(12) United States Patent
Kotake et al.

(10) Patent No.: US 7,550,503 B2
(45) Date of Patent: Jun. 23, 2009

(54) PHYSIOLOGICALLY ACTIVE SUBSTANCES

(75) Inventors: Yoshihiko Kotake, Ibaraki (JP); Jun Niijima, Ibaraki (JP); Yoshio Fukuda, Ibaraki (JP); Mitsuo Nagai, Ibaraki (JP); Regina Mikie Kanada, Ibaraki (JP); Takashi Nakashima, Shizuoka (JP); Masahi Yoshida, Shizuoka (JP); Toshio Tsuchida, Shizuoka (JP)

(73) Assignees: Eisai R& D Management Co., Ltd., Tokyo (JP); Merican Corporation, Tokyo (JP)

( * ) Notice: Subject to any disclaimer, the term of this patent is extended or adjusted under 35 U.S.C. 154(b) by 135 days.

(21) Appl. No.: 11/473,201

(22) Filed: Jun. 23, 2006

(65) Prior Publication Data

US 2006/0241171 A1   Oct. 26, 2006

Related U.S. Application Data

(63) Continuation of application No. 10/515,647, filed on Jul. 20, 2005, now abandoned.

(51) Int. Cl.
- A01N 43/02 (2006.01)
- A61K 31/335 (2006.01)
- C07D 313/00 (2006.01)
- C07D 313/04 (2006.01)

(52) U.S. Cl. .................. 514/450; 549/266; 549/271
(58) Field of Classification Search .................. 514/450; 549/271, 266
See application file for complete search history.

(56) References Cited

U.S. PATENT DOCUMENTS

| | | | |
|---|---|---|---|
| 6,712,617 B2 * | 3/2004 | Detmar et al. | 434/407 |
| 7,026,352 B1 * | 4/2006 | Mizui et al. | 514/450 |
| 7,256,178 B2 * | 8/2007 | Kotake et al. | 514/28 |
| 2008/0021226 A1 * | 1/2008 | Kanada et al. | 549/215 |

FOREIGN PATENT DOCUMENTS

| | | |
|---|---|---|
| JP | 4-352783 A | 12/1992 |
| WO | WO-00/75126 A1 | 12/2000 |
| WO | WO-02/12533 A2 | 2/2002 |
| WO | WO-02/060890 A1 | 8/2002 |
| WO | WO-03/099813 A1 | 12/2003 |

OTHER PUBLICATIONS

Ryuichi Morishita, Circ Journal, vol. 66, pp. 1077-1086.*
Moon-Seok Cha, Biochemical and Biophysical Research Comunications, vol. 282, pp. 1061-1066.*
Ryuichi Morishita. "Recent Progress in Gene Therapy for Cardiovascular Disease", Circ Journal, vol. 66, pp. 1077-1086.
Moon-Seok Cha, "Endogenous Production of Nitric Oxide by vascular Endothelial Growth Factor Down-Regulates Proliferation of Choriocarcinoma Cells", Biochemical and Biophysical Research Communications, vol. 282, pp. 1061-1066.

Seki-Asano, Mitsuko et al., "Isolation and Characterization of a New 12-Membered Macrolide FD-895", J. Antibiot., 1994, vol. 47, No. 12, pp. 1395 to 1401.
Bestmann, Hans Jurgen. Synthesis, 1989, vol. 6, pp. 419-423.
Bestmann, Jans Jurgen. Angew. Chem., 1983, vol. 95, No. 10, pp. 810-811.
Furstner, Alois et al. Efficient Total Syntheses of Resin Glycosides and Analogues by Ring-Closing Olefin Metathesis, J. Am. Chem. Soc., 1999, vol. 121, pp. 7814-7821.
Gunawardana, Geewananda, et al. J. Am. Chem. Soc. 1999, vol. 121, pp. 6092-6093.
Rohr, Jurgen. Angew Chem. Int. Ed., 2000, vol. 39, No. 16, pp. 2847-2849.
Kobayashi, Jun'ichi et al. Tetrahedron Letters, 1996, vol. 37, No. 9, pp. 1449-1450.
Hamberg, Mats. Lipids, 2000, vol. 35, No. 4, pp. 353-363.
Hamberg, Mats. Chem. Phys. Lipids, 1988, vol. 46, No. 4, pp. 235-243.
Sakai et al., "Shinki ko-shuyo kassei busshitsu pladienolide ni kansuru kenkyu (1)-shinki 12-inkan macrolide pladeienolide B no tanri to kozo", Japan Society for Bioscience, Biotechnology, and Agrochemistry, Taikai Koen Yoshishu, Mar. 2003, p. 123.
Akifumi et al., "Shinki ko-shuyo kassei busshitsu pladienolide ni kansuru kenkyu (2) VEGF sansei yokusei kassei o shihyo to shita pladienolide-rui no kozo kassei sokan", Japan Society for Bioscience, Biotechnology, and Agrochemistry, Taikai Koen Yoshishu, Mar. 2003, p. 124.
Keiji et al., "Shinki ko-shuyo kassei busshitsu pladienolide ni kansuru kenkyu (3)- pladienolide-rui no yakuri kassei (in vitro, in vivo)", Japan Society for Bioscience, Biotechnology, and Agrochemistry, Taikai Koen Yoshishu, Mar. 2003, p. 124.

(Continued)

Primary Examiner—D. Margaret Seaman
Assistant Examiner—Niloofar Rahmani
(74) Attorney, Agent, or Firm—Birch, Stewart, Kolasch & Birch, LLP

(57) ABSTRACT

The present invention relates to a compound represented by the formula (I):

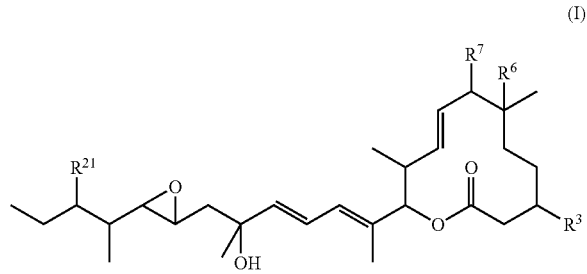

(wherein, $R^3$, $R^6$, $R^7$ and $R^{21}$ are the same as or different from one another and each represents a hydroxyl group etc.), a pharmacologically acceptable salt thereof or a hydrate of them. The compound (I) of the present invention suppresses angiogenesis, in particular, suppresses VEGF production in a hypoxic condition and is useful as a therapeutic agent for treating solid cancer.

26 Claims, No Drawings

OTHER PUBLICATIONS

Proceedings for 2003 Annual Meeting of Japan Society for Bioscience, Biotechnology, and Agrochemistry, pp. 123-124, (2003).
Ronald A. Lemahieu et al.; The Journal of Antibiotics, Jul. 1976, vol. 29, No. 7, pp. 728-734.
Roberto Spagnoli et al.; The Journal of Antibiotics, Apr. 1983, vol. 36, No. 4, pp. 365-375.
A. Anadon; Research in Veterinary Science, Jun. 1999, vol. 66, No. 3, pp. 197-203.
D.J. Farrell et al.; Journal of Antimicrobial Chemotherapy, Sep. 2002, vol. 50, Suppl., pp. 39-47.
Eskens et al., "First-in-human clinical, pharmacokinetic (PK) and pharmacodynamic (PD) phase I study of the first-in-class spliceosome inhibitor E7107 administered IV (bolus) on days 1, 8, and 15 every 28 days to patients with solid tumors", Abstract submission to: American Society of Clinical Oncology, date of submission: Jan. 6, 2009.

* cited by examiner

PHYSIOLOGICALLY ACTIVE SUBSTANCES

CROSS-REFERENCE TO RELATED APPLICATIONS

The present application is a 37 C.F.R. §1.53(b) continuation of U.S. patent application Ser. No. 10/515,647 filed Jul. 20, 2005 now abandoned, which claims priority on Japanese Patent Application No. 2002-155853, filed May 29, 2002, Japanese Patent Application No. 2002-223355, Jul. 31, 2002, and Japanese Patent Application No. 2003-63176 filed on Mar. 10, 2003, the entire contents of which are hereby incorporated by reference and for which priority is claimed under 35 U.S.C. § 120.

TECHNICAL FIELD

The present invention relates to a 12-membered ring macrolide compound useful as a medicament, preparation thereof and use thereof.

BACKGROUND OF THE INVENTION

Compounds having cytotoxicity have been used as antitumor agents, and many screenings have been carried out using cytotoxicity as an index. As a result, most of pre-existing antitumor agents give affection to cancer cells and simultaneously to normal tissues in which a proliferation of cell is active, for example, to bone marrow, intestine epithelium and the like. Thus, the improvement of QOL of patients has not been sufficiently accomplished yet.

Further, although it can be expected that treatments by the antitumor agents are rather effective for leukemia, it cannot be always said that they are effective for solid cancer. Therefore strong demands have been made to provide antitumor agents that are effective for solid cancer and are highly safe.

Screenings for fermentation products of microorganism have been carried out using the cytotoxicity in vitro as an index, expecting that they might also be used as antitumor agents. Many compounds having cytotoxicity have been found, however, most of them show cytotoxic activities only in vitro, and few compounds of them show antitumor activities in vivo, and very few compounds exhibit effectiveness for solid cancer.

DISCLOSURE OF THE INVENTION

It is the object of the present invention to find out compounds which show antitumor activity not only in vitro but also in vivo and have antitumor activities for solid cancer from fermentation products of microorganism or derivatives thereof.

It is considered that tumorgenesis of a normal cell is caused by mutation of a gene in the cell occurs and an abnormal gene is expressed. Accordingly, the present inventors have made intensive investigations based on the inference that the growth of a tumor cell can be suppressed by changing the gene expression of the tumor cell, namely, the growth of the tumor cell can be controlled by changing the gene expression of oncogene or tumor suppressor gene, or by changing the gene expression involved in cell cycle. The present inventors have considered that a compound changing of the gene expression, in particular, a compound suppressing VEGF (vascular endothelial growth factor) production at a hypoxic condition could suppress angiogenesis by a tumor and has an antitumor activities for solid cancer. Then, they carried out screening for fermentation products of microorganism and derivatives thereof using the VEGF production by U251 cell under hypoxic stimulation as an index. As the results, the inventors have found out novel physiologically active compounds, 12-membered ring macrolide compounds, named 11107 and analogues thereof which suppress the VEGF production at a hypoxic condition in vitro, and further suppress the growth of solid tumor cells in vivo.

The present inventors have further found that 1107D among the 11107 analogues is stable even in an aqueous solution, and that compounds obtained by chemical modifications of 11107D (hereinafter, these are referred to as 11107D derivatives) inherit the property of stability in an aqueous solution from 11107D and inhibit the growth of solid tumor cells in vivo experiments in much more degree. The present invention has been accomplished based on these findings.

As a related art of a 12-membered ring macrolide compound which is most structurally similar to the compounds of the present invention, a 12-membered ring macrolide compound FD-895 (JP-A 4-352783) represented by the formula (XIV):

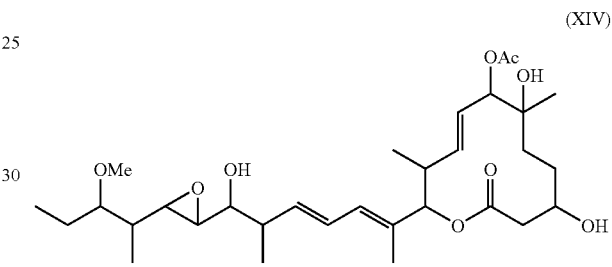

is mentioned. The publication discloses that FD-895 has in vitro cell growth inhibitory activities against P388 mouse leukemia cell, L-1210 mouse leukemia cell and HL-60 human leukemia cell in RPM-1640 medium (column 6, Table 2). However, it has been reported that FD-895 did not show antitumor activities in an in vivo experiment using P388 mouse leukemia cell (Seki-Asano M. et al, J. Antibiotics, 47, 1395-1401, 1994).

In addition, FD-895 is unstable in an aqueous solution as described later and is expected to be inappropriate to mix with an infusion solution upon administration. Thus, it cannot be said that FD-895 has sufficient qualities as an antitumor agent.

That is, the present invention relates to:
(1) a compound represented by the formula (I):

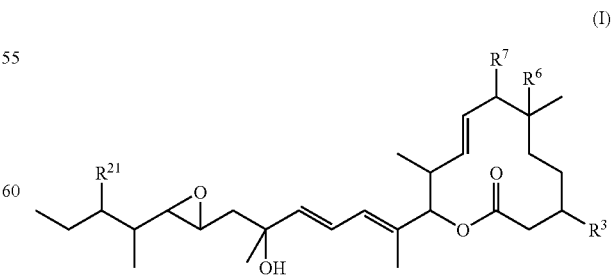

(in the formula, $R^3$, $R^6$, $R^7$ and $R^{21}$ are the same as or different from one another and each represents 1) a hydroxyl group or an oxo group formed together with the carbon atom to which each of $R^3$, $R^6$, $R^7$ and $R^{21}$ is bound, provided that $R^6$ is limited to a hydroxyl group,
2) an optionally substituted $C_{1-22}$ alkoxy group,
3) an optionally substituted unsaturated $C_{2-22}$ alkoxy group,
4) an optionally substituted $C_{7-22}$ aralkyloxy group,
5) an optionally substituted 5 to 14-membered heteroaralkyloxy group,
6) RCO—O— (wherein R represents
   a) a hydrogen atom,
   b) an optionally substituted $C_{1-22}$ alkyl group,
   c) an optionally substituted unsaturated $C_{2-22}$ alkyl group,
   d) an optionally substituted $C_{6-14}$ aryl group,
   e) an optionally substituted 5 to 14-membered heteroaryl group,
   f) an optionally substituted $C_{7-22}$ aralkyl group,
   g) an optionally substituted 5 to 14-membered heteroaralkyl group,
   h) an optionally substituted $C_{1-22}$ alkoxy group,
   i) an optionally substituted unsaturated $C_{2-22}$ alkoxy group,
   j) an optionally substituted $C_{6-14}$ aryloxy group or
   k) an optionally substituted 5 to 14-membered heteroaryloxy group), 7) $R^{S1}R^{S2}R^{S3}SiO$— (wherein $R^{S1}$, $R^{S2}$ and $R^{S3}$ are the same as or different from one another and each represents
   a) a $C_{1-6}$ alkyl group or
   b) a $C_{6-14}$ aryl group),
8) a halogen atom,
9) $R^{N1}R^{N2}N$—$R^M$— (wherein $R^M$ represents
   a) a single bond,
   b) —CO—O—,
   c) —SO$_2$—O—,
   d) —CS—O— or
   e) —CO—NR$^{N3}$— (wherein $R^{N3}$ represents a hydrogen atom or an optionally substituted $C_{1-6}$ alkyl group), provided that each of the leftmost bond in b) to e) is bound to the nitrogen atom; and
$R^{N1}$ and $R^{N2}$ are the same as or different from each other and each represents
   a) a hydrogen atom,
   b) an optionally substituted $C_{1-22}$ alkyl group,
   c) an optionally substituted unsaturated $C_{2-22}$ alkyl group,
   d) an optionally substituted aliphatic $C_{2-22}$ acyl group,
   e) an optionally substituted aromatic $C_{7-15}$ acyl group,
   f) an optionally substituted $C_{6-14}$ aryl group,
   g) an optionally substituted 5 to 14-membered heteroaryl group,
   h) an optionally substituted $C_{7-22}$ aralkyl group,
   i) an optionally substituted $C_{1-22}$ alkylsulfonyl group,
   j) an optionally substituted $C_{6-14}$ arylsulfonyl group,
   k) an optionally substituted 3 to 14-membered non-aromatic heterocyclic group formed by $R^{N1}$ and $R^{N2}$ together with the nitrogen atom to which $R^{N1}$ and $R^{N2}$ are bound, and the non-aromatic heterocyclic group may have substituents,
   l) an optionally substituted 5 to 14-membered heteroaralkyl group,
   m) an optionally substituted $C_{3-14}$ cycloalkyl group or
   n) an optionally substituted 3 to 14-membered non-aromatic heterocyclic group),
10) $R^{N4}SO_2$—O— (wherein $R^{N4}$ represents
   a) an optionally substituted $C_{1-22}$ alkyl group,
   b) an optionally substituted $C_{6-14}$ aryl group,
   c) an optionally substituted $C_{1-22}$ alkoxy group,
   d) an optionally substituted unsaturated $C_{2-22}$ alkoxy group,
   e) an optionally substituted $C_{6-14}$ aryloxy group,
   f) an optionally substituted 5 to 14-membered heteroaryloxy group,
   g) an optionally substituted $C_{7-22}$ aralkyloxy group or
   h) an optionally substituted 5 to 14-membered heteroaralkyloxy group),
11) $(R^{N5}O)_2PO$—O— (wherein $R^{N5}$ represents
   a) an optionally substituted $C_{1-22}$ alkyl group,
   b) an optionally substituted unsaturated $C_{2-22}$ alkyl group,
   c) an optionally substituted $C_{6-14}$ aryl group,
   d) an optionally substituted 5 to 14-membered heteroaryl group,
   e) an optionally substituted $C_{7-22}$ aralkyl group or
   f) an optionally substituted 5 to 14-membered heteroaralkyl group),
12) $(R^{N1}R^{N2}N)_2PO$—O— (wherein $R^{N1}$ and $R^{N2}$ have the same meanings as defined above) or
13) $(R^{N1}R^{N2}N)(R^{N5}O)_2PO$—O— (wherein $R^{N1}$, $R^{N2}$ and $R^{N5}$ have the same meanings as defined above), provided that a compound in which $R^3$, $R^6$, $R^7$ and $R^{21}$ are all hydroxyl groups, and a compound in which $R^3$, $R^6$ and $R^{21}$ are all hydroxyl groups and $R^7$ is an acetoxy group are excluded), a pharmacologically acceptable salt thereof or a hydrate of them;
(2) the compound described in (1) represented by the formula (I-a):

(I-a)

(in the formula, $R^{3a}$, $R^{6a}$, $R^{7a}$ and $R^{21a}$ are the same as or different from one another and each represents
1) a hydroxyl group or an oxo group formed together with the carbon atom to which each of $R^{3a}$, $R^{6a}$, $R^{7a}$ and $R^{21a}$ is bound, provided that $R^{6a}$ is limited to a hydroxyl group,
2) an optionally substituted $C_{1-22}$ alkoxy group,
3) $R^aCO$—O— (wherein $R^a$ represents
   a) a hydrogen atom,
   b) an optionally substituted $C_{1-22}$ alkyl group,
   c) an optionally substituted unsaturated $C_{2-22}$ alkyl group,
   d) an optionally substituted $C_{6-14}$ aryl group,
   e) an optionally substituted 5 to 14-membered heteroaryl group,
   f) an optionally substituted $C_{7-22}$ aralkyl group,
   g) an optionally substituted 5 to 14-membered heteroaralkyl group,
   h) an optionally substituted $C_{1-22}$ alkoxy group,
   i) an optionally substituted unsaturated $C_{2-22}$ alkoxy group,
   j) an optionally substituted $C_{6-14}$ aryloxy group or k) an optionally substituted 5 to 14-membered heteroaryloxy group),
4) $R^{aS1}R^{aS2}R^{aS3}SiO$— (wherein $R^{aS1}$, $R^{aS2}$ and $R^{aS3}$ are the same as or different from one another and each represents
   a) a $C_{1-6}$ alkyl group or
   b) a $C_{6-14}$ aryl group),
5) a halogen atom or
6) $R^{aN1}R^{aN2}N$—$R^{aM}$— (wherein $R^{aM}$ represents
   a) a single bond,
   b) —CO—O—,
   c) —$SO_2$—O—,
   d) —CS—O— or
   e) —CO—$NR^{aN3}$— (wherein $R^{aN3}$ represents a hydrogen atom or an optionally substituted $C_{1-6}$ alkyl group, provided that each of the leftmost bond in b) to e) is bound to the nitrogen atom); and
$R^{aN1}$ and $R^{aN2}$ are the same as or different from each other and each represents
   a) a hydrogen atom,
   b) an optionally substituted $C_{1-22}$ alkyl group,
   c) an optionally substituted unsaturated $C_{2-22}$ alkyl group,
   d) an optionally substituted aliphatic $C_{2-22}$ acyl group,
   e) an optionally substituted aromatic $C_{7-15}$ acyl group,
   f) an optionally substituted $C_{6-14}$ aryl group,
   g) an optionally substituted 5 to 14-membered heteroaryl group,
   h) an optionally substituted $C_{7-22}$ aralkyl group,
   i) an optionally substituted $C_{1-22}$ alkylsulfonyl group,
   j) an optionally substituted $C_{6-14}$ arylsulfonyl group,
   k) an optionally substituted 3 to 14-membered non-aromatic heterocyclic group formed by $R^{aN1}$ and $R^{aN2}$ together with the nitrogen atom to which $R^{aN1}$ and $R^{aN2}$ are bound, and the non-aromatic heterocyclic group may have substituents,
   l) an optionally substituted 5 to 14-membered heteroaralkyl group,
   m) an optionally substituted $C_{3-14}$ cycloalkyl group or
   n) an optionally substituted 3 to 14-membered non-aromatic heterocyclic group)), a pharmacologically acceptable salt thereof or a hydrate of them;
(3) the compound described in (1) represented by the formula (I-b):

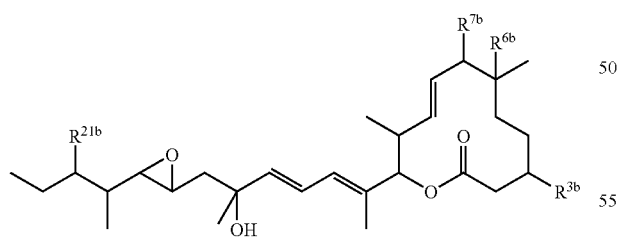

(I-b)

(in the formula, $R^{3b}$, $R^{6b}$, $R^{7b}$ and $R^{21b}$ are the same as or different from one another and each represents
   1) a hydroxyl group or an oxo group formed together with the carbon atom to which each of $R^{3b}$, $R^{6b}$, $R^{7b}$ and $R^{21b}$ is bound, provided that $R^{6b}$ is limited to a hydroxyl group,
   2) an optionally substituted $C_{1-22}$ alkoxy group,
   3) $R^{b}CO$—O— (wherein $R^{b}$ represents
      a) a hydrogen atom,
      b) an optionally substituted $C_{1-22}$ alkyl group,
      c) an optionally substituted unsaturated $C_{2-22}$ alkyl group,
      d) an optionally substituted $C_{6-14}$ aryl group,
      e) an optionally substituted 5 to 14-membered heteroaryl group,
      f) an optionally substituted $C_{7-22}$ aralkyl group,
      g) an optionally substituted 5 to 14-membered heteroaralkyl group,
      h) an optionally substituted $C_{1-22}$ alkoxy group,
      i) an optionally substituted unsaturated $C_{2-22}$ alkoxy group,
      j) an optionally substituted $C_{6-14}$ aryloxy group or
      k) an optionally substituted 5 to 14-membered heteroaryloxy group),
4) $R^{bS1}R^{bS2}R^{bS3}SiO$— (wherein $R^{bS1}$, $R^{bS2}$ and $R^{bS3}$ are the same as or different from one another and each represents
   a) a $C_{1-6}$ alkyl group or
   b) a $C_{6-14}$ aryl group) or
5) $R^{bN1}R^{bN2}N$—$R^{bM}$— (wherein $R^{bM}$ represents
   a) —CO—O— or
   b) —CS—O—, provided that each of the leftmost bond in a) and b) is bound to the nitrogen atom; and
$R^{bN1}$ and $R^{bN2}$ are the same as or different from each other and each represents
   a) a hydrogen atom,
   b) an optionally substituted $C_{1-22}$ alkyl group,
   c) an optionally substituted unsaturated $C_{2-22}$ alkyl group,
   d) an optionally substituted aliphatic $C_{2-22}$ acyl group,
   e) an optionally substituted aromatic $C_{7-15}$ acyl group,
   f) an optionally substituted $C_{6-14}$ aryl group,
   g) an optionally substituted 5 to 14-membered heteroaryl group,
   h) an optionally substituted $C_{7-22}$ aralkyl group,
   i) an optionally substituted $C_{1-22}$ alkylsulfonyl group,
   j) an optionally substituted $C_{6-14}$ arylsulfonyl group,
   k) an optionally substituted 3 to 14-membered non-aromatic heterocyclic group formed by $R^{bN1}$ and $R^{bN2}$ together with the nitrogen atom to which $R^{bN1}$ and $R^{bN2}$ are bound, and the non-aromatic heterocyclic group may have substituents,
   l) an optionally substituted 5 to 14-membered heteroaralkyl group,
   m) an optionally substituted $C_{3-14}$ cycloalkyl group or
   n) an optionally substituted 3 to 14-membered non-aromatic heterocyclic group)), a pharmacologically acceptable salt thereof or a hydrate of them;
(4) the compound described in (1) represented by the formula (I-c):

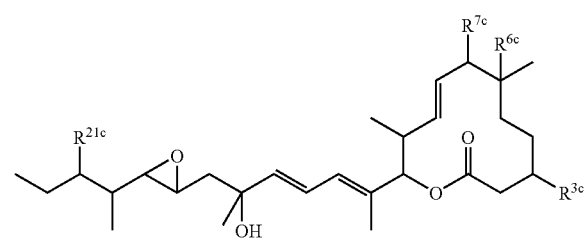

(I-c)

(in the formula, $R^{3c}$, $R^{6c}$, $R^{7c}$ and $R^{21c}$ are the same as or different from one another and each represents 1) a hydroxyl group or an oxo group formed together with the carbon atom to which each of $R^{3c}$, $R^{6c}$, $R^{7c}$ and $R^{21c}$ is bound, provided that $R^{6c}$ is limited to a hydroxyl group,
2) an optionally substituted $C_{1-22}$ alkoxy group,
3) $R^c CO—O—$ (wherein $R^c$ represents
  a) an optionally substituted $C_{1-22}$ alkyl group,
  b) an optionally substituted $C_{6-14}$ aryl group,
  c) an optionally substituted $C_{7-22}$ aralkyl group or
  d) an optionally substituted $C_{6-14}$ aryloxy group),
4) $R^{cS1}R^{cS2}R^{cS3}SiO—$ (wherein $R^{cS1}$, $R^{cS2}$ and $R^{cS3}$ are the same as or different from one another and each represents
  a) a $C_{1-6}$ alkyl group or
  b) a $C_{6-14}$ aryl group) or
5) $R^{cN1}R^{cN2}N—R^{cM}—$ (wherein $R^{cM}$ represents
  a) —CO—O— or
  b) —CS—O—, provided that each of the leftmost bond in a) and b) is bound to the nitrogen atom; and
$R^{cN1}$ and $R^{cN2}$ are the same as or different from each other and each represents
  a) a hydrogen atom,
  b) an optionally substituted $C_{1-22}$ alkyl group,
  c) an optionally substituted 3 to 14-membered non-aromatic heterocyclic group formed by $R^{cN1}$ and $R^{cN2}$ together with the nitrogen atom to which $R^{cN1}$ and $R^{cN2}$ are bound, and the non-aromatic heterocyclic group may have substituents,
  d) an optionally substituted 5 to 14-membered heteroaralkyl group,
  e) an optionally substituted $C_{3-14}$ cycloalkyl group or
  f) an optionally substituted 3 to 14-membered non-aromatic heterocyclic group, and the non-aromatic heterocyclic group may have substituents)), a pharmacologically acceptable salt thereof or a hydrate of them;
(5) the compound described in (1) represented by the formula (I-d):

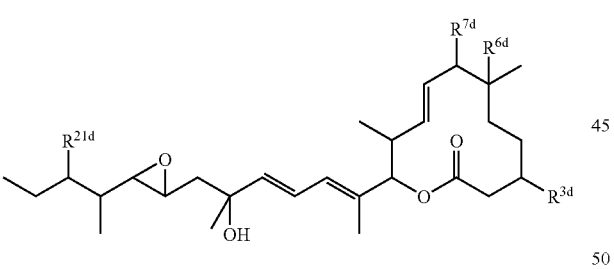

(I-d)

(in the formula, $R^{3d}$ represents
1) a hydroxyl group or an oxo group formed together with the carbon atom to which $R^{3d}$ is bound,
2) an optionally substituted $C_{1-22}$ alkoxy group,
3) an optionally substituted unsaturated $C_{2-22}$ alkoxy group,
4) an optionally substituted $C_{7-22}$ aralkyloxy group,
5) $R^d CO—O—$ (wherein $R^d$ represents
  a) a hydrogen atom,
  b) an optionally substituted $C_{1-22}$ alkyl group,
  c) an optionally substituted unsaturated $C_{2-22}$ alkyl group,
  d) an optionally substituted $C_{6-14}$ aryl group,
  e) an optionally substituted 5 to 14-membered heteroaryl group,
  f) an optionally substituted $C_{7-22}$ aralkyl group,
  g) an optionally substituted 5 to 14-membered heteroaralkyl group,
  h) an optionally substituted $C_{1-22}$ alkoxy group,
  i) an optionally substituted unsaturated $C_{2-22}$ alkoxy group,
  j) an optionally substituted $C_{6-14}$ aryloxy group or
  k) an optionally substituted 5 to 14-membered heteroaryloxy group) or
6) $R^{dN1}R^{dN2}N—CO—O—$ (wherein $R^{dN1}$ and $R^{dN2}$ are the same as or different from each other and each represents
  a) a hydrogen atom,
  b) an optionally substituted $C_{1-22}$ alkyl group,
  c) an optionally substituted unsaturated $C_{2-22}$ alkyl group,
  d) an optionally substituted $C_{6-14}$ aryl group,
  e) an optionally substituted 5 to 14-membered heteroaryl group,
  f) an optionally substituted $C_{7-22}$ aralkyl group,
  g) an optionally substituted 5 to 14-membered heteroaralkyl group,
  h) an optionally substituted $C_{3-14}$ cycloalkyl group,
  i) an optionally substituted 3 to 14-membered non-aromatic heterocyclic group or
  j) an optionally substituted 3 to 14-membered non-aromatic heterocyclic group formed by $R^{dN1}$ and $R^{dN2}$ together with the nitrogen atom to which $R^{dN1}$ and $R^{dN2}$ are bound, and the non-aromatic heterocyclic group may have substituents); and
$R^{6d}$, $R^{7d}$ and $R^{21d}$ are the same as or different from one another and each represents
1) a hydroxyl group or an oxo group formed together with the carbon atom to which each of $R^{6d}$, $R^{7d}$ and $R^{21d}$ is bound, provided that $R^{6d}$ is limited to a hydroxyl group,
2) an optionally substituted $C_{1-22}$ alkoxy group,
3) an optionally substituted unsaturated $C_{2-22}$ alkoxy group,
4) an optionally substituted $C_{7-22}$ aralkyloxy group,
5) $R^d CO—O—$ (wherein $R^d$ has the same meaning as defined above),
6) $R^{dN1}R^{dN2}N—CO—O—$ (wherein $R^{dN1}$ and $R^{dN2}$ have the same meanings as defined above),
7) $R^{dN1}R^{dN2}N—SO_2—O—$ (wherein $R^{dN1}$ and $R^{dN2}$ have the same meanings as defined above),
8) $R^{dN1}R^{dN2}N—CS—O—$ (wherein $R^{dN1}$ and $R^{dN2}$ have the same meanings as defined above),
9) $R^{dN3}SO_2—$ (wherein $R^{dN3}$ represents
  a) an optionally substituted $C_{1-22}$ alkyl group,
  b) an optionally substituted $C_{1-22}$ alkoxy group,
  c) an optionally substituted unsaturated $C_{2-22}$ alkoxy group,
  d) an optionally substituted $C_{6-14}$ aryl group,
  e) an optionally substituted $C_{6-14}$ aryloxy group,
  f) an optionally substituted 5 to 14-membered heteroaryloxy group,
  g) an optionally substituted $C_{7-22}$ aralkyloxy group or
  h) an optionally substituted 5 to 14-membered heteroaralkyloxy group),
10) $(R^{dN5}O)_2PO—$ (wherein $R^{dN5}$ represents
  a) an optionally substituted $C_{1-22}$ alkyl group,
  b) an optionally substituted unsaturated $C_{2-22}$ alkyl group,
  c) an optionally substituted $C_{6-14}$ aryl group,
  d) an optionally substituted 5 to 14-membered heteroaryl group,
  e) an optionally substituted $C_{7-22}$ aralkyl group or
  f) an optionally substituted 5 to 14-membered heteroaralkyl group), 11) $(R^{dN1}R^{dN2}N)_2PO-$ (wherein $R^{dN1}$ and $R^{dN2}$ have the same meanings as defined above) or 12) $R^{dN1}R^{dN2})(R^{dN5}O)PO-$ (wherein $R^{dN1}$, $R^{dN2}$ and $R^{dN5}$ have the same meanings as defined above), provided that a compound in which $R^{3d}$, $R^{6d}$, $R^{7d}$ and $R^{21d}$ are all hydroxyl groups, and a compound in which $R^{3d}$, $R^{6d}$ and $R^{21d}$ are hydroxyl groups and $R^{7d}$ is an acetoxy group are excluded), a pharmacologically acceptable salt thereof or a hydrate of them;

(6) the compound described in (1), wherein $R^6$ and/or $R^7$ represents $R^{N1}R^{N2}N-R^M-$ (wherein $R^M$ represents
 a) $-CO-O-$ or
 b) $-CS-O-$; and
$R^{N1}$ and $R^{N2}$ have the same meanings as defined above, provided that each of the leftmost bond in a) and b) is bound to the nitrogen atom), a pharmacologically acceptable salt thereof or a hydrate of them;

(7) the compound described in (1), a pharmacologically acceptable salt thereof or a hydrate of them, wherein $R^{21}$ is an oxo group formed together with the carbon atom to which $R^{21}$ is bound;

(8) the compound described in (5) represented by the formula (I-e):

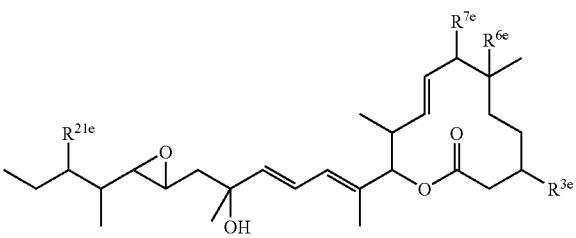

(I-e)

(in the formula, $R^{3e}$ and $R^{21e}$ are the same as or different from each other and each represents
 1) a hydroxyl group or an oxo group formed together with the carbon atom to which each of $R^{3e}$ and $R^{21e}$ is bound,
 2) an optionally substituted $C_{1-6}$ alkoxy group,
 3) an optionally substituted unsaturated $C_{2-10}$ alkoxy group,
 4) an optionally substituted $C_{7-10}$ aralkyloxy group,
 5) an optionally substituted aliphatic $C_{2-6}$ acyloxy group or
 6) $R^{eN1}R^{eN2}N-CO-O-$ (wherein $R^{eN1}$ and $R^{eN2}$ are the same as or different from each other and each represents
  A) a hydrogen atom or
  B) an optionally substituted $C_{1-6}$ alkyl group); and
$R^{6e}$ and $R^{7e}$ are the same as or different from each other and each represents
 1) a hydroxyl group or an oxo group formed together with the carbon atom to which each of $R^{6e}$ and $R^{7e}$ is bound, provided that $R^{6e}$ is limited to a hydroxyl group,
 2) an optionally substituted $C_{1-6}$ alkoxy group,
 3) an optionally substituted unsaturated $C_{2-10}$ alkoxy group,
 4) an optionally substituted $C_{7-10}$ aralkyloxy group,
 5) an optionally substituted aliphatic $C_{2-6}$ acyloxy group or
 6) $R^eC(=Y^e)-O-$ (wherein $Y^e$ represents an oxygen atom or a sulfur atom; and $R^e$ represents
  a) a hydrogen atom,
  b) an optionally substituted $C_{1-6}$ alkyl group,
  c) an optionally substituted $C_{7-10}$ aralkyl group,
  d) an optionally substituted 5 to 14-membered heteroaralkyl group, e) the formula (III):

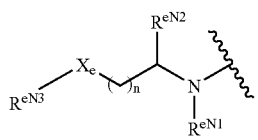

(III)

(in the formula,
 A) n represents an integer of 0 to 4;
$X_e$ represents
 i) $-CHR^{eN4}-$,
 ii) $-NR^{eN5}-$,
 iii) $-O-$,
 iv) $-S-$,
 v) $-SO-$ or
 vi) $-SO_2-$;
$R^{eN1}$ represents
 i) a hydrogen atom or
 ii) a $C_{1-6}$ alkyl group;
$R^{eN2}$ represents
 i) hydrogen atom or
 ii) a $C_{1-6}$ alkyl group;
$R^{eN3}$ and $R^{eN4}$ are the same as or different from each other and each represents
 i) a hydrogen atom,
 ii) an optionally substituted $C_{1-6}$ alkyl group,
 iii) an optionally substituted unsaturated $C_{2-10}$ alkyl group,
 iv) an optionally substituted $C_{6-14}$ aryl group,
 v) an optionally substituted 5 to 14-membered heteroaryl group,
 vi) an optionally substituted $C_{7-10}$ aralkyl group,
 vii) an optionally substituted $C_{3-8}$ cycloalkyl group,
 viii) an optionally substituted $C_{4-9}$ cycloalkyl alkyl group,
 ix) an optionally substituted 5 to 14-membered heteroaralkyl group,
 x) an optionally substituted 5 to 14-membered non-aromatic heterocyclic group,
 xi) $-NR^{eN6}R^{eN7}$ (wherein $R^{eN6}$ and $R^{eN7}$ are the same as or different from each other and each represents a hydrogen atom or an optionally substituted $C_{1-6}$ alkyl group) or
 xii) an optionally substituted 5 to 14-membered non-aromatic heterocyclic group formed by $R^{eN3}$ and $R^{eN4}$ together with the carbon atom to which $R^{N3}$ and $R^{N4}$ are bound, and the non-aromatic heterocyclic group may have substituents; and
$R^{eN5}$ represents
 i) a hydrogen atom,
 ii) an optionally substituted $C_{1-6}$ alkyl group,
 iii) an optionally substituted unsaturated $C_{2-10}$ alkyl group,
 iv) an optionally substituted $C_{6-14}$ aryl group,
 v) an optionally substituted 5 to 14-membered heteroaryl group,
 vi) an optionally substituted $C_{7-10}$ aralkyl group,
 vii) an optionally substituted $C_{3-8}$ cycloalkyl group,
 viii) an optionally substituted $C_{4-9}$ cycloalkyl alkyl group,
 ix) an optionally substituted 5 to 14-membered heteroaralkyl group,
 x) an optionally substituted 5 to 14-membered non-aromatic heterocyclic group or
 xi) an optionally substituted 5 to 14-membered non-aromatic heterocyclic group formed by $R^{N3}$ and $R^{N5}$ together with the nitrogen atom to which $R^{eN3}$ and $R^{eN5}$ are bound, and the non-aromatic heterocyclic group may have substituents,
B) $X_e$, n, $R^{eN3}$, $R^{eN4}$ and $R^{eN5}$ each represents the group as defined above; and $R^{eN1}$ and $R^{eN2}$ together form an optionally substituted 5 to 14-membered non-aromatic heterocyclic group,
C) $X_e$, n, $R^{eN2}$, $R^{eN4}$ and $R^{eNn5}$ each represents the group as defined above; and $R^{eN1}$ and $R^{eN3}$ together form an optionally substituted 5 to 14-membered non-aromatic heterocyclic group or
D) $X_e$, n, $R^{eN1}$, $R^{eN4}$ and $R^{eN5}$ each represents the group as defined above; and $R^{eN2}$ and $R^{eN3}$ together form an optionally substituted 5 to 14-membered non-aromatic heterocyclic group) or
f) the formula (IV):

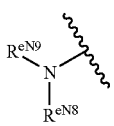

(IV)

(in the formula, $R^{eN8}$ and $R^{eN9}$ are the same as or different from each other and each represents
i) a hydrogen atom,
ii) an optionally substituted $C_{1-6}$ alkyl group,
iii) an optionally substituted $C_{6-14}$ aryl group,
iv) an optionally substituted 5 to 14-membered heteroaryl group,
v) an optionally substituted $C_{7-10}$ aralkyl group or
vi) an optionally substituted 5 to 14-membered heteroaralkyl group))), a pharmacologically acceptable salt thereof or a hydrate of them;
(9) the compound described in (5), wherein $R^{6d}$ and/or $R^{7d}$ represents $R^{d1}C(=Y^{d1})$—O— (wherein $Y^{d1}$ represents an oxygen atom or a sulfur atom; and $R^{d1}$ represents
1) a hydrogen atom,
2) an optionally substituted $C_{1-6}$ alkyl group,
3) an optionally substituted $C_{7-10}$ aralkyl group or
4) an optionally substituted 5 to 14-membered heteroaralkyl group), a pharmacologically acceptable salt thereof or a hydrate of them;
(10) the compound described in (5), wherein $R^{6d}$ and/or $R^{7d}$ represents $R^{d2}C(=Y^{d2})$—O— (wherein $Y^{d2}$ represents an oxygen atom or a sulfur atom; and $R^{d2}$ represents the formula (III'):

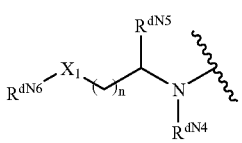

(III')

(in the formula, n represents an integer of 0 to 4; $X_1$ represents
1) —$CHR^{dN7}$—,
2) —$NR^{dN8}$—,
3) —O—,
4) —S—,
5) —SO— or
6) —$SO_2$—;
$R^{dN4}$ and $R^{dN5}$ are the same as or different from each other and each represents 1) a hydrogen atom or
2) a $C_{1-6}$ alkyl group;
$R^{dN6}$ and $R^{dN7}$ are the same as or different from each other and each represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group,
10) an optionally substituted 5 to 14-membered non-aromatic heterocyclic group,
11) —$NR^{dN9}R^{dN10}$ (wherein $R^{dN9}$ and $R^{dN10}$ are the same as or different from each other and each represents a hydrogen atom or an optionally substituted $C_{1-6}$ alkyl group) or
12) an optionally substituted 5 to 14-membered non-aromatic heterocyclic group formed together by $R^{dN6}$ and $R^{dN7}$, and the non-aromatic heterocyclic group may have substituents; and
$R^{dN8}$ represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group,
10) an optionally substituted 5 to 14-membered non-aromatic heterocyclic group,
11) an optionally substituted 5 to 14-membered non-aromatic heterocyclic group formed by $R^{dN4}$, $R^{dN5}$ or $R^{dN6}$ together with the nitrogen atom to which each of $R^{dN4}$, $R^{dN5}$ and $R^{dN6}$ is bound, and the non-aromatic heterocyclic group may have substituents or
12) an optionally substituted 5 to 14-membered non-aromatic heterocyclic group formed by two substituents selected from the group consisting of $R^{dN4}$, $R^{dN5}$ and $R^{dN6}$ together with the nitrogen atom to which it is bound, and the non-aromatic heterocyclic group may have substituents)), a pharmacologically acceptable salt thereof or a hydrate of them;
(11) the compound described in (10), a pharmacologically acceptable salt thereof or a hydrate of them, wherein $X_1$ represents —$NR^{dN8}$— (wherein $NR^{dN8}$ has the same meanings as defined above);
(12) the compound described in (5) represented by the formula (I-f):

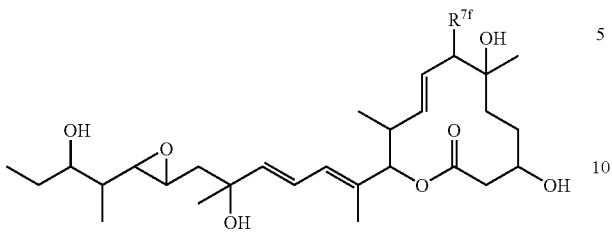

(I-f)

(in the formula, $R^{7f}$ represents $R^{f}C(=Y^{f})$—O— (wherein $Y^{f}$ represents an oxygen atom or a sulfur atom; and $R^{f}$ represents the formula (V):

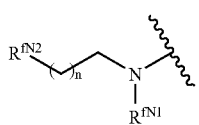

(V)

(wherein n represents an integer of 0 to 4;
$R^{fN1}$ represents
  1) a hydrogen atom,
  2) a methyl group or
  3) an ethyl group; and
$R^{fN2}$ represents
  1) a hydrogen atom,
  2) a methylamino group,
  3) a dimethylamino group,
  4) an ethylamino group,
  5) a diethylamino group,
  6) an ethylmethylamino group,
  7) a pyridinyl group,
  8) a pyrrolidin-1-yl group,
  9) a piperidin-1-yl group,
  10) a morpholin-4-yl group or
  11) a 4-methylpiperazin-1-yl group))), a pharmacologically acceptable salt thereof or a hydrate of them;

(13) the compound described in (5), wherein $R^{6d}$ and/or $R^{7d}$ represents $R^{d3}CO$—O— (wherein $R^{d3}$ represents the formula (VI):

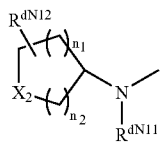

(VI)

(wherein $n_1$ and $n_2$ are the same as or different from each other and each represents an integer of 0 to 4;
$X_2$ represents
  1) —$CHR^{dN13}$—,
  2) —$NR^{d14}$—,
  3) —O—,
  4) —S—,
  5) —SO— or
  6) —$SO_2$—;
$R^{dN11}$ represents 1) a hydrogen atom or
  2) an optionally substituted $C_{1-6}$ alkyl group;
$R^{dN12}$ represents
  1) a hydrogen atom,
  2) an optionally substituted $C_{1-6}$ alkyl group,
  3) an optionally substituted $C_{6-14}$ aryl group or
  4) an optionally substituted $C_{7-10}$ aralkyl group;
$R^{dN13}$ represents
  1) a hydrogen atom,
  2) an optionally substituted $C_{1-6}$ alkyl group,
  3) an optionally substituted unsaturated $C_{2-10}$ alkyl group,
  4) an optionally substituted $C_{6-14}$ aryl group,
  5) an optionally substituted 5 to 14-membered heteroaryl group,
  6) an optionally substituted $C_{7-10}$ aralkyl group,
  7) an optionally substituted $C_{3-8}$ cycloalkyl group,
  8) an optionally substituted $C_{4-9}$ cycloalkyl alkyl group,
  9) an optionally substituted 5 to 14-membered heteroaralkyl group,
  10) —$NR^{dN15}R^{dN16}$ (wherein $R^{dN15}$ and $R^{dN16}$ are the same as or different from each other and each represents a hydrogen atom or an optionally substituted $C_{1-6}$ alkyl group) or
  11) an optionally substituted 5 to 14-membered non-aromatic heterocyclic group; and
$R^{dN14}$ represents
  1) a hydrogen atom,
  2) an optionally substituted $C_{1-6}$ alkyl group,
  3) an optionally substituted unsaturated $C_{2-10}$ alkyl group,
  4) an optionally substituted $C_{6-14}$ aryl group,
  5) an optionally substituted 5 to 14-membered heteroaryl group,
  6) an optionally substituted $C_{7-10}$ aralkyl group,
  7) an optionally substituted $C_{3-8}$ cycloalkyl group,
  8) an optionally substituted $C_{4-9}$ cycloalkyl alkyl group,
  9) an optionally substituted 5 to 14-membered heteroaralkyl group or
  10) an optionally substituted 5 to 14-membered non-aromatic heterocyclic group)), a pharmacologically acceptable salt thereof or a hydrate of them;

(14) the compound described in (5) represented by the formula (I-g):

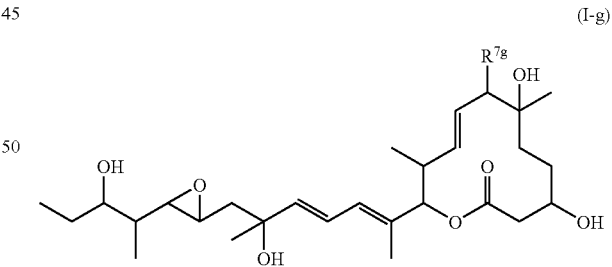

(I-g)

(in the formula, $R^{7g}$ represents $R^{g}CO$—O— (wherein $R^{g}$ represents the formula (VII):

(VII)

(wherein $n_3$ represents 1 or 2;
$R^{dN17}$ represents
  1) a hydrogen atom,
  2) a methyl group or
  3) an ethyl group; and
$R^{dN18}$ represents
  1) a hydrogen atom,
  2) a methyl group or
  3) an ethyl group))), a pharmacologically acceptable salt thereof or a hydrate of them;
(15) the compound described in (5), wherein $R^{6d}$ and/or $R^{7d}$ represents $R^{d4}CO-O-$ (wherein $R^{d4}$ represents the formula (VIII):

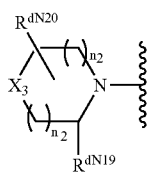

(VIII)

(wherein $n_1$ and $n_2$ are the same as or different from each other and each represents an integer of 0 to 4;
$X_3$ represents
  1) $-CHR^{dN21}-$,
  2) $-NR^{dN22}-$,
  3) $-O-$,
  4) $-S-$,
  5) $-SO-$ or
  6) $-SO_2-$;
$R^{dN19}$ represents
  1) a hydrogen atom or
  2) a $C_{1-6}$ alkyl group;
$R^{dN20}$ represents
  1) a hydrogen atom,
  2) an optionally substituted $C_{1-6}$ alkyl group,
  3) an optionally substituted $C_{6-14}$ aryl group or
  4) an optionally substituted $C_{7-10}$ aralkyl group;
$R^{dN21}$ represents
  1) a hydrogen atom,
  2) an optionally substituted $C_{1-6}$ alkyl group,
  3) an optionally substituted unsaturated $C_{2-10}$ alkyl group,
  4) an optionally substituted $C_{1-6}$ alkoxy group,
  5) an optionally substituted $C_{6-14}$ aryl group,
  6) an optionally substituted 5 to 14-membered heteroaryl group,
  7) an optionally substituted $C_{7-10}$ aralkyl group,
  8) an optionally substituted $C_{3-8}$ cycloalkyl group,
  9) an optionally substituted $C_{4-9}$ cycloalkyl alkyl group,
  10) an optionally substituted 5 to 14-membered heteroaralkyl group,
  11) $-NR^{dN23}R^{dN24}$ (wherein $R^{dN23}$ and $R^{dN24}$ are the same as or different from each other and each represents a hydrogen atom or an optionally substituted $C_{1-6}$ alkyl group) or
  12) an optionally substituted 5 to 14-membered non-aromatic heterocyclic group; and
$R^{dN22}$ represents
  1) a hydrogen atom,
  2) an optionally substituted $C_{1-6}$ alkyl group,
  3) an optionally substituted unsaturated $C_{2-10}$ alkyl group,
  4) an optionally substituted $C_{6-14}$ aryl group,
  5) an optionally substituted 5 to 14-membered heteroaryl group,
  6) an optionally substituted $C_{7-10}$ aralkyl group,
  7) an optionally substituted $C_{3-8}$ cycloalkyl group,
  8) an optionally substituted $C_{4-9}$ cycloalkyl alkyl group,
  9) an optionally substituted 5 to 14-membered heteroaralkyl group or
  10) an optionally substituted 5 to 14-membered non-aromatic heterocyclic group)), a pharmacologically acceptable salt thereof or a hydrate of them;
(16) the compound described in (5) represented by the formula (I-h):

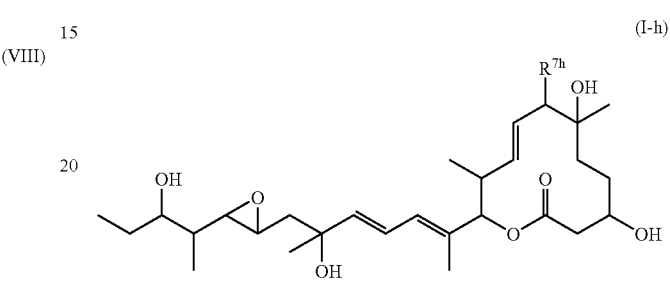

(I-h)

(in the formula, $R^{7h}$ represents $R^h CO-O-$ (wherein $R^h$ represents the formula (IX):

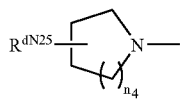

(IX)

(wherein $n_4$ represents an integer of 1 to 3; and
$R^{dN25}$ represents
  1) an amino group,
  2) a methylamino group,
  3) a dimethylamino group,
  4) a pyrrolidin-1-yl group,
  5) a piperidin-1-yl group or
  6) a morpholin-4-yl group))), a pharmacologically acceptable salt thereof or a hydrate of them;
(17) the compound described in (5) represented by the formula (I-i):

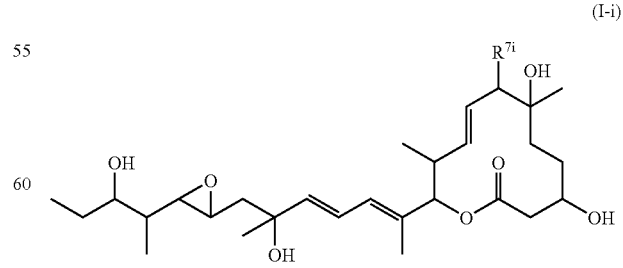

(I-i)

(in the formula, $R^{7i}$ represents $R^i CO-O-$ (wherein $R^i$ represents the formula (X):

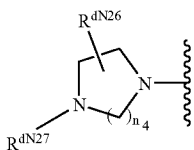

(wherein $n_4$ represents an integer of 1 to 3;
$R^{dN26}$ represents
1) a hydrogen atom,
2) an optionally substituted $C_{1-6}$ alkyl group,
3) an optionally substituted $C_{6-14}$ aryl group or
4) an optionally substituted $C_{7-10}$ aralkyl group; and
$R^{dN27}$ represents
1) a hydrogen atom,
2) an optionally substituted $C_{1-6}$ alkyl group,
3) an optionally substituted $C_{3-8}$ cycloalkyl group,
4) an optionally substituted 3 to 8-membered non-aromatic heterocyclic group,
5) an optionally substituted $C_{6-14}$ aryl group,
6) an optionally substituted 5 to 14-membered heteroaryl group,
7) an optionally substituted $C_{7-10}$ aralkyl group,
8) an optionally substituted 5 to 14-membered heteroaralkyl group or
9) an optionally substituted $C_{4-9}$ cycloalkyl alkyl group))), a pharmacologically acceptable salt thereof or a hydrate of them;

(18) the compound described in (5) represented by the formula (I-j):

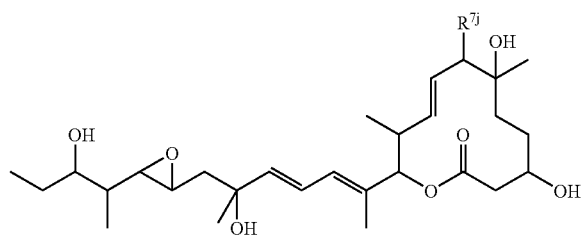

(in the formula, $R^{7j}$ represents $R^{j}CO$—O— (wherein $R^{j}$ represents the formula (XI):

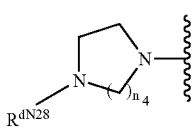

(wherein $n_4$ represents an integer of 1 to 3; and
$R^{dN28}$ represents
1) a hydrogen atom,
2) an optionally substituted $C_{1-6}$ alkyl group,
3) a $C_{3-8}$ cycloalkyl group,
4) a $C_{4-9}$ cycloalkyl alkyl group,
5) a $C_{7-10}$ aralkyl group,
6) a pyridinyl group or 7) a tetrahydropyranyl group))), a pharmacologically acceptable salt thereof or a hydrate of them;

(19) the compound described in (5) represented by the formula (I-k):

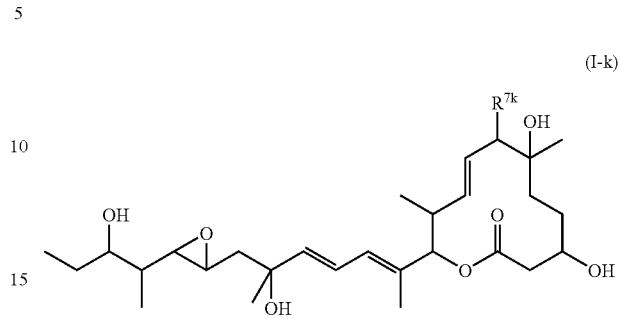

(in the formula, $R^{7k}$ represents $R^{k}CO$—O— (wherein $R^{k}$ represents the formula (XII):

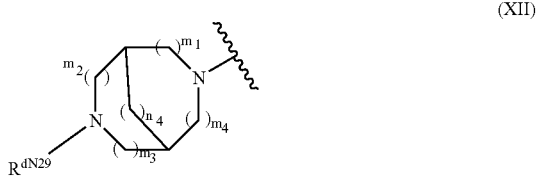

(wherein $m_1$, $m_2$, $m_3$ and $m_4$ are the same as or different from one another and each represents 0 or 1;
$n_4$ represents an integer of 1 to 3; and
$R^{dN29}$ represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group or
10) an optionally substituted 5 to 14-membered non-aromatic heterocyclic group))), a pharmacologically acceptable salt thereof or a hydrate of them;

(20) the compound described in (5) represented by the formula (I-m):

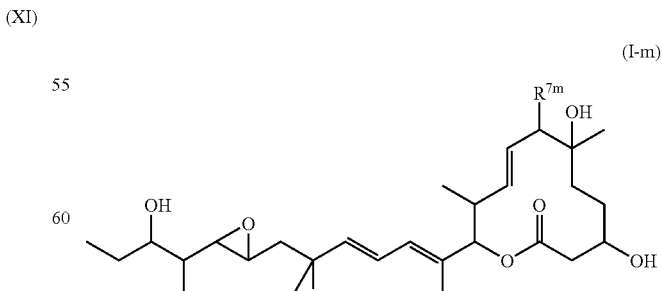

(in the formula, $R^{7m}$ represents $R^{m}CO$—O— (wherein $R^{m}$ represents the formula (XIII):

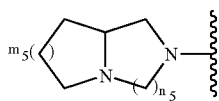

(wherein m₅ represents an integer of 1 to 3; and n₅ represents 2 or 3))), a pharmacologically acceptable salt thereof or a hydrate of them;

(21) the compound described in (5) represented by the formula (I-n):

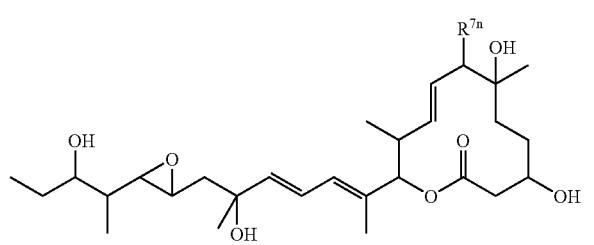

(in the formula, $R^{7n}$ represents R″CO—O— (wherein R″ is a group represented by the formula (XIV):

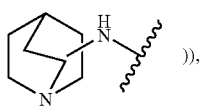

a pharmacologically acceptable salt thereof or a hydrate of them;

(22) the compound described in (1), which is selected from: (8E,12E,14E)-7-(N-(2-(N',N'-Dimethylamino)ethyl)-N-methylcarbamoyloxy)-3,6,16,21-tetrahydroxy-6,10,12,16,20-pentamethyl-18,19-epoxytricosa-8,12,14-trien-11-olide (Compound 6); (8E,12E,14E)-3,6,16,21-Tetrahydroxy-6,10,12,16,20-pentamethyl-7-((4-methylhomopiperazin-1-yl)carbonyl)oxy-18,19-epoxytricosa-8,12,14-trien-11-olide (Compound 9); (8E,12E,14E)-3,6,16,21-Tetrahydroxy-6,10,12,16,20-pentamethyl-7-((4-methylpiperazin-1-yl)carbonyl)oxy-18,19-epoxytricosa-8,12,14-trien-11-olide (Compound 12); (8E,12E,14E)-7-((4-Butylpiperazin-1-yl)carbonyl)oxy-3,6,16,21-tetrahydroxy-6,10,12,16,20-pentamethyl-18,19-epoxytricosa-8,12,14-trien-11-olide (Compound 16); (8E,12E,14E)-7-((4-Ethylpiperazin-1-yl)carbonyl)oxy-3,6,16,21-tetrahydroxy-6,10,12,16,20-pentamethyl-18,19-epoxytricosa-8,12,14-trien-11-olide (Compound 21); (8E,12E,14E)-3,6,16,21-Tetrahydroxy-6,10,12,16,20-pentamethyl-7-((4-propylpiperazin-1-yl)carbonyl)oxy-18,19-epoxytricosa-8,12,14-trien-11-olide (Compound 25); (8E,12E,14E)-7-((4-Cyclohexylpiperazin-1-yl)carbonyl)oxy-3,6,16,21-tetrahydroxy-6,10,12,16,20-pentamethyl-18,19-epoxytricosa-8,12,14-trien-11-olide (Compound 26); (8E,12E,14E)-7-((4-(Cyclopylmethyl)piperazin-1-yl)carbonyl)oxy-3,6,16,21-tetrahydroxy-6,10,12,16,20-pentamethyl-18,19-epoxytricosa-8,12,14-trien-11-olide (Compound 27); (8E,12E,14E)-3,6,16,21-Tetrahydroxy-6,10,12,16,20-pentamethyl-7-((4-propylhomopiperazin-1-yl)carbonyl)oxy-18,19-epoxytricosa-8,12,14-trien-11-olide (Compound 31); (8E,12E,14E)-7-((4-(Cyclopropylmethyl)homopiperazin-1-yl)carbonyl)oxy-3,6,16,21-tetrahydroxy-6,10,12,16,20-pentamethyl-18,19-epoxytricosa-8,12,14-trien-11-olide (Compound 36); (8E,12E,14E)-7-((4-Cyclopentylpiperazin-1-yl)carbonyl)oxy-3,6,16,21-tetrahydroxy-6,10,12,16,20-pentamethyl-18,19-epoxytricosa-8,12,14-trien-11-olide (Compound 38); (8E,12E,14E)-3,6,16,21-Tetrahydroxy-7-((4-isopropylpiperazin-1-yl)carbonyl)oxy-6,10,12,16,20-pentamethyl-18,19-epoxytricosa-8,12,14-trien-11-olide (Compound 44); (8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide (Compound 45); (8E,12E,14E)-7-(N-(2-(N',N'-Diethylamino)ethyl)-N-methylcarbamoyloxy)-3,6,16,21-tetrahydroxy-6,10,12,16,20-pentamethyl-18,19-epoxytricosa-8,12,14-trien-11-olide (Compound 75); (8E,12E,14E)-3,6,16,21-Tetrahydroxy-7-((4-isobutylhomopiperazin-1-yl)carbonyl)oxy-6,10,12,16,20-pentamethyl-18,19-epoxytricosa-8,12,14-trien-11-olide (Compound 54); (8E,12E,14E)-7-((4-Ethylhomopiperazin-1-yl)carbonyl)oxy-3,6,16,21-tetrahydroxy-6,10,12,16,20-pentamethyl-18,19-epoxytricosa-8,12,14-trien-11-olide (Compound 63); (8E,12E,14E)-7-((4-Butylhomopiperazin-1-yl)carbonyl)oxy-3,6,16,21-tetrahydroxy-6,10,12,16,20-pentamethyl-18,19-epoxytricosa-8,12,14-trien-11-olide (Compound 64); (8E,12E,14E)-3,16,21-Trihydroxy-6-methoxy-6,10,12,16,20-pentamethyl-7-((4-methylpiperazin-1-yl)carbonyl)oxy-18,19-epoxytricosa-8,12,14-trien-11-olide (Compound 85); (8E,12E,14E)-3,16,21-Trihydroxy-6-methoxy-6,10,12,16,20-pentamethyl-7-((4-(piperidin-1-yl)piperidin-1-yl)carbonyl)oxy-18,19-epoxytricosa-8,12,14-trien-11-olide (Compound 109); (8E,12E,14E)-7-((4-(2,2-Dimethylpropyl)homopiperazin-1-yl)carbonyl)oxy-3,6,16,21-tetrahydroxy-6,10,12,16,20-pentamethyl-18,19-epoxytricosa-8,12,14-trien-11-olide (Compound 69); and (8E,12E,14E)-3,6,16-Trihydroxy-21-methoxy-6,10,12,16,20-pentamethyl-7-((4-methylpiperazin-1-yl)carbonyl)oxy-18,19-epoxytricosa-8,12,14-trien-11-olide (Compound 131);

(23) the compound described in (1), which is selected from: (8E,12E,14E)-3,6,16,21-Tetrahydroxy-6,10,12,16,20-pentamethyl-7-((4-methylhomopiperazin-1-yl)carbonyl)oxy-18,19-epoxytricosa-8,12,14-trien-11-olide (Compound 9); (8E,12E,14E)-3,6,16,21-Tetrahydroxy-6,10,12,16,20-pentamethyl-7-((4-methylpiperazin-1-yl)carbonyl)oxy-18,19-epoxytricosa-8,12,14-trien-11-olide (Compound 12); (8E,12E,14E)-7-((4-Cyclohexylpiperazin-1-yl)carbonyl)oxy-3,6,16,21-tetrahydroxy-6,10,12,16,20-pentamethyl-18,19-epoxytricosa-8,12,14-trien-11-olide (Compound 26); (8E,12E,14E)-3,6,16,21-Tetrahydroxy-7-((4-isopropylpiperazin-1-yl)carbonyl)oxy-6,10,12,16,20-pentamethyl-18,19-epoxytricosa-8,12,14-trien-11-olide (Compound 44); (8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide (Compound 45); and (8E,12E,14E)-7-(N-(2-(N',N'-Diethylamino)ethyl)-N-methylcarbamoyloxy)-3,6,16,21-tetrahydroxy-6,10,12,16,20-pentamethyl-18,19-epoxytricosa-8,12,14-trien-11-olide (Compound 75);

(24) a medicament comprising the compound described in any one of (1) to (23), a pharmacologically acceptable salt thereof or a hydrate of them as an active ingredient;

(25) a pharmaceutical composition comprising the compound described in any one of (1) to (23), a pharmacologically acceptable salt thereof or a hydrate of them as an active ingredient;
(26) the medicament described in (24), which is an agent for preventing or treating a disease against which a regulation of gene expression is efficacious;
(27) the medicament described in (24), which is an agent for preventing or treating a diseases against which suppression of VEGF production is efficacious;
(28) the medicament described in (24), which is an agent for preventing or treating a disease against which an antiangiogenic effect is efficacious;
(29) the medicament described in (24), which is an angiogenesis inhibitor;
(30) the medicament described in (24), which is an antitumor agent;
(31) the medicament described in (24), as a therapeutic agent for treating angioma;
(32) the medicament described in (24), which is a cancer metastasis inhibitor;
(33) the medicament described in (24), which is a therapeutic agent for treating retinal neovascularization or diabetic retinopathy;
(34) the medicament described in (24), which is a therapeutic agent for treating inflammatory disease;
(35) the medicament described in (24), which is a therapeutic agent for treating inflammatory diseases consisting of deformans arthritis, rheumatoid arthritis, psoriasis and delayed hypersensitivity reaction;
(36) the medicament described in (24), which is a therapeutic agent for treating atherosclerosis;
(37) the medicament described in (24), which is a therapeutic agent for treating solid cancer;
(38) the medicament described in (37), wherein the solid cancer is lung cancer, brain tumor, breast cancer, prostate cancer, ovarian cancer, colon cancer or melanoma;
(39) the medicament described in (24), which is a therapeutic agent for treating leukemia;
(40) the medicament described in (24), which is an antitumor agent based on a regulation of gene expression;
(41) the medicament described in (24), which is an antitumor agent based on suppression of VEGF production;
(42) the medicament described in (24), which is an antitumor agent based on an effect of angiogenesis inhibition;
(43) a method for preventing or treating a disease against which a regulation of gene expression is efficacious, which comprises administering a pharmacologically effective dose of the medicament described in (24) to a patient;
(44) a method for preventing or treating a disease against which suppression of VEGF production is efficacious, which comprises administering a pharmacologically effective dose of the medicament described in (24) to a patient;
(45) a method for preventing or treating a disease against which an angiogenesis inhibition is efficacious, which comprises administering a pharmacologically effective dose of the medicament described in (24) to a patient;
(46) use of the compound described in any one of (1) to (23), a pharmacologically acceptable salt thereof or a hydrate of them, for manufacturing an agent for preventing or treating a disease against which a regulation of gene expression is efficacious;
(47) use of the compound described in any one of (1) to (23), a pharmacologically acceptable salt thereof or a hydrate of them, for manufacturing an agent for preventing or treating a disease against which suppression of VEGF production is efficacious;
(48) use of the compound described in any one of (1) to (23), a pharmacologically acceptable salt thereof or a hydrate of them, for manufacturing an agent for preventing or treating a disease against which an angiogenesis inhibition is efficacious; and
(49) use of the compound described in any one of (1) to (23), a pharmacologically acceptable salt thereof or a hydrate of them, for producing an agent for preventing or treating solid cancers.

The terms, symbols and the like used in the present specification will be illustrated below.

In the present specification, the chemical formula of the compound according to the present invention is illustrated as a planimetric chemical formula for convenience but the compound can include certain isomers drawn from the chemical formula. The present invention can include all isomers and mixtures of the isomers such as a geometric isomer which is generated from the configuration of the compound, an optical isomer based on an asymmetric carbon, a rotamer, a stereoisomer and a tautomer. The present invention is not limited to the expediential description of the chemical formula, and can include either of isomers or a mixture thereof. Accordingly, when the compound of the present invention has an asymmetric carbon in the molecule, and its optically active substance and racemate exist, any one is included. Further, when polymorphic crystals exist, the crystal form of the present invention is not specifically limited to one form, and any one of the crystal forms may be single or a mixture of the crystal forms. The compound represented by the formula (I) according to the present invention or a salt thereof may be an anhydrate or a hydrate, and both are included in the present invention. The metabolite which is generated in vivo by decomposition of the compound of the formula (I) according to the present invention and the prodrug of the compound of the formula (I) according to the present invention or a salt thereof are also included in the present invention.

The "halogen atom" used in the specification of the present application means a fluorine atom, a chlorine atom, a bromine atom and an iodine atom. Among them, for example, a fluorine atom, a chlorine atom or a bromine atom is preferred, of which a fluorine atom or a chlorine atom is typically preferred.

The "$C_{1-22}$ alkyl group" used in the specification of the present application indicates a linear or branched alkyl group having 1 to 22 carbon atoms, such as methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group, n-heptyl group, n-octyl group, n-nonyl group or n-decyl group; preferably a linear or branched alkyl group having 1 to 6 carbon atoms, such as methyl group, ethyl group, n-propyl group, iso-propyl group, n-butyl group, iso-butyl group, sec-butyl group, tert-butyl group or n-pentyl group; and more preferably, for example, methyl group, ethyl group, propyl group, iso-propyl group, n-butyl group, iso-butyl group or tert-butyl group.

The "unsaturated $C_{2-22}$ alkyl group" used in the specification of the present application indicates a linear or branched alkenyl group having 2 to 22 carbon atoms or a linear or branched alkynyl group having 2 to 22 carbon atoms, such as vinyl group, allyl group, 1-propenyl group, isopropenyl group, 2-methyl-1-propenyl group, 2-methyl-2-propenyl group, 1-butenyl group, 2-butenyl group, 3-butenyl group, 1-pentenyl group, 1-hexenyl group, 1,3-hexadienyl group, 1,5-hexadienyl group, ethynyl group, 1-propynyl group, 2-propynyl group, 1-butynyl group, 2-butynyl group, 3-butynyl group, 1-ethynyl-2-propynyl group, 2-methyl-3-butynyl group, 1-pentynyl group, 1-hexynyl group, 1,3-hexanediynyl group or 1,5-hexanediynyl group. It preferably indicates a linear or branched alkenyl group having 2 to 10 carbon atoms or a linear or branched alkynyl group having 2 to 10 carbon atoms, such as vinyl group, allyl group, 1-propenyl group, 2-propenyl group, isopropenyl group, 3-methyl-2-butenyl group, 3,7-dimethyl-2,6-octadienyl group, ethynyl group, 1-propynyl group, 2-propynyl group, 1-butynyl group, 2-butynyl group, 3-butynyl group or 3-methyl-1-propynyl group.

The "$C_{6-14}$ aryl group" used in the specification of the present application means an aromatic cyclic hydrocarbon group having 6 to 14 carbon atoms, and a monocyclic group and condensed rings such as a bicyclic group and a tricyclic group are included. Examples thereof are phenyl group, indenyl group, 1-naphthyl group, 2-naphthyl group, azulenyl group, heptalenyl group, indacenyl group, acenaphthyl group, fluorenyl group, phenalenyl group, phenanthrenyl group and anthracenyl group; of which a preferred example is phenyl group, 1-naphthyl group or 2-naphthyl group.

The "5 to 14-membered heteroaryl group" used in the specification of the present application means a monocyclic, bicyclic or tricyclic 5 to 14-membered aromatic heterocyclic group which contains one or more of hetero atoms selected from the group consisting of nitrogen atom, sulfur atom and oxygen atom. Preferred examples thereof are a nitrogen-containing aromatic heterocyclic group such as pyrrolyl group, pyridinyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolinyl group, isoquinolinyl group, quinolizinyl group, phthalazinyl group, naphthyridinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridinyl group, imidazopyrimidinyl group, pyrazolopyridinyl group or pyrazolopyridinyl group; a sulfur-containing aromatic heterocyclic group such as thienyl group or benzothienyl group; and an oxygen-containing aromatic heterocyclic group such as furyl group, pyranyl group, cyclopentapyranyl group, benzofuryl group or isobenzofuryl group; an aromatic heterocyclic group containing two or more different hetero atoms, such as thiazolyl group, isothiazolyl group, benzothiazolyl group, benzthiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group or pyridoxazinyl group, of which a preferred example is thienyl group, furyl group, pyridinyl group, pyridazinyl group, pyrimidinyl group or pyrazinyl group.

The "3 to 14-membered non-aromatic heterocyclic group" used in the specification of the present application indicates a monocyclic, bicyclic or tricyclic 3 to 14-membered non-aromatic heterocyclic group which may contain one or more hetero atoms selected from the group consisting of nitrogen atom, sulfur atom and oxygen atom. Preferred examples thereof are aziridinyl group, azetidinyl group, pyrrolidinyl group, pyrrolyl group, piperidinyl group, piperazinyl group, homopiperidinyl group, homopiperazinyl group, imidazolyl group, pyrazolidinyl group, imidazolidinyl group, morpholinyl group, thiomorpholinyl group, imidazolinyl group, oxazolinyl group, 2,5-diazabicyclo[2.2.1]heptyl group, 2,5-diazabicyclo[2.2.2]octyl group, 3,8-diazabicyclo[3.2.1]octyl group, 1,4-diazabicyclo[4.3.0]nonyl group, quinuclidinyl group, tetrahydrofuranyl group and tetrahydrothiophenyl group. The non-aromatic heterocyclic group also includes a group derived from a pyridone ring, and a non-aromatic fused ring (e.g., a group derived from, for example, phthalimide ring or succinimide ring).

The "$C_{7-22}$ aralkyl group" used in the specification of the present application means a group corresponding to the above-defined "$C_{1-22}$ alkyl group" of which substitutable moiety is replaced by the above-defined "$C_{6-14}$ aryl group". Specific examples thereof are benzyl group, phenethyl group, 3-phenylpropyl group, 4-phenylbutyl group, 1-naphthylmethyl group and 2-naphthylmethyl group, of which an aralkyl group having 7 to 10 carbon atoms such as benzyl group or phenethyl group is preferred.

The "5 to 14-membered heteroaralkyl group" used in the specification of the present application means a group corresponding to the above-defined "$C_{1-22}$ alkyl group" of which substitutable moiety is replaced by the above-defined "5 to 14-membered heteroaryl group". Specific examples thereof are thienylmethyl group, furylmethyl group, pyridinylmethyl group, pyridazinylmethyl group, pyrimidinylmethyl group and pyrazinylmethyl group, of which a preferred example is thienylmethyl group, furylmethyl group or pyridinylmethyl group.

The "$C_{3-14}$ cycloalkyl group" used in the specification of the present application indicates a cycloalkyl group having 3 to 14 carbon atoms, and suitable examples thereof are cyclopropyl group, cyclobutyl group, cyclopentyl group, cyclohexyl group, cycloheptyl group and cyclooctyl group, of which a preferred example is cyclopentyl group, cyclohexyl group, cycloheptyl group or cyclooctyl group.

The "$C_{4-9}$ cycloalkyl alkyl group" used in the specification of the present application means a group corresponding to the above-defined "$C_{1-22}$ alkyl group" of which substitutable moiety is replaced by the above-defined "$C_{3-14}$ cycloalkyl group". Specific examples thereof are cyclopropylmethyl group, cyclobutylmethyl group, cyclopentylmethyl group, cyclohexylmethyl group, cycloheptylmethyl group and cyclooctylmethyl group, of which a preferred example is cyclopropylmethyl group, cyclobutylmethyl group or cyclopentylmethyl group.

The "$C_{1-22}$ alkoxy group" used in the specification of the present application means a group corresponding to the above-defined "$C_{1-22}$ alkyl group" to which end an oxygen atom is bonded. Suitable examples thereof are methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropoxy group, 1,2-dimethylpropoxy group, 2,2-dimethylpropoxy group, 1-methyl-2-ethylpropoxy group, 1-ethyl-2-methylpropoxy group, 1,1,2-trimethylpropoxy group, 1,2,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and hexyloxy group, of which a preferred example is methoxy group, ethoxy group, n-propoxy group, iso-propoxy group, iso-butoxy group or 2,2-dimethylpropoxy group.

The "unsaturated $C_{2-22}$ alkoxy group" used in the specification of the present application means a group corresponding to the above-defined "unsaturated $C_{2-22}$ alkyl group" to which end an oxygen atom is bonded. Suitable examples thereof are vinyloxy group, allyloxy group, 1-propenyloxy group, 2-propenyloxy group, isopropenyloxy group, 2-methyl-1-propenyloxy group, 2-methyl-2-propenyloxy group, 1-butenyloxy group, 2-butenyloxy group, 3-butenyloxy group, 1-pentenyloxy group, 1-hexenyloxy group, 1,3-hexadienyloxy group, 1,5-hexadienyloxy group, propargyloxy group and 2-butynyloxy group, of which a preferred example is allyloxy group, propargyloxy group or 2-butynyloxy group.

The "$C_{6-14}$ aryloxy group" used in the specification of the present application means a group corresponding to the above-defined "$C_{6-14}$ aryl group" to which end an oxygen atom is bonded. Specific examples thereof are phenyloxy group, indenyloxy group, 1-naphthyloxy group, 2-naphthyloxy group, azulenyloxy group, heptalenyloxy group, indacenyloxy group, acenaphthyloxy group, fluorenyloxy group, phenalenyloxy group, phenanthrenyloxy group and anthracenyloxy group, of which a preferred example is phenyloxy group, 1-naphthyloxy group or 2-naphthyloxy group.

The "$C_{7-22}$ aralkyloxy group" used in the specification of the present application means a group corresponding to the above-defined "$C_{7-22}$ aralkyl group" to which end an oxygen atom is bonded. Specific examples thereof are benzyloxy group, phenethyloxy group, 3-phenylpropyloxy group, 4-phenylbutyloxy group, 1-naphthylmethyloxy group and 2-naphthylmethyloxy group, of which a preferred example is benzyloxy group.

The "5 to 14-membered heteroaralkyloxy group" used in the specification of the present application means a group corresponding to the above-defined "5 to 14-membered heteroaralkyl group" to which end an oxygen atom is bonded. Specific examples thereof are thienylmethyloxy group, furylmethyloxy group, pyridinylmethyloxy group, pyridazinylmethyloxy group, pyrimidinylmethyloxy group and pyrazinylmethyloxy group, of which a preferred example is thienylmethyloxy group, furylmethyloxy group or pyridinylmethyloxy group.

The "5 to 14-membered heteroaryloxy group" used in the specification of the present application means a group corresponding to the above-defined "5 to 14-membered heteroaryl group" to which end an oxygen atom is bonded. Specific examples thereof are pyrrolyloxy group, pyridinyloxy group, pyridazinyloxy group, pyrimidinyloxy group, pyrazinyloxy group, triazolyloxy group, tetrazolyloxy group, benzotriazolyloxy group, pyrazolyloxy group, imidazolyloxy group, benzimidazolyloxy group, indolyloxy group, isoindolyloxy group, indolizinyloxy group, purinyloxy group, indazolyloxy group, quinolinyloxy group, isoquinolinyloxy group, quinolizinyloxy group, phthalazinyloxy group, naphthyridinyloxy group, quinoxalinyloxy group, quinazolinyloxy group, cinnolinyloxy group, pteridinyloxy group, imidazotriazinyloxy group, pyrazinopyridazinyloxy group, acridinyloxy group, phenanthridinyloxy group, carbazolyloxy group, carbazolinyloxy group, perimidinyloxy group, phenanthrolinyloxy group, phenazinyloxy group, imidazopyridinyloxy group, imidazopyrimidinyloxy group, pyrazolopyridinyloxy group, pyrazolopyridinyloxy group, thienyloxy group, benzothienyloxy group, furyloxy group, pyranyloxy group, cyclopentapyranyloxy group, benzofuryloxy group, isobenzofuryloxy group, thiazolyloxy group, isothiazolyloxy group, benzothiazolyloxy group, benzothiadiazolyloxy group, phenothiazinyloxy group, isoxazolyloxy group, furazanyloxy group, phenoxazinyloxy group, oxazolyloxy group, isoxazolyloxy group, benzoxazolyloxy group, oxadiazolyloxy group, pyrazolooxazolyloxy group, imidazothiazolyloxy group, thienofuranyloxy group, furopyrrolyloxy group and pyridoxazinyloxy group, of which a preferred example is thienyloxy group, pyridinyloxy group, pyrimidinyloxy group or pyrazinyloxy group.

The "aliphatic $C_{2-22}$ acyl group" used in the specification of the present application means a group corresponding to the above-defined "$C_{1-22}$ alkyl group" or "unsaturated $C_{2-22}$ alkyl group" to which end a carbonyl group is bonded. Examples thereof are acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group, arachidoyl group, acryloyl group, propioloyl group, crotonoyl group, iso-crotonoyl group, oleoyl group and linolenoyl group, of which a preferred example is an acyl group having 2 to 6 carbon atoms, such as acetyl group, propionyl group, butyryl group, iso-butyryl group or acryloyl group.

The "aromatic $C_{7-15}$ acyl group" used in the specification of the present application means a group corresponding to the above-defined "$C_{6-14}$ aryl group" or "5 to 14-membered heteroaryl group" to which end a carbonyl group is bonded. Examples thereof are benzoyl group, 1-naphthoyl group, 2-naphthoyl group, picolinoyl group, nicotinoyl group, isonicotinoyl group, furoyl group and thiophenecarbonyl group, of which a preferred example is benzoyl group, picolinoyl group, nicotinoyl group or isonicotinoyl group.

The "$C_{1-22}$ alkylsulfonyl group" used in the specification of the present application means a sulfonyl group to which the above-defined "$C_{1-22}$ alkyl group" is bound. Specific examples thereof are methanesulfonyl group, ethanesulfonyl group, n-propanesulfonyl group and iso-propanesulfonyl group, of which a preferred example is methanesulfonyl group.

The "$C_{6-14}$ arylsulfonyl group" used in the specification of the present application means a sulfonyl group to which the above-defined "$C_{6-14}$ aryl group" is bound. Specific examples thereof are benzenesulfonyl group, 1-naphthalenesulfonyl group and 2-naphthalenesulfonyl group, of which a preferred example is benzenesulfonyl group.

The "aliphatic $C_{2-22}$ acyloxy group" used in the specification of the present application means a group corresponding to the above-defined "aliphatic $C_{2-22}$ acyl group" to which end an oxygen atom is bonded. Specific examples thereof are acetoxy group, propionyloxy group and acryloxy group, of which a preferred example is acetoxy group or propionyloxy group.

The "$C_{2-22}$ alkoxycarbonyl group" used in the specification of the present application means a group corresponding to the above-defined "$C_{1-22}$ alkoxy group" to which end a carbonyl group is bonded. Examples thereof are methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group and tert-butoxycarbonyl group, of which a preferred example is ethoxycarbonyl group, iso-propoxycarbonyl group or tert-butoxycarbonyl group.

The "unsaturated $C_{3-22}$ alkoxycarbonyl group" used in the specification of the present application means a group corresponding to the above-defined "unsaturated $C_{2-22}$ alkoxy group" to which end a carbonyl group is bonded. Examples thereof are vinyloxycarbonyl group, allyloxycarbonyl group, 1-propenyloxycarbonyl group, isopropenyloxycarbonyl group, propargyloxycarbonyl group and 2-butynyloxycarbonyl group, of which a preferred example is allyloxycarbonyl group.

The "$C_{1-22}$ alkylthio group" used in the specification of the present application means a group corresponding to the above-defined "$C_{1-22}$ alkyl group" to which end a sulfur atom is bonded. Examples thereof are methylthio group, ethylthio group, n-propylthio group and iso-propylthio group, of which a preferred example is methylthio group or ethylthio group.

The "$C_{1-22}$ alkylsulfinyl group" used in the specification of the present application means a group corresponding to the above-defined "$C_{1-22}$ alkyl group" to which end a sulfinyl group is bonded. Examples thereof are methanesulfinyl group, ethanesulfinyl group, n-propanesulfinyl group and iso-propanesulfinyl group, of which a preferred example is methanesulfinyl group or ethanesulfinyl group.

The "$C_{1-22}$ alkylsulfonyloxy group" used in the specification of the present application means a group corresponding to the above-defined "$C_{1-22}$ alkylsulfonyl group" to which end an oxygen atom is bonded. Examples thereof are methanesulfonyloxy group, ethanesulfonyloxy group, n-propanesulfonyloxy group and iso-propanesulfonyloxy group, of which a preferred example is methanesulfonyloxy group.

The substituent of the phrase "an optionally substituted" used in the specification of the present application may be one or more groups selected from:

(1) a halogen atom,
(2) a hydroxyl group,
(3) a thiol group,
(4) a nitro group,
(5) a nitroso group,
(6) a cyano group,
(7) a carboxyl group,
(8) a hydroxysulfonyl group,
(9) a amino group,
(10) a $C_{1-22}$ alkyl group (for example, methyl group, ethyl group, n-propyl group, iso-propyl group, n-butyl group, iso-butyl group, sec-butyl group and tert-butyl group),
(11) an unsaturated $C_{2-22}$ alkyl group (for example, vinyl group, allyl group, 1-propenyl group, 2-propenyl group, isopropenyl group, ethynyl group, 1-propynyl group, 2-propynyl group, 1-butynyl group, 2-butynyl group and 3-butynyl group),
(12) a $C_{6-14}$ aryl group (for example, phenyl group, 1-naphthyl group and 2-naphthyl group),
(13) a 5 to 14-membered heteroaryl group (for example, thienyl group, furyl group, pyridinyl group, pyridazinyl group, pyrimidinyl group and pyrazinyl group),
(14) a 3 to 14-membered non-aromatic heterocyclic group (for example, aziridinyl group, azetidyl group, pyrrolidinyl group, pyrrolyl group, piperidinyl group, piperazinyl group, homopiperidinyl group, homopiperazinyl group, imidazolyl group, pyrazolidinyl group, imidazolidinyl group, morpholinyl group, thiomorpholinyl group, imidazolinyl group, oxazolinyl group and quinuclidinyl group),
(15) a $C_{3-14}$ cycloalkyl group (for example, cyclopropyl group, cyclobutyl group, cyclopentyl group, cyclohexyl group, cycloheptyl group and cyclooctyl group),
(16) a $C_{1-22}$ alkoxy group (for example, methoxy group, ethoxy group, n-propoxy group, iso-propoxy group, sec-propoxy group, n-butoxy group, iso-butoxy group and tert-butoxy group),
(17) an unsaturated $C_{2-22}$ alkoxy group (for example, vinyloxy group, allyloxy group, 1-propenyloxy group, 2-propenyloxy group, isopropenyloxy group, ethynyloxy group, 1-propynyloxy group, 2-propynyloxy group, 1-butynyloxy group and 2-butynyloxy group),
(18) a $C_{6-14}$ aryloxy group (for example, phenyloxy group, 1-naphthyloxy group and 2-naphthyloxy group),
(19) a $C_{7-22}$ aralkyloxy group (for example, benzyloxy group, phenethyloxy group, 3-phenylpropyloxy group, 4-phenylbutyloxy group, 1-naphthylmethyloxy group and 2-naphthylmethyloxy group),
(20) a 5 to 14-membered heteroaralkyloxy group (for example, thienylmethyloxy group, furylmethyloxy group, pyridinylmethyloxy group, pyridazinylmethyloxy group, pyrimidinylmethyloxy group and pyrazinylmethyloxy group),
(21) a 5 to 14-membered heteroaryloxy group (for example, thienyloxy group, furyloxy group, pyridinyloxy group, pyridazinyloxy group, pyrimidinyloxy group and pyrazinyloxy group),
(22) an aliphatic $C_{2-22}$ acyl group (for example, acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group, arachidoyl group, acryloyl group, propioloyl group, crotonoyl group, iso-crotonoyl group, oleoyl group and linolenoyl group),
(23) an aromatic $C_{7-15}$ acyl group (for example, benzoyl group, 1-naphthoyl group and 2-naphthoyl group),
(24) an aliphatic $C_{2-22}$ acyloxy group (for example, acetoxy group, propionyloxy group and acryloxy group),
(25) a $C_{2-22}$ alkoxycarbonyl group (for example, methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group and tert-butoxycarbonyl group),
(26) an unsaturated $C_{3-22}$ alkoxycarbonyl group (for example, vinyloxycarbonyl group, allyloxycarbonyl group, 1-propenyloxycarbonyl group, 2-propenyloxycarbonyl group, iso-propenyloxycarbonyl group, propargyloxycarbonyl group and 2-butynyloxycarbonyl group),
(27) a $C_{1-22}$ alkylthio group (for example, methylthio group, ethylthio group, n-propylthio group and iso-propylthio group),
(28) a $C_{1-22}$ alkylsulfinyl group (for example, methanesulfinyl group, ethanesulfinyl group, n-propanesulfinyl group and iso-propanesulfinyl group),
(29) a $C_{1-22}$ alkylsulfonyl group (for example, methanesulfonyl group, ethanesulfonyl group, n-propanesulfonyl group and iso-propanesulfonyl group),
(30) a $C_{6-14}$ arylsulfonyl group (for example, benzenesulfonyl group, 1-naphthalenesulfonyl group and 2-naphthalenesulfonyl group),
(31) a $C_{1-22}$ alkylsulfonyloxy group (for example, methanesulfonyloxy group, ethanesulfonyloxy group, n-propanesulfonyloxy group and iso-propanesulfonyloxy group),
(32) carbamoyl group, and
(33) formyl group.

Among them, a preferred example is an amino group, a $C_{1-22}$ alkyl group, an unsaturated $C_{2-22}$ alkyl group, a $C_{6-14}$ aryl group, a 5 to 14-membered heteroaryl group, a 3 to 14-membered non-aromatic heterocyclic group and a $C_{3-14}$ cycloalkyl group, and a more preferred example is an amino group, a $C_{1-22}$ alkyl group, a 3 to 14-membered non-aromatic heterocyclic group and a $C_{3-14}$ cycloalkyl group. The above-mentioned (9) an amino group and (31) a carbamoyl group as the substituent in "an optionally substituted" may each be further substituted with one or two of a $C_{1-22}$ alkyl group, an unsaturated $C_{2-22}$ alkyl group or a $C_{6-14}$ aryl group.

The compounds of the formula (I) according to the present invention will be elucidated below.

The compounds of the formula (I) suppress VEGF production under a hypoxic condition and possess a growth inhibitory activities to solid tumor cells in in vivo. Among them, the compounds of the formula (I-a) are preferred, of which the compounds of the formula (I-b) are more preferred and the compounds of the formula (I-c) are typically advantageous.

The compounds of the formula (I) are structurally characterized by the 6-position side chain and/or 7-position side chain, and the group of more preferred compounds can be defined as the compounds of the formula (I-d). In addition to the compounds of the formula (I-d), the compounds of the formula (I), in which $R^{21}$ forms an oxo group together with the carbon atom to which $R^{21}$ is bound, belong to the group of compounds having good activities. As detailed embodiments of more preferred compounds among the compounds of the formula (I-d), the compounds of the above-mentioned "5." to "19." of the present invention may be exemplified.

Preferred examples of the compounds of the formula (I) will be illustrated below. The group of the preferred compounds inclusive of compounds described later in Examples include, for example, Compound 6, Compound 9, Compound 12, Compound 15, Compound 16, Compound 20, Compound 21, Compound 22, Compound 25, Compound 26, Compound 27, Compound 31, Compound 34, Compound 36, Compound 38, Compound 39, Compound 40, Compound 41, Compound 43, Compound 44, Compound 45, Compound 48, Compound 51, Compound 53, Compound 54, Compound 55, Compound 57, Compound 58, Compound 62, Compound 63, Compound 64, Compound 65, Compound 69, Compound 70, Compound 72, Compound 74, Compound 75, Compound 77, Compound 79, Compound 85, Compound 88, Compound 105, Compound 106, Compound 108, Compound 109 and Compound 131. Among them, examples of more preferred compounds are Compound 6, Compound 9, Compound 12, Compound 16, Compound 21, Compound 25, Compound 26, Compound 27, Compound 31, Compound 36, Compound 38, Compound 44, Compound 45, Compound 54, Compound 63, Compound 64, Compound 69, Compound 75, Compound 85, Compound 109 and Compound 131, of which, for example, Compound 9, Compound 12, Compound 26, Compound 44, Compound 45 and Compound 75 are typically preferred.

Next, the preparation of the compound of the formula (I) according to the present invention will be illustrated.

The compound of the formula (I) can be prepared by culturing a strain belonging to the genus *Streptomyces* which has an ability of producing the bioactive substance 11107D [the compound of the formula (I), in which $R^3$, $R^6$ and $R^{21}$ are hydroxyl groups, and $R^7$ is an acetoxy group] under aerobic conditions, collecting the compound from the microorganism cell and culture, and chemically modifying the obtained compound as a key compound according to a conventional procedure.

Initially, the process for preparation of 11107D will be elucidated below.

The following deposit microorganism strain can be used for the microorganism for producing 11107D. The strain was internationally deposited to International Patent Organism Depositary (IPOD) National Institute of Advanced Industrial Science and Technology (Tsukuba Central 6, 1-1, Higashi 1-Chome Tsukuba-shi, Ibaraki-ken 305-8566 Japan). Specifically, *Streptomyces* sp. Mer-11107 was deposited as FERM P-18144 at the National Institute of Bioscience and Human-Technology Agency of Industrial Science and Technology (1-3, Higashi 1-chome Tsukuba-shi, Ibaraki-ken 305-8566 Japan). Further, this was transferred to International Deposit FERM BP-7812 at International Patent Organism Depositary (IPOD) National Institute of Advanced Industrial Science and Technology (Tsukuba Central 6, 1-1, Higashi 1-Chome Tsukuba-shi, Ibaraki-ken 305-8566 Japan).

The strain for producing 11107D is not specifically limited and also includes variants of such strains, as long as the strain is belonging to the genus *Streptomyces* and has an ability of producing 11107D. Examples of the strain are *Streptomyces* sp. A-1532, *Streptomyces* sp. A-1533 and *Streptomyces* sp. A-1534, in addition to the above-mentioned strain. These strains were also internationally deposited to International Patent Organism Depositary (IPOD) National Institute of Advanced Industrial Science and Technology (Tsukuba Central 6, 1-1, Higashi 1-Chome Tsukuba-shi, Ibaraki-ken 305-8566 Japan) as FERM BP-7849, FERM BP-7850 and FERM BP-7851, respectively.

Detailed description of 1. the property of separated microorganism, 2. the fermentation method of the microorganism and 3. the purification method of an active substance in the preparation of 11107D will be made below.

1. The Property of Separated Microorganism

As the strain for use in the present invention, it is expected that any one of strains belonging to the genus *Streptomyces* and having an ability of producing 11107D can be used. However, as a typical strain used in the present invention, a strain which was named as "Mer-11107 strain" by the inventors is exemplified. The taxonomical properties of this strain are as follows.

(1) Morphological Characteristics

Aerial hyphae that bore spirales is extended from vegetative hypha in this strain. Spore chain consisting of about 10 to 20 of columnar spores are formed at the edge of the ripened aerial hyphae. The size of the spores is about 0.7×1.0 µm, the surface of the spores is smooth, and specific organs such as sporangium, sclerotium and flagellum are not observed.

(2) Cultural Characteristics on Various Media

Cultural characteristics of the strain after incubation at 28° C. for two weeks on various media are shown below. The color tone is described by the color name and codes which are shown in the parenthesis of the Color Harmony Manual (Container Corporation of America).

1) Yeast Extract-Malt Extract Agar Medium

The strain grew well, the aerial hyphae grew up on the surface, and light gray spores (Light gray; d) were observed. The reverse side of colony was Light melon yellow (3ea). Soluble pigment was not produced.

2) Oatmeal Agar Medium

The strain grew in the middle level, the aerial hyphae grew slightly on the surface, and gray spores (Gray; g) were observed. The reverse side of colony was Nude tan (4gc) or Putty (1½ec). Soluble pigment was not produced.

3) Inorganic Salt-Starch Agar Medium

The strain grew well, the aerial hyphae grew up on the surface, and gray spores (Gray; e) were observed. The reverse side of colony was Fawn (4ig) or Gray (g). Soluble pigment was not produced.

4) Glycerol-Asparagine Agar Medium

The strain grew well, the aerial hyphae grew up on the surface, and white spores (White; a) were observed. The reverse side of colony was Pearl pink (3ca). Soluble pigment was not produced.

5) Peptone-Yeast Extract-Iron Agar Medium

The strain growth was bad, and the aerial hyphae did not grow on the surface. The reverse side of colony was Light melon yellow (3ea). Soluble pigment was not produced.

6) Tyrosine Agar Medium

The strain grew well, the aerial hyphae grew up on the surface, and white spores (White; a) were observed. The reverse side of colony was Pearl pink (3ca). Soluble pigment was not produced.

(3) Utilization of Various Carbon Sources

Various carbon sources are added in Pridham-Gottlieb agar medium, growth of the strain after incubation at 28° C. for two weeks are shown below.
1) L-arabinose ±
2) D-xylose ±
3) D-glucose +
4) D-fructose +
5) sucrose +
6) inositol +
7) L-rhamnose –
8) D-mannitol +
9) D-raffinose +

(+: positive, ±: slightly positive, –: negative)

(4) Physiological Properties

The physiological properties of the strain are as shown below.
(a) Range of growth temperature (yeast extract-malt extract agar medium, incubation for 2 weeks) 12° C. to 37° C.
(b) Range of optimum temperature (yeast extract-malt extract agar medium, incubation for 2 weeks) 21° C. to 33° C.
(c) Liquefaction of gelatin (glucose-peptone-gelatin agar medium) negative
(d) Coagulation of milk (skim milk agar medium) negative
(e) Peptonization of milk (skim milk agar medium) negative
(f) Hydrolysis of starch (inorganic salt-starch agar medium) positive
(g) Formation of melanoid pigment (peptone-yeast extract-iron agar medium) negative (tyrosine medium) negative
(h) Production of hydrogen sulfide (peptone-yeast extract-iron agar medium) negative
(i) Reduction of nitrate (broth containing 0.1% potassium nitrate) negative
(j) Sodium chloride tolerance (yeast extract-malt extract agar medium, incubation for 2 weeks) grown at a salt content of 4% or less (5) Chemotaxonomy LL-diaminopimelic acid and glycine were detected from the cell wall of the present strain.

It is considered that the present strain is a strain of the genus *Streptomyces* from the above-mentioned microbial characteristics. Accordingly, the present inventors have named the present microbial strain as *Streptomyces* sp. Mer-11107 and have deposited the strain as FERM P-18144 at the National Institute of Bioscience and Human-Technology Agency of Industrial Science and Technology.

2. Fermentation Method of Producing Microorganism

The physiologically active substance 11107D according to the present invention can be produced by inoculating the strain on a nutrition source medium and carrying out aerobic fermentation. The strain for producing the physiologically active substance 11107D is not limited to the above-mentioned strain, and any strain belonging to the genus *Streptomyces* and having an ability of producing 11107D can be used in the present invention.

The fermentation method of the above-mentioned microorganism is according to the general fermentation method of microorganism, but it is preferably carried out under aerobic conditions such as shaking culture or aeration-agitation fermentation using liquid medium. The medium used for culture may be a medium containing a nutrition source which can be utilized by microorganism belonging the genus *Streptomyces*, therefore all of various synthetic, a semi-synthetic medium, an organic medium and the like can be utilized. As the carbon source in the medium composition, there can be used a single or a combination of glucose, sucrose, fructose, glycerin, dextrin, starch, molasses, soybean oil and the like.

As the nitrogen source, there can be used a single or a combination of organic nitrogen sources such as pharma media, peptone, meat extract, soybean powder, casein, amino acid, yeast extract and urea, and inorganic nitrogen sources such as sodium nitrate and ammonium sulfate. Additionally, for example, there can be added and used salts such as sodium chloride, potassium chloride, calcium carbonate, magnesium sulfate, sodium phosphate, potassium phosphate and cobalt chloride; heavy metal salts, vitamins such as vitamin B or biotin, if necessary. Further, when foaming is remarkable during culture, various defoaming agents can be appropriately added in the medium as necessary. When the defoaming agent is added, it is required to set at a concentration for not adversely affecting the production of an objective substance, and for example, the use concentration is desirably 0.05% or less.

The culture condition can be appropriately selected within the range at which the microbial strain grows well and can produce the above-mentioned substance. For example, the pH of a medium is about 5 to 9, and preferably nearby neutral in general. The temperature of fermentation is usually kept at 20° C. to 40° C. and preferably 28° C. to 35° C. The fermentation period is about 2 to 8 days, and usually about 3 to 5 days. The above-mentioned fermentation conditions can be suitably changed in accordance with the kind and property of microorganism used, external conditions and the like, and it is needless to say that an optimum condition can be selected. The physiologically active substance 11107D of the present invention which was accumulated in the cultured broth can be collected by usual separation procedures utilizing its property such as a solvent extraction method and an absorbing resin method.

The physiologically active substance 11107D can also be prepared, for example, by using a microorganism belonging to the genus *Streptomyces* (for example, *Streptomyces* sp. AB-1704 strain (FERM P-18999)) and using 11107B substance (the compound described in Example A4 of WO 02/060890, as shown in Referential Examples 6 to 10.

3. Purification Method for the Bioactive Substance

General methods for separation and purification which are used for isolation of microbial metabolites from the cultured broth can be employed in order to collect 11107D from the cultured medium after the fermentation. For example, there can be corresponded all methods such as extraction by an organic solvent typically using methanol, ethanol, butanol, ethyl acetate or chloroform; various kinds of ion-exchange chromatography; gel filtration chromatography using Sephadex LH-20; the treatment of adsorption and desorption by absorption chromatography typically using active carbon or silica gel or by thin layer chromatography; or high performance liquid chromatography typically using a reverse phase column, to this. Further, the purification methods for 11107D are not specifically limited to the methods shown here.

The compound 11107D can be isolated and purified by using these methods alone or in combination or repeatedly using them.

Next, the preparation for the compounds of the formula (I) other than 11107D will be elucidated.

The compounds of the formula (I) can be synthesized from 11107D isolated and purified as a starting compound by converting the hydroxyl group and/or acetoxy group of the compound according to general organic synthetic procedures. Typical examples of the synthesis methods are A. a preparation for an urethane derivative, B. a preparation for a thiourethane derivative, C. a preparation for an ether derivative, D. a preparation for an ester derivative, E. a preparation for a phosphoric ester or amidophosphoric ester derivative, F. a preparation for a sulfuric ester or amidosulfuric ester derivative, G. a preparation for a halogen derivative, H. a preparation for a sulfonic ester derivative, I. a preparation for an amine derivative, and J. a preparation for an oxo-derivative by oxidation of a hydroxyl group. The introduction and removal of a protecting group for a hydroxyl group can be carried out according to need by the method described in document (Protective Groups in Organic Synthesis, T. W. Greene, John Wiley & Sons, Inc. 3rd Edition) or a method analogous thereto, while depending on the type of the protecting group and the stability of the compound relating to the preparation. The compounds of the formula (I) can be prepared by using the introduction and removal reactions for the hydroxyl-protecting group and the preparation described above in a suitable combination. More specifically, the compounds of the formula (I) in which $R^3$, $R^6$, $R^7$ and $R^{21}$ are the substituents listed in above-mentioned 9) can be prepared by using the preparation for a urethane derivative, a thiourethane derivative, an amidosulfuric ester or an amine derivative; those in which $R^3$, $R^6$, $R^7$ and $R^{21}$ are the substituents listed in above-mentioned 2) to 5) can be prepared by using the preparation for an ether derivative; those in which $R^3$, $R^6$, $R^7$ and $R^{21}$ are the substituents listed in above-mentioned 6) can be prepared by using the preparation for an ester derivative; those in which $R^3$, $R^6$, $R^7$ and $R^{21}$ are the substituents listed in above-mentioned 11) to 13) can be prepared by using the preparation for a phosphoric ester or amidophosphoric ester derivative; those in which $R^3$, $R^6$, $R^7$ and $R^{21}$ are the substituents listed in above-mentioned 10) can be prepared by using the preparation for a sulfuric ester or sulfonic ester derivative; those in which $R^3$, $R^6$, $R^7$ and $R^{21}$ are the substituents listed in above-mentioned 8) can be prepared by using the preparation for a halogen derivative; those in which $R^3$, $R^6$, $R^7$ and $R^{21}$ are the substituents listed in above-mentioned 7) can be prepared by using the introduction and removal reactions of a hydroxyl-protecting group; and the oxo-derivative in which $R^3$, $R^6$, $R^7$ and $R^{21}$ are the substituents listed in above-mentioned 1) can be prepared by using the preparation for an oxo-derivative by oxidation of a hydroxyl group.

Next, synthetic methods for preparing the compounds of the formula (I) will be elucidated.

A. A Preparation for a Urethane Derivative

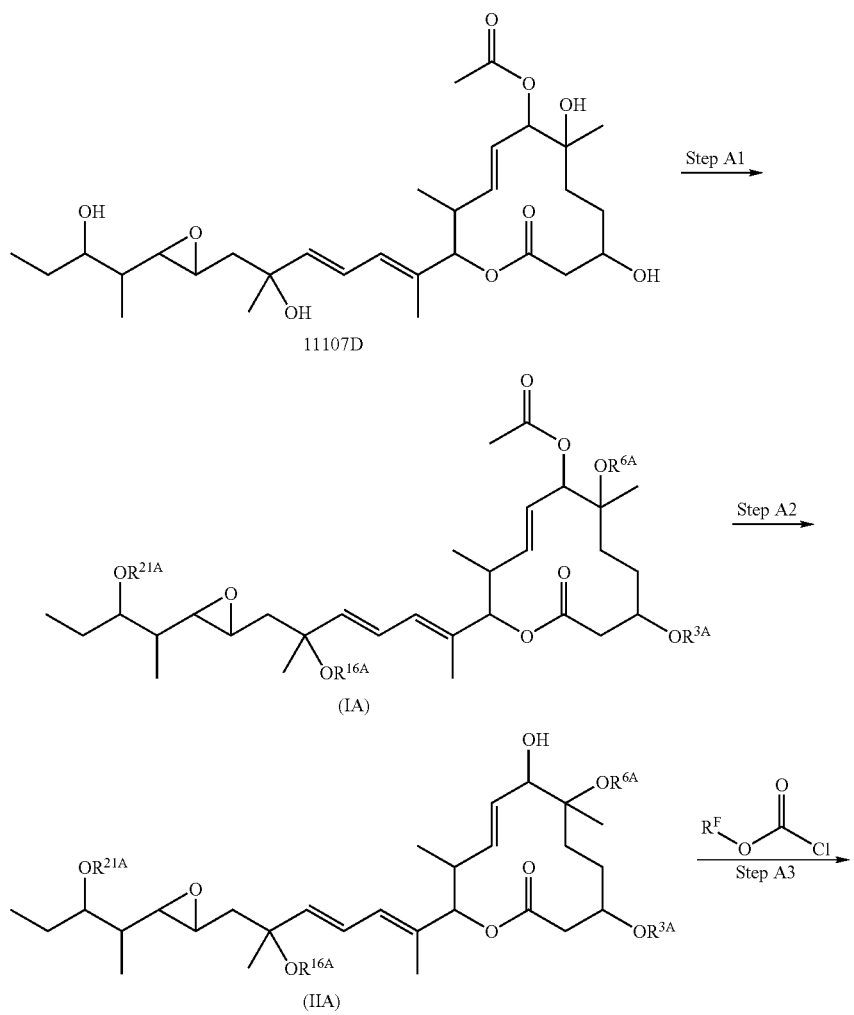

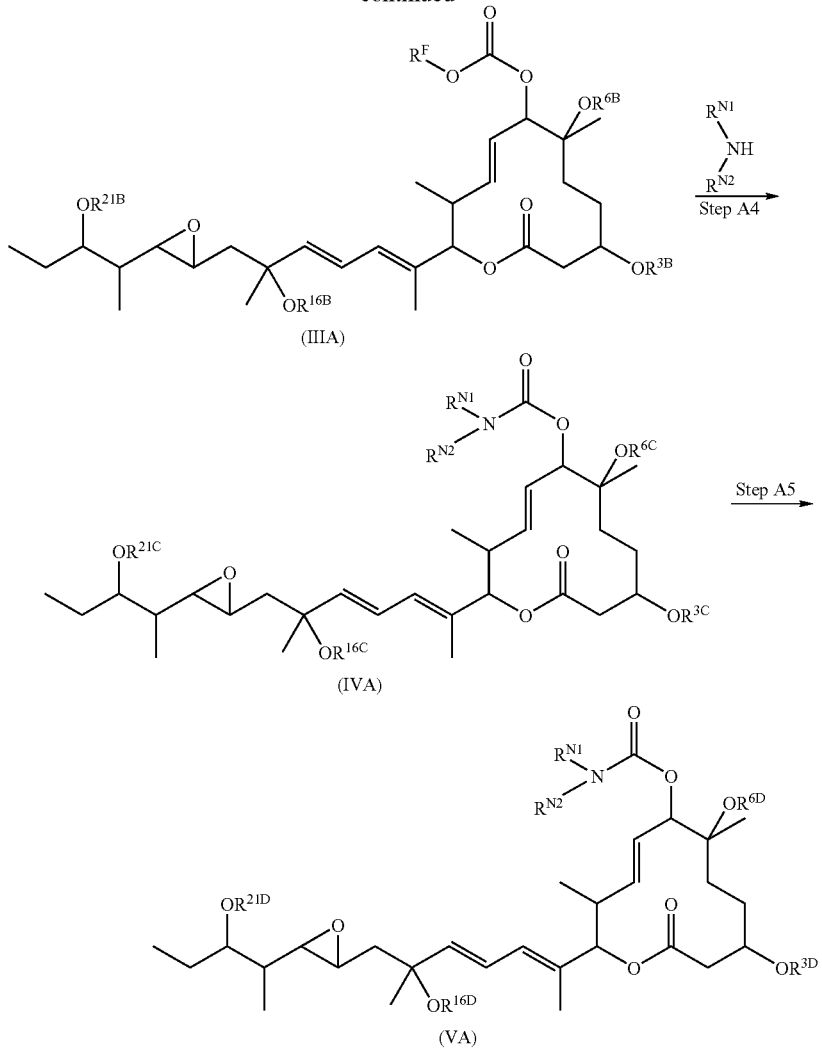

In the formula, $R^{3A}$, $R^{6A}$, $R^{16A}$ and $R^{21A}$ each represents a hydrogen atom or a protecting group, provided that $R^{3A}$, $R^{6A}$, $R^{16A}$ and $R^{21A}$ do not concurrently represent hydrogen atoms; $R^{3B}$, $R^{6B}$, $R^{16B}$ and $R^{21B}$ each represents a hydrogen atom, a protecting group or a group represented by the formula $R^FO$—$CO$— (wherein $R^F$ represents an optionally substituted $C_{6-14}$ aryl group), provided that $R^{3B}$, $R^{6B}$, $R^{16B}$ and $R^{21B}$ do not concurrently represent hydrogen atoms; $R^{3C}$, $R^{6C}$, $R^{16C}$ and $R^{21C}$ each represents a hydrogen atom, a protecting group or a group represented by the formula $R^{N1}R^{N2}N$—$CO$— (wherein $R^{N1}$ and $R^{N2}$ each represents the group as defined above); and $R^{3D}$, $R^{6D}$, $R^{16D}$ and $R^{21D}$ each represents a hydrogen atom or a group represented by the formula $R^{N1}R^{N2}N$—$CO$— (wherein $R^{N1}$ and $R^{N2}$ each represents the group as defined above).

The step A1 is a step for preparing the compound of the formula (IA). This step is carried out by protecting the hydroxyl group(s) of 11107D.

The reaction for protecting the hydroxyl group(s) is carried out according to a procedure well known in organic synthetic chemistry, while being selected depending on the type of the protecting group.

Examples of the protecting group are 1-ethoxyethyl, tetrahydropyranyl, 1-methyl-1-methoxyethyl, 1-(2-chloroethoxy)ethyl, 1-methoxycyclohexyl, 4-methoxytetrahydropyranyl, 4-methoxytetrahydrothiopyranyl, 4-methoxytetrahydrothiopyranyl S,S-dioxide, methoxymethyl, methylthiomethyl, methoxyethoxymethyl, trichloroethoxymethyl, trimethylsilylethyl, trimethylsilylethoxymethyl, tert-butyldimethylsilyl, triethylsilyl, diethylisopropylsilyl, trimethylsilyl, triisopropylsilyl, methyl-di-tert-butylsilyl, diphenylmethylsilyl, benzyl, p-methoxybenzyl, p-methylbenzyl, p-nitrobenzyl, p-chlorobenzyl and triphenylmethyl. All or part of the hydroxyl groups can be appropriately protected by these protecting groups.

For example, hydroxyl-protected derivatives protected by 1-ethoxyethyl, tetrahydropyranyl, 1-methoxycyclohexyl, 4-methoxytetrahydropyranyl, 4-methoxytetrahydrothiopyranyl or 4-methoxytetrahydrothiopyranyl-S,S-dioxide can be synthesized by treating 11107D with a corresponding vinyl ether such as ethylvinyl ether or dihydropyran in the presence of an acid. Examples of the acid are general acids including organic acids such as pyridinium p-toluenesulfonate (PPTS), p-toluenesulfonic acid, camphorsulfonic acid, acetic acid, trifluoroacetic acid or methanesulfonic acid; and inorganic acids such as hydrogen chloride, nitric acid, hydrochloric acid or sulfuric acid. Among them, a preferred example is pyridinium p-toluenesulfonate (PPTS), p-toluenesulfonic acid or camphorsulfonic acid. The solvent used in the reaction is not specifically limited, but an inert solvent which cannot easily react with a starting material is desirable. Examples of such solvents are ethers such as tetrahydrofuran, diethyl ether, diisopropyl ether, dioxane and dimethoxyethane; halogenated hydrocarbons such as dichloromethane, chloroform, carbon tetrachloride and 1,2-dichloroethane; hydrocarbons such as hexane, benzene and toluene; ketones such as acetone and methyl ethyl ketone; nitriles such as acetonitrile; amides such as N,N-dimethylformamide, N,N-dimethylacetamide, N-methyl-2-pyridone and hexamethylphosphoramide; and sulfoxides such as dimethyl sulfoxide, of which a preferred example is dichloromethane, chloroform or tetrahydrofuran. The reaction time is 10 minutes to 5 days and is preferably 1 day to 2 days. The reaction temperature is a temperature of −78° C. to heating under reflux and is preferably room temperature. The amounts of the vinyl ether and acid used in the reaction are 1 to 200 equivalents and 0.05 to 2 equivalents, and preferably 30 to 50 equivalents and 0.1 to 0.3 equivalent, respectively, to 11107D.

Examples of other protecting groups are methoxymethyl, methylthiomethyl, methoxyethoxymethyl, trichloroethoxymethyl, trimethylsilylethyl, trimethylsilylethoxymethyl, tert-butyldimethylsilyl, triethylsilyl, trimethylsilyl, diethylisopropylsilyl, triisopropylsilyl, di-tert-butylmethylsilyl, diphenylmethylsilyl, benzyl, p-methoxybenzyl, p-methylbenzyl, p-nitrobenzyl, p-chlorobenzyl and triphenylmethyl. Such hydroxyl-protected derivatives can be synthesized by reacting a starting material with a chloride, bromide or trifluoromethanesulfonate of the respective protecting groups in the presence of a base. The base is a general organic base or inorganic base. Examples of the organic base are an aromatic base such as imidazole, 4-(N,N-dimethylamino)pyridine (the 4-dimethylaminopyridine, N,N-dimethylaminopyridine and dimethylaminopyridine used in the present specification have the same meaning), pyridine, 2,6-lutidine or collidine; a tertiary amine such as N-methylpiperidine, N-methylpyrrolidine, triethylamine, trimethylamine, di-iso-propylethylamine, cyclohexyldimethylamine, N-methylmorpholine or 1,8-bis(dimethylamino)naphthalene; a secondary amine such as di-iso-butylamine or dicyclohexylamine; an alkyllithium such as methyllithium or butyllithium; a metal alkoxide such as sodium methoxide or sodium ethoxide. Examples of the inorganic base are an alkali metal hydride such as sodium hydride or potassium hydride; an alkaline earth metal hydride such as calcium hydride; an alkali metal hydroxide such as sodium hydroxide or potassium hydroxide; an alkali metal carbonate such as sodium carbonate, potassium carbonate or cesium carbonate; and an alkali metal hydrogen carbonate such as sodium bicarbonate. Preferred examples of the base for the protection of the hydroxyl group by a silyl protecting group are an aromatic base such as imidazole or 4-dimethylaminopyridine; and a tertiary amine such as triethylamine. The solvent used in the reaction is not specifically limited, but one which does not easily react with a starting material is desirable. Examples of such solvents are the above-mentioned inert solvents, of which a preferred example is tetrahydrofuran, dichloromethane or N,N-dimethylformamide. The reaction time is 10 minutes to 3 days and is preferably 1 day to 2 days. The reaction temperature is a temperature of −78° C. to heating under reflux and is preferably −10° C. to 50° C. The amounts of the chloride, bromide or trifluoromethanesulfate and the base used in the reaction are 1 to 20 equivalents and 0.5 to 30 equivalents, preferably 1 to 15 equivalents and 0.5 to 20 equivalents, respectively, to 11107D.

The hydroxyl groups of 11107D can be selectively protected by selecting the reagent and equivalence thereof for use in the protection of the hydroxyl groups. For example, a compound in which the hydroxyl groups at the 3-position and 21-position are selectively protected can be obtained by carrying out the reaction at room temperature using chlorotriethylsilane, triethylamine and 4-dimethylaminopyridine in dichloromethane or using tert-butylchlorodimethylsilane and imidazole in N,N-dimethylformamide. In this procedure, for example, the hydroxyl group at the 3-position can be selectively protected by controlling the equivalence of chlorotriethylsilane or tert-butylchlorodimethylsilane. Further, it is possible that two or three of the four hydroxyl groups are protected by a silyl group, and then the other two or one hydroxyl group is protected by the above-mentioned ethoxyethyl or the like.

The step A2 is a step for preparing the compound of the formula (IIA). This step is carried out by converting the acetoxy group of the compound of the formula (IA) into the hydroxyl group by the treatment of a base in an inert solvent. Examples of the base used herein are inorganic bases including an alkali metal hydride such as sodium hydride or potassium hydride; an alkaline earth metal hydride such as calcium hydride; an alkali metal hydroxide such as lithium hydroxide, sodium hydroxide or potassium hydroxide; an alkali metal carbonate such as lithium carbonate, sodium carbonate or potassium carbonate; an alkali metal hydrogen carbonate such as sodium bicarbonate; and a metal alkoxide such as lithium methoxide, sodium methoxide, sodium ethoxide or potassium tert-butoxide, as well as bases such as guanidine or ammonia. Preferred examples of the base are potassium carbonate and guanidine.

Examples of the inert solvent used herein include, in addition to the above-mentioned inert solvents, an alcohol solvent such as methanol, ethanol, isopropanol or tert-butanol, and water. These solvents can be used in combination as a mixture. A preferred solvent is an alcohol solvent or a mixture of an alcohol and a halogen solvent. The reaction time is 10 minutes to 5 days and is preferably 30 minutes to 1 day. The reaction temperature is a temperature of −78° C. to heating under reflux and is preferably room temperature. The amount of the base used in the reaction is 1 to 10 equivalents and preferably 2 to 5 equivalents to the compound of the formula (IA).

The step A3 is a step for preparing the compound of the formula (IIIA). This step is carried out by treating the hydroxyl group of the compound of the formula (IIA) with a chloroformate derivative or carbonyldiimidazole in the presence of a base. Examples of the chloroformate derivative are 4-nitrophenyl chloroformate, phenyl chloroformate, 4-chlorophenyl chloroformate, 4-bromophenyl chloroformate and 2,4-dinitrophenyl chloroformate. Examples of the base are the above-mentioned organic bases and inorganic bases, of which, for example, diisopropylethylamine, 4-dimethylaminopyridine, triethylamine, pyridine, 2,6-lutidine or sodium hydride is preferably used. The solvent used in the reaction is not specifically limited, but a solvent that does not easily react with a starting material is desirable. Examples of such solvents are the above-mentioned inert solvents, of which, for example, tetrahydrofuran, dichloromethane or N,N-dimethylformamide is preferably used. The amounts of the chloroformate derivative and base for use in the reaction are 1 to 10 equivalents and 1 to 20 equivalents, and preferably 1 to 5 equivalents and 1 to 10 equivalents, respectively, to the compound of the formula (IIA). The reaction time is 10 minutes to 30 hours and is preferably 1 to 4 hours. The reaction temperature is a temperature of −78° C. to heating under reflux and is preferably −10° C. to 50° C.

For the hydroxyl compound (IA) in which one to three of $OR^{3,4}$, $OR^{6,4}$, $OR^{16,4}$ and $OR^{21,4}$ have not been protected in the step A1, the hydroxyl groups can be converted into carbonic ester groups by the step A3. More specifically, the hydroxyl groups of the compound (IA) other than the hydroxyl group at the 7-position can be converted into carbonic ester groups by the same way as the hydroxyl group at the 7-position by treatment with a base and a chloroformate derivative in equivalents corresponding to the number of hydroxyl groups to be converted into carbonic ester groups.

The step A4 is a step for preparing the compound of the formula (IVA). This step is carried out by treating the carbonic ester of the formula (IIIA) with an amine ($R^{N1}R^{N2}$H) that can form a desired compound of the formula (I) in an inert solvent in the presence of a base or with the amine alone.

Examples of the amine used herein are methylamine, ethylamine, propylamine, butylamine, octylamine, decylamine, cyclopropylamine, cyclopentylamine, cyclohexylamine, dimethylamine, diethylamine, ethylmethylamine, ethylenediamine, 1,3-propanediamine, 1,4-butanediamine, N,N-dimethylethylenediamine, N,N-dimethyl-1,3-propanediamine, N,N-dimethyl-1,4-butanediamine, N,N-diethylethylenediamine, N,N-diethyl-1,3-propanediamine, N,N-diethyl-1,4-butanediamine, N,N,N'-trimethylethylenediamine, N,N,N'-trimethyl-1,3-propanediamine, N,N,N'-trimethyl-1,4-butanediamine, N-ethyl-N',N'-dimethylethylenediamine, N-ethyl-N',N'-dimethyl-1,3-propanediamine, N-ethyl-N',N'-dimethyl-1,4-butanediamine, N,N,N'-triethylethylenediamine, N,N,N'-triethyl-1,3-propanediamine, N,N,N'-triethyl-1,4-butanediamine, N,N-diethyl-N'-methylethylenediamine, N,N-diethyl-N'-methyl-1,3-propanediamine, N,N-diethyl-N'-methyl-1,4-butanediamine, N,N'-dimethyl-N-phenylethylenediamine, N,N'-dimethyl-N-phenyl-1,3-propanediamine, N-benzyl-N,N'-dimethylethylenediamine, N-benzyl-N,N'-dimethyl-1,3-propanediamine, morpholine, thiomorpholine, thiomorpholine-S-oxide, thiomorpholine-S,S-dioxide, pyrrolidine, piperidine, piperazine, homopiperazine, 4-hydroxypiperidine, 4-methoxypiperidine, 1-methylpiperazine, 1-ethylpiperazine, 1-propylpiperazine, 1-butylpiperazine, 1-isopropylpiperazine, 1-cyclobutylpiperazine, 1-cyclopentylpiperazine, 1-cyclohexylpiperazine, 1-cycloheptylpiperazine, 1-cyclooctylpiperazine, 1-(cyclopropylmethyl)piperazine, 1-benzylpiperazine, 1-methylhomopiperazine, 1-ethylhomopiperazine, 1-(2-aminoethyl)pyrrolidine, 1-(2-(N-methylamino)ethyl)pyrrolidine), 1-(3-aminopropyl)pyrrolidine, 1-(3-(N-methylamino)propyl)pyrrolidine), 1-(2-aminoethyl)piperidine, 1-(2-(N-methylamino)ethyl)piperidine), 1-(3-aminopropyl)piperidine, 1-(3-(N-methylamino)propyl)piperidine), 4-(2-aminoethyl)morpholine, 4-(2-(methylamino)ethyl)morpholine), 4-(3-aminopropyl)morpholine, 4-(3-(N-methylamino)propyl)morpholine), 1-(2-aminoethyl)-4-methylpiperazine, 1-(3-aminopropyl)-4-methylpiperazine, 1-(3-(N-methylamino)propyl)-4-methylpiperazine, 1-amino-4-methylpiperidine, 1-methylamino-4-methylpiperidine, 1-ethyl-4-(N-methylamino)piperidine, 1-methylamino-4-propylpiperidine, 1-butyl-4-(N-methylamino)piperidine, 1-(N,N-dimethylamino)piperidine, 1-(N,N-diethylamino)piperidine, 4-(pyrrolidin-1-yl)piperidine, 4-(piperidin-1-yl)piperidine, 3-aminoquinuclidine, 3-(N-methylamino)quinuclidine, aniline, N-methylaniline, N,N-dimethyl-p-phenylenediamine, N,N-dimethyl-m-phenylenediamine, N,N,N'-trimethyl-p-phenylenediamine, N,N,N'-trimethyl-m-phenylenediamine, 1-naphthylamine, 2-naphthylamine, benzylamine, N-methylbenzylamine, phenethylamine, N-methylphenethylamine, 2-picolylamine, 3-picolylamine, 4-picolylamine, N-methyl-2-picolylamine, N-methyl-3-picolylamine, N-methyl-4-picolylamine, 2,5-diazabicyclo[2.2.1]heptane, 2-methyl-2,5-diazabicyclo[2.2.1]heptane, 3,8-diazabicyclo[3.2.1]octane and 1,4-diazabicyclo[4.3.0]nonane.

Examples of the base are the above-mentioned organic bases and inorganic bases, of which, for example, diisopropylethylamine, dimethylaminopyridine, triethylamine, pyridine, 2,6-lutidine or sodium hydride is preferably used. The solvent used in the reaction is not specifically limited, but a solvent that does not easily react with a starting material is desirable. Examples of such solvents are the above-mentioned inert solvents, of which, for example, tetrahydrofuran, dichloromethane or N,N-dimethylformamide is preferably used. The amounts of the amine and base used in the reaction are 1 to 10 equivalents and 2 to 20 equivalents, and preferably 1.5 to 5 equivalents and 2 to 10 equivalents, respectively, to the compound of the formula (IIIA). The reaction time is 10 minutes to 30 hours and is preferably 1 to 2 hours. The reaction temperature is a temperature of −78° C. to heating under reflux and is preferably −10° C. to 50° C.

The compound of the formula (IVA) can also be prepared by treating the compound of the formula (IIA) with an isocyanate in an inert solvent in the presence of a base and/or cuprous chloride. The isocyanate is not specifically limited and includes, for example, ethyl isocyanate, methyl isocyanate and phenyl isocyanate. Examples of the base are the above-mentioned organic bases and inorganic bases, of which, for example, diisopropylethylamine, dimethylaminopyridine, triethylamine, pyridine, 2,6-lutidine or sodium hydride is preferably used. The solvent used in the reaction is not specifically limited, but a solvent that does not easily react with a starting material is desirable. Examples of such solvents are the above-mentioned inert solvents, of which, for example, tetrahydrofuran, dichloromethane or N,N-dimethylformamide is preferably used. The amounts of the base and isocyanate used in the reaction are 3 to 100 equivalents and 1 to 20 equivalents, preferably 5 to 20 equivalents and 3 to 10 equivalents, respectively, to the compound of the formula (IIIA). In the case where cuprous chloride is used, the amount thereof is 1 to 10 equivalents and preferably 2 to 6 equivalents. The reaction time is 10 minutes to 30 hours and is preferably 1 to 2 hours. The reaction temperature is a temperature of −78° C. to heating under reflux and is preferably −10° C. to 50° C.

The hydroxyl compound in which one to three of $OR^{3,4}$, $OR^{6,4}$, $OR^{16,4}$ and $OR^{21,4}$ have not been protected in the step A1 can be converted into a derivative having a plurality of urethane structures by converting those hydroxyl groups into carbonic ester groups in the step A3 and further converting them into carbamoyloxy groups in the step A4.

The step A5 is a step for producing the compound of the formula (VA). This step is carried out by subjecting the urethane derivative of the formula (IVA) to a deprotection treatment mentioned below in an inert solvent. The deprotection reaction for the protecting groups of the hydroxyl groups varies depending on the type of the protecting group but is carried out by a method well known in organic synthetic chemistry.

For the respective hydroxyl group protected by, for example, 1-ethoxyethyl, tetrahydropyranyl, 1-methoxycyclohexyl, 4-methoxytetrahydropyranyl, 4-methoxytetrahydrothiopyranyl or 4-methoxytetrahydrothiopyranyl-S,S-dioxide, the deprotection reaction can be easily carried out by treatment with an acid in an inert solvent. Examples of the acid are the above-mentioned organic acids and inorganic acid, of which, for example, pyridinium p-toluenesulfonate, p-toluenesulfonic acid or camphorsulfonic acid is preferred. The solvent used in the reaction is not specifically limited, but a solvent that does not easily react with a starting material is desirable. Preferred examples thereof are an alcohol solvent such as methanol, ethanol, isopropanol or tert-butanol, or a mixture of the alcohol and the above-mentioned inert solvent. The amount of the acid used in the reaction is 0.5 to 5 equivalents and is preferably 1 to 3 equivalents to the compound of the formula (IVA). The reaction time is 10 minutes to 10 days and is preferably 1 day to 4 days. The reaction temperature is a temperature of −78° C. to heating under reflux and is preferably −10° C. to 50° C.

When the hydroxyl group is protected by the other protecting group such as tert-butyldimethylsilyl, triethylsilyl, diethylisopropylsilyl, trimethylsilyl, triisopropylsilyl, di-tert-butylmethylsilyl or diphenylmethylsilyl, it can be deprotected by the treatment of a fluoride anion or an acid. Examples of the fluoride anion are tetrabutylammonium fluoride, hydrogen fluoride, potassium fluoride and hydrogen fluoride-pyridine. Examples of the acid are the above-mentioned organic acids and inorganic acids, of which a preferred example is acetic acid, formic acid, trifluoroacetic acid, pyridinium p-toluenesulfonate or camphorsulfonic acid. The solvent used in the reaction is not specifically limited, but a solvent that does not easily react with a starting material is desirable. Examples thereof are the above-mentioned inert solvents, of which, for example, tetrahydrofuran, diethyl ether or water is preferably used. The amounts of the fluoride anion and acid used in the reaction are 1 to 5 equivalents and 0.5 to 5 equivalents, preferably 1 to 4 equivalents and 0.5 to 3 equivalents, respectively, to the compound of the formula (IVA). The reaction time is 10 minutes to 30 hours and is preferably 1 to 2 hours. The reaction temperature is a temperature of −78° C. to heating under reflux and is preferably −10° C. to 50° C.

By a combination of the various protection methods for hydroxyl groups described in the step A1 and the various deprotection methods described in the step A5, the respective hydroxyl groups at the 3-position, 6-position and 21-position can be converted into urethane derivatives selectively. For example, a urethane derivative having a hydroxyl group at the 6-position can be synthesized by subjecting the hydroxyl group at the 6-position of the compound (IA) in which $R^{3,4}$, $R^{16,4}$ and $R^{21,4}$ are triethylsilyl groups to the step A3, the step A4 and the step A5 sequentially.

The selective modification of the hydroxyl group at the 3-position, 6-position or 21-position which is carried out by a combination of the protection and the deprotection procedures can also be applied to the other modification methods described below.

B. A Preparation for a Thiourethane Derivative

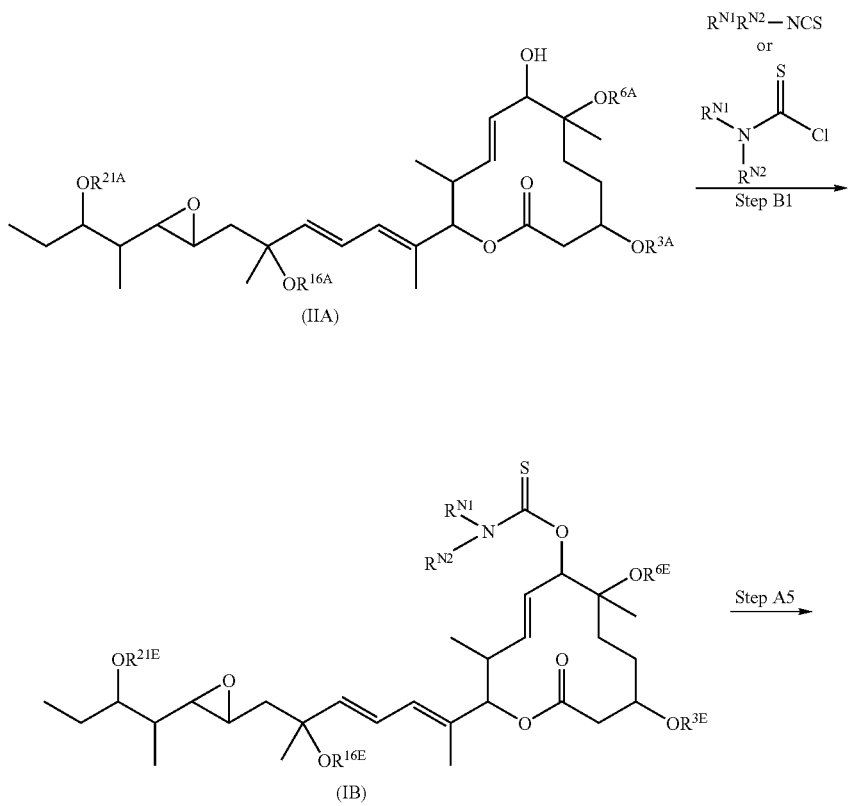

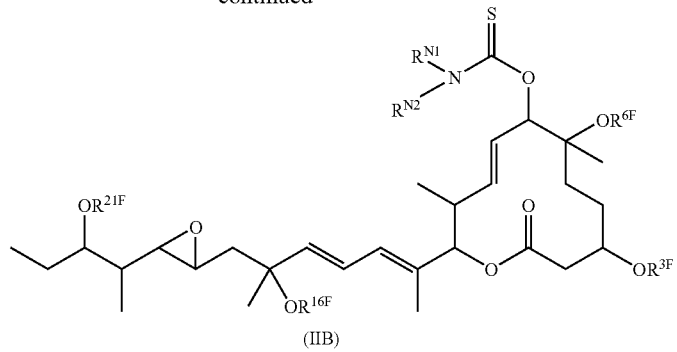

(IIB)

In the formula, $R^{3A}$, $R^{6A}$, $R^{16A}$ and $R^{21A}$ each represents the same group as defined above; $R^{3E}$, $R^{6E}$, $R^{16E}$ and $R^{21E}$ each represents a hydrogen atom, a protecting group or a group represented by the formula $R^{N1}R^{N2}N$—CS— (wherein $R^{N1}$ and $R^{N2}$ each represents the same group as defined above), provided that $R^{3E}$, $R^{6E}$, $R^{16E}$ and $R^{21E}$ do not concurrently represent hydrogen atoms; and $R^{3F}$, $R^{6F}$, $R^{16F}$ and $R^{21F}$ each represents hydrogen atom or a group represented by the formula $R^{N1}R^{N2}N$—CS— (wherein $R^{N1}$ and $R^{N2}$ each represents the same group as defined above).

The step B1 is a step for preparing the compound of the formula (IB) by using a thioisocyanate or a thiocarbamoyl chloride instead of the isocyanate. This step is carried out by treating the compound of the formula (IIA) with an isothiocyanate or a thiocarbamoyl chloride in an inert solvent in the presence of a base or bis(tributyltin)oxide. The isothiocyanate used herein is not specifically limited and includes, for example, ethyl isothiocyanate, methyl isothiocyanate, phenyl isothiocyanate, benzyl isothiocyanate, allyl isothiocyanate, 2-(N,N-dimethylamino)ethyl isothiocyanate, 2-(N,N-diethylamino)ethyl isothiocyanate, 3-(N,N-dimethylamino)propyl isothiocyanate, 3-(N,N-diethylamino)propyl isothiocyanate, 2-(morpholin-4-yl)ethyl isothiocyanate, 2-(piperidin-1-yl) ethyl isothiocyanate and 2-(pyrrolidin-1-yl)ethyl isothiocyanate. The thiocarbamoyl chloride used herein is not specifically limited and includes, for example, N,N-dimethylthiocarbamoyl chloride, N-phenyl-N-methylthiocarbamoyl chloride, (morpholin-4-yl) thiocarbamoyl chloride, (4-methylpiperazin-1-yl) thiocarbamoyl chloride and (4-methylhomopiperazin-1-yl) thiocarbamoyl chloride. Examples of the base are the above-mentioned organic bases and inorganic bases, of which, for example, diisopropylethylamine, 4-dimethylaminopyridine, triethylamine, pyridine, 2,6-lutidine or sodium hydride is preferably used. The solvent used in the reaction is not specifically limited, but a solvent that does not easily react with a starting material is desirable. Examples of such solvents are the above-mentioned inert solvents, of which, for example, tetrahydrofuran, dichloromethane, N,N-dimethylformamide or toluene is preferably used. The amounts of the base or bis(tributyltin)oxide, and isothiocyanate or thiocarbamoyl chloride are 1 to 5 equivalents and 1 to 10 equivalents, preferably 1 to 3 equivalents and 2 to 5 equivalents, respectively, to the compound of the formula (IIA). The reaction time is 10 minutes to 72 hours and is preferably 1 to 24 hours. The reaction temperature is a temperature of −78° C. to heating under reflux and is preferably −10° C. to 70° C.

A compound of the formula (IB) having a plurality of thiocarbamoyl groups can be synthesized by converting the hydroxyl group(s) of the compound represented by the formula (IIA), in which one to three of $OR^{3A}$, $OR^{6A}$, $OR^{16A}$ and $OR^{21A}$ are not protected, into thiocarbamoyloxy group(s) in the step B1.

The thiourethane derivative of the formula (IIB) can be synthesized by deprotecting the protecting group of the hydroxyl group by the step A5.

C. A Preparation for an Ether Derivative

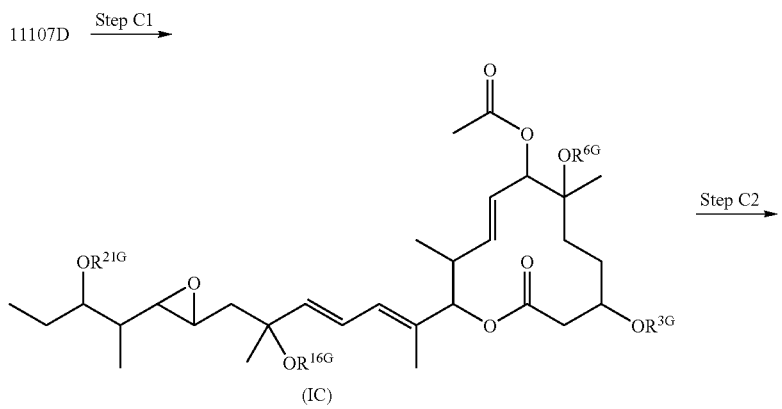

(IC)

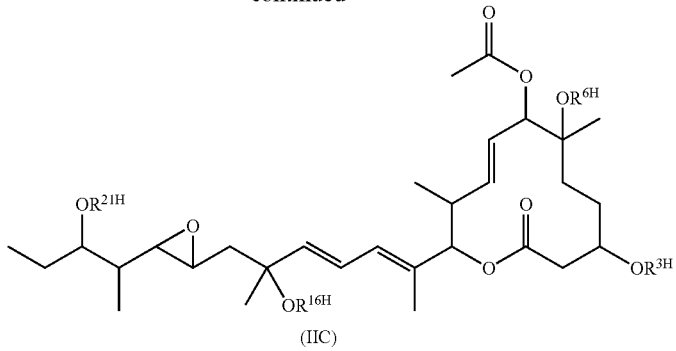

(IIC)

In the formula, $R^{3G}$, $R^{6G}$, $R^{16G}$ and $R^{21G}$ each represents a hydrogen atom or a protecting group, provided that $R^{3G}$, $R^{6G}$, $R^{16G}$ and $R^{21G}$ do not concurrently represent hydrogen atoms and at least one of them represents a hydrogen atom; and $R^{3H}$, $R^{6H}$, $R^{16H}$ and $R^{21H}$ each represents a protecting group or an optionally substituted $C_{1-22}$ alkyl group.

The step C1 is a step for synthesizing the compound of the formula (IC). This step is carried out by the same way as in the reaction corresponding to the step A1 of the preparation A, except that one to three hydroxyl groups are to be protected.

On this step, alternatively, a compound in which one at the 3-position, 6-position or 21-position is a hydroxyl group and the other hydroxyl groups are protected can be synthesized by using a combination of the various protection methods for the hydroxyl group corresponding to the step A1 and deprotection methods for a protected hydroxyl group corresponding to the step A5 in the preparation.

The step C2 is a step for synthesizing the compound of the formula (IIC). This step is carried out by alkylating the unprotected hydroxyl group(s) of the compound (IC).

The alkylation can be carried out by the treatment of an alkylating agent of the formula $R^m$—X in the presence of a base. The substituent $R^m$ represents a $C_{1-22}$ alkyl group which may have substituents and includes, for example, methyl group, ethyl group and benzyl group. X represents a leaving group. Examples of the leaving group are chloro group, bromo group, iodo group and trifluoromethanesulfonyl group. Examples of the base are the above-mentioned organic bases and inorganic bases, of which preferred examples are sodium hydride, lithium bis(trimethylsilyl)amide, lithium diisopropylamide, lithium dicyclohexylamide, potassium carbonate, cesium carbonate and 1,8-bis(N,N-dimethylamino)naphthalene. The solvent used in the reaction is not specifically limited, but a solvent that does not easily react with a starting material is desirable. Examples thereof are the above-mentioned inert solvents, of which, for example, diethyl ether, tetrahydrofuran, dimethoxyethane or toluene is preferably used. The amounts of the alkylating agent and base used in the reaction are 3 to 20 equivalents and 5 to 30 equivalents, preferably 3 to 5 equivalents and 5 to 10 equivalents, respectively, to the compound of the formula (IC). The reaction time is 10 minutes to 48 hours and is preferably 1 to 24 hours. The reaction temperature is a temperature of −78° C. to heating under reflux and is preferably −10° C. to 70° C.

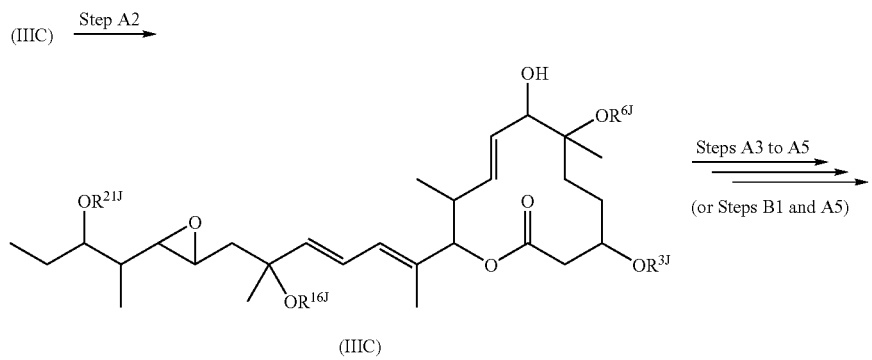

(IIIC)

-continued

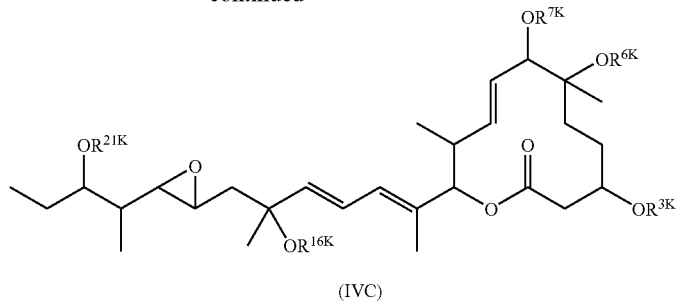

(IVC)

In the formula, $R^{3J}$, $R^{6J}$, $R^{16J}$ and $R^{21J}$ each represents an alkyl group or a protecting group; $R^{3K}$, $R^{6K}$, $R^{16K}$ and $R^{21K}$ each represents an alkyl group or a hydrogen atom; and $R^{7K}$ represents a carbamoyl group or a thiocarbamoyl group, and each may have substituents on the nitrogen atom.

If desired, a derivative having a carbamoyl group introduced into the hydroxyl group at the 7-position and an alkyl group introduced into one or two of the hydroxyl groups at the 3-position, 6-position and 21-position can be obtained by further subjecting the compound of the formula (IIC) to the steps A2, A3, A4 and A5.

Alternatively, a derivative having a thiocarbamoyl group introduced into the hydroxyl group at the 7-position and an alkyl group introduced into one or two of the hydroxyl groups at the 3-position, 6-position and 21-position can be obtained by subjecting the compound of the formula (IIIC) to the step B1 and then to the step A5.

In the formula, $R^{3A}$, $R^{6A}$, $R^{16A}$ and $R^{21A}$ each represents the same group as defined above; and $R^{3L}$, $R^{6L}$, $R^{7L}$, $R^{16L}$ and $R^{21L}$ each represents a hydrogen atom or an alkyl group.

The ether derivative represented by the formula (IIC'), in which the hydroxyl group at the 7-position is alkylated can be prepared by subjecting the compound of the formula (IIA) to the step C2 and then to the step A5 in a similar way as described above.

Further, a corresponding ether derivative can be prepared by using, instead of the alkylating agent, an unsaturated-alkylating agent, aralkylating agent or heteroaralkylating agent that can parepare a desired compound of the formula (I).

D. A preparation for an Ester Derivative

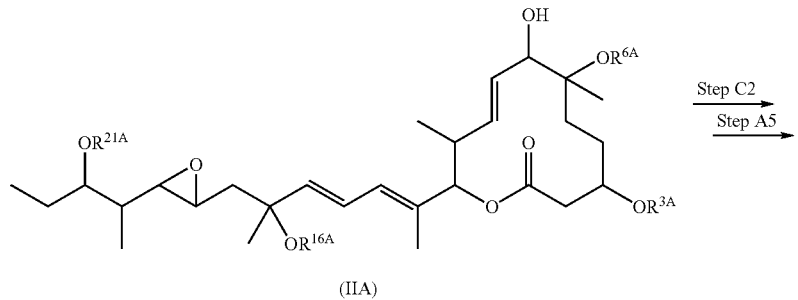

(IIA)

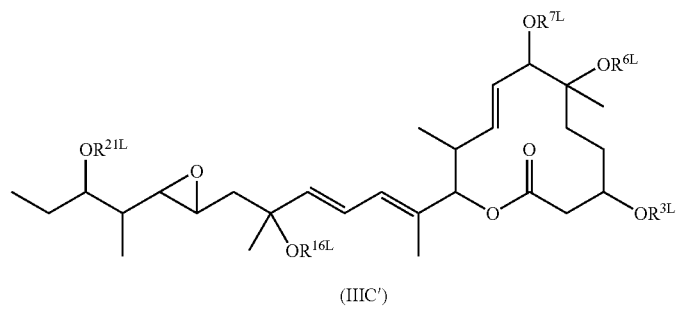

(IIIC')

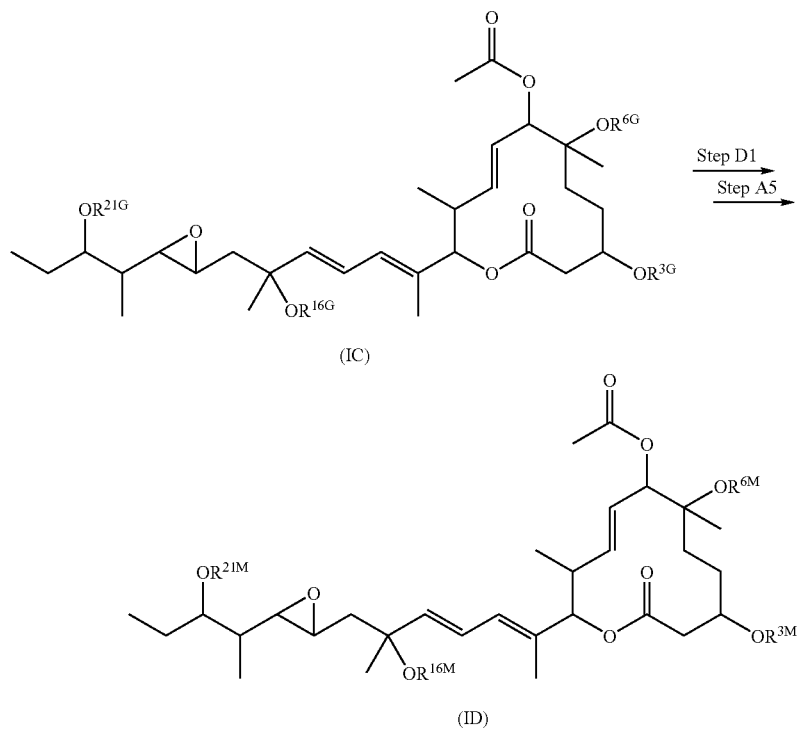

(IC)

(ID)

In the formula, $R^{3G}$, $R^{6G}$, $R^{16G}$ and $R^{21G}$ each represents the same group as defined above; and $R^{3M}$, $R^{6M}$, $R^{16M}$ and $R^{21M}$ each represents a hydrogen atom, a protecting group or a group represented by the formula $R^{co}CO$— (wherein $R^{co}$ represents a hydrogen atom, an optionally substituted $C_{1-22}$ alkyl group, an optionally substituted unsaturated $C_2$-$C_{22}$ alkyl group, an optionally substituted $C_{6-14}$ aryl group, an optionally substituted 5 to 14-membered heteroaryl group, an optionally substituted $C_{7-22}$ aralkyl group or an optionally substituted 5 to 14-membered heteroaralkyl group), provided that $R^{3M}$, $R^{6M}$, $R^{16M}$ and $R^{21M}$ do not concurrently represent hydrogen atoms.

The step D1 is a step for converting the unprotected hydroxyl group into an ester group by using the compound of the formula (IC) synthesized in the step C1 as a starting material.

The esterification is carried out, for example, by using an acid anhydride with a base, an acid halide with a base, a carboxylic acid with a condensing agent or by carrying out Mitsunobu reaction. As the acid anhydride, a variety of anhydrides of carboxylic acids are used. Examples thereof are a mixed anhydride comprising, for example, acetic acid, propionic acid, butyric acid, valeric acid and benzoic acid; a symmetrical anhydride; a cyclic anhydride such as succinic anhydride, glutaric anhydride or adipic anhydride. Preferred examples are acetic anhydride, propionic anhydride, butyric anhydride and benzoic anhydride. As the acid halide, for example, various acid chlorides and bromides are used, of which a preferred example is acetyl chloride, propionyl chloride, benzoyl chloride or benzoyl bromide. Examples of the base are the above-mentioned organic bases and inorganic bases, of which a preferred example is imidazole, 4-dimethylaminopyridine, pyridine or sodium hydride. As the carboxylic acid, various carboxylic acids are used, of which a preferred example is acetic acid or propionic acid. Preferred examples of the condensing agent are, for example, dicyclohexylcarbodiimide, trifluoroacetic anhydride, carbonyldiimidazole, N,N-diisopropylcarbodiimide and 1-ethyl-3-(3-dimethylaminopropyl)carbodiimide. In the Mitsunobu reaction, a variety of carboxylic acids can be substituted in the presence of triphenylphosphine and diethyl azodicarboxylate or diisopropyl azodicarboxylate. The solvent used in each of the reactions is not specifically limited, but a solvent that does not easily react with a starting material is desirable. Examples thereof are the above-mentioned inert solvents, of which, for example, dichloromethane, chloroform or tetrahydrofuran is preferably used. The amounts of the acid anhydride with the base, the acid halide with the base, and the carboxylic acid with the condensing agent are 1 to 10 equivalents with 3 to 20 equivalents, 1 to 10 equivalents with 3 to 20 equivalents, and 1 to 20 equivalents with 1 to 20 equivalents, preferably 1 to 5 equivalents with 2 to 10 equivalents, 1 to 5 equivalents with 2 to 10 equivalents, and 1 to 5 equivalents with 1 to 5 equivalents, respectively, to the compound of the formula (IC). The reaction can be accelerated by adding 0.2 to 2 equivalents of 4-dimethylaminopyridine as the case requires. The reaction time is 10 minutes to 30 hours and is preferably 1 to 2 hours. The reaction temperature is a temperature of −78° C. to heating under reflux and is preferably −10° C. to 50° C.

The compound of the formula (ID) can be produced by subjecting the thus-synthesized ester derivative to a reaction similar to the step A5 to thereby deprotect the protecting group of a hydroxyl group.

It is also possible to esterify one to four hydroxyl groups by carrying out an esterification similar to the step D1 using 11107D as a starting material.

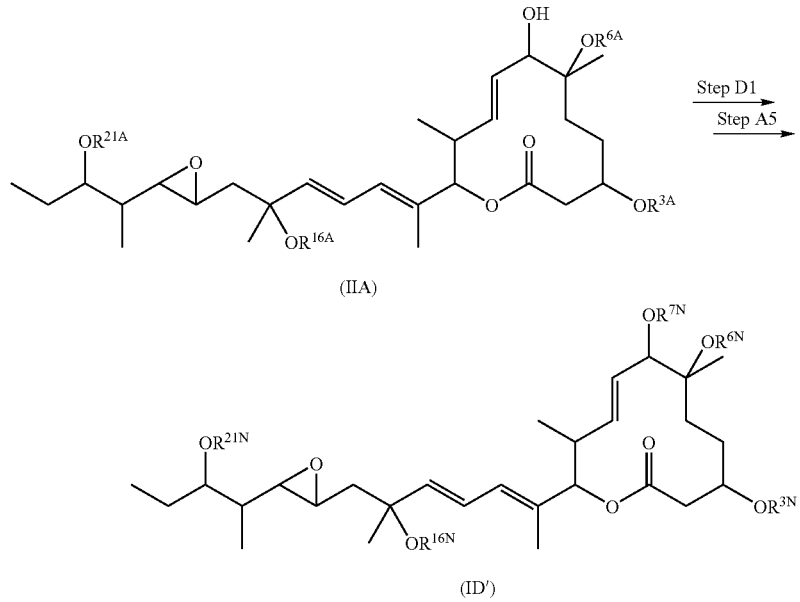

(IIA)

(ID')

In the formula, $R^{3A}$, $R^{6A}$, $R^{16A}$ and $R^{21A}$ each represents the same group as defined above; and $R^{3N}$, $R^{6N}$, $R^{7N}$, $R^{16N}$ or $R^{21N}$ represents a hydrogen atom or a group represented by the formula $R^{co}CO$— (wherein $R^{co}$ represents the same group as defined above).

The derivative represented by the formula (ID') in which the hydroxyl group at the 7-position is esterified can be synthesized by subjecting the compound of the formula (IIA) to the step D1 and then to the step A5 in a similar way as described above.

E. A preparation for a Phosphoric Ester or Amidophosphoric Ester Derivative

In the formula, $R^{3A}$, $R^{6A}$, $R^{16A}$ and $R^{21A}$ each represents the same group as defined above; $R^{3P}$, $R^{6P}$, $R^{7P}$, $R^{16P}$ and $R^{21P}$ each represents a hydrogen atom, a group represented by the formula $(R^{N3}O)_2PO$—, the formula $(R^{N1}R^{N2}N)_2PO$— or the formula $(R^{N1}R^{N2}N)(R^{N3}O)PO$— (wherein $R^{N1}$, $R^{N2}$ and $R^{N3}$ each represents the same group as defined above).

The step E1 is a step for converting the hydroxyl group of the compound of the formula (IIA) as a starting material into a phosphoric ester or an amidophosphoric ester.

The phosphoric-esterification is carried out, for example, by using a phosphoryl halide and a base. Various phosphoryl halides can be used herein, and examples thereof are a

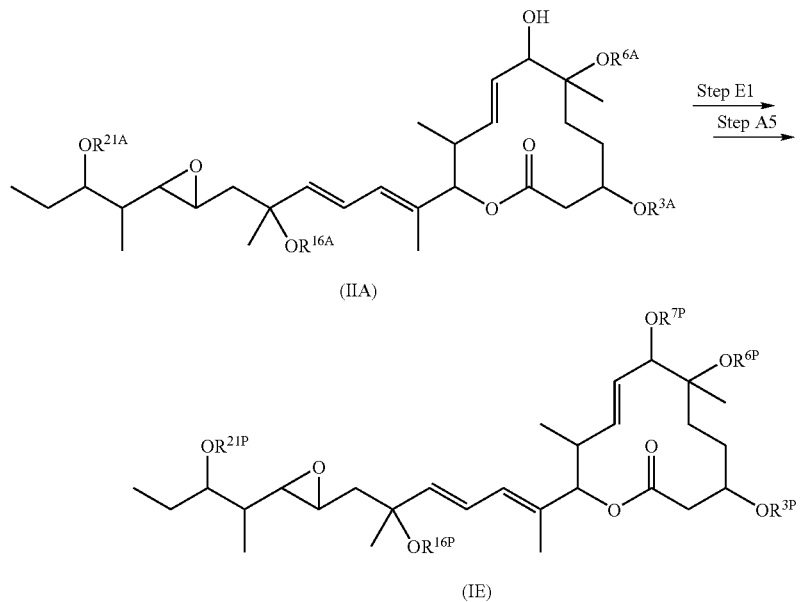

(IIA)

(IE)

dialkoxyphosphoryl chloride, a diphenyloxyphosphoryl chloride, an alkoxy(N,N-disubstituted amino)phosphoryl chloride, an allyloxy(N,N-disubstituted amino)phosphoryl chloride, an alkoxy(N-substituted amino)phosphoryl chloride and an allyloxy(N-substituted amino)phosphoryl chloride. Examples of the base are the above-mentioned organic bases and inorganic bases, of which a preferred example is pyridine, 4-dimethylaminopyridine, triethylamine, ethyldiisopropylamine, sodium hydride, n-butyllithium, potassium carbonate or sodium carbonate. The solvent used in each of the reactions is not specifically limited, but a solvent that does not easily react with a starting material is desirable. Examples thereof are the above-mentioned inert solvents, of which, for example, dichloromethane, chloroform, tetrahydrofuran or N,N-dimethylformamide is preferably used. The reaction time is 10 minutes to 72 hours and is preferably 1 to 24 hours. The amounts of the phosphoryl halide and base used in the reaction are 1 to 10 equivalents and 2 to 20 equivalents, preferably 1 to 5 equivalents and 2 to 10 equivalents, respectively, to the compound of the formula (IIA). The reaction temperature is a temperature of −78° C. to heating under reflux and is preferably −10° C. to 50° C.

The compound of the formula (IE) can be prepared by subjecting the thus-synthesized phosphoric ester derivative to a similar reaction as the step A5 to thereby deprotect the protecting group of a hydroxyl group.

It is also possible to convert one to four hydroxyl groups into phosphoric esters by carrying out phosphoric-esterification of 11107D as a starting material by a similar way as described for the step E1.

F. A preparation for a Sulfuric Ester or Amidosulfuric Ester Derivative by $R^{N1}R^{N2}N-SO_2-$ or $R^{N3}O-SO_2-$ (wherein $R^{N1}$, $R^{N2}$ and $R^{N3}$ each represents the same group as defined above).

The step F1 is a step for converting the hydroxyl group of the compound of the formula (IIA) as a starting material into a sulfuric ester.

The sulfuric-esterification is carried out, for example, by using a sulfonyl halide and a base. Various sulfonyl halides can be used herein, and examples thereof are an alkoxysulfonyl chloride and an N,N-disubstituted sulfamoyl chloride. Examples of the base are the above-mentioned organic bases and inorganic bases, of which a preferred example is pyridine, 4-dimethylaminopyridine, triethylamine, ethyldiisopropylamine, sodium hydride, n-butyllithium, potassium carbonate or sodium carbonate. The solvent used in each of the reactions is not specifically limited, but a solvent that does not easily react with a starting material is desirable. Examples thereof are the above-mentioned inert solvents, of which, for example, dichloromethane, chloroform, tetrahydrofuran or N,N-dimethylformamide is preferably used. The amounts of the sulfonyl halide and base used in the reaction are 1 to 10 equivalents and 2 to 20 equivalents, preferably 1 to 5 equivalents and 2 to 10 equivalents, respectively, to the compounds of the formula (IIA). The reaction time is 10 minutes to 72 hours and is preferably 1 to 24 hours. The reaction temperature is a temperature of −78° C. to heating under reflux and is preferably −10° C. to 50° C.

The compound of the formula (IF) can be synthesized by subjecting the those synthesized sulfuric ester derivative to a similar reaction as the step A5 to thereby deprotect the hydroxyl-protecting group.

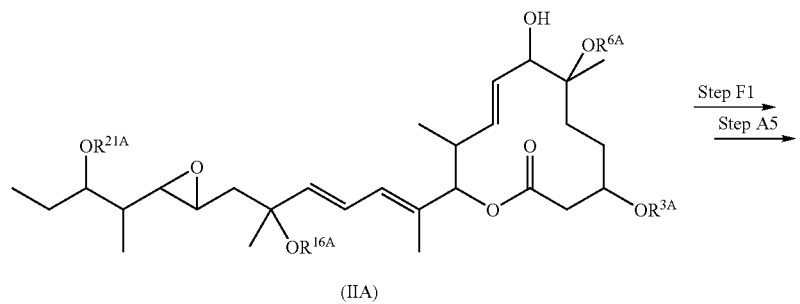

(IIA)

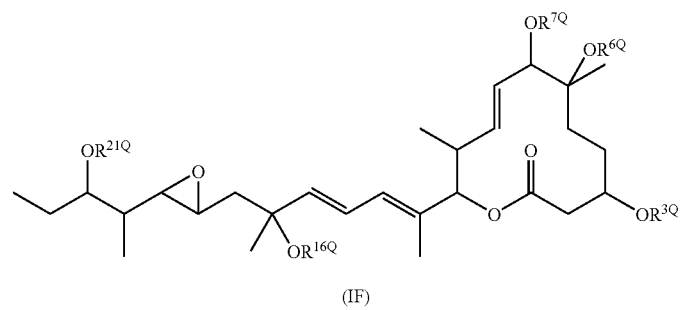

(IF)

In the formula, $R^{3A}$, $R^{6A}$, $R^{16A}$ and $R^{21A}$ each represents the same group as defined above; and $R^{3Q}$, $R^{6Q}$, $R^{7Q}$, $R^{16Q}$ and $R^{21Q}$ each represents a hydrogen atom or a group represented It is also possible to convert one to four of the hydroxyl groups into sulfuric acid esters by subjecting 11107D as a starting material to sulfuric-esterification by a similar way as the step F1.

G. A preparation for a Halogen Derivative

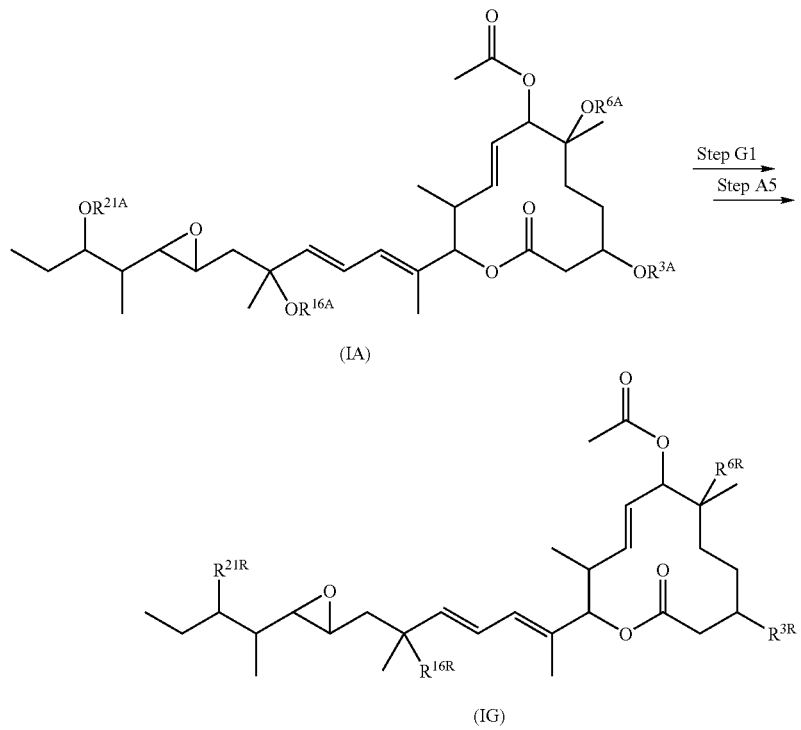

In the formula, $R^{3A}$, $R^{6A}$, $R^{16A}$ and $R^{21A}$ each represents the same group as defined above; $R^{3R}$, $R^{6R}$, $R^{16R}$ and $R^{21R}$ each represents a hydroxyl group or a halogen atom.

The step G1 is a step for converting the hydroxyl group of the compound of the formula (IA) as a starting material into a halogen.

The halogenation is carried out, for example, by treating diethylaminosulfur trifluoride (DAST) or triphenylphosphine with carbon tetrabromide, bromine, phosphorus tribromide, iodine or carbon tetrachloride in the presence of a base. The base used herein includes, for example, general organic bases and inorganic bases such as diisopropylethylamine, dimethylaminopyridine, triethylamine, pyridine, 2,6-lutidine and sodium hydride. The solvent used in the reaction is not specifically limited, but a solvent that does not easily react with a starting material is desirable. Examples thereof are tetrahydrofuran, dichloromethane and N,N-dimethylformamide. Among them, fluorination with diethylaminosulfur trifluoride is preferred. The amount of diethylaminosulfur trifluoride (DAST) is 1 to 5 equivalents, and preferably 1 to 3 equivalents to the compound of the formula (IIA). The reaction time is 10 minutes to 10 hours. The reaction temperature is a temperature of −78° C. to room temperature.

The compound of the formula (IG) can be synthesized by subjecting the those synthesized halogen derivative to the procedure of the step A5 to thereby remove the protecting group of a hydroxyl group.

H. A Preparation for a Sulfonic Ester Derivative

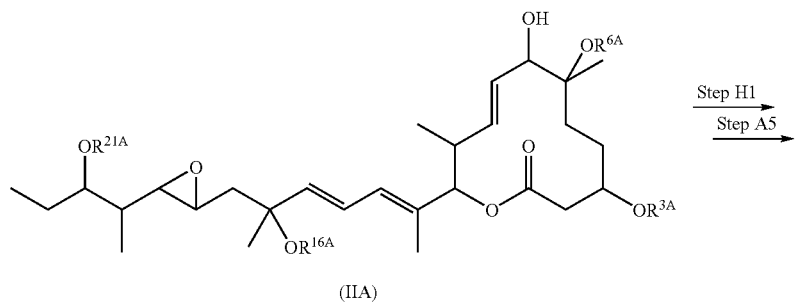

-continued

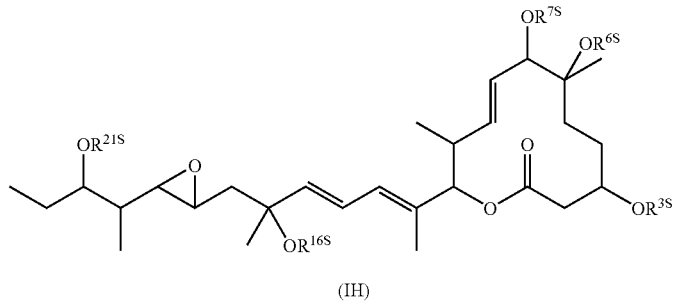

(IH)

In the formula, $R^{3A}$, $R^{6A}$, $R^{16A}$ and $R^{21A}$ each represents the same group as defined above; and $R^{3S}$, $R^{6S}$, $R^{7S}$, $R^{16S}$ and $R^{21S}$ each represents a hydrogen atom or a group represented by $R^{N3}SO_2$— (wherein $R^{N3}$ represents the same group as defined above).

The step H1 is a step for sulfonylating the hydroxyl group of the compound of the formula (IIA) as a starting material.

The sulfonylation can be carried out, for example, by the treatment of a sulfonyl chloride such as p-toluenesulfonyl chloride, methanesulfonyl chloride or benzenesulfonyl chloride in the presence of a base. Examples of the base are general organic bases and inorganic bases such as diisopropylethylamine, dimethylaminopyridine, triethylamine, pyridine, 2,6-lutidine and sodium hydride. The solvent used in the reaction is not specifically limited, but a solvent that does not easily react with a starting material is desirable. Examples thereof are tetrahydrofuran, dichloromethane and N,N-dimethylformamide. The amounts of the sulfonyl chloride and base used in the reaction are 1 to 5 equivalents and 2 to 10 equivalents, preferably 1 to 3 equivalents and 2 to 6 equivalents, respectively, to the compound of the formula (IIA). The reaction time is 10 minutes to 30 hours. The reaction temperature is a temperature of −78° C. to heating under reflux.

The derivative represented by the formula (IH) in which the hydroxyl group at the 7-position is sulfonylated can be synthesized by subjecting the those synthesized sulfonic ester derivative to the step A5 to deprotect the protecting group of a hydroxyl group.

It is also possible that 11107D as a starting material is subjected to sulfonylation by a similar procedure as the step H1 to thereby sulfonylate one to four of the hydroxyl groups.

I. A Preparation for an Amine Derivative

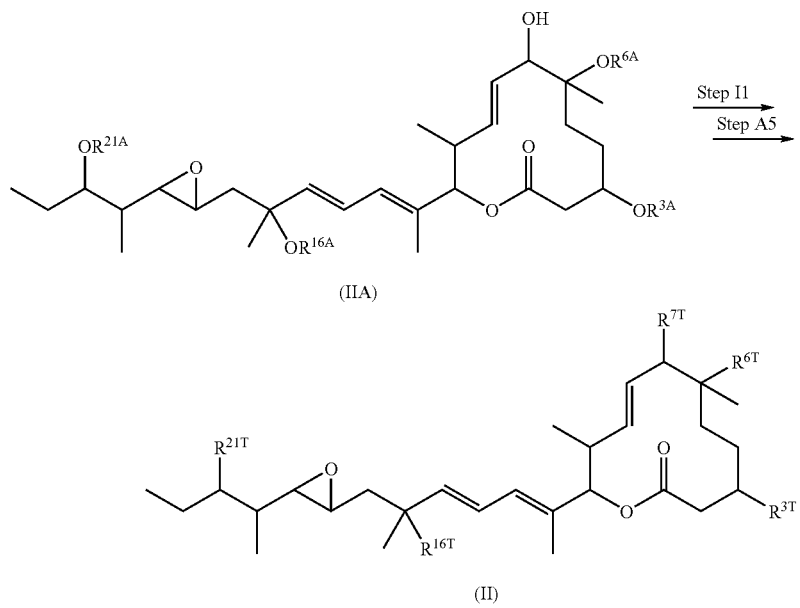

In the formula, $R^{3A}$, $R^{6A}$, $R^{16A}$ and $R^{21A}$ each represents the same group as defined above; and $R^{3T}$, $R^{6T}$, $R^{7T}$, $R^{6T}$ and $R^{21T}$ each represents a hydroxyl group or the formula $R^{N1}R^{N2}N$- (wherein $R^{N1}$ and $R^{N2}$ each represents the same group as defined above).

The step I1 is a step for converting the hydroxyl group of the compound of (IIA) directly into an amine or into a good leaving group, then into an azide and then into an amine by reduction.

In the case where the hydroxyl group is converted into an azide, examples of reagents used in the reaction are 1) diphenylphosphoryl azide (DPPA), diethyl azodicarboxylate and triphenylphosphine, 2) DPPA and 1,8-diazabicyclo[5.4.0]undec-7-ene (DBU), 3) hydrogen azide, diethyl azodicarboxylate and triphenylphosphine, 4) DPPA, tetramethylazodicarboxamide (TMAD) and tributylphosphine, and 5) sodium azide in the presence of a base. Examples of the base are the above-mentioned organic bases and inorganic bases, of which, for example, diisopropylethylamine, dimethylaminopyridine, triethylamine, pyridine, 2,6-lutidine or sodium hydride is preferably used. It is also possible to convert into an azide by the treatment of sodium azide in the presence of a palladium catalyst. An example of the palladium catalyst is $Pd(PPh_3)_4$. The solvent used in the reaction is not specifically limited, but a solvent that does not easily react with a starting material is desirable. Examples thereof are tetrahydrofuran, dichloromethane, N,N-dimethylformamide, toluene and benzene. The reaction time is 10 minutes to 30 hours. The reaction temperature is a temperature of −78° C. to heating under reflux.

The reduction from the azide to the amine can be carried out by using, for example, triphenylphosphine or lithium aluminum hydride. The azide can be also reduced into the amine, for example, by using a catalyst such as palladium-carbon or Lindlar catalyst under hydrogen atmosphere. The solvent used in the reaction is not specifically limited, but a solvent that does not easily react with a starting material is desirable. Examples thereof are tetrahydrofuran, diethyl ether and ethanol. The reaction time is 10 minutes to 30 hours. The reaction temperature is a temperature of −78° C. to heating under reflux.

The conversion of a hydroxyl group into a good leaving group can be carried out by the similar procedure of the step G1 (halogenation) or the step H1 (sulfonylation). Examples of the good leaving group are chloro group, bromo group, iodo group, methanesulfonyl group and p-toluenesulfonyl group. Next, by treating the converted compound having a leaving group with an amine in an inert solvent in the presence of a base, the compound in which the hydroxyl group is converted into an amino group or substituted amino group can be synthesized.

Examples of the amine used herein are methylamine, ethylamine, dimethylamine and diethylamine. Examples of the base are the above-mentioned organic bases and inorganic bases, of which, for example, diisopropylethylamine, dimethylaminopyridine, triethylamine, pyridine, 2,6-lutidine or sodium hydride is preferably used. The solvent used in the reaction is not specifically limited, but a solvent that does not easily react with a starting material is desirable. Examples thereof are the above-mentioned inert solvents, of which, for example, tetrahydrofuran, dichloromethane or N,N-dimethylformamide is preferably used. The reaction time is 10 minutes to 30 hours and is preferably 1 to 2 hours. The reaction temperature is a temperature of −78° C. to heating under reflux and is preferably −10° C. to 50° C.

The compound of the formula (II) can be prepared by subjecting the those synthesized amine derivative to deprotect the protecting group of a hydroxyl group the by a similar way as the step A5. It is also possible to convert one or two of the hydroxyl groups of 11107D as a starting material into amino groups by amination by a similar way as the step 11.

The compound of the formula (I) can be also prepared by alkylating, acylating, carbamoylating or sulfonylating the amino group of the compound of the formula (II) by methods well known in organic synthetic chemistry and the above-mentioned methods.

J. A Preparation for an Oxo-compound (Oxidation of a Hydroxyl Group)

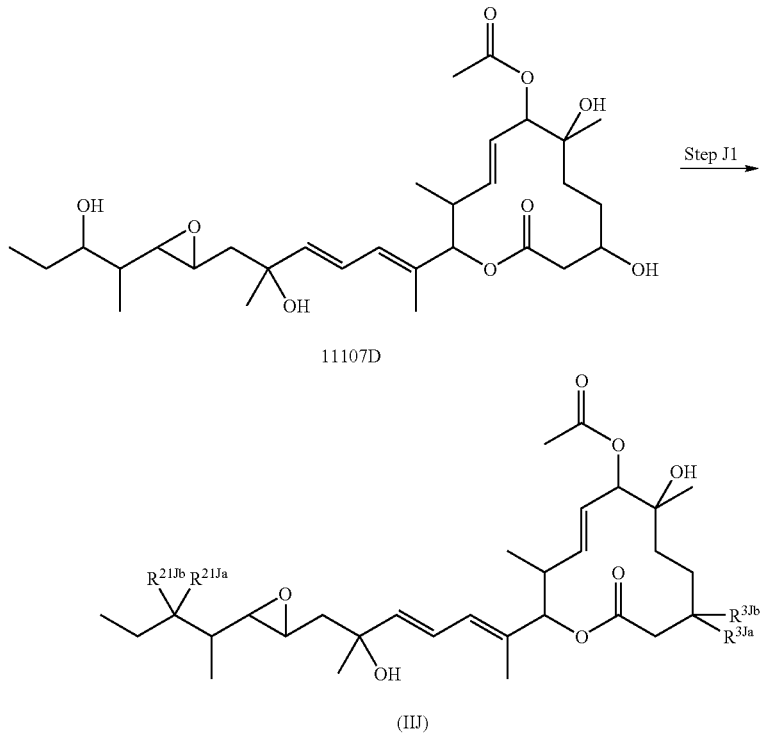

In the formula, either one of $R^{3Ja}$ and $R^{3Ja}$ represents a hydroxyl group and the other represents a hydrogen atom, or $R^{3Ja}$ and $R^{3Ja}$ together with the carbon atom to which $R^{3Ja}$ and $R^{3Ja}$ are bound represent an oxo group, either one of $R^{21Ja}$ and $R^{21Ja}$ represents a hydroxyl group and the other represents a hydrogen atom, or $R^{21Ja}$ and $R^{21Ja}$ together with the carbon atom to which $R^{21Ja}$ and $R^{21Ja}$ are bound represent an oxo group.

The step J1 is a step for synthesizing the oxo-compound represented by the formula (IIJ) by oxidizing the hydroxyl group of 11107D as a starting material.

Examples of the oxidizing agent used in this step are manganese dioxide, pyridinium chlorochromate, pyridinium dichromate, Dess-Martin reagent and reagents used in Swern oxidation. The solvent used in the reaction is not specifically limited, but a solvent that does not easily react with a starting material is desirable. Examples thereof are tetrahydrofuran, dichloromethane, chloroform and toluene. The reaction temperature is a temperature of −78° C. to heating under reflux. The reaction time is 10 minutes to 78 hours. Among these reactions, for example, the reaction using Dess-Martin reagent, manganese dioxide or reagents used in Swern oxidation is preferred, of which the reaction using a Dess-Martin reagent is typically preferred. As the solvent for use in the oxidation using Dess-Martin reagent, dichloromethane or chloroform is typically preferred. The amount of the oxidizing agent used herein is 1 to 20 equivalents and is preferably 1 to 5 equivalents to the compound (11107D). The reaction temperature is preferably 0° C. to room temperature. The reaction time is 30 minutes to 24 hours and is preferably 1 to 8 hours.

A compound in which the hydroxyl group at the 3-position or 21-position of these derivatives has been converted into an oxo moiety can be synthesized by subjecting, for example, an urethane derivative, thiourethane derivative, ester derivative or alkyl derivative, which is precedently prepared by the above-mentioned methods to the step J1 instead of 11107D. Further, a 7-oxo compound can be obtained by oxidizing the hydroxyl group at the 7-position of the compound represented by the formula (IIA).

Further, the hydroxyl group at the 3-position, 7-position and/or 21-position can be selectively converted into an oxo moiety by a various combination of the protection and deprotection conditions of the step A1 and the step A5 with the step J1. In addition, a compound which has both an oxo moiety and a urethane, thiourethane, ester or alkyl moiety can be respectively synthesized by subjecting a compound, which is precedently converted into an oxo moiety, to the above-mentioned methods for a urethane derivative, thiourethane derivative, ester derivative or alkyl derivative.

The compounds represented by the formula (I) can be synthesized by an appropriate combination of the reactions A to J and protection and deprotection procedures of the hydroxyl group.

After termination of the reaction, the target product in the respective reaction is isolated from a reaction mixture according to a conventional procedure. For example, the target compound can be obtained by filtration, if insoluble matter is present, and evaporation of the solvent, or by diluting the reaction mixture with an organic solvent such as ethyl acetate, washing the organic layer with water, drying over anhydrous magnesium sulfate and evaporating the solvent. The compound can be further purified by a conventional procedure such as column chromatography, thin layer chromatography or high performance liquid chromatography as the case requires.

To illustrate the usefulness of the present invention specifically, the VEGF transcription-suppressing activity, growth inhibitory activity on WiDr human colon cancer cell, growth inhibitory activity on solid cancer, body weight loss (acute toxicity) and stability in an aqueous solution of representative compounds of the compounds of the formula (I) according to the present invention were determined.

TEST EXAMPLE 1

Construction of Reporter System for Screening Compound Which Suppresses the Transcription of VEGF In order to prepare reporter system reflecting transcription from VEGF promoter, VEGF promoter sequence was cloned, and inserted in secretory alkaline phosphatase (PLAP) vector to construct reporter vector.

In order to obtain the promoter region of human VEGF, VEGF genomic DNA was cloned from phage library. PCR primers having the sequences described in Sequence Numbers 1 and 2 were designed based on VEGF cDNA (GenBank accession number: X62568) and a fragment having about 340 bp was obtained by carrying out PCR. Human genomic phage library (Human genomic library, Clontech Co.) was screened using this as a probe to obtain VEGF genomic DNA. The DNA was digested by EcoRI, and the resultant fragments were inserted in the EcoRI site of pUC18. Finally, pUC18-VEGFA containing about 5.4 kb of VEGF 5' flanking region was obtained. The pUC18-VEGFA was digested by KpnI/NheI, VEGF promoter region of about 2.3 kb obtained was inserted in the multi cloning site KpnI/NheI of secretory alkaline phosphatase (PLAP) vector (Goto et al, Mol. Pharmacol., 49, 860-873, 1996), and thus, VEGF-PLAP vector was constructed.

The above-mentioned VEGF-PLAP vector was transfected in the U251 cell cultured in the DULBECCO-modified eagle medium (DMEM; manufactured by SIGMA Co., Ltd.) containing 10% fetal calf serum, and the cells were cultured in the presence of 1 mg/mL G418 (Merck Co.) to establish G418 resistant stable clone (U251/1-8 cell).

It was confirmed that U251/1-8 cell secreted PLAP under hypoxic condition (2% $O_2$ incubator) in the same manner as in the report (Cell. Mol. Biol. Res. 40, 35-39, 1994) and was a reporter system reflecting the transcription from VEGF promoter. The screening of the compound suppressing VEGF production which was induced by hypoxic stimulation was carried out below using the clone.

TEST EXAMPLE 2

VEGF Transcription-Suppressing Activities of Various 11107 Analogues and Derivatives In order to remove the influence of alkaline phosphates in serum, U251/1-8 cells were rinsed twice with the adequate amount of PBS (Phosphate buffered saline), diluted in the DMEM medium containing 10% of serum in which alkaline phosphates was inactivated by the treatment of 65° C. for 20 min., and dispensed in 96-well plates by $4 \times 10^4$ cells/180 µL.

After culturing at 37° C. overnight in a $CO_2$ incubator (5% $CO_2$), 20 µL of the above-mentioned incubation solution containing the test compound diluted with 3-fold succession was added, and then they were incubated in a hypoxic (2% $CO_2$) incubator for 18 hours. With respect to the PLAP activity in the culture supernatants, 10 µL of the supernatants was added to 50 µL of 0.28 M $Na_2CO_3$—$NaHCO_3$ buffer solution (pH 10.0, 8.0 mM $MgSO_4$), and finally 50 µL of alkaline phosphatase substrate (LUMISTEIN, Genomescience Co.) was added. After reacting for one hour, the alkaline phosphatase activity of the PLAP was measured by detecting the chemical luminescence by a micro plate reader (Perkin-Elmer Co.). The PLAP activity under normoxia was set as 0%, the PLAP activity of cell which was treated under hypoxia was set as 100%, and the concentration suppressing the PLAP activity by 50% was set as the $IC_{50}$ value of PLAP. The $IC_{50}$ values of 11107D derivatives shown in Examples were measured, and the $IC_{50}$ values of representative 11107D derivatives are shown in Table 1. The 11107D derivatives showed strong VEGF transcription-suppressing activities.

TABLE 1

| Compound | VEGF transcription-suppressing activities ($IC_{50}$: nM) |
|---|---|
| 6 | 32.0 |
| 9 | 12.9 |
| 12 | 10.2 |
| 16 | 3.1 |
| 17 | 3.9 |
| 21 | 6.1 |
| 22 | 25.6 |
| 24 | 5.5 |
| 25 | 2.9 |
| 26 | 2.8 |
| 27 | 3.7 |
| 44 | 3.9 |
| 45 | 1.9 |
| 75 | 9.1 |
| 95 | 1.2 |
| 109 | 3.3 |
| 122 | 4.4 |
| 127 | 2.4 |
| 131 | 1.7 |
| 136 | 1.2 |
| 142 | 11.2 |

TEST EXAMPLE 3

Growth Inhibitory Activities on WiDr Human Colon Cancer Cells

WiDr human colon cancer cells cultured in DULBECCO-modified eagle medium (DMEM; manufactured by SIGMA Co., Ltd.) containing 10% fetal calf serum, penicillin (100 unit/mL) and streptomycin (100 μg/mL) were dispensed in 96-well plates by $2\times10^3$ cells/well. After culturing overnight in a $CO_2$ incubator, 20 μL of the above-mentioned incubation solution containing the test compound diluted with 3-fold succession was added, followed by incubation. After three days, 50 μL of 3.3 mg/mL MTT solution was added, followed by culturing for further one hour. Then, formazan formed by the reduction by the action of living cells was extracted with 100 μL of DMSO, the absorbance (A540/A660) was determined and was set as the index of the number of living cells.

The concentrations of the compounds of the formula (I) at which the growth of WiDr human colon cancer cells are inhibited 50% were determined. The $IC_{50}$ values of representative compounds are shown in Table 2. The compounds of the formula (I) showed strong growth inhibitory activities on WiDr human colon cancer cells.

TABLE 2

| Compound | Growth inhibitory activities on WiDr human colon cancer cells ($IC_{50}$: nM) |
|---|---|
| 6 | 12.5 |
| 9 | 5.5 |
| 16 | 2.0 |
| 17 | 2.6 |

TABLE 2-continued

| Compound | Growth inhibitory activities on WiDr human colon cancer cells ($IC_{50}$: nM) |
|---|---|
| 21 | 3.2 |
| 22 | 14.6 |
| 24 | 5.3 |
| 25 | 1.2 |
| 26 | 1.6 |
| 27 | 1.2 |
| 44 | 2.1 |
| 45 | 0.7 |
| 75 | 4.1 |
| 95 | 0.5 |
| 109 | 1.5 |
| 122 | 1.1 |
| 127 | 0.7 |
| 131 | 0.7 |
| 136 | 0.8 |
| 142 | 4.9 |

TEST EXAMPLE 4

Solid Tumor Growth Inhibitory Activities

In order to study solid tumor growth inhibitory activities of the compounds of the formula (I) in vivo, WiDr human colon cancer cells were implanted subcutaneously into the flanks of nude mice. transplanted to the subcutaneous body sides of mice. The animals were grouped so that the average of the volumes of the respective groups became uniform, when it reached about 100 mm³. Control group was made up of 10 mice and 11107D-administering groups were made up of 5 mice. The derivatives were administered for the administering groups for 5 consecutive days by intravenous injection so as to be any of 0.625 mg, 1.25 mg, 2.5 mg, 5 mg and 10 mg/kg/day, and a vehicle was administered to the control group. The tumor volumes on Day 15 were measured, and relative tumor volume ratios (T/C %) were determined setting the tumor volume of the control group as 100%. The T/C % of representative compounds of the formula (I) are shown in Table 3. The body weights on Day 1, Day 5, Day 8, Day 12 and Day 15 (or 16) were measured, and relative body weight variations were determined setting the body weight on Day 1 as 100%. The relative body weight ratios on the day where the body weight reached the minimum were defined as the minimum relative weight ratios and are shown in Table 3.

TABLE 3

| Compound | Dose (mg/kg) | Growth inhibitory activities in the WiDr human solid tumor model (T/C %) | the minimum relative weight ratios |
|---|---|---|---|
| 6 | 1.25 | 35 | 0.81 |
| 9 | 5.0 | 10 | 0.86 |
| 12 | 2.5 | 21 | 0.85 |
| 15 | 2.5 | 36 | 0.82 |
| 16 | 2.5 | 28 | 0.90 |
| 21 | 2.5 | 28 | 0.80 |
| 22 | 5.0 | 39 | 0.74 |
| 26 | 2.5 | 42 | 0.93 |
| 44 | 5.0 | 19 | 0.89 |
| 45 | 5.0 | 20 | 0.90 |
| 75 | 5.0 | 17 | 0.82 |
| 109 | 0.625 | 36 | 0.89 |
| 131 | 2.5 | 28 | 0.83 |

The compounds of the formula (I) showed growth inhibitory activities in the WiDr human colon tumor model even in a dose without remarkable weight loss also in

TEST EXAMPLE 5

Stability in an Aqueous Solution

The compounds of the formula (I) were dissolved in DMSO in concentrations of 10 to 20 mM, and these were diluted about 500 folds with Britton-Robinson's buffer solution of pH 7. Each of the solutions as sample solutions was incubated at 25° C. for 24 hours.

The sample solutions were analyzed by high performance liquid chromatography before and after incubation, and the residual ratios of the tested substances in the sample solutions after incubation were determined from the peak areas of the obtained chromatograms.

| Example | Peak area (mAU × sec) | | The residual ratios (%) |
|---|---|---|---|
| | initial | after 24 hours | |
| FD895 | 1197 | 993 | 83.0 |
| 11107D | 3994 | 3817 | 95.6 |
| Compound 9 | 5690 | 5476 | 96.2 |
| Compound 12 | 5450 | 5169 | 94.9 |
| Compound 22 | 4713 | 4514 | 95.8 |
| Compound 44 | 4031 | 3820 | 94.8 |
| Compound 45 | 5291 | 5024 | 95.0 |
| Compound 75 | 2594 | 2478 | 95.5 |
| Compound 109 | 2224 | 2111 | 94.9 |
| Compound 122 | 4872 | 4620 | 94.8 |
| Compound 130 | 4819 | 4583 | 95.1 |
| Compound 131 | 168 | 157 | 93.2 |
| Compound 136 | 3750 | 3579 | 95.4 |
| Compound 142 | 3916 | 3705 | 94.6 |

The results show that the content of FD895 decreased to 83% after 24 hours, but that the contents of Compounds 9, 12 and 22 as representative compounds of the compounds of the formula (I) remained 95 to 96%, indicating that the 11107D derivatives are stable in an aqueous solution.

As is evident from the above Pharmacological Test Examples, the compounds of the formula (I) according to the present invention especially suppress VEGF production by varying the gene expression and are expected to use as an antitumor agent, in particular, as a treating agent for solid cancer, a carcinoma metastasis suppressor, as well as an agent for treating diabetic retinopathy, rheumatoid arthritis and anginoma. Further, as is evident from the toxicity test of Test Example 4, the compounds of the formula (I) show growth inhibitory activities in the WiDr human colon tumor model in such a dose as to not cause remarkable weight loss of the tested mice and are safe compounds. Accordingly, they are efficacious as an agent for preventing or treating a disease against which gene expression control is efficacious, a disease against which VEGF production suppressing activity is efficacious and a disease against which angiogenesis inhibiting activity is efficacious. The "preventing or treating" indicates either of preventing or treating, or both of them. More specifically, the compounds of the formula (I) of the present invention are effective as an antitumor agent, and in particular, as an antitumor agent and a carcinoma metastasis suppressor for solid cancer. As the solid cancer, for example, pancreatic cancer, gastric cancer, colon cancer, breast cancer, prostate cancer, lung cancer, kidney cancer, brain tumor, head and neck cancer, esophageal cancer, skin cancer, liver cancer, uterus cancer, cervix uteri cancer, urinary bladder cancer, thyroid cancer, testicular cancer, chorionic carcinoma, osteosarcoma, soft tissue sarcoma, and ovarian cancer may be proposed, of which a cancer such as colon cancer, breast cancer, prostate cancer, lung cancer, head and neck cancer or ovarian cancer is preferred. Further, they are also effective as an antitumor agent for leukemia. Further, they are also effective as an agent for treating hematoma. Furthermore, they are also effective as an agent for treating diabetic retinopathy, rheumatoid arthritis and hematoma, which is based on VEGF production suppressing action. In addition, they are also effective as an agent for treating inflammatory diseases consisting of osteoarthritis, psoriasis and prolonged hypersensitivity reaction, and atherosclerosis.

When the compounds are prepared as an injection, a pH regulator, a buffer, a stabilizer, a solubilizer and the like are added to the main drug, if necessary, to prepare an subcutaneous, intramuscular, intra-articular or intravenous injection according to a conventional procedure.

When the compound is administered as a preventive or therapeutic agent for various diseases, it may be orally administered as tablets, powders, granules, capsules, syrups and the like, and may be parenterally or parenterally administered as a spray, a suppository, an injection, an external preparation or a drip. The dose remarkably varies according to the severity of symptom, age, the kind of liver disease etc., and approximately 1 mg to 100 mg per day for an adult is administered in general at one time or several times.

Conventional excipients are used at production of pharmaceuticals, and the pharmaceutical products are prepared by a conventional method. Namely, when a solid formulation for oral use is prepared, a filler is added to the main drug, and if necessary, a binder, a disintegrant, a lubricant, a colorant, a flavoring agent and the like are added thereto, and then tablets, coated tablets, granules, powders, capsules and the like are prepared. It is needless to say that sugar coating, gelatin coating or suitable coating may conducted on the tablet and granule, if necessary.

According to the present invention, the compounds of the formula (I) of the present invention suppress, in particular, VEGF production by varying the gene expression and show excellent antitumor activities in in vivo solid tumor models. Further, the compounds of the formula (I) of the present invention are stable in an aqueous solution and can provide, for example, an agent for treating cancer, in particular, an agent for treating solid cancer, a carcinoma metastasis suppressor, an agent for treating diabetic retinopathy, rheumatoid arthritis and angioma.

EXAMPLES

The present invention will be illustrated in further detail with reference to Examples and Referential Examples below, which are not intended to limit the scope of the present invention.

The symbols used in the chemical structural formulae in Examples will be illustrated below.

DEIPS: diethylisopropylsilyl group
Et: ethyl group
EE: 1-ethoxyethyl group
Me: methyl group
TES: triethylsilyl group

Example 1

Fermentation of Mer-11107 Strain and Purification of 11107D

One loopful of the slant culture (ISP-2) of Mer-1107 strain was inoculated into a 500 ml Erlenmeyer flask containing 50 mL of seed medium (2% of glycerin, 2% of glucose, 2% of soybean meal (ESUSAN-MEAT manufactured by Ajinomoto Co. Ltd.), 0.5% of yeast extract, 0.25% of sodium chloride, 0.32% of calcium carbonate, 0.0005% of copper sulfate, 0.0005% of manganese chloride, 0.0005% of zinc sulfate, pH 7.4), and it was cultured at 28° C. for three days on a shaker to give the first seed culture. The seed culture (0.6 mL) was inoculated into a 500 mL Erlenmeyer flask containing 60 mL of the producing medium (5% of soluble starch, 0.5% of corn steep liquor, 0.5% of dry yeast, 0.5% of gluten meal, 0.1% of calcium carbonate) and it was fermented at 28° C. for four days on a rotary shaker to give a fermentation cultured broth.

The cultured broth (10 L) was extracted with 1-butanol (10 L), then thus acquired butanol layer was evaporated to dryness to give 100 g of crude active fraction. The crude active fraction was applied on Sephadex LH-20 (1500 mL; manufactured by Pharmacia Co. Ltd.), and eluted with tetrahydrofuran-methanol (1:1) as a solvent. An eluted fraction from 540 mL to 660 mL was concentrated to dryness, to give a residue (660 mg). The resulting residue was dissolved in a mixture of ethyl acetate and methanol (9:1; v/v) and subjected to silica gel column chromatography (WAKO GEL C-200, 50 g). The column was eluted with a mixture (2 L) consisting of n-hexane and ethyl acetate (1:9, v/v), the fractions eluted from 1440 mL to 1566 mL were collected, evaporated to give 15 mg of a crude active fraction.

The obtained crude active fraction was subjected to preparative high performance liquid chromatography (HPLC) under the following preparative HPLC condition (A), and the fractions eluted at the retention time of 17 minutes were collected. After removing acetonitrile, the respective fractions were desalted by HPLC under the following preparative HPLC condition (B) to give 11107D (Retention time: 36 minutes, 1.8 mg).

Preparative HPLC Conditions A:
Column: YMC-PACK ODS-AM F20 mm×250 mm (manufactured by YMC Co.)
Flow rate: 10 ml/min.
Detection: 240 nm
Eluent: acetonitrile/0.15% aqueous potassium dihydrogenphosphate (pH 3.5) (2:8 to 8:2, v/v, 0 to 50 min., linear gradient)

Preparative HPLC conditions B:
Column: YMC-PACK ODS-AM F20 mm×250 mm (manufactured by YMC Co.)
Flow rate: 10 mL/min.
Detection: 240 nm
Eluent: methanol/water (2:8 to 10:0, v/v, 0 to 40 min., linear gradient)

Example 2

Physico-Chemical Properties of 11107D

The physico-chemical properties of 11107D are shown below. The structure of 11107D was determined as shown below.
1. Appearance: colorless powder
2. Molecular weight: 552, ESI-MS m/z 551 (M-H)$^-$, 575 (M+Na)$^+$
3. Molecular formula: $C_{30}H_{48}O_9$
4. Solubility: soluble in dimethyl sulfoxide, pyridine, methanol and acetone, and slightly soluble in water
5. Color reaction: positive for iodine and sulfuric acid
6. Ultraviolet absorption spectrum (methanol, maximum value) nm: 239 ($\epsilon$ 33100)
7. Infrared absorption spectrum (KBr) cm$^{-1}$: 3417, 2967, 1732, 1714, 1455, 1372, 1248, 1176
8. $^1$H-NMR spectrum (CD$_3$OD, 500 MHz): δ ppm (integral, multiplicity, coupling constant J (Hz)):

0.93 (3H, d, J=7.0 Hz), 0.95 (3H, d, J=6.8 Hz), 0.98(3H, t, J=8.0 Hz), 1.23 (3H, s), 1.30 (1H, m), 1.36-1.66 (9H, m), 1.70 (1H, dd, J=6.4, 14.2 Hz), 1.82 (3H, d, J=1.0 Hz), 1.90 (1H, dd, J=6.4, 14.2 Hz), 2.10 (3H, s), 2.52 (2H, m), 2.62 (1H, m), 2.72 (1 H, dd, J=2.4, 8.3 Hz), 2.94 (1H, dt, J=2.4, 5.7 Hz), 3.55 (1H, dt, J=8.3, 4.4 Hz), 3.82 (1H, m), 5.10 (1H, d, J=9.8 Hz), 5.11 (1H, d, J=10.8 Hz), 5.60 (1H, dd, J=9.8, 15.2 Hz), 5.74 (1H, dd, J=8.3, 15.2 Hz), 5.92 (1H, d, J=15.2 Hz), 6.18 (1H, d, J=10.8 Hz), 6.57 (1H, dd, J=10.8, 15.2 Hz)

9. $^{13}$C-NMR Spectrum (CD$_3$ OD, 125 MHz):δ ppm (multiplicity):

10.52(q), 10.82(q), 11.98(q), 16.84(q), 21.07(q), 24.21(q), 28.62(t), 28.79(q), 30.46(t), 37.53(t), 40.10(t), 41.80(d), 42.58(d), 45.97(t), 55.99(d), 62.53(d), 70.42(d), 73.09(s), 74.11(s), 75.30(d), 80.31(d), 84.19(d), 123.64(d), 127.10 (d), 131.76(d), 133.81(s), 141.61(d), 143.22(d), 171.75(s), 172.18(s)

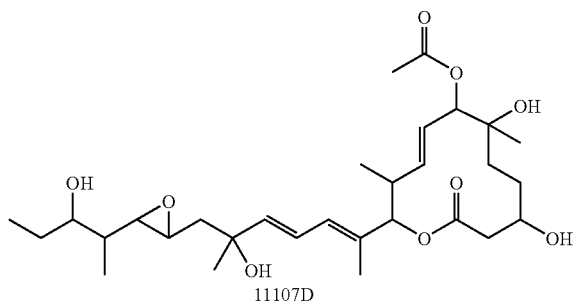

11107D

Example 3

(8E,12E,14E)-3,6,16,21-Tetrahydroxy-6,10,12,16,20-pentamethyl-7-((4-(pyrrolidin-1-yl)piperidin-1-yl)carbonyl)oxy-18,19-epoxytricosa-8,12,14-trien-11-olide (Compound 3)

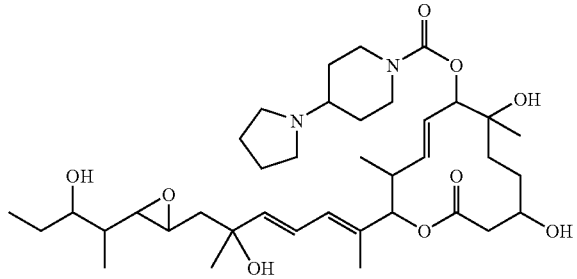

Example 3-1

(8E,12E,14E)-7-Acetoxy-3,6,16,21-tetrakis(1-ethoxyethoxy)-6,10,12,16,20-pentamethyl-18,19-epoxytricosa-8,12,14-trien-11-olide (Formula XV) and (8E,12E,14E)-7-acetoxy-3,16,21-tris(1-ethoxyethoxy)-6-hydroxy-6,10,12,16,20-pentamethyl-18,19-epoxytricosa-8,12,14-trien-11-olide (Formula XVI)

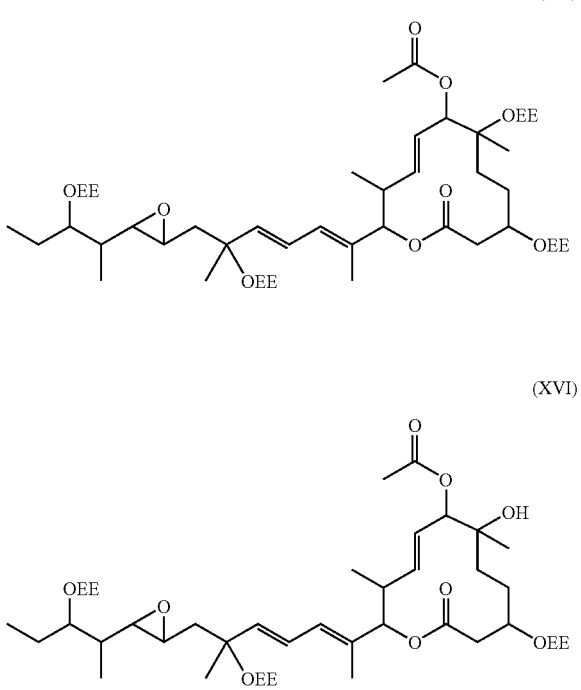

(XV)

(XVI)

To a solution of (8E,12E,14E)-7-acetoxy-3,6,16,21-tetrahydroxy-6,10,12,16,20-pentamethyl-18,19-epoxytricosa-8,12,14-trien-11-olide (50 mg, 0.09 mmol) in dichloromethane (2.5 mL) were added ethyl vinyl ether (326 mg, 4.5 mmol) and pyridinium p-toluenesulfonate (6.8 mg, 27 μmol) at room temperature, followed by stirring at the same temperature for 19 hours. The reaction mixture was diluted with ethyl acetate and washed with a saturated aqueous solution of sodium bicarbonate and brine. The organic layer was dried over anhydrous magnesium sulfate, filtrated and evaporated. The resulting residue was purified by silica gel column chromatography (Kanto silica gel 60N, 40 to 100 μm; ethyl acetate:hexane=30:70) to give (8E,12E,14E)-7-acetoxy-3,6,16,21-tetrakis(1-ethoxyethoxy)-6,10,12,16,20-pentamethyl-18,19-epoxytricosa-8,12,14-trien-11-olide (60 mg, 79%) as a colorless oil (Formula XV).

ESI-MS m/z 863 (M+Na)$^+$.

Next, (8E,12E,14E)-7-acetoxy-3,16,21-tris(1-ethoxyethoxy)-6-hydroxy-6,10,12,16,20-pentamethyl-18,19-epoxytricosa-8,12,14-trien-11-olide (6 mg, 9%) was obtained as a colorless oil (Formula XVI) from an eluted fraction of ethyl acetate:hexane=50:50.

ESI-MS m/z 791 (M+Na)$^+$.

Example 3-2

(8E,12E,14E)-3,6,16,21-Tetrakis(1-ethoxyethoxy)-7-hydroxy-6,10,12,16,20-pentamethyl-18,19-epoxytricosa-8,12,14-trien-11-olide To a solution of (8E,12E,14E)-7-acetoxy-3,6,16,21-tetrakis(1-ethoxyethoxy)-6,10,12,16,20-pentamethyl-18,19-epoxytricosa-8,12,14-trien-11-olide (145 mg, 0.17 mmol) in methanol (2.5 mL) was added potassium carbonate (95 mg, 0.69 mmol) at room temperature, followed by stirring at the same temperature for two hours and 30 minutes. The reaction mixture was diluted with ethyl acetate and then washed with brine. The organic layer was dried over anhydrous magnesium sulfate, filtrated and evaporated. The resulting residue was purified by silica gel column chromatography (Kanto silica gel 60N, 40 to 100 μm; ethyl acetate:hexane=40:60) to give the title compound (128 mg, 93%) as a colorless oil.

ESI-MS m/z 821 (M+Na)$^+$.

Example 3-3

(8E,12E,14E)-3,6,16,21-Tetrakis(1-ethoxyethoxy)-6,10,12,16,20-pentamethyl-7-(4-nitrophenoxy)carboxy-18,19-epoxytricosa-8,12,14-trien-11-olide To a solution of (8E,12E,14E)-3,6,16,21-tetrakis(1-ethoxyethoxy)-7-hydroxy-6,10,12,16,20-pentamethyl-18,19-epoxytricosa-8,12,14-trien-11-olide (139 mg, 0.17 mmol) in dichloromethane (2.5 mL) were added triethylamine (88 mg, 0.87 mmol), N,N-dimethylaminopyridine (64 mg, 0.52 mmol) and 4-nitrophenyl chloroformate (105 mg, 0.52 mmol) under ice cooling, followed by stirring at room temperature under nitrogen atmosphere for one hour. The reaction mixture was diluted with ethyl acetate, and then washed with a saturated aqueous solution of sodium bicarbonate and brine. The organic layer was dried over anhydrous magnesium sulfate, filtrated and evaporated. The resulting residue was purified by silica gel column chromatography (Kanto silica gel 60N, 40 to 100 μm; ethyl acetate:hexane=20:80) to give the title compound (134 mg, 80%) as a colorless oil.

ESI-MS m/z 986 (M+Na)$^+$.

Example 3-4

(8E,12E,14E)-3,6,16,21-Tetrakis(1-ethoxyethoxy)-6,
10,12,16,20-pentamethyl-7-((4-(pyrrolidin-1-yl)piperidin-1-yl)carbonyl)oxy-18,19-epoxytricosa-8,12,14-trien-11-olide

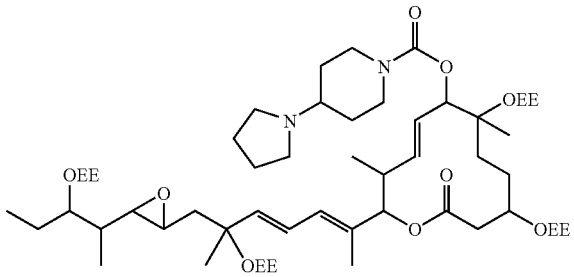

To (8E,12E,14E)-3,6,16,21-tetrakis(1-ethoxyethoxy)-6,10,12,16,20-pentamethyl-7-(4-nitrophenoxy)carboxy-18,19-epoxytricosa-8,12,14-trien-11-olide (11.4 mg, 12 μmol) was added a solution of 4-(pyrrolidin-1-yl)piperidine (2.4 mg, 16 μmol) in tetrahydrofuran (0.5 mL) at room temperature. To the mixture was added triethylamine (2.3 mg, 24 μmol) at room temperature, followed by stirring at the same temperature for three hours. The reaction mixture was evaporated to give the compound (11 mg) as a crude product (a pale yellow oil).

Example 3-5

(8E,12E,14E)-3,6,16,21-Tetrahydroxy-6,10,12,16,20-pentamethyl-7-((4-(pyrrolidin-1-yl)piperidin-1-yl)carbonyl)oxy-18,19-epoxytricosa-8,12,14-trien-11-olide (Compound 3)

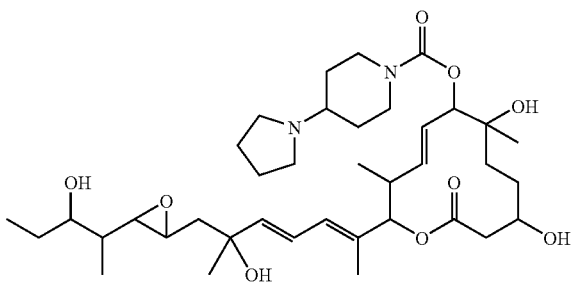

To the crude product of (8E,12E,14E)-3,6,16,21-tetrakis(1-ethoxyethoxy)-6,10,12,16,20-pentamethyl-7-((4-(pyrrolidin-1-yl)piperidin-1-yl)carbonyl)oxy-18,19-epoxytricosa-8,12,14-trien-11-olide (11 mg, 11 μmol) was added a solution of pyridinium p-toluenesulfonate (11.4 mg, 45 μmol) in a mixture of tetrahydrofuran:2-methyl-2-propanol=1:1 (1 mL) at room temperature. To the mixture was added molecular sieves 4 Å (10 mg), followed by stirring at room temperature for 18.5 hours. Additional pyridinium p-toluenesulfonate (11.4 mg, 45 μmol) was added, followed by stirring at room temperature for 72 hours. The reaction mixture was evaporated, and the resulting residue was diluted with ethyl acetate, and then washed with a saturated aqueous solution of sodium bicarbonate and brine. The organic layer was dried over anhydrous sodium sulfate, filtrated and evaporated. The resulting residue was purified by thin layer chromatography (Fuji Silysia, NH Silica gel Plate, methanol:dichloromethane=1:19) to give the title compound (2.88 mg, 35%, two steps) as a colorless oil.

$^1$H-NMR Spectrum (CD$_3$OD, 400 MHz) δ(ppm): 0.89 (3H, d, J=6.4 Hz), 0.90 (3H, d, J=6.8 Hz), 0.92 (3H, t, J=7.2 Hz), 1.21 (3H, s), 1.22-1.68 (8H, m), 1.34 (3H, s), 1.77 (3H, s), 1.78-2.00 (9H, m), 2.48-2.62 (3H, m), 2.67 (1H, dd, J=2.4, 8.0 Hz), 2.68-2.92 (9H, m), 3.46-3.54 (1H, m), 3.72-3.82 (1H, m), 4.24-4.40 (1H, m), 4.92 (1H, d, J=10.8 Hz), 5.06 (1H, d, J=10.8 Hz), 5.57 (1H, dd, J=9.6, 14.8 Hz), 5.72 (1H, dd, J=9.2, 14.8 Hz), 5.86 (1H, d, J=14.8 Hz), 6.13 (1H, d, J=10.8 Hz), 6.53 (1H, dd, J=11.2, 15.2 Hz); ESI-MS m/z 691 (M+H)$^+$.

Example 4

(8E,12E,14E)-7-(N-Ethylcarbamoyloxy)-3,6,16,21-tetrahydroxy-6,10,12,16,20-pentamethyl-18,19-epoxytricosa-8,12,14-trien-11-olide (Compound 4)

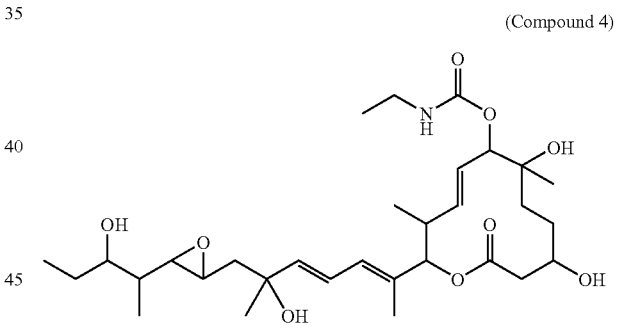

The title compound (a colorless oil) was synthesized by a similar method as described for Example 3.

$^1$H-NMR Spectrum (CD$_3$OD, 400 MHz) δ(ppm): 0.88 (3H, d, J=6.8 Hz), 0.90 (3H, d, J=6.8 Hz), 0.94 (3H, t, J=7.6 Hz), 1.10 (3H, t, J=7.6 Hz), 1.20 (3H, s), 1.22-1.62 (7H, m), 1.34 (3H, s), 1.65 (1H, dd, J=6.6, 13.7 Hz), 1.77 (3H, s), 1.86 (1H, dd, J=5.7, 13.7 Hz), 2.50-2.53 (2H, m), 2.53-2.60 (1H, m), 2.67 (1H, dd, J=2.4, 7.6 Hz), 2.89 (1H, dt, J=2.0, 6.0 Hz), 3.12 (2H, q, J=7.2 Hz), 3.49-3.54 (1H, m), 3.74-3.81 (1H, m), 4.82-4.98 (1H, covered with H$_2$O), 5.06 (1H, d, J=10.8 Hz), 5.55 (1H, dd, J=9.6, 15.2 Hz), 5.69 (1H, dd, J=9.2, 15.2 Hz), 5.87 (1H, d, J=15.2 Hz), 6.13 (1H, d, J=11.2 Hz), 6.52 (1H, dd, J=10.8, 15.2 Hz); ESI-MS m/z 604 (M+Na)$^+$.

Example 5

(8E,12E,14E)-3,6,16,21-Tetrahydroxy-6,10,12,16,20-pentamethyl-7-(N-(3-(morpholin-4-yl)propyl)carbamoyloxy)-18,19-epoxytricosa-8,12,14-trien-11-olide (Compound 5)

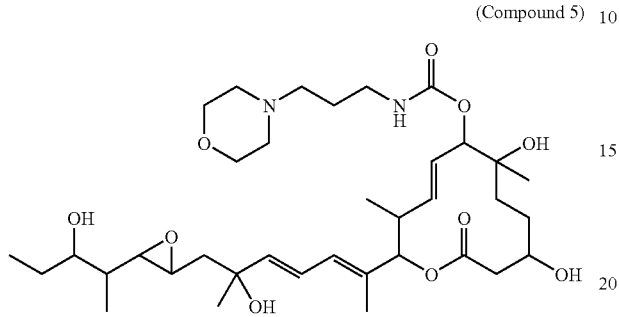

The title compound (a colorless oil) was synthesized by a similar method as described for Example 3.

$^1$H-NMR Spectrum (CD$_3$OD, 400 MHz) δ(ppm): 0.89 (3H, d, J=6.4 Hz), 0.90 (3H, d, J=7.2 Hz), 0.94 (3H, t, J=7.6 Hz), 1.20 (3H, s), 1.26-1.73 (10H, m), 1.34 (3H, s), 1.77 (3H, s), 1.86 (1H, dd, J=5.4, 14.1 Hz), 2.35-2.60 (9H, m), 2.67 (1H, dd, J=2.4, 7.6 Hz), 2.89 (1H, dt, J=2.4, 6.0 Hz), 3.15 (2H, t, J=7.2 Hz), 3.48-3.54 (1H, m), 3.68 (4H, t, J=4.8 Hz), 3.74-3.82 (1H, m), 4.82-4.98 (1H, covered with H$_2$O), 5.06 (1H, d, J=10.8 Hz), 5.55 (1H, dd, J=10.0, 15.2 Hz), 5.69 (1H, dd, J=9.6, 15.2 Hz), 5.87 (1H, d, J=15.2 Hz), 6.13 (1H, d, J=10.4 Hz), 6.52 (1H, dd, J=11.2, 15.2 Hz); ESI-MS m/z 681 (M+H)$^+$.

Example 6

(8E,12E,14E)-7-(N-(2-(N',N'-Dimethylamino)ethyl)-N-methylcarbamoyloxy)-3,6,16,21-tetrahydroxy-6,10,12,16,20-pentamethyl-18,19-epoxytricosa-8,12,14-trien-11-olide (Compound 6)

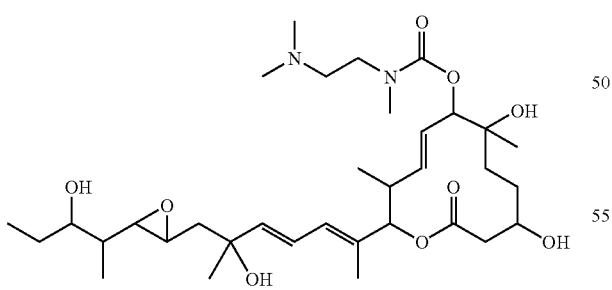

The title compound (a colorless oil) was synthesized by a similar method as described for Example 3.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.2 Hz), 1.22 (3H, s), 1.24-1.68 (8H, m), 1.34 (3H, s), 1.77 (3H, s), 1.86 (1H, dd, J=5.2, 14.0 Hz), 2.28 (6H, s), 2.45-2.62 (7H, m), 2.67 (1H, dd, J=2.4, 8.0 Hz), 2.86-2.99 (4H, m), 3.49-3.56 (1H, m), 3.75-3.82 (1H, m), 4.92 (1H, d, J=10.0 Hz), 5.06 (1H, d, J=10.8 Hz), 5.57 (1H, dd, J=10.0, 15.6 Hz), 5.72 (1H, dd, J=9.6, 15.2 Hz), 5.87 (1H, d, J=14.8 Hz), 6.14 (1H, d, J=10.8 Hz), 6.53 (1H, dd, J=11.2, 15.2 Hz); ESI-MS m/z 639 (M+H)$^+$.

Example 7

(8E,12E,14E)-(7-N-(3-(N',N'-Dimethylamino)propyl)-N-methylcarbamoyloxy)-3,6,16,21-tetrahydroxy-6,10,12,16,20-pentamethyl-18,19-epoxytricosa-8,12,14-trien-11-olide (Compound 7)

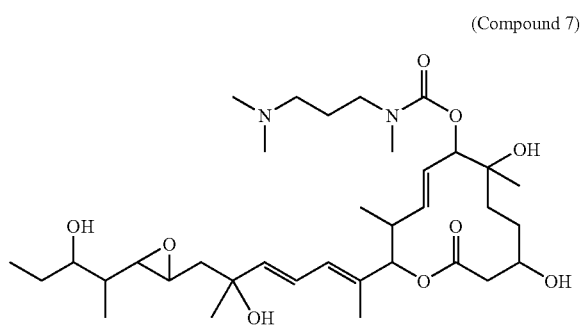

The title compound (a colorless oil) was synthesized by a similar method as described for Example 3.

$^1$H-NMR Spectrum (CD$_3$OD, 400 MHz) δ(ppm): 0.89 (3H, d, J=6.4 Hz), 0.90 (3H, d, J=6.8 Hz), 0.94 (3H, t, J=7.6 Hz), 1.21 (3H, s), 1.24-1.75 (10H, m), 1.34 (3H, s), 1.77 (3H, s), 1.86 (1H, dd, J=5.9, 13.7 Hz), 2.28 (6H, s), 2.37 (2H, t, J=7.6 Hz), 2.48-2.62 (5H, m), 2.67 (1H, dd, J=2.4, 7.6 Hz), 2.86-2.99 (4H, m), 3.48-3.58 (1H, m), 3.74-3.82 (1H, m), 4.93 (1H, d, J=10.4 Hz), 5.06 (1H, d, J=10.8 Hz), 5.57 (1H, dd, J=9.6, 15.2 Hz), 5.73 (1H, dd, J=9.6, 15.2 Hz), 5.87 (1H, d, J=15.6 Hz), 6.13 (1H, d, J=11.2 Hz), 6.52 (1H, dd, J=11.2, 15.2 Hz); ESI-MS m/z 653 (M+H)$^+$.

Example 8

(8E,12E,14E)-7-(N-(2-(N',N'-Dimethylamino)ethyl)carbamoyloxy)-3,6,16,21-tetrahydroxy-6,10,12,16,20-pentamethyl 18,19-epoxytricosa-8,12,14-trien-11-olide (Compound 8)

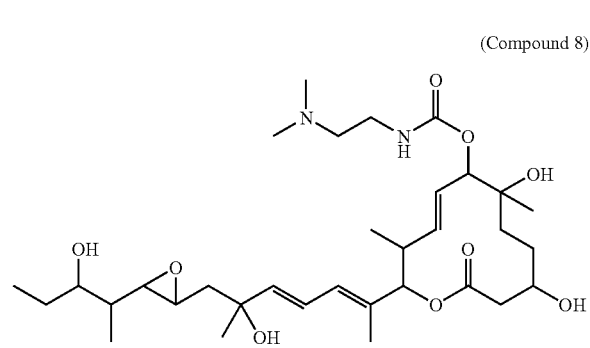

The title compound (a colorless oil) was synthesized by a similar method as described for Example 3.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.2

Hz), 1.21 (3H, s), 1.22-1.68 (8H, m), 1.34 (3H, s), 1.77 (3H, s), 1.86 (1H, dd, J=5.7, 14.3 Hz), 2.29 (6H, s), 2.44-2.62 (7H, m), 2.67 (1H, dd, J=2.4, 8.0 Hz), 2.89 (1H, dt, J=2.0, 6.0 Hz), 3.49-3.56 (1H, m), 3.74-3.82 (1H, m), 4.82-4.98 (1H, covered with H$_2$O peak), 5.06 (1H, d, J=10.8 Hz), 5.55 (1H, dd, J=10.4, 15.2 Hz), 5.69 (1H, dd, J=9.6, 15.2 Hz), 5.87 (1H, d, J=15.2 Hz), 6.13 (1H, d, J=10.8 Hz), 6.52 (1H, dd, J=11.2, 15.2 Hz); ESI-MS m/z 625 (M+H)$^+$.

Example 9

(8E,12E,14E)-3,6,16,21-Tetrahydroxy-6,10,12,16,20-pentamethyl-7-((4-methylhomopiperazin-1-yl)carbonyl)oxy-18,19-epoxytricosa-8,12,14-trien-11-olide (Compound 9)

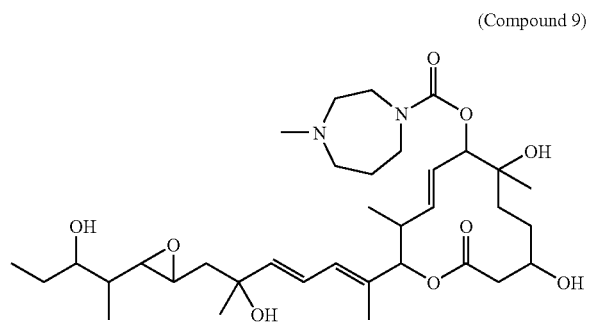

The title compound (a colorless oil) was synthesized by a similar method as described for Example 3.

$^1$H-NMR Spectrum (CD$_3$ OD, 400 MHz) δ(ppm): 0.887 (3H, d, J=6.6 Hz), 0.894 (3H, d, J=7.0 Hz), 0.93 (3H, t, J=7.3 Hz), 1.23-1.27 (4H, m), 1.33 (3H, s), 1.33-1.68 (7H, m), 1.77 (3H, d, J=0.7 Hz), 1.82-1.91 (3H, m), 2.35 (3H, s), 2.50-2.66 (7H, m), 2.66 (1H, dd, J=2.2, 7.7 Hz), 2.89 (1H, dt, J=2.2, 5.5 Hz), 3.49-3.56 (3H, m), 3.58-3.67 (2H, m), 3.75-3.81 (1H, m), 4.94 (1H, d, J=9.5 Hz), 5.06 (1H, d, J=10.6 Hz), 5.57 (1H, dd, J=9.9, 15.0 Hz), 5.72 (1H, dd, J=9.5, 15.0 Hz), 5.86 (1H, d, J=15.0 Hz), 6.13 (1H, d, J=9.9 Hz), 6.52 (1H, dd, J=11.0, 15.0 Hz); ESI-MS m/z 651 (M+H)$^+$.

Example 10

(8E,12E,14E)-7-(N-(3-(N',N'-Dimethylamino)propyl)carbamoyloxy)-3,6,16,21-tetrahydroxy-6,10,12,16,20-pentamethyl-18,19-epoxytricosa-8,12,14-trien-11-olide (Compound 10)

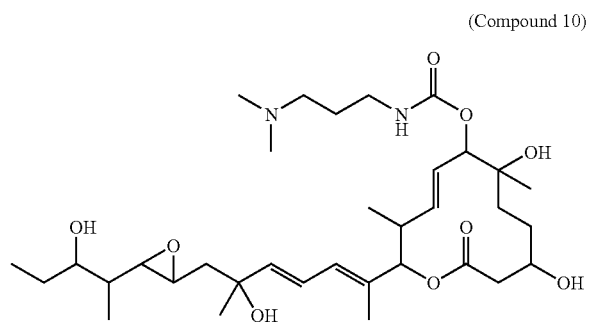

The title compound (a colorless oil) was synthesized by a similar method as described for Example 3.

$^1$H-NMR Spectrum (CD$_3$ OD, 400 MHz) δ(ppm): 0.88 (3H, d, J=6.6 Hz), 0.89 (3H, d, J=7.0 Hz), 0.93 (3H, t, J=7.3 Hz), 1.20 (3H, s), 1.20-1.26 (1H, m), 1.33 (3H, s), 1.33-1.71 (9H, m), 1.77 (3H, s), 1.86 (1H, dd, J=5.5, 14.3 Hz), 2.25 (6H, s), 2.36 (2H, t, J=7.3 Hz), 2.49-2.61 (3H, m), 2.66 (1H, dd, J=2.2, 8.1 Hz), 2.89 (1H, dt, J=2.2, 5.5 Hz), 3.13 (2H, t, J=6.6 Hz), 3.52 (1H, dt, J=4.4, 8.1 Hz), 3.75-3.81 (1H, m), 4.89 (1H, d, J=9.5 Hz), 5.05 (1H, d, J=10.6 Hz), 5.55 (1H, dd, J=9.5, 15.4 Hz), 5.69 (1H, dd, J=9.5, 15.4 Hz), 5.86 (1H, d, J=15.4 Hz), 6.13 (1H, d, J=10.6 Hz), 6.52 (1H, dd, J=10.6, 15.4 Hz); ESI-MS m/z 639 (M+H)$^+$.

Example 11

(8E,12E,14E)-3,6,16,21-Tetrahydroxy-6,10,12,16,20-pentamethyl-7-(N-((pyridin-4-yl)methyl)carbamoyloxy)-18,19-epoxytricosa-8,12,14-trien-11-olide (Compound 11)

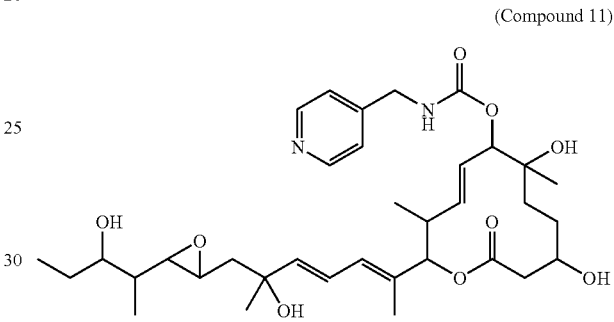

The title compound (a colorless oil) was synthesized by a similar method as described for Example 3.

$^1$H-NMR Spectrum (CD$_3$ OD, 400 MHz) δ(ppm): 0.88 (3H, d, J=5.1 Hz), 0.89 (3H, d, J=7.0 Hz), 0.94 (3H, t, J=7.3 Hz), 1.23 (3H, s), 1.23-1.27 (1H, m), 1.33 (3H, s), 1.33-1.62 (6H, m), 1.65 (1H, dd, J=6.2, 14.3 Hz), 1.77 (3H, s), 1.86 (1H, dd, J=6.2, 14.3 Hz), 2.48-2.65 (3H, m), 2.66 (1H, dd, J=2.2, 8.1 Hz), 2.89 (1H, dt, J=2.2, 6.2 Hz), 3.52 (1H, dt, J=4.4, 8.1 Hz), 3.74-3.80 (1H, m), 4.35 (2H, s), 4.93 (1H, d, J=9.5 Hz), 5.06 (1H, d, J=10.6 Hz), 5.56 (1H, dd, J=9.5, 15.4 Hz), 5.73 (1H, dd, J=9.5, 15.4 Hz), 5.86 (1H, d, J=15.0 Hz), 6.13 (1H, d, J=11.0 Hz), 6.52 (1H, d, J=11.0, 15.0 Hz), 7.33 (2H, d, J=5.9 Hz), 8.45 (2H, dd, J=1.5, 4.4 Hz); ESI-MS m/z 645 (M+H)$^+$.

Example 12

(8E,12E,14E)-3,6,16,21-Tetrahydroxy-6,10,12,16,20-pentamethyl-7-((4-methylpiperazin-1-yl)carbonyl)oxy-18,19-epoxytricosa-8,12,14-trien-11-olide (Compound 12)

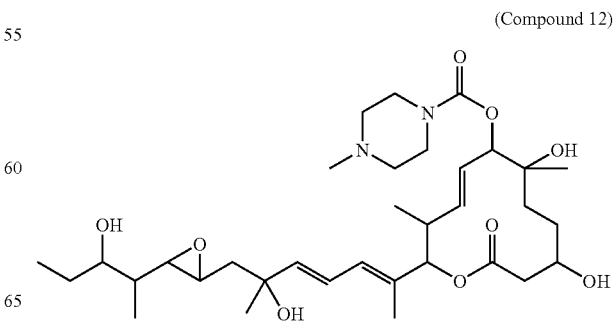

First Step (8E,12E,14E)-6-(1-Ethoxyethoxy)-6,10,12,16,20-pentamethyl-7-((4-methylpiperazin-1-yl)carbonyl)oxy-3,16,21-tris(triethylsiloxy)-18,19-epoxytricosa-8,12,14-trien-11-olide (Compound 12-1)

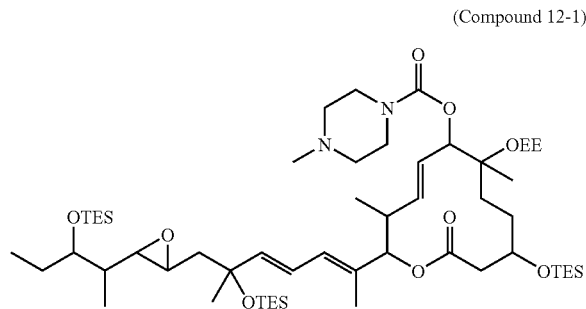

A solution of Compound 46-4 (8E,12E,14E)-6-(1-ethoxyethoxy)-6,10,12,16,20-pentamethyl-7-(4-nitrophenoxy)carboxy-3,16,21-tris(triethylsiloxy)-18,19-epoxytricosa-8,12,14-trien-11-olide (628 mg, 0.575 mmol) obtained in the fourth step of Example 46 in tetrahydrofuran (7 mL) was cooled to 5° C., and a solution of 1-methylpiperazine (118 mg, 1.152 mmol) in tetrahydrofuran (1.5 mL) and a solution of triethylamine (236 mg, 2.305 mmol) in tetrahydrofuran (1.5 mL) were added dropwise thereto. The reaction mixture was stirred at room temperature for 1.5 hours. The reaction mixture was diluted with ethyl acetate, and washed with an aqueous solution of sodium bicarbonate and brine. The organic layer was dried over anhydrous magnesium sulfate, filtrated and evaporated. The resulting residue was purified by silica gel column chromatography (Kanto silica gel 60N, 40 to 50 μm; ethyl acetate-hexane-methanol, 1:1:0 to 4:1:0 to 9:1:0 to 1:0:0 to 39:0:1 to 19:0:1) to give the title compound (514 mg, 85%) as a colorless oil.

Second Step (8E,12E,14E)-6-(1-Ethoxyethoxy)-3,16,21-trihydroxy-6,10,12,16,20-pentamethyl-7-((4-methylpiperazin-1-yl)carbonyl)oxy-18,19-epoxytricosa-8,12,14-trien-11-olide (Compound 12-2)

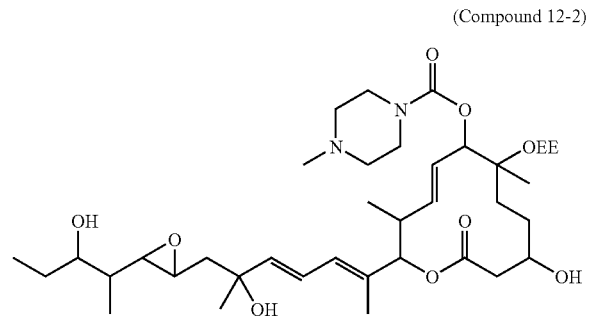

A solution of Compound 12-1 (8E,12E,14E)-6-(1-ethoxyethoxy)-6,10,12,16,20-pentamethyl-7-((4-methylpiperazin-1-yl)carbonyl)oxy-3,16,21-tris(triethylsiloxy)-18,19-epoxytricosa-8,12,14-trien-11-olide (514 mg, 0.489 mmol) obtained in the first step in tetrahydrofuran (10 mL) was cooled to 5° C., and tetrabutylammonium fluoride (1.0 M tetrahydrofuran solution, 1.62 mL, 1.62 mmol) was added dropwise thereto. The reaction mixture was stirred at room temperature for two hours. Additional tetrabutylammonium fluoride (1.0 M tetrahydrofuran solution, 0.3 mL, 0.3 mmol) was added dropwise, and the reaction mixture was stirred at room temperature for one hour. The reaction mixture was diluted with ethyl acetate and washed with an aqueous solution of sodium bicarbonate. The organic layer was dried over anhydrous magnesium sulfate, filtrated and evaporated. The resulting residue was purified by silica gel column chromatography (Fuji Silysia, NH Silica gel, 200 to 350 mesh; ethyl acetate-hexane-methanol, 1:1:0 to 4:1:0 to 1:0:0 to 49:0:1 to 19:0:1) to give the title compound (364 mg, 99%) as a colorless oil.

ESI-MS m/z 709 (M+H)$^+$

Third Step (8E,12E,14E)-3,6,16,21-Tetrahydroxy-6,10,12,16,20-pentamethyl-7-((4-methylpiperazin-1-yl)carbonyl)oxy-18,19-epoxytricosa-8,12,14-trien-11-olide (Compound 12)

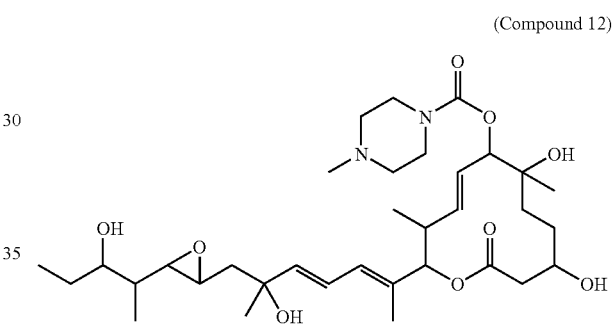

To a solution of Compound 12-2 (8E,12E,14E)-6-(1-ethoxyethoxy)-3,16,21-trihydroxy-6,10,12,16,20-pentamethyl-7-((4-methylpiperazin-1-yl)carbonyl)oxy-18,19-epoxytricosa-8,12,14-trien-11-olide (364 mg, 0.489 mmol) obtained in the second step in a mixture of tetrahydrofuran:2-methyl-2-propanol=1:1 (10 mL) was added pyridinium p-toluenesulfonate (184 mg, 0.734 mmol), and the reaction mixture was stirred at room temperature for 19 hours. After triethylamine (75 mg, 0.734 mmol) was added dropwise to the reaction mixture, the mixture was evaporated. The resulting residue was dissolved in ethyl acetate and washed with a saturated aqueous solution of sodium bicarbonate. The organic layer was dried over anhydrous magnesium sulfate, filtrated and evaporated. The resulting residue was purified by silica gel column chromatography (Fuji Silysia, NH Silica gel, 200 to 350 mesh; ethyl acetate-hexane-methanol, 1:1:0 to 2:1:0 to 4:1:0 to 1:0:0 to 39:0:1 to 29:0:1 to 19:0:1). The crude purified fraction was evaporated, and the residue was purified by thin layer chromatography (Fuji Silysia, NH Silica gel Plate; methanol-dichloromethane, 1:29) to give the title compound (286 mg, 92%) as a colorless oil.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.6 Hz), 1.19-1.28 (4H, m), 1.32-1.68 (10H, m), 1.77 (3H, d, J=0.8 Hz), 1.86 (1H, dd, J=5.6, 14.4 Hz), 2.30 (3H, s), 2.36-2.44 (4H, m), 2.50-2.64 (3H, m), 2.66 (1H, dd, J=2.4, 8.0 Hz), 2.89 (1H, dt, J=2.4, 6.0 Hz), 3.38-3.70 (5H, m), 3.75-3.81 (1H, m), 4.93 (1H, d, J=10.0 Hz), 5.06 (1H, d, J=10.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 637 (M+H)+.

Example 13

(8E,12E,14E)-3,6,16,21-Tetrahydroxy-6,10,12,16, 20-pentamethyl-7-((piperazin-1-yl)carbonyl)oxy-18, 19-epoxytricosa-8,12,14-trien-11-olide (Compound 13)

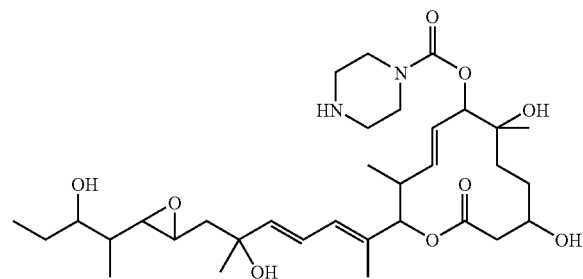

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=7.2 Hz), 0.94 (3H, t, J=7.6 Hz), 1.20-1.30 (4H, m), 1.32-1.68 (10H, m), 1.77 (3H, d, J=0.8 Hz), 1.86 (1H, dd, J=5.6, 14.4 Hz), 2.50-2.64 (3H, m), 2.67 (1H, dd, J=2.4, 8.0 Hz), 2.76 (4H, t, J=5.2 Hz), 2.89 (1H, dt, J=2.4, 5.6 Hz), 3.34-3.68 (5H, m), 3.75-3.81 (1H, m), 4.94 (1H, d, J=9.6 Hz), 5.06 (1H, d, J=10.8 Hz), 5.57 (1H, dd, J=9.6, 15.2 Hz), 5.72 (1H, dd, J=9.6, 15.2 Hz), 5.87 (1H, d, J=15.2 Hz), 6.13 (1H, d, J=11.2 Hz), 6.53 (1H, dd, J=11.2, 15.2 Hz); ESI-MS m/z 623 (M+H)+.

Example 14

(8E,12E,14E)-3,6,16,21-Tetrahydroxy-6,10,12,16, 20-pentamethyl-7-((4-(pyridin-4-yl)piperazin-1-yl) carbonyl)oxy-18,19-epoxytricosa-8,12,14-trien-11-olide (Compound 14)

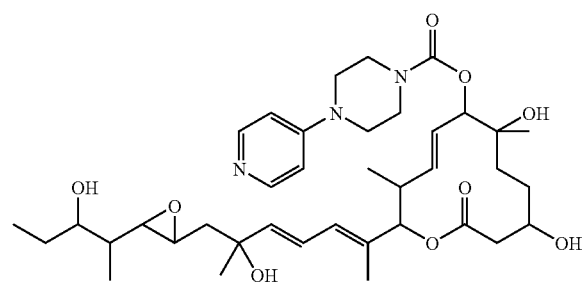

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 1.20-1.30 (4H, m), 1.32-1.69 (10H, m), 1.77 (3H, d, J=0.8 Hz), 1.86 (1H, dd, J=5.6, 14.4 Hz), 2.50-2.64 (3H, m), 2.66 (1H, dd, J=2.4, 8.0 Hz), 2.89 (1H, dt, J=2.4, 6.0 Hz), 3.38-3.46 (4H, m), 3.49-3.84 (6H, m), 4.97 (1H, d, J=10.0 Hz), 5.06 (1H, d, J=10.8 Hz), 5.59 (1H, dd, J=10.0, 15.2 Hz), 5.74 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz), 6.86 (2H, d, J=6.8 Hz), 8.13 (2H, d, J=6.8 Hz); ESI-MS m/z 700 (M+H)+.

Example 15

(8E,12E,14E)-3,6,16,21-Tetrahydroxy-6,10,12,16, 20-pentamethyl-7-(N-methyl-N-(1-methylpiperidin-4-yl)carbamoyloxy)-18,19-epoxytricosa-8,12,14-trien-11-olide (Compound 15)

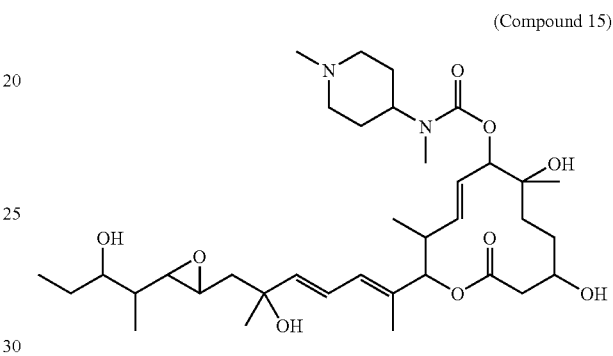

The title compound (a colorless oil) was synthesized by a similar method as described for Example 3.

¹H-NMR Spectrum (CD₃ OD, 400 MHz) δ(ppm): 0.88 (3H, d, J=6.4 Hz), 0.90 (3H, d, J=6.8 Hz), 0.94 (3H, t, J=7.6 Hz), 1.19-1.30 (4H, m), 1.32-1.69 (12H, m), 1.72-1.90 (6H, m), 2.06-2.22 (2H, m), 2.28 (3H, s), 2.50-2.64 (3H, m), 2.66 (1H, dd, J=2.4, 8.0 Hz), 2.76-2.98 (6H, m), 3.52 (1H, dt, J=4.4, 8.4 Hz), 3.75-3.82 (1H, m), 3.85-4.14 (1H, m), 4.95 (1H, d, J=10.0 Hz), 5.06 (1H, d, J=10.8 Hz), 5.57 (1H, dd, J=10.0, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 665 (M+H)+.

Example 16

(8E,12E,14E)-7-((4-Butylpiperazin-1-yl)carbonyl) oxy-3,6,16,21-tetrahydroxy-6,10,12,16,20-pentamethyl-18,19-epoxytricosa-8,12,14-trien-11-olide (Compound 16)

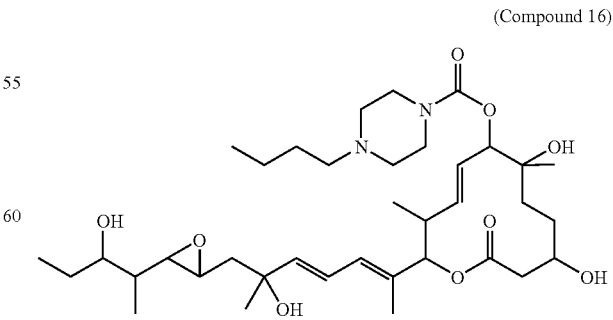

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 0.94 (3H, t, J=7.6 Hz), 1.19-1.69 (18H, m), 1.77 (3H, d, J=1.2 Hz), 1.86 (1H, dd, J=5.6, 14.0 Hz), 2.34-2.64 (9H, m), 2.67 (1H, dd, J=2.4, 8.0 Hz), 2.89 (1H, dt, J=2.4, 6.4 Hz), 3.38-3.72 (5H, m), 3.75-3.82 (1H, m), 4.93 (1H, d, J=9.6 Hz), 5.06 (1H, d, J=10.8 Hz), 5.57 (1H, dd, J=9.6, 15.2 Hz), 5.71 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 679 (M+H)⁺.

Example 17

(8E,12E,14E)-7-((4-Benzylhomopiperazin-1-yl)carbonyl)oxy-3,6,16,21-tetrahydroxy-6,10,12,16,20-pentamethyl-18,19-epoxytricosa-8,12,14-trien-11-olide (Compound 17)

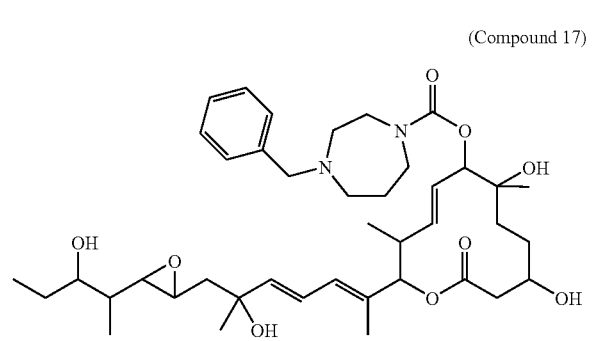

The title compound (a colorless oil) was synthesized by a similar method as described for Example 3.

¹H-NMR Spectrum (CD₃ OD, 400 MHz) δ(ppm): 0.85-0.92 (6H, m), 0.94 (3H, t, J=7.6 Hz), 1.19-1.30 (4H, m), 1.32-1.69 (10H, m), 1.78 (3H, s), 1.79-1.90 (3H, m), 2.50-2.72 (8H, m), 2.89 (1H, dt, J=2.4, 6.0 Hz), 3.42-3.68 (7H, m), 3.75-3.82 (1H, m), 4.91-4.97 (1H, m), 5.06 (1H, d, J=10.8 Hz), 5.53-5.62 (1H, m), 5.67-5.77 (1H, m), 5.87 (1H, d, J=15.2 Hz), 6.13 (1H, d, J=10.8 Hz), 6.53 (1H, dd, J=11.2, 15.2 Hz), 7.21-7.35 (5H, m); ESI-MS m/z 727 (M+H)⁺.

Example 18

(8E,12E,14E)-7-((4-(3-Chloropropyl)homopiperazin-1-yl)carbonyl)oxy-3,6,16,21-tetrahydroxy-6,10,12,16,20-pentamethyl-18,19-epoxytricosa-8,12,14-trien-11-olide (Compound 18)

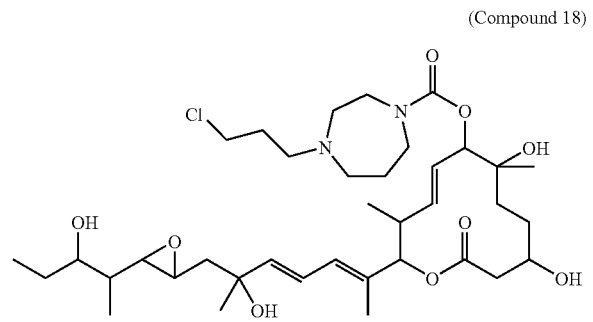

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 1.19-1.30 (4H, m), 1.32-1.69 (10H, m), 1.77 (3H, d, J=0.8 Hz), 1.80-1.96 (5H, m), 2.49-2.74 (10H, m), 2.89 (1H, dt, J=2.4, 6.4 Hz), 3.41-3.69 (7H, m), 3.75-3.81 (1H, m), 4.92-4.97 (1H, m), 5.07 (1H, d, J=10.4 Hz), 5.57 (1H, dd, J=9.6, 15.2 Hz), 5.73 (1H, dd, J=10.0, 15.2 Hz), 5.87 (1H, d, J=15.2 Hz), 6.13 (1H, d, J=11.2, 15.2 Hz), 6.53 (1H, dd, J=11.2, 15.2 Hz); ESI-MS m/z 713 (M)⁺.

Example 19

(8E,12E,14E)-7-((4-(N,N-Dimethylamino)piperidin-1-yl)carbonyl)oxy-3,6,16,21-tetrahydroxy-6,10,12,16,20-pentamethyl-18,19-epoxytricosa-8,12,14-trien-11-olide (Compound 19)

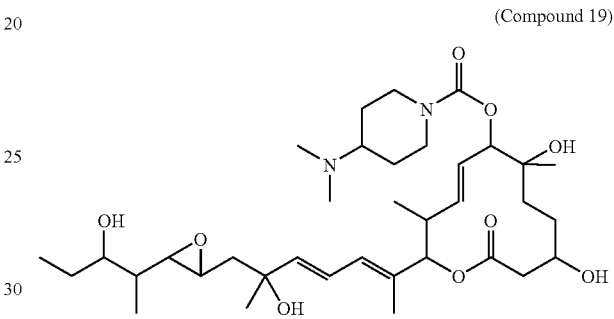

The title compound (a colorless oil) was synthesized by a similar method as described for Example 3.

¹H-NMR Spectrum (CD₃ OD, 400 MHz) δ(ppm): 0.89 (3H, d, J=6.4 Hz), 0.90 (3H, d, J=6.8 Hz), 0.94 (3H, t, J=7.6 Hz), 1.19-1.68 (16H, m), 1.77 (3H, d, J=0.8 Hz), 1.83-1.93 (3H, m), 2.28 (6H, s), 2.38 (1H, tt, J=3.6, 11.6 Hz), 2.49-2.62 (3H, m), 2.67 (1H, dd, J=2.4, 8.0 Hz), 2.71-2.88 (2H, m), 2.89 (1H, dt, J=2.4, 6.0 Hz), 3.52 (1H, dt, J=4.4, 8.4 Hz), 3.75-3.82 (1H, m), 4.08-4.45 (2H, m), 4.92 (1H, d, J=10.0 z), 5.06 (1H, d, J=10.8 Hz), 5.57 (1H, dd, J=10.0, 15.2 Hz), 5.72 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 665 (M+H)⁺.

Example 20

(8E,12E,14E)-7-((1,4-Diazabicyclo[4,3,0]nonane-4-yl)carbonyl)oxy-3,6,16,21-tetrahydroxy-6,10,12,16,20-pentamethyl-18,19-epoxytricosa-8,12,14-trien-11-olide (Compound 20)

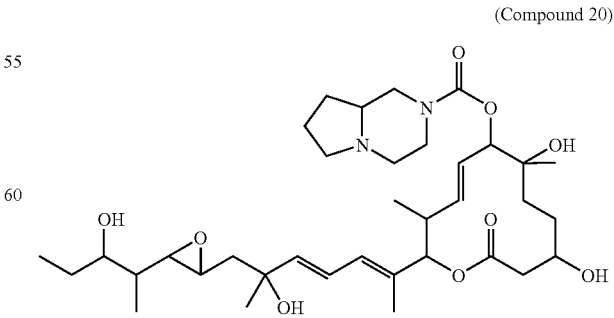

The title compound (a colorless oil) was synthesized by a similar method as described for Example 3.

¹H-NMR Spectrum (CD₃ OD, 400 MHz) δ(ppm): 0.89 (3H, d, J=6.4 Hz), 0.90 (3H, d, J=6.8 Hz), 0.94 (3H, t, J=7.6 Hz), 1.19-1.30 (4H, m), 1.32-1.69 (10H, m), 1.73-2.02 (6H, m), 2.09-2.22 (2H, m), 2.49-2.71 (6H, m), 2.87-3.12 (6H, m), 3.52 (1H, dt, J=4.4, 8.0 Hz), 3.75-3.82 (1H, m), 4.01-4.51 (2H, m), 4.88-4.99 (1H, m), 5.06 (1H, d, J=10.8 Hz), 5.57 (1H, dd, J=9.6, 14.8 Hz), 5.72 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 663 (M+H)⁺.

Example 21

(8E,12E,14E)-7-((4-Ethylpiperazin-1-yl)carbonyl)oxy-3,6,16,21-tetrahydroxy-6,10,12,16,20-pentamethyl-18,19-epoxytricosa-8,12,14-trien-11-olide (Compound 21)

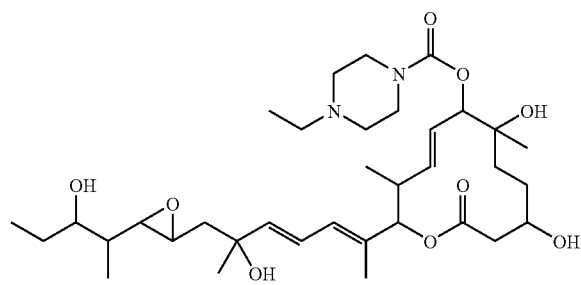

The title compound (a colorless oil) was synthesized by a similar method as described for Example 3.

¹H-NMR Spectrum (CD₃ OD, 400 MHz) δ(ppm): 0.88 (3H, d, J=6.8 Hz), 0.90 (3H, d, J=6.8 Hz), 0.94 (3H, t, J=7.6 Hz), 1.11 (3H, t, J=7.6 Hz), 1.21 (3H, s), 1.22-1.64 (7H, m), 1.34 (3H, s), 1.65 (1H, dd, J=6.2, 14.2 Hz), 1.77 (3H, s), 1.86 (1H, dd, J=5.2, 14.0 Hz), 2.39-2.49 (6H, m), 2.50-2.53 (2H, m), 2.53-2.62 (1H, m), 2.66 (1H, dd, J=2.4, 7.6 Hz), 2.89 (1H, dt, J=2.0, 6.0 Hz), 3.34-3.72 (5H, m), 3.74-3.82 (1H, m), 4.93 (1H, d, J=9.6 Hz), 5.05 (1H, d, J=10.4 Hz), 5.56 (1H, dd, J=10.0, 15.2 Hz), 5.71 (1H, dd, J=9.6, 15.2 Hz), 5.87 (1H, d, J=15.2 Hz), 6.13 (1H, d, J=10.8 Hz), 6.52 (1H, dd, J=11.2, 15.2 Hz); ESI-MS m/z 651 (M+H)⁺.

Example 22

(8E,12E,14E)-3,6,16,21-Tetrahydroxy-6,10,12,16,20-pentamethyl-7-((4-(piperidin-1-yl)piperidin-1-yl)carbonyl)oxy-18,19-epoxytricosa-8,12,14-trien-11-olide (Compound 22)

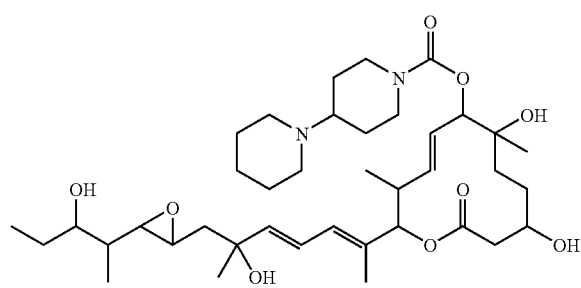

The title compound (a colorless oil) was synthesized by a similar method as described for Example 3.

¹H-NMR Spectrum (CD₃ OD, 400 MHz) δ(ppm): 0.88 (3H, d, J=6.4 Hz), 0.90 (3H, d, J=7.2 Hz), 0.94 (3H, t, J=7.6 Hz), 1.21 (3H, s), 1.20-1.69 (16H, m), 1.34 (3H, s), 1.77 (3H, s), 1.83-1.93 (3H, m), 2.45-2.65 (8H, m), 2.66 (1H, dd, J=2.4, 7.6 Hz), 2,70-2.85 (2H, m), 2.89 (1H, dt, J=2.4, 6.0 Hz), 3.51 (1H, td, J=4.4, 8.0 Hz), 3.74-3.82 (1H, m), 4.12-4.25 (1H, m), 4.30-4.45 (1H, m), 4.92 (1H, d, J=9.6 Hz), 5.06 (1H, d, J=10.4 Hz), 5.56 (1H, dd, J=10.0, 15.2 Hz), 5.71 (1H, dd, J=10.0, 15.6 Hz), 5.87 (1H, d, J=15.2 Hz), 6.13 (1H, d, J=11.2 Hz), 6.52 (1H, dd, J=11.2, 15.2 Hz); ESI-MS m/z 705 (M+H)⁺.

Example 23

(8E,12E,14E)-7-((Homopiperazin-1-yl)carbonyl)oxy-3,6,16,21-tetrahydroxy-6,10,12,16,20-pentamethyl-18,19-epoxytricosa-8,12,14-trien-11-olide (Compound 23)

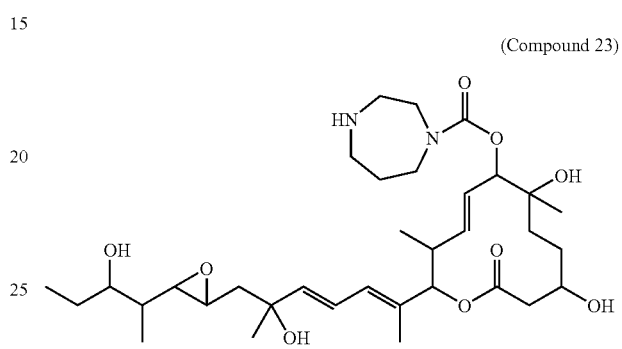

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.4 Hz), 1.23 (3H, s), 1.24-1.69 (8H, m), 1.34 (3H, s), 1.77 (3H, s), 1.78-1.90 (3H, m), 2.48-2.62 (3H, m), 2.66 (1H, dd, J=2.4, 8.0 Hz), 2.72-2.93 (5H, m), 3.43-3.67 (5H, m), 3.74-3.82 (1H, m), 4.94 (1H, d, J=9.6 Hz), 5.06 (1H, d, J=10.4 Hz), 5.57 (1H, dd, J=10.4, 15.2 Hz), 5.72 (1H, dd, J=9.8, 15.4 Hz), 5.86 (1H, d, J=15.2 Hz), 6.13 (1H, d, J=10.8 Hz), 6.53 (1H, dd, J=11.0, 15.4 Hz); EI-MS m/z 637 (M+H)⁺.

Example 24

(8E,12E,14E)-7-((4-Benzylpiperazin-1-yl)carbonyl)oxy-3,6,16,21-tetrahydroxy-6,10,12,16,20-pentamethyl-18,19-epoxytricosa-8,12,14-trien-11-olide (Compound 24)

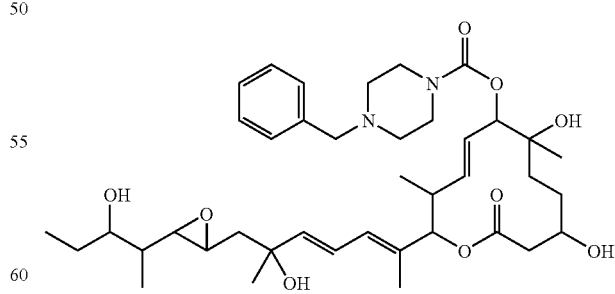

The title compound (a colorless oil) was synthesized by a similar method as described for Example 3.

¹H-NMR Spectrum (CD₃ OD, 400 MHz) δ(ppm): 0.88 (3H, d, J=6.8 Hz), 0.89 (3H, d, J=6.8 Hz), 0.94 (3H, t, J=7.6 Hz), 1.20 (3H, s), 1.22-1.65 (7H, m), 1.34 (3H, s), 1.65 (1H, dd, J=6.2, 14.2 Hz), 1.77 (3H, s), 1.87 (1H, dd, J=5.4, 14.2 Hz), 2.39-2.49 (4H, m), 2.50-2.64 (3H, m), 2.67 (1H, dd, J=2.4, 8.0 Hz), 2.89 (1H, dt, J=2.0, 5.6 Hz), 3.36-3.72 (7H, m), 3.74-3.83 (1H, m), 4.92 (1H, d, J=9.6 Hz), 5.06 (1H, d, J=10.8 Hz), 5.56 (1H, dd, J=10.0, 15.2 Hz), 5.71 (1H, dd, J=9.6, 15.2 Hz), 5.87 (1H, d, J=15.2 Hz), 6.13 (1H, d, J=11.2 Hz), 6.53 (1H, dd, J=11.2, 15.2 Hz), 7.22-7.37 (5H, m); ESI-MS m/z 713 (M+H)$^+$.

Example 25

(8E,12E,14E)-3,6,16,21-Tetrahydroxy-6,10,12,16,20-pentamethyl-7-((4-propylpiperazin-1-yl)carbonyl)oxy-18,19-epoxytricosa-8,12,14-trien-11-olide (Compound 25)

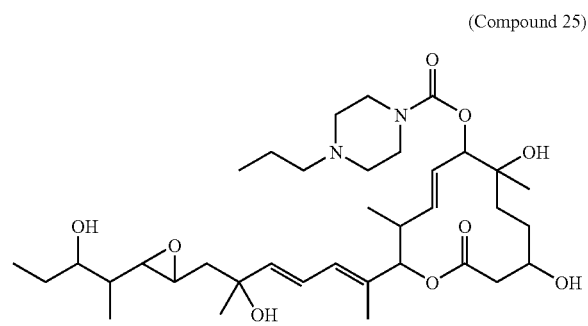

The title compound (a colorless oil) was synthesized by a similar method as described for Example 3.

$^1$H-NMR Spectrum (CD$_3$ OD, 400 MHz) δ(ppm): 0.86-0.97 (12H, m), 1.21 (3H, s), 1.21-1.68 (10H, m), 1.34 (3H, s), 1.77 (3H, s), 1.87 (1H, dd, J=5.2, 14.0 Hz), 2.30-2.36 (2H, m), 2.38-2.47 (4H, m), 2.49-2.63 (3H, m), 2.66 (1H, dd, J=2.4, 7.6 Hz), 2.89 (1H, dt, J=2.0, 6.0 Hz), 3.35-3.72 (5H, m), 3.74-3.83 (1H, m), 4.93 (1H, d, J=9.6 Hz), 5.06 (1H, d, J=10.8 Hz), 5.57 (1H, dd, J=10.0, 15.2 Hz), 5.71 (1H, dd, J=1.0, 15.2 Hz), 5.87 (1H, d, J=15.2 Hz), 6.13 (1H, d, J=10.0 Hz), 6.52 (1H, dd, J=10.8, 15.2 Hz); ESI-MS m/z 665 (M+H)$^+$.

Example 26

(8E,12E,14E)-7-((4-Cyclohexylpiperazin-1-yl)carbonyl)oxy-3,6,16,21-tetrahydroxy-6,10,12,16,20-pentamethyl-18,19-epoxytricosa-8,12,14-trien-11-olide (Compound 26)

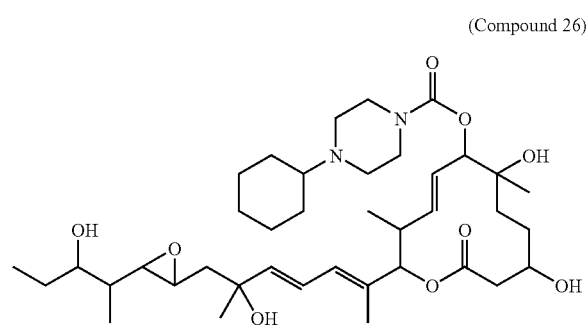

The title compound (a colorless oil) was synthesized by a similar method as described for Example 3.

$^1$H-NMR Spectrum (CD$_3$ OD, 400 MHz) δ(ppm): 0.89 (3H, d, J=6.8 Hz), 0.90 (3H, d, J=6.8 Hz), 0.94 (3H, t, J=7.6 Hz), 1.10-1.69 (15H, m), 1.21 (3H, s), 1.34 (3H, s), 1.78 (3H, s), 1.78-1.93 (4H, m), 2.26-2.35 (1H, m), 2.47-2.64 (7H, m), 2.67 (1H, dd, J=2.0, 8.0 Hz), 2.89 (1H, dt, J=2.0, 6.0 Hz), 3.36-3.70 (5H, m), 3.75-3.82 (1H, m), 4.93 (1H, d, J=9.6 Hz), 5.06 (1H, d, J=10.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 705 (M+H)$^+$.

Example 27

(8E,12E,14E)-7-((4-(Cyclopropylmethyl)piperazin-1-yl)carbonyl)oxy-3,6,16,21-tetrahydroxy-6,10,12,16,20-pentamethyl-18,19-epoxytricosa-8,12,14-trien-11-olide (Compound 27)

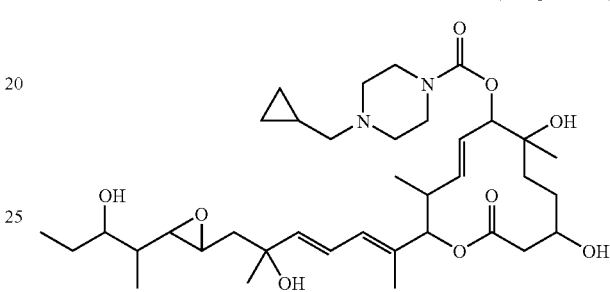

The title compound (a colorless oil) was synthesized by a similar method as described for Example 3.

$^1$H-NMR Spectrum (CD$_3$ OD, 400 MHz) δ(ppm): 0.12-0.17 (2H, m), 0.52-0.58 (2H, m), 0.89 (3H, d, J=6.8 Hz), 0.90 (3H, d, J=6.8 Hz), 0.90-0.97 (4H, m), 1.21 (3H, s), 1.21-1.69 (8H, m), 1.34 (3H, s), 1.78 (3H, s), 1.86 (1H, dd, J=5.2, 14.0 Hz), 2.29 (2H, d, J=6.8 Hz), 2.47-2.64 (7H, m), 2.67 (1H, dd, J=2.0, 8.0 Hz), 2.89 (1H, dt, J=2.0, 6.0 Hz), 3.40-3.72 (5H, m), 3.74-3.82 (1H, m), 4.93 (1H, d, J=9.6 Hz), 5.06 (1H, d, J=10.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 677 (M+H)$^+$.

Example 28

(8E,12E,14E)-3,6,16,21-Tetrahydroxy-6,10,12,16,20-pentamethyl-7-((4-(morpholin-4-yl)piperidin-1-yl)carbonyl)oxy-18,19-epoxytricosa-8,12,14-trien-11-olide (Compound 28)

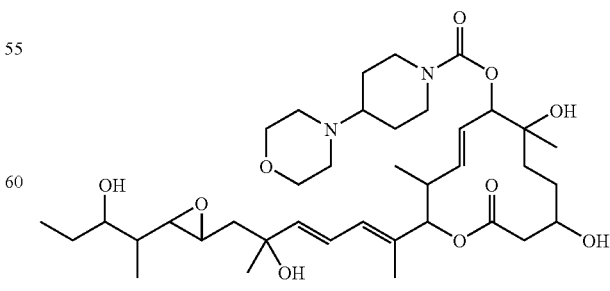

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 19-1.30 (4H, m), 1.31-1.68 (12H, m), 1.77 (3H, d, J=1.2 Hz), 1.83-1.95 (3H, m), 2.34-2.43 (1H, m), 2.50-2.64 (7H, m), 2.67 (1H, dd, J=2.4, 8.0 Hz), 2.73-2.89 (2H, m), 2.89 (1H, dt, J=2.4, 6.0 Hz), 3.52 (1H, td, J=4.4, 8.0 Hz), 3.66-3.72 (4H, m), 3.75-3.81 (1H, m), 4.07-4.44 (2H, m), 4.92 (1H, d, J=9.6 Hz), 5.06 (1H, d, J=10.4 Hz), 5.57 (1H, dd, J=10.0, 15.2 Hz), 5.72 (1H, dd, J=9.6, 15.2 Hz), 5.87 (1H, d, J=15.2 Hz), 6.13 (1H, d, J=11.2 Hz), 6.53 (1H, dd, J=10.8, 15.2 Hz); ESI-MS m/z 707 (M+H)⁺.

Example 29

(8E,12E,14E)-3,6,16,21-Tetrahydroxy-6,10,12,16, 20-pentamethyl-7-((4-(3,3,3-trifluoropropyl)piper- azin-1-yl)carbonyl)oxy-18,19-epoxytricosa-8,12,14- trien-11-olide (Compound 29)

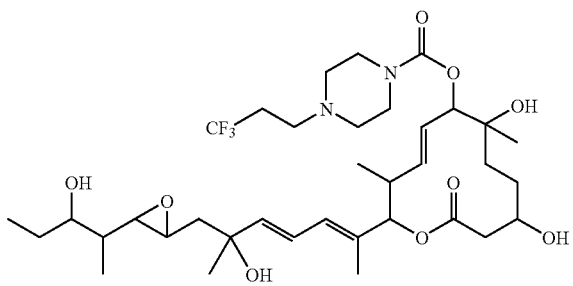

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 1.19-1.30 (4H, m), 1.31-1.69 (10H, m), 1.77 (3H, d, J=1.2 Hz), 1.86 (1H, dd, J=5.6, 14.0 Hz), 2.35-2.66 (11H, m), 2.67 (1H, dd, J=2.4, 8.0 Hz), 2.89 (1H, dt, J=2.0, 6.0 Hz), 3.38-3.71 (5H, m), 3.75-3.82 (1H, m), 4.93 (1H, d, J=10.0 Hz), 5.06 (1H, d, J=10.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=11.2 Hz), 6.53 (1H, dd, J=10.8, 15.2 Hz); ESI-MS m/z 719 (M+H)⁺, 741 (M+Na)⁺.

Example 30

(8E,12E,14E)-3,6,16,21-Tetrahydroxy-6,10,12,16, 20-pentamethyl-7-((4-(4,4,4-trifluorobutyl)piper- azin-1-yl)carbonyl)oxy-18,19-epoxytricosa-8,12,14- trien-11-olide (Compound 30)

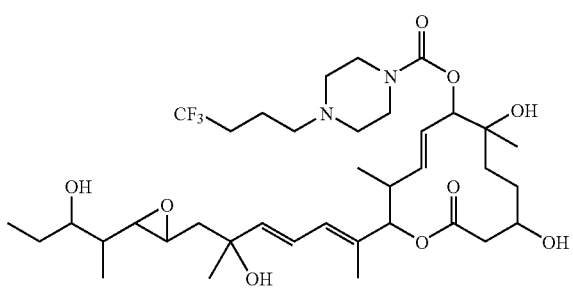

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 1.19-1.30 (4H, m), 1.32-1.69 (10H, m), 1.70-1.81 (5H, m), 1.86 (1H, dd, J=5.6, 14.0 Hz), 2.14-2.28 (2H, m), 2.38-2.49 (6H, m), 2.50-2.64 (3H, m), 2.67 (1H, dd, J=2.4, 8.0 Hz), 2.89 (1H, dt, J=2.4, 6.0 Hz), 3.39-3.72 (5H, m), 3.75-3.82 (1H, m), 4.93 (1H, d, J=10.0 Hz), 5.06 (1H, d, J=10.4 Hz), 5.57 (1H, dd, J=10.0, 15.2 Hz), 5.72 (1H, dd, J=10.0, 15.2 Hz), 5.87 (1H, d, J=15.2 Hz), 6.13 (1H, d, J=11.2 Hz), 6.53 (1H, dd, J=10.8, 15.2 Hz); ESI-MS m/z 733 (M+H)⁺, 755 (M+Na)⁺.

Example 31

(8E,12E,14E)-3,6,16,21-Tetrahydroxy-6,10,12,16, 20-pentamethyl-7-((4-propylhomopiperazin-1-yl) carbonyl)oxy-18,19-epoxytricosa-8,12,14-trien-11- olide (Compound 31)

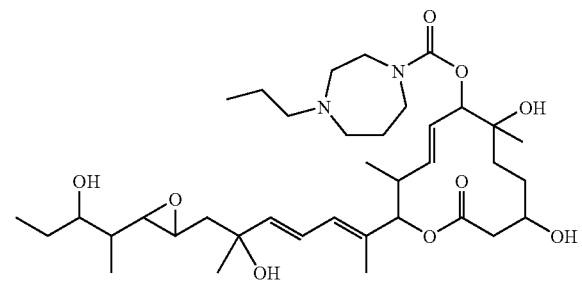

The title compound (a colorless oil) was synthesized by a similar method as described for Example 3.

¹H-NMR Spectrum (CD₃ OD, 400 MHz) δ(ppm): 0.87-0.92 (9H, m), 0.94 (3H, t, J=7.6 Hz), 1.20-1.30 (4H, m), 1.32-1.69 (12H, m), 1.77 (3H, d, J=0.8 Hz), 1.82-1.91 (3H, m), 2.41-2.49 (2H, m), 2.50-2.77 (8H, m), 2.89 (1H, dt, J=2.4, 6.0 Hz), 3.42-3.67 (5H, m), 3.75-3.82 (1H, m), 4.94 (1H, d, J=9.6 Hz), 5.07 (1H, d, J=10.8 Hz), 5.57 (1H, dd, J=10.0, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 679 (M+H)⁺.

Example 32

(8E,12E,14E)-3,6,16,21-Tetrahydroxy-7-((4-(2-methoxyethyl)piperazin-1-yl)carbonyl)oxy-6,10,12, 16,20-pentamethyl-18,19-epoxytricosa-8,12,14-trien-11-olide (Compound 32)

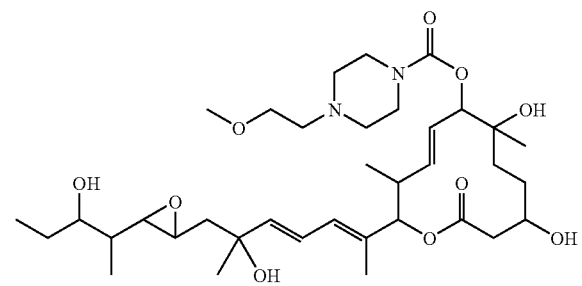

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 1.19-1.30 (4H, m), 1.31-1.69 (10H, m), 1.77 (3H, d, J=1.2 Hz), 1.86 (1H, dd, J=5.6, 14.0 Hz), 2.44-2.64 (9H, m), 2.67 (1H, dd, J=2.4, 8.0 Hz), 2.89 (1H, dt, J=2.4, 6.0 Hz), 3.33 (3H, s), 3.39-3.71 (7H, m), 3.75-3.82 (1H, m), 4.93 (1H, d, J=9.6 Hz), 5.06 (1H, d, J=10.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 681 (M+H)⁺.

Example 33

(8E,12E,14E)-7-((4-Cyclobutylpiperazin-1-yl)carbonyl)oxy-3,6,16,21-tetrahydroxy-6,10,12,16,20-pentamethyl-18,19-epoxytricosa-8,12,14-trien-11-olide (Compound 33)

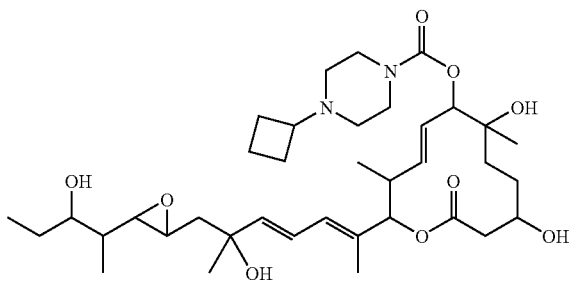

The title compound (a colorless oil) was synthesized by a similar method as described for Example 3.

¹H-NMR Spectrum (CD₃ OD, 400 MHz) δ(ppm): 0.89 (3H, d, J=6.8 Hz), 0.90 (3H, d, J=6.8 Hz), 0.94 (3H, t, J=7.6 Hz), 1.19-1.30 (4H, m), 1.32-1.69 (10H, m), 1.70-1.81 (5H, m), 1.83-1.95 (3H, m), 2.02-2.11 (2H, m), 2.27-2.37 (4H, m), 2.49-2.64 (3H, m), 2.67 (1H, dd, J=2.4, 8.0 Hz), 2.72-2.81 (1H, m), 2.89 (1H, dt, J=2.4, 6.0 Hz), 3.37-3.71 (5H, m), 3.75-3.82 (1H, m), 4.93 (1H, d, J=9.6 Hz), 5.06 (1H, d, J=10.8 Hz), 5.57 (1H, dd, J=9.6, 15.2 Hz), 5.71 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 677 (M+H)⁺.

Example 34

(8E,12E,14E)-7-((4-(1-Ethylpropyl)piperazin-1-yl)carbonyl)oxy-3,6,16,21-tetrahydroxy-6,10,12,16,20-pentamethyl-18,19-epoxytricosa-8,12,14-trien-11-olide (Compound 34)

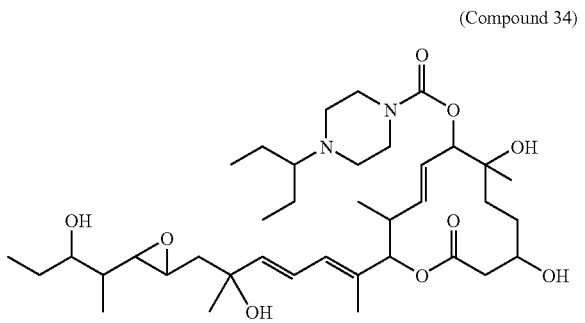

The title compound (a colorless oil) was synthesized by a similar method as described for Example 3.

¹H-NMR Spectrum (CD₃ OD, 400 MHz) δ(ppm): 0.87-0.97 (15H, m), 1.19-1.69 (18H, m), 1.77 (3H, d, J=0.8 Hz), 1.86 (1H, dd, J=5.2, 14.0 Hz), 2.15-2.23 (1H, m), 2.45-2.64 (7H, m), 2.67 (1H, dd, J=2.4, 8.0 Hz), 2.89 (1H, dt, J=2.4, 6.0 Hz), 3.34-3.65 (5H, m), 3.75-3.82 (1H, m), 4.93 (1H, d, J=10.0 Hz), 5.06 (1H, d, J=10.8 Hz), 5.57 (1H, dd, J=9.6, 15.2 Hz), 5.72 (1H, dd, J=9.6, 15.2 Hz), 5.87 (1H, d, J=15.2 Hz), 6.13 (1H, d, J=11.2 Hz), 6.53 (1H, dd, J=11.2, 15.2 Hz); ESI-MS m/z 693 (M+H)⁺.

Example 35

(8E,12E,14E)-3,6,16,21-Tetrahydroxy-6,10,12,16,20-pentamethyl-7-((4-(tetrahydropyran-4-yl)piperazin-1-yl)carbonyl)oxy-18,19-epoxytricosa-8,12,14-trien-11-olide (Compound 35)

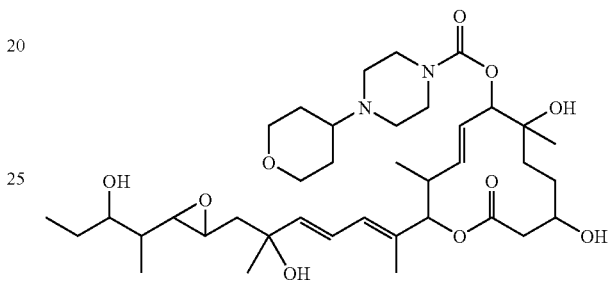

The title compound (a colorless oil) was synthesized by a similar method as described for Example 3.

¹H-NMR Spectrum (CD₃ OD, 400 MHz) δ(ppm): 0.88 (3H, d, J=6.8 Hz), 0.90 (3H, d, J=6.8 Hz), 0.94 (3H, t, J=7.6 Hz), 1.21 (3H, s), 1.21-1.69 (10H, m), 1.34 (3H, s), 1.77 (3H, s), 1.77-1.90 (3H, m), 2.42-2.62 (8H, m), 2.66 (1H, dd, J=2.0, 7.6 Hz), 2.89 (1H, dt, J=2.0, 6.0 Hz), 3.34-3.71 (7H, m), 3.74-3.82 (1H, m), 3.94-4.02 (2H, m), 4.93 (1H, d, J=9.6 Hz), 5.05 (1H, d, J=10.4 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=10.4 Hz), 6.53 (1H, dd, J=10.8, 15.2 Hz); ESI-MS m/z 707 (M+H)⁺.

Example 36

(8E,12E,14E)-7-((4-(Cyclopropylmethyl)homopiperazin-1-yl)carbonyl)oxy-3,6,16,21-tetrahydroxy-6,10,12,16,20-pentamethyl-18,19-epoxytricosa-8,12,14-trien-11-olide (Compound 36)

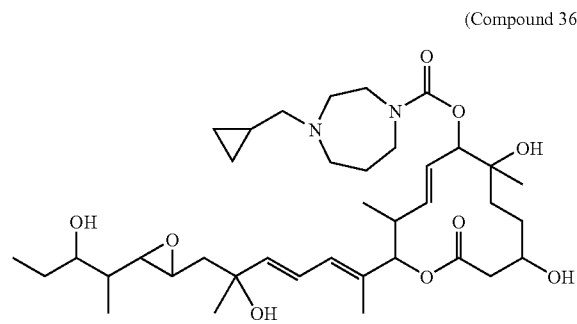

The title compound (a colorless oil) was synthesized by a similar method as described for Example 3.

¹H-NMR Spectrum (CD₃OD, 400 MHz) δ(ppm): 0.08-0.14 (2H, m), 0.48-0.54 (2H, m), 0.83 (3H, d, J=6.8 Hz), 0.88 (3H, d, J=7.2 Hz), 0.89-0.94 (4H, m), 1.20-1.67 (8H, m), 1.21 (3H, s), 1.31 (3H, s), 1.75 (3H, s), 1.80-1.90 (3H, m), 2.37 (2H, d, J=6.4), 2.47-2.61 (3H, m), 2.62-2.82 (5H, m), 2.87 (1H, dt, J=2.4, 6.0 Hz), 3.43-3.69 (5H, m), 3.73-3.80 (1H, m), 4.92 (1H, d, J=9.6 Hz), 5.04 (1H, d, J=10.8 Hz), 5.55 (1H, dd, J=10.0, 15.2 Hz), 5.70 (1H, dd, J=9.6, 15.2 Hz), 5.84 (1H, d, J=15.2 Hz), 6.11 (1H, d, J=11.2 Hz), 6.50 (1H, dd, J=10.8, 15.2 Hz); ESI-MS m/z 691 (M+H)⁺.

Example 37

(8E,12E,14E)-3,6,16,21-Tetrahydroxy-6,10,12,16,20-pentamethyl-7-((4-(2,2,2-trifluoroethyl)piperazin-1-yl)carbonyl)oxy-18,19-epoxytricosa-8,12,14-trien-11-olide (Compound 37)

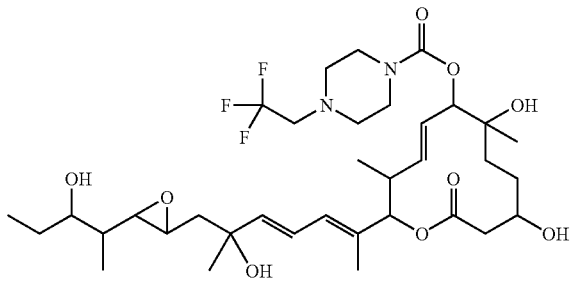

The title compound (a colorless oil) was synthesized by a similar method as described for Example 3.

¹H-NMR Spectrum (CD₃OD, 400 MHz) δ(ppm): 0.89 (3H, d, J=6.4 Hz), 0.90 (3H, d, J=6.8 Hz), 0.94 (3H, t, J=7.6 Hz), 1.21 (3H, s), 1.20-1.69 (8H, m), 1.34 (3H, s), 1.77 (3H, s), 1.86 (1H, dd, J=5.2, 14.4 Hz), 2.50-2.69 (8H, m), 2.86-2.92 (1H, m), 3.38-3.72 (2H, m), 3.04-3.14 (5H, m), 3.74-3.82 (1H, m), 4.93 (1H, d, J=10.0 Hz), 5.05 (1H, d, J=10.8 Hz), 5.57 (1H, dd, J=10.0, 15.2 Hz), 5.71 (1H, dd, J=10.0, 15.2 Hz), 5.87 (1H, d, J=15.6 Hz), 6.13 (1H, d, J=11.2 Hz), 6.52 (1H, dd, J=11.2, 15.2 Hz); ESI-MS m/z 727 (M+Na)⁺.

Example 38

(8E,12E,14E)-7-((4-Cyclopentylpiperazin-1-yl)carbonyl)oxy-3,6,16,21-tetrahydroxy-6,10,12,16,20-pentamethyl-18,19-epoxytricosa-8,12,14-trien-11-olide (Compound 38)

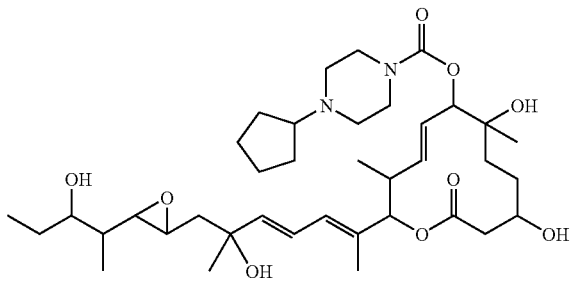

The title compound (a colorless oil) was synthesized by a similar method as described for Example 3.

¹H-NMR Spectrum (CD₃OD, 400 MHz) δ(ppm): 0.89 (3H, d, J=6.4 Hz), 0.90 (3H, d, J=6.8 Hz), 0.94 (3H, t, J=7.6 Hz), 1.21 (3H, s), 1.21-1.76 (14H, m), 1.34 (3H, s), 1.77 (3H, s), 1.83-1.95 (3H, m), 2.46-2.62 (8H, m), 2.66 (1H, dd, J=2.4, 7.6 Hz), 2.88 (1H, dt, J=2.4, 6.4 Hz), 3.34-3.72 (5H, m), 3.74-3.82 (1H, m), 4.93 (1H, d, J=10.0 Hz), 5.05 (1H, d, J=10.4 Hz), 5.57 (1H, dd, J=10.0, 15.2 Hz), 5.71 (1H, dd, J=10.0, 15.2 Hz), 5.87 (1H, d, J=15.6 Hz), 6.13 (1H, d, J=11.2 Hz), 6.52 (1H, dd, J=11.2, 15.2 Hz); ESI-MS m/z 691 (M+H)⁺.

Example 39

(8E,12E,14E)-7-((4-Isobutylpiperazin-1-yl)carbonyl)oxy-3,6,16,21-tetrahydroxy-6,10,12,16,20-pentamethyl-18,19-epoxytricosa-8,12,14-trien-11-olide (Compound 39)

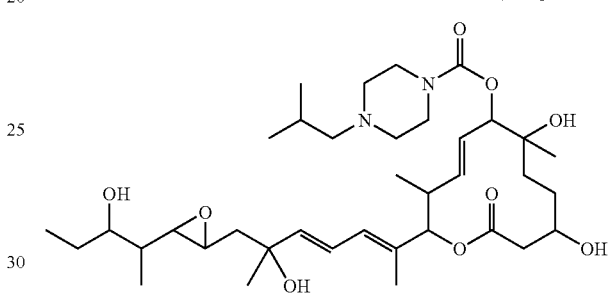

The title compound (a colorless oil) was synthesized by a similar method as described for Example 3.

¹H-NMR Spectrum (CD₃OD, 400 MHz) δ(ppm): 0.87-0.97 (15H, m), 1.21 (3H, s), 1.21-1.69 (8H, m), 1.34 (3H, s), 1.77 (3H, s), 1.78-1.90 (2H, m), 2.11 (2H, d, J=7.2 Hz), 2.32-2.41 (4H, m), 2.50-2.63 (3H, m), 2.67 (1H, dd, J=2.4, 8.0 Hz), 2.89 (1H, dt, J=2.0, 6.0 Hz), 3.38-3.70 (5H, m), 3.74-3.82 (1H, m), 4.93 (1H, d, J=9.6 Hz), 5.05 (1H, d, J=10.4 Hz), 5.57 (1H, dd, J=9.6, 15.2 Hz), 5.71 (1H, dd, J=10.0, 15.2 Hz), 5.87 (1H, d, J=15.6 Hz), 6.13 (1H, d, J=11.2 Hz), 6.52 (1H, dd, J=11.2, 15.2 Hz); ESI-MS m/z 679 (M+H)⁺.

Example 40

(8E,12E,14E)-7-(((1S,4S)-5-Benzyl-2,5-diazabicyclo[2.2.1]heptan-2-yl)carbonyl)oxy-3,6,16,21-tetrahydroxy-6,10,12,16,20-pentamethyl-18,19-epoxytricosa-8,12,14-trien-11-olide (Compound 40)

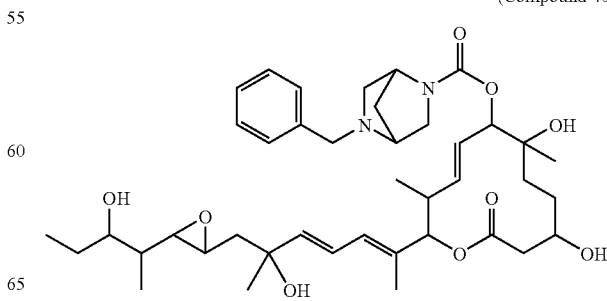

The title compound (a colorless oil) was synthesized by a similar method as described for Example 3.

$^1$H-NMR Spectrum (CD$_3$ OD, 400 MHz) δ(ppm): 0.84 (3H, d, J=7.0 Hz), 0.85 (3H, d, J=7.0 Hz), 0.89 (3H, t, J=7.3 Hz), 1.14-1.27 (4H, m), 1.27-1.65 (7H, m), 1.30 (3H, s), 1.65-1.92 (6H, m), 2.44-2.66 (5H, m), 2.79-2.88 (2H, m), 3.16 (0.6H, dd, J=1.8, 10.3 Hz), 3.25-3.31 (0.4H, m), 3.45-3.78 (6H, m), 4.29 (0.4H, brs), 4.52 (0.6H, brs), 4.89 (1H, d, J=9.9 Hz), 5.02 (1H, d, J=10.6 Hz), 5.54 (1H, dd, J=9.9, 15.0 Hz), 5.68 (0.6H, dd, J=9.9, 15.0 Hz), 5.73 (0.4H, dd, J=9.9, 15.0 Hz), 5.82 (1H, d, J=15.4 Hz), 6.09 (1H, d, J=11.0 Hz), 6.48 (1H, d, J=11.0, 15.4 Hz), 7.16-7.32 (5H, m); ESI-MS m/z 725 (M+H)$^+$.

Example 41

(8E,12E,14E)-7-(N-(2-(N',N'-Dimethylamino)ethyl)-N-ethylcarbamoyloxy)-3,6,16,21-tetrahydroxy-6,10,12,16,20-pentamethyl-18,19-epoxytricosa-8,12,14-trien-11-olide (Compound 41)

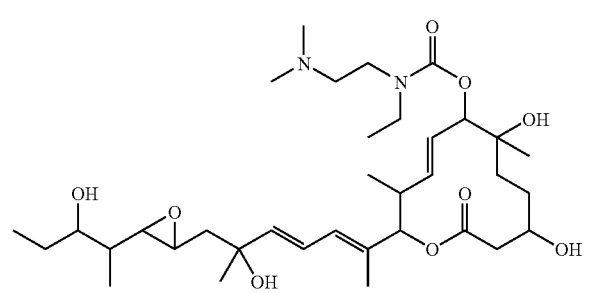

The title compound (a colorless oil) was synthesized by a similar method as described for Example 3.

$^1$H-NMR Spectrum (CD$_3$ OD, 400 MHz) δ(ppm): 0.88 (3H, d, J=7.0 Hz), 0.89 (3H, d, J=7.0 Hz), 0.93 (3H, t, J=7.3 Hz), 1.08-1.14 (3H, m), 1.20-1.29 (1H, m), 1.22 (3H, s), 1.31-1.68 (7H, m), 1.33 (3H, s), 1.77 (3H, d, J=0.7 Hz), 1.86 (1H, dd, J=5.5, 14.3 Hz), 2.28 (6H, s), 2.43-2.62 (5H, m), 2.66 (1H, dd, J=2.2, 8.1 Hz), 2.89 (1H, dt, J=2.2, 5.5 Hz), 3.23-3.52 (4H, m), 3.52 (1H, dt, J=4.4, 8.4 Hz), 3.74-3.82 (1H, m), 4.92 (1H, d, J=9.9 Hz), 5.06 (1H, d, J=10.6 Hz), 5.56 (1H, dd, J=9.9, 15.0 Hz), 5.73 (1H, dd, J=9.9, 15.0 Hz), 5.86 (1H, d, J=15.0 Hz), 6.13 (1H, dd, J=1.1, 11.0 Hz), 6.52 (1H, dd, J=11.0, 15.0 Hz); ESI-MS m/z 653 (M+H)$^+$.

Example 42

(8E,12E,14E)-7-(N-(2-(N',N'-Diethylamino)ethyl)-N-ethylcarbamoyloxy)-3,6,16,21-tetrahydroxy-6,10,12,16,20-pentamethyl-18,19-epoxytricosa-8,12,14-trien-11-olide (Compound 42)

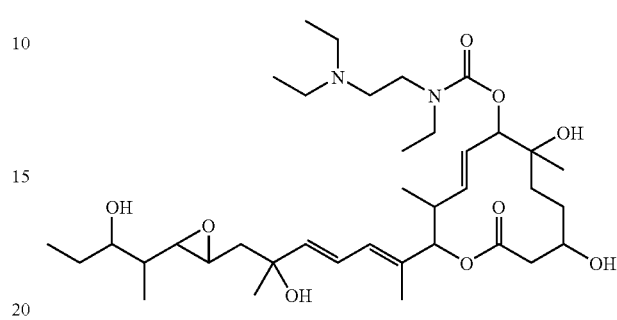

The title compound (a colorless oil) was synthesized by a similar method as described for Example 3.

$^1$H-NMR Spectrum (CD$_3$ OD, 400 MHz) δ(ppm): 0.88 (3H, d, J=6.6 Hz), 0.89 (3H, d, J=7.0 Hz), 0.93 (3H, t, J=7.3 Hz), 1.06 (6H, t, J=7.0 Hz), 1.06-1.15 (3H, m), 1.20-1.29 (1H, m), 1.22 (3H, s), 1.31-1.68 (7H, m), 1.33 (3H, s), 1.77 (3H, d, J=1.1 Hz), 1.86 (1H, dd, J=5.5, 14.3 Hz), 2.48-2.66 (5H, m), 2.59 (4H, q, J=7.0 Hz), 2.66 (1H, dd, J=2.2, 8.1 Hz), 2.89 (1H, dt, J=2.2, 5.5 Hz), 3.21-3.60 (4H, m), 3.52 (1H, dt, J=4.4, 8.4 Hz), 3.74-3.81 (1H, m), 4.93 (1H, d, J=9.9 Hz), 5.06 (1H, d, J=10.6 Hz), 5.57 (1H, dd, J=9.9, 15.0 Hz), 5.73 (1H, dd, J=9.9, 15.0 Hz), 5.86 (1H, d, J=15.4 Hz), 6.13 (1H, d, J=11.0 Hz), 6.52 (1H, dd, J=11.0, 15.4 Hz); ESI-MS m/z 681 (M+H)$^+$.

Example 43

(8E,12E,14E)-7-Acetoxy-3,16,21-trihydroxy-6-methoxy-6,10,12,16,20-pentamethyl-18,19-epoxytricosa-8,12,14-trien-11-olide (Compound 43)

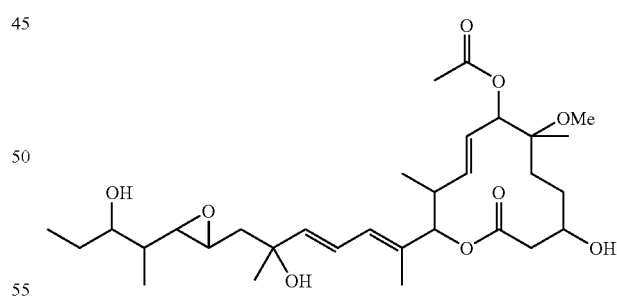

(8E,12E,14E)-7-Acetoxy-3,16,21-tris(1-ethoxyethoxy)-6-hydroxy-6,10,12,16,20-pentamethyl-18,19-epoxytricosa-8,12,14-trien-11-olide (34 mg, 44 μmol) obtained in Example 3 and 1,8-bis(N,N-dimethylamino)naphthalene (57 mg, 266 μmol) were dissolved in toluene (2 mL). Methyl trifluoromethanesulfonate (22 mg, 133 μmol) was added to this solution, and the reaction mixture was stirred at 65° C. for 11 hours. After removing the precipitate by filtration, the reaction mixture was diluted with ethyl acetate, and an aqueous solution of ammonium chloride was added, followed by vigorous stirring for 5 minutes. The organic layer was washed with a saturated aqueous solution of sodium bicarbonate and brine, dried over anhydrous magnesium sulfate, and concentrated. The resulting residue was purified by silica gel column chromatography (Kanto silica gel 60N spherical, neutral, 40 to 100 µm; hexane:ethyl acetate=1:1) to give (8E,12E,14E)-7-acetoxy-3,16,21-tris(1-ethoxyethoxy)-6-methoxy-6,10,12,16,20-pentamethyl-18,19-epoxytricosa-8,12,14-trien-11-olide (14 mg) as a colorless oil.

The obtained compound was subjected to deprotection of ethoxyethyl group by a similar method as described for Example 3, to give the title compound (5.7 mg, 22.9%, two steps) as a colorless oil.

$^1$H-NMR Spectrum (CD$_3$OD, 500 MHz) δ(ppm): 0.88 (3H, d, J=6.5 Hz), 0.91 (3H, d, J=7.5 Hz), 0.94 (3H, t, J=7.5 Hz), 1.21 (3H, s), 1.22-1.32 (1H, m), 1.34 (3H, s), 1.40-1.70 (7H, m), 1.78 (3H, s), 1.86 (1H, dd, J=5.5, 14.0 Hz), 2.06 (3H, s), 2.46-2.63 (3H, m), 2.67 (1H, d, J=8.5 Hz), 2.99 (1H, brs), 3.33 (3H, s), 3.50-3.56 (1H, m), 3.78-3.86 (1H, m), 5.06 (1H, d, J=10.5 Hz), 5.12 (1H, d, J=10.0 Hz), 5.56 (1H, dd, J=10.0, 15.5 Hz), 5.72 (1H, dd, J=10.5, 15.5 Hz), 5.87 (1H, d, J=15.5 Hz), 6.14 (1H, d, J=10.5 Hz), 6.53 (1H, dd, J=10.5, 15.5 Hz); ESI-MS m/z 589 (M+Na)$^+$.

Example 44

(8E,12E,14E)-3,6,16,21-Tetrahydroxy-7-((4-isopropylpiperazin-1-yl)carbonyl)oxy-6,10,12,16,20-pentamethyl-18,19-epoxytricosa-8,12,14-trien-11-olide (Compound 44)

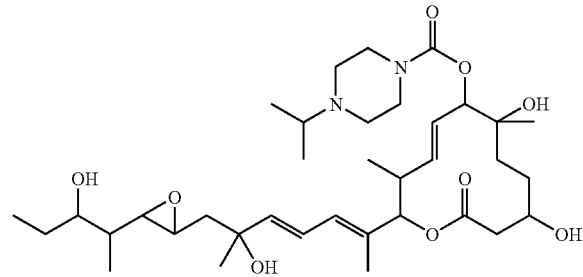

First Step (8E,12E,14E)-6-(1-Ethoxyethoxy)-7-((4-isopropylpiperazin-1-yl)carbonyl)oxy-6,10,12,16,20-pentamethyl-3,16,21-tris(triethylsiloxy)-18,19-epoxytricosa-8,12,14-trien-11-olide (Compound 44-1)

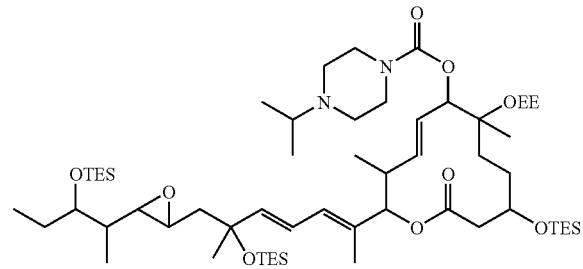

To a solution of Compound 46-4 (8E,12E,14E)-6-(1-ethoxyethoxy)-6,10,12,16,20-pentamethyl-7-(4-nitrophenoxy)carboxy-3,16,21-tris(triethylsiloxy)-18,19-epoxytricosa-8,12,14-trien-11-olide (1.27 g, 1.16 mmol) obtained in the fourth step of Example 46 in tetrahydrofuran (25 mL) were added triethylamine (470 mg, 4.64 mmol) and isopropylpiperazine (298 mg, 2.32 mmol) at room temperature, and the reaction mixture was stirred at the same temperature for 1.5 hours. The reaction mixture was diluted with ethyl acetate and then washed with a saturated aqueous solution of sodium bicarbonate and brine. The organic layer was dried over anhydrous magnesium sulfate, filtrated and concentrated. The resulting residue was purified by silica gel column chromatography (Kanto silica gel 60N, 40 to 100 µm; hexane:ethyl acetate=1:1 to ethyl acetate to ethyl acetate:methanol=97:3) to give the title compound (1.12 g, 89%) as a colorless oil.

$^1$H-NMR Spectrum (CD$_3$OD, 400 MHz) δ(ppm): 0.58-0.70 (27H, m), 0.80-1.72 (53H, m), 1.76 (3H, s), 1.88-1.98 (1H, m), 2.33-2.64 (8H, m), 2.64-2.76 (1H, m), 2.80-2.90 (1H, m), 3.38-3.66 (6H, m), 3.68-3.78 (1H, m), 3.85-3.98 (1H, m), 4.88-4.99 (2H, m), 5.05 (0.4H, q, J=5.2 Hz), 5.13 (0.6H, q, J=5.2 Hz), 5.57 (1H, dd, J=10.0, 15.2 Hz), 5.72-5.80 (1H, m), 5.82 (1H, d, J=14.8 Hz), 6.13 (1H, d, J=10.8 Hz), 6.50 (1H, dd, J=10.8, 15.2 Hz).

Second Step (8E,12E,14E)-6-(1-Ethoxyethoxy)-3,16,21-trihydroxy-7-((4-isopropylpiperazin-1-yl)carbonyl)oxy-6,10,12,16,20-pentamethyl-18,19-epoxytricosa-8,12,14-trien-11-olide (Compound 44-2)

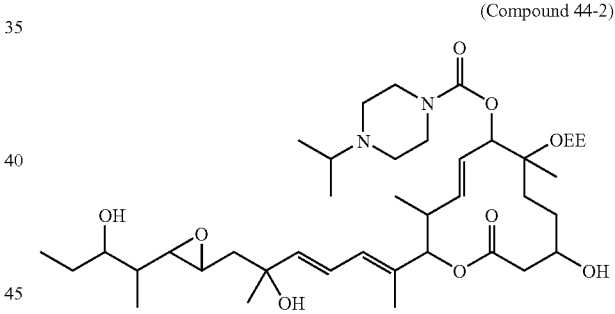

To a solution of Compound 44-1 (8E,12E,14E)-6-(1-ethoxyethoxy)-7-((4-isopropylpiperazin-1-yl)carbonyl)oxy-6,10,12,16,20-pentamethyl-3,16,21-tris(triethylsiloxy)-18,19-epoxytricosa-8,12,14-trien-11-olide (1.12 g, 1.03 mmol) obtained in the first step in tetrahydrofuran (20 mL) was added tetrabutylammonium fluoride (4.1 mL, 1.0 M tetrahydrofuran solution) at room temperature, and the reaction mixture was stirred at the same temperature for 4 hours. The reaction mixture was diluted with ethyl acetate and then washed with a saturated aqueous solution of sodium bicarbonate and brine. The organic layer was dried over anhydrous magnesium sulfate, filtrated and evaporated. The resulting residue was purified by silica gel column chromatography (Fuji Silysia, NH Silica gel, 200-350 mesh; ethyl acetate to ethyl acetate:methanol=95:5) to give the title compound (0.76 g, 99%) as a colorless oil.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.6 Hz), 1.06 (6H, d, J=6.4 Hz), 1.12-1.70 (20H, m), 1.78 (3H, s), 1.86 (1H, dd, J=2.4, 7.6 Hz), 2.42-2.62 (7H, m), 2.64-2.76

(2H, m), 2.89 (1H, dt, J=2.0, 6.0 Hz), 3.38-3.66 (7H, m), 3.75-3.84 (1H, m), 4.98 (1H, d, J=9.6 Hz), 5.02-5.16 (2H, m), 5.56 (1H, dd, J=10.0, 15.6 Hz), 5.72-5.80 (1H, m), 5.87 (1H, d, J=15.6 Hz), 6.13 (1H, d, J=10.8 Hz), 6.53 (1H, dd, J=10.8, 15.2 Hz); ESI-MS m/z 737 (M+H)$^+$.

Third Step (8E,12E,14E)-3,6,16,21-Tetrahydroxy-7-((4-isopropylpiperazin-1-yl)carbonyl)oxy-6,10,12,16,20-pentamethyl-18,19-epoxytricosa-8,12,14-trien-11-olide (Compound 44)

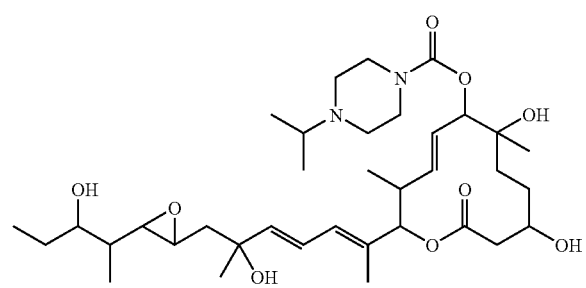

To a solution of Compound 44-2 (8E,12E,14E)-6-(1-ethoxyethoxy)-3,16,21-trihydroxy-7-((4-isopropylpiperazin-1-yl)carbonyl)oxy-6,10,12,16,20-pentamethyl-18,19-epoxytricosa-8,12,14-trien-11-olide (0.76 g, 1.03 mmol) obtained in the second step in a mixture of tetrahydrofuran: 2-methyl-2-propanol=1:1 (20 mL) was added pyridinium p-toluenesulfonate (0.39 g, 1.55 mmol) at room temperature, and the reaction mixture was stirred at the same temperature for 16 hours. Triethylamine (0.25 g, 3.10 mmol) was added to the reaction mixture at room temperature, and the organic solvent was evaporated. The resulting residue was diluted with ethyl acetate and washed with a saturated aqueous solution of sodium bicarbonate and brine. The organic layer was dried over anhydrous sodium sulfate, filtrated and evaporated. The resulting residue was purified by silica gel column chromatography (Fuji Silysia, NH Silica gel, 200-350 mesh; ethyl acetate to ethyl acetate:methanol=95:5) to give the title compound (0.76 g, 85%) as a colorless oil.

$^1$H-NMR Spectrum (CD$_3$OD, 400 MHz) δ(ppm): 0.89 (3H, d, J=6.6 Hz), 0.90 (3H, d, J=6.9 Hz), 0.94 (3H, t, J=7.4 Hz), 1.07 (6H, d, J=6.4 Hz), 1.14-1.67 (14H, m), 1.77 (3H, brs), 1.86 (1H, dd, J=5.4, 14.2 Hz), 2.46-2.63 (7H, m), 2.66 (1H, dd, J=2.4, 8.0 Hz), 2.64-2.79 (1H, m), 2.89 (1H, dt, J=2.4, 6.0 Hz), 3.36-3.67 (5H, m), 3.72-3.81 (1H, m), 4.93 (1H, d, J=9.7 Hz), 5.06 (1H, d, J=10.8 Hz), 5.57 (1H, dd, J=9.7, 15.1 Hz), 5.71 (1H, dd, J=9.7, 15.2 Hz), 5.87 (1H, d, J=15.2 Hz), 6.13 (1H, d, J=10.8 Hz), 6.53 (1H, dd, J=10.8, 15.2 Hz); ESI-MS m/z 665 (M+H)$^+$.

Example 45

(8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide (Compound 45)

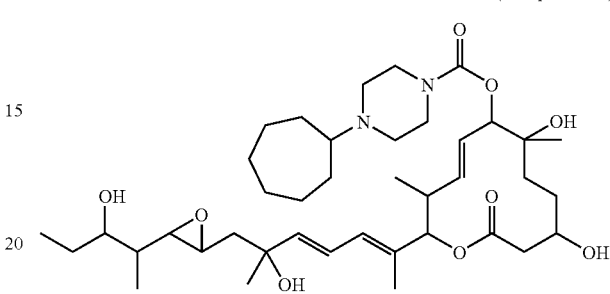

First Step (8E,12E,14E)-7-((4-Cycloheptylpiperazin-1-yl)carbonyl)oxy-6-(1-ethoxyethoxy)-6,10,12,16,20-pentamethyl-3,16,21-tris(triethylsiloxy)-18,19-epoxytricosa-8,12,14-trien-11-olide (Compound 45-1)

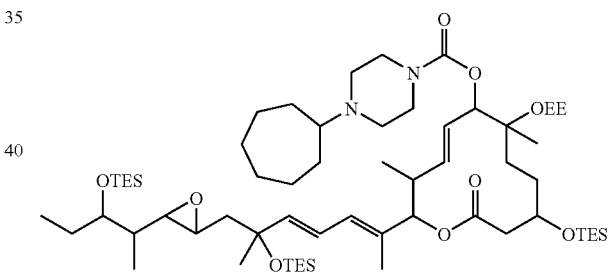

To a solution of Compound 46-4 (8E,12E,14E)-6-(1-ethoxyethoxy)-6,10,12,16,20-pentamethyl-7-(4-nitrophenoxy)carboxy-3,16,21-tris(triethylsiloxy)-18,19-epoxytricosa-8,12,14-trien-11-olide (1.368 g, 1.254 mmol) obtained in the fourth step of Example 46 in tetrahydrofuran (20 mL) were sequentially added dropwise 1-cycloheptylpiperazine (462 mg, 2.51 mmol) and triethylamine (513 mg, 5.02 mmol). Then, tetrahydrofuran (8 mL) was added thereto, and the reaction mixture was stirred at room temperature for 1.5 hours. The reaction mixture was diluted with ethyl acetate and washed with an aqueous solution of sodium bicarbonate and brine. The organic layer was dried over anhydrous magnesium sulfate, filtrated and concentrated. The resulting residue was purified by silica gel column chromatography (Kanto silica gel 60N, 40-50 μm; ethyl acetate-hexane, 1:9 to 1:4 to 1:3) to give the title compound (1.455 g, 99%) as a colorless oil.

Second Step (8E,12E,14E)-7-((4-Cycloheptylpiperazin-1-yl)car-
bonyl)oxy-6-(1-ethoxyethoxy)-3,16,21-trihydroxy-6,
10,12,16,20-pentamethyl-18,19-epoxytricosa-8,12,
14-trien-11-olide (Compound 45-2)

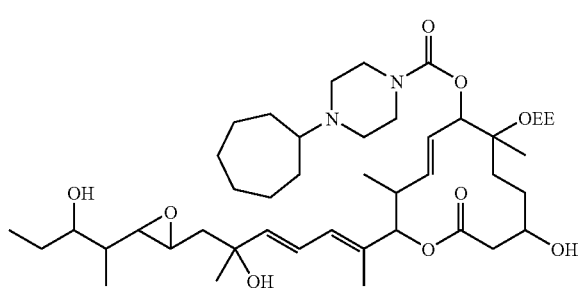

A solution of Compound 45-1 (8E,12E,14E)-7-((4-cyclo-heptylpiperazin-1-yl)carbonyl)oxy-6-(1-ethoxyethoxy)-6,10,12,16,20-pentamethyl-3,16,21-tris(triethylsiloxy)-18,19-epoxytricosa-8,12,14-trien-11-olide (1.454 g, 1.254 mmol) obtained in the first step in tetrahydrofuran (30 mL) was cooled to 5° C., tetrabutylammonium fluoride (1.0 M tetrahydrofuran solution, 4.5 mL, 4.5 mmol) was added dropwise thereto, and the reaction mixture was stirred at room temperature for 1.5 hours. Tetrabutylammonium fluoride (1.0 M tetrahydrofuran solution, 0.52 mL, 0.52 mmol) was further added dropwise, and the reaction mixture was stirred at room temperature for two hours. The reaction mixture was diluted with ethyl acetate and washed with an aqueous solution of sodium bicarbonate and brine. The organic layer was dried over anhydrous magnesium sulfate, filtrated and concentrated. The resulting residue was purified by silica gel column chromatography (Fuji Silysia, NH Silica gel, 200-350 mesh; ethyl acetate-hexane, 1:1 to 4:1 to 9:1 to 1:0) to give the title compound (965 mg, 97%) as a colorless oil.

ESI-MS m/z 791 (M+H)$^+$

Third Step (8E,12E,14E)-7-((4-Cycloheptylpiperazin-1-yl)car-
bonyl)oxy-3,6,16,21-tetrahydroxy-6,10,12,16,20-
pentamethyl-18,19-epoxytricosa-8,12,14-trien-11-
olide (Compound 45)

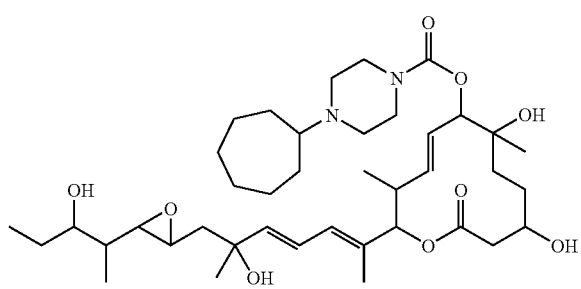

To a solution of Compound 45-2 (8E,12E,14E)-7-((4-cy-cloheptylpiperazin-1-yl)carbonyl)oxy-6-(1-ethoxyethoxy)-3,16,21-trihydroxy-6,10,12,16,20-pentamethyl-18,19-epoxytricosa-8,12,14-trien-11-olide (964 mg, 1.218 mmol) obtained in the second step in a mixture of tetrahydrofuran:2-methyl-2-propanol=1:1 (22 mL) was added pyridinium p-toluenesulfonate (459 mg, 1.827 mmol), and the reaction mixture was stirred at room temperature for 16 hours. The reaction mixture was diluted with ethyl acetate and washed with an aqueous solution of sodium bicarbonate and brine. The organic layer was dried over anhydrous magnesium sulfate, filtrated and concentrated. The resulting residue was purified by silica gel column chromatography (Fuji Silysia, NH Silica gel, 200 to 350 mesh; ethyl acetate-hexane-methanol, 2:1:0 to 4:1:0 to 99:0:1 to 98:0:1 to 97:0:1), and the crude fraction was concentrated. The resulting residue was purified by silica gel column chromatography (Kanto silica gel 60N, 40-50 μm; methanol-dichloromethane, 1:29 to 1:19 to 1:17 to 1:14 to 1:9) to give the title compound (866 mg, 99%) as a colorless oil.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.2 Hz), 1.10-1.77 (24H, m), 1.77 (3H, brs), 1.79-1.90 (3H, m), 2.42-2.74 (9H, m), 2.85-2.92 (1H, m), 3.36-3.70 (5H, m), 3.72-3.84 (1H, m), 4.92 (1H, d, J=10.0 Hz), 5.06 (1H, d, J=10.8 Hz), 5.57 (1H, dd, J=9.6, 15.2 Hz), 5.71 (1H, dd, J=10.0, 15.2 Hz), 5.87 (1H, d, J=15.2 Hz), 6.13 (1H, d, J=11.2 Hz), 6.52 (1H, dd, J=11.2, 15.2 Hz); ESI-MS m/z 719 (M+H)$^+$.

Example 46

(8E,12E,14E)-7-((4-Allylpiperazin-1-yl)carbonyl)
oxy-6-(1-ethoxyethoxy)-3,16,21-trihydroxy-6,10,12,
16,20-pentamethyl-18,19-epoxytricosa-8,12,14-
trien-11-olide (Compound 46)

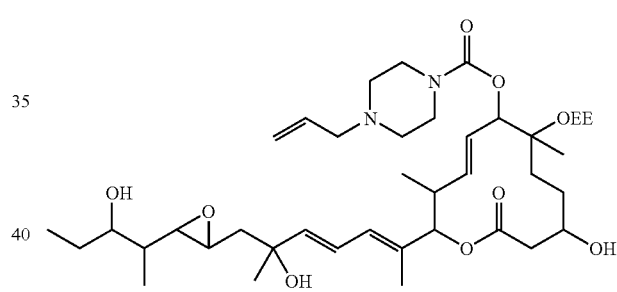

First Step (8E,12E,14E)-7-Acetoxy-6-hydroxy-6,10,12,16,20-
pentamethyl-3,16,21-tris(triethylsiloxy)-18,19-ep-
oxytricosa-8,12,14-trien-11-olide (Compound 46-1)

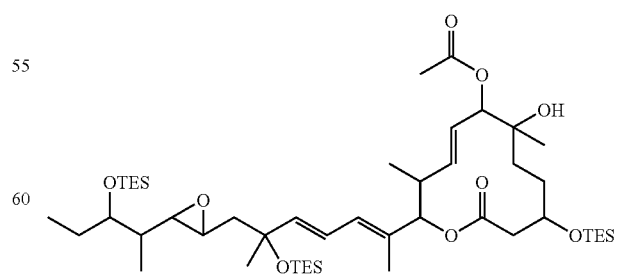

To a solution of (8E,12E,14E)-7-acetoxy-6,3,16,21-tetrahydroxy-6,10,12,16,20-pentamethyl-18,19-epoxytricosa-8,12,14-trien-11-olide (100 mg, 0.18 mmol) in dichloromethane (6 mL) were added N,N-dimethylaminopyridine (221 mg, 1.8 mmol) and chlorotriethylsilane (272 mg, 1.8 mmol) at room temperature, and the reaction mixture was stirred at the same temperature for 18 hours. The reaction mixture was diluted with ethyl acetate and washed with saturated aqueous solution of ammonium chloride and brine. The organic layer was dried over anhydrous magnesium sulfate, filtrated and concentrated. The resulting residue was purified by silica gel column chromatography (Kanto silica gel 60N, 40-100 μm; ethyl acetate:hexane=20:80) to give the title compound (159 mg, 98%) as a colorless oil.

ESI-MS m/z 918 (M+Na)$^+$.

Second Step (8E,12E,14E)-7-Acetoxy-6-(1-ethoxyethoxy)-6,10, 12,16,20-pentamethyl-3,16,21-tris(triethylsiloxy)-18, 19-epoxytricosa-8,12,14-trien-11-olide (Compound 46-2)

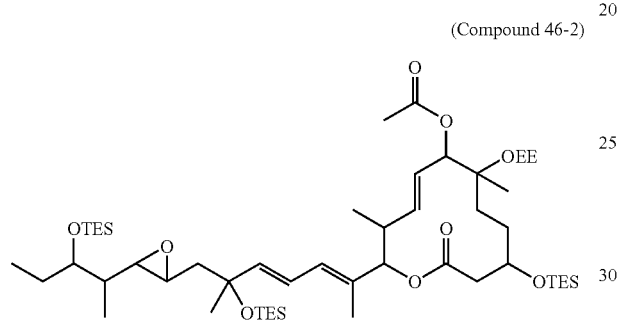

To a solution of Compound 46-1 (8E,12E,14E)-7-acetoxy-6-hydroxy-6,10,12,16,20-pentamethyl-3,16,21-tris(triethylsiloxy)-18,19-epoxytricosa-8,12,14-trien-11-olide (1.6 g, 1.8 mmol) obtained in the first step in dichloromethane (35 mL) were added ethyl vinyl ether (2.6 g, 36 mmol) and pyridinium p-toluenesulfonate (22 mg, 89 μmol) at room temperature, and the resulting mixture was stirred at the same temperature for 19 hours. The reaction mixture was washed with a saturated aqueous solution of sodium bicarbonate and brine. The organic layer was dried over anhydrous magnesium sulfate, filtrated and concentrated. The resulting residue was purified by silica gel column chromatography (Kanto silica gel 60N, 40-100 μm; ethyl acetate:hexane=10:90) to give the title compound (1.6 g, 93%) as a colorless oil.

ESI-MS m/z 990 (M+Na)$^+$.

Third Step (8E,12E,14E)-6-(1-Ethoxyethoxy)-7-hydroxy-6,10, 12,16,20-pentamethyl-3,16,21-tris(triethylsiloxy)-18, 19-epoxytricosa-8,12,14-trien-11-olide (Compound 46-3)

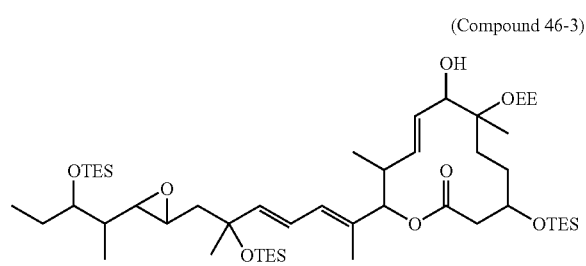

To Compound 46-2 (8E,12E,14E)-7-acetoxy-6-(1-ethoxyethoxy)-6,10,12,16,20-pentamethyl-3,16,21-tris(triethylsiloxy)-18,19-epoxytricosa-8,12,14-trien-11-olide (1.6 g, 1.7 mmol) obtained in the second step was added guanidine/guanidine nitrate (41 mL, 0.2M dichloromethane:methanol=10:90 solution) at room temperature, followed by stirring at the same temperature for three hours. The reaction mixture was diluted with ethyl acetate and washed with a saturated aqueous solution of ammonium chloride and brine. The organic layer was dried over anhydrous magnesium sulfate, filtrated and concentrated. The resulting residue was purified by silica gel column chromatography (Kanto silica gel 60N, 40-100 μm; ethyl acetate:hexane=20:80) to give the title compound (1.3 g, 84%) as a colorless oil.

ESI-MS m/z 948 (M+Na)$^+$.

Fourth Step (8E,12E,14E)-6-(1-Ethoxyethoxy)-6,10,12,16,20-pentamethyl-7-(4-nitrophenoxy)carboxy-3,16,21-tris (triethylsiloxy)-18,19-epoxytricosa-8,12,14-trien-11-olide (Compound 46-4)

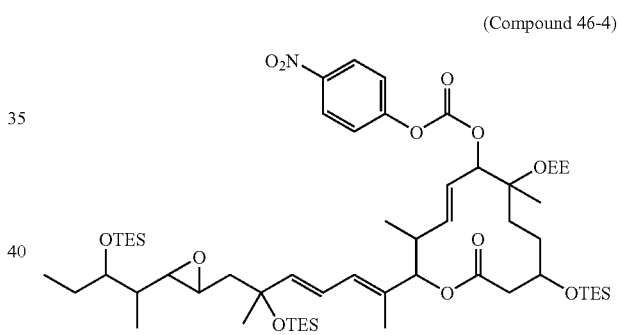

To a solution of Compound 46-3 (8E,12E,14E)-6-(1-ethoxyethoxy)-7-hydroxy-6,10,12,16,20-pentamethyl-3,16, 21-tris(triethylsiloxy)-18,19-epoxytricosa-8,12,14-trien-11-olide (1.3 g, 1.4 mmol) obtained in the third step in dichloromethane (30 mL) were added triethylamine (826 mg, 8.2 mmol), N,N-dimethylaminopyridine (831 mg, 6.8 mmol) and 4-nitrophenyl chloroformate (823 mg, 4.1 mmol) at room temperature, and the resulting mixture was stirred at the same temperature for 1.5 hours. The reaction mixture was diluted with dichloromethane and washed with a saturated aqueous solution of ammonium chloride, a saturated aqueous solution of sodium bicarbonate and brine. The organic layer was dried over anhydrous magnesium sulfate, filtrated and concentrated. The resulting residue was purified by silica gel column chromatography (Kanto silica gel 60N, 40-100 μm; ethyl acetate:hexane=10:90) to give the title compound (1.4 g, 97%) as a colorless oil.

ESI-MS m/z 1114 (M+Na)$^+$.

Fifth Step (8E,12E,14E)-7-((4-Allylpiperazin-1-yl)carbonyl)oxy-6-(1-ethoxyethoxy)-6,10,12,16,20-pentamethyl-3,16,21-tris(triethylsiloxy)-18,19-epoxytricosa-8,12,14-trien-11-olide (Compound 46-5)

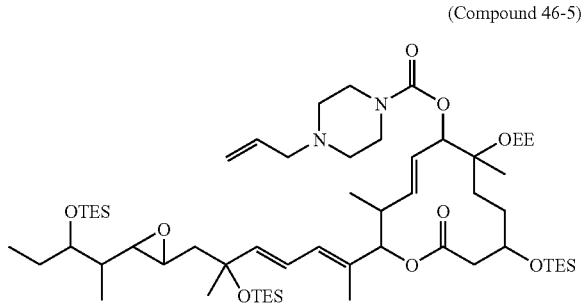

To a solution of Compound 46-4 (8E,12E,14E)-6-(1-ethoxyethoxy)-6,10,12,16,20-pentamethyl-7-(4-nitrophenoxy)carboxy-3,16,21-tris(triethylsiloxy)-18,19-epoxytricosa-8,12,14-trien-11-olide (37 mg, 34 μmol) obtained in the fourth step in tetrahydrofuran (2 mL) were added triethylamine (14 mg, 0.14 mmol) and allylpiperazine (8.5 mg, 68 μmol) at room temperature, and the resulting mixture was stirred at the same temperature for 1.5 hours. The reaction mixture was diluted with ethyl acetate and washed with a saturated aqueous solution of sodium bicarbonate and brine. The organic layer was dried over anhydrous magnesium sulfate, filtrated and concentrated. The resulting residue was purified by silica gel column chromatography (Kanto silica gel 60N, 40-100 μm; ethyl acetate:hexane=30:70) to give the title compound (28 mg, 77%) as a colorless oil.

ESI-MS m/z 1078 (M+H)$^+$.

Sixth Step (8E,12E,14E)-7-((4-Allylpiperazin-1-yl)carbonyl)oxy-6-(1-ethoxyethoxy)-3,16,21-trihydroxy-6,10,12,16,20-pentamethyl-18,19-epoxytricosa-8,12,14-trien-11-olide (Compound 46)

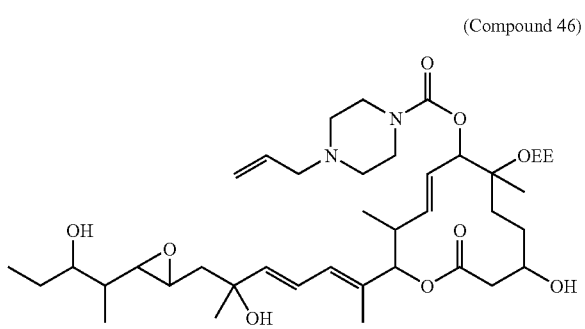

To a solution of Compound 46-5 (8E,12E,14E)-7-((4-allylpiperazin-1-yl)carbonyl)oxy-6-(1-ethoxyethoxy)-6,10,12,16,20-pentamethyl-3,16,21-tris(triethylsiloxy)-18,19-epoxytricosa-8,12,14-trien-11-olide (26 mg, 24 μmol) obtained in the fifth step in tetrahydrofuran (2.5 mL) was added tetrabutylammonium fluoride (79 μL, 1.0 M tetrahydrofuran solution) at room temperature, and this mixture was stirred at the same temperature for three hours. The reaction mixture was diluted with ethyl acetate and washed with a saturated aqueous solution of sodium bicarbonate and brine. The organic layer was dried over anhydrous magnesium sulfate, filtrated and concentrated. The resulting residue was purified by thin layer chromatography (Fuji Silysia, NH Silica gel Plate; methanol:dichloromethane=5:95) to give the title compound (13 mg, 72%) as a colorless oil.

$^1$H-NMR Spectrum (CD$_3$OD, 400 MHz) δ(ppm): 0.85-0.90 (6H, m), 0.94 (3H, t, J=7.6 Hz), 1.12-1.68 (20H, m), 1.78 (3H, s), 1.86 (1H, dd, J=2.4, 7.6 Hz), 2.38-2.62 (7H, m), 2.67 (1H, dd, J=2.4, 8.0 Hz), 2.89 (1H, dt, J=2.0, 6.0 Hz), 3.03 (2H, d, J=6.4 Hz), 3.44-3.62 (7H, m), 3.76-3.84 (1H, m), 4.94-5.14 (3H, m), 5.16-5.26 (2H, m), 5.56 (1H, dd, J=10.0, 15.6 Hz), 5.70-5.82 (3H, m), 6.13 (1H, d, J=10.8 Hz), 6.53 (1H, dd, J=10.8, 15.2 Hz); ESI-MS m/z 735 (M+H)$^+$.

Example 47

(8E,12E,14E)-7-((4-Allylpiperazin-1-yl)carbonyl)oxy-3,6,16,21-tetrahydroxy-6,10,12,16,20-pentamethyl-18,19-epoxytricosa-8,12,14-trien-11-olide (Compound 47)

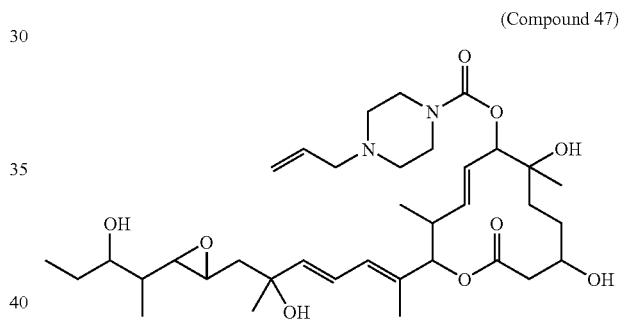

To Compound 46 (8E,12E,14E)-7-((4-allylpiperazin-1-yl)carbonyl)oxy-6-(1-ethoxyethoxy)-3,16,21-trihydroxy-6,10,12,16,20-pentamethyl-18,19-epoxytricosa-8,12,14-trien-11-olide (8.7 mg, 12 μmol) obtained in Example 46 was added a solution of pyridinium p-toluenesulfonate (3.3 mg, 13 μmol) in a mixture of tetrahydrofuran:2-methyl-2-propanol=1:1 (1 mL) at room temperature, and the reaction mixture was stirred at the same temperature for 17 hours. The reaction mixture was concentrated. The resulting residue was purified by thin layer chromatography (Fuji Silysia, NH Silica gel Plate; methanol:dichloromethane=5:95) to give the title compound (5.5 mg, 70%) as a colorless oil.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.2 Hz), 1.21 (3H, s), 1.34 (3H, s), 1.22-1.68 (8H, m), 1.78 (3H, s), 1.86 (1H, dd, J=2.4, 7.6 Hz), 2.38-2.46 (4H, m), 2.48-2.60 (3H, m), 2.67 (1H, dd, J=2.0, 8.0 Hz), 2.89 (1H, dt, J=2.0, 5.6 Hz), 3.04 (2H, d, J=6.8 Hz), 3.42-3.64 (5H, m), 3.74-3.82 (1H, m), 4.92 (1H, d, J=9.6 Hz), 5.06 (1H, d, J=10.8 Hz), 5.16-5.26 (2H, m), 5.57 (1H, dd, J=10.0, 15.6 Hz), 5.71 (1H, dd, J=9.6, 15.2 Hz), 5.82-5.92 (2H, m), 6.13 (1H, d, J=11.2 Hz), 6.53 (1H, dd, J=11.2, 15.2 Hz); ESI-MS m/z 663 (M+H)$^+$.

Example 48

(8E,12E,14E)-7-((4-(3,7-Dimethyl-2,6-octadien-1-yl)piperazin-1-yl)carbonyl)oxy-3,6,16,21-tetrahydroxy-6,10,12,16,20-pentamethyl-18,19-epoxytricosa-8,12,14-trien-11-olide (Compound 48)

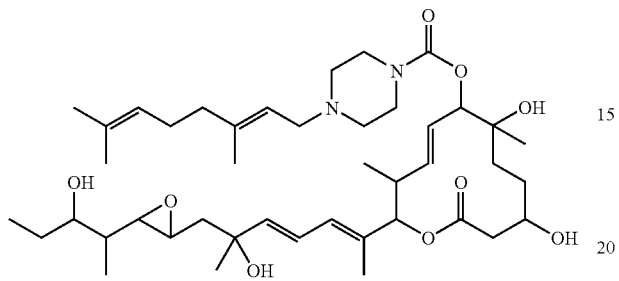

The title compound (a colorless oil) was synthesized by a similar method as described for Examples 46 and 47.

$^1$H-NMR Spectrum (CD$_3$OD, 400 MHz) δ(ppm): 0.89 (3H, d, J=6.4 Hz), 0.90 (3H, d, J=6.8 Hz), 0.94 (3H, t, J=7.2 Hz), 1.21 (3H, s), 1.34 (3H, s), 1.24-1.68 (8H, m), 1.60 (3H, s), 1.66 (6H, s), 1.77 (3H, s), 1.86 (1H, dd, J=5.6, 14.0 Hz), 2.04-2.16 (4H, m), 2.40-2.46 (4H, m), 2.48-2.62 (3H, m), 2.67 (1H, dd, J=2.4, 8.0 Hz), 2.89 (1H, dt, J=2.0, 5.2 Hz), 3.02 (2H, d, J=6.8 Hz), 3.42-3.64 (5H, m), 3.75-3.82 (1H, m), 4.93 (1H, d, J=10.0 Hz), 5.02-5.12 (2H, m), 5.24 (1H, t, J=7.2 Hz), 5.57 (1H, dd, J=10.0, 15.2 Hz), 5.72 (1H, dd, J=9.6, 15.2 Hz), 5.87 (1H, d, J=15.2 Hz), 6.14 (1H, d, J=11.2 Hz), 6.53 (1H, dd, J=10.8, 15.2 Hz); ESI-MS m/z 760 (M+H)$^+$.

Example 49

(8E,12E,14E)-3,6,16,21-Tetrahydroxy-6,10,12,16,20-pentamethyl-7-((4-pentylpiperazin-1-yl)carbonyl)oxy-18,19-epoxytricosa-8,12,14-trien-11-olide (Compound 49)

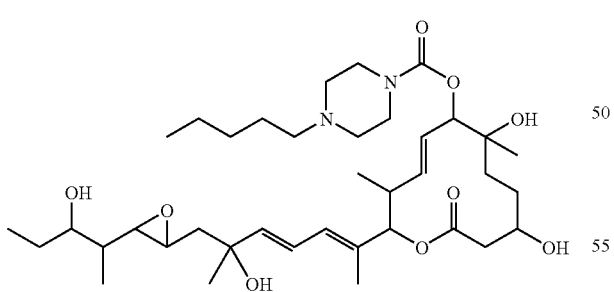

The title compound (a colorless oil) was synthesized by a similar method as described for Examples 46 and 47.

$^1$H-NMR Spectrum (CD$_3$OD, 400 MHz) δ(ppm): 0.89 (3H, d, J=7.2 Hz), 0.90 (3H, d, J=7.2 Hz), 0.94 (3H, t, J=7.6 Hz), 1.21 (3H, s), 1.22-1.68 (20H, m), 1.77 (3H, s), 1.86 (1H, dd, J=5.6, 13.7 Hz), 2.32-2.60 (9H, m), 2.67 (1H, dd, J=2.4, 8.0 Hz), 2.89 (1H, dt, J=1.6, 5.6 Hz), 3.40-3.70 (5H, m), 3.74-3.82 (1H, m), 4.93 (1H, d, J=9.6 Hz), 5.06 (1H, d, J=10.8 Hz), 5.57 (1H, dd, J=10.8, 15.2 Hz), 5.72 (1H, dd, J=10.8, 15.2 Hz), 5.87 (1H, d, J=15.2 Hz), 6.13 (1H, d, J=9.2 Hz), 6.53 (1H, dd, J=10.8, 15.2 Hz); ESI-MS m/z 693 (M+H)$^+$.

Example 50

(8E,12E,14E)-3,6,16,21-Tetrahydroxy-7-((((1S,4S)-5-isopropyl-2,5-diazabicyclo[2.2.1]heptan-2-yl)carbonyl)oxy-6,10,12,16,20-pentamethyl-18,19-epoxytricosa-8,12,14-trien-11-olide (Compound 50)

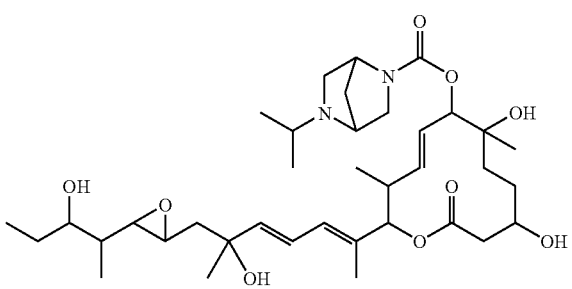

The title compound (a colorless oil) was synthesized by a similar method as described for Examples 46 and 47.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.2 Hz), 1.06-1.12 (6H, m), 1.18-1.68 (16H, m), 1.78 (3H, s), 1.86 (1H, dd, J=5.7, 13.7 Hz), 2.47-2.62 (7H, m), 2.67 (1H, dd, J=2.4, 8.0 Hz), 2.89 (1H, dt, J=2.4, 6.4 Hz), 3.05 (1H, t, J=10.0 Hz), 3.19 (1H, dd, J=2.4, 10.8 Hz), 3.48-3.68 (2H, m), 3.78 (1H, brs), 4.92 (1H, d, J=9.6 Hz), 5.06 (1H, d, J=10.4 Hz), 5.58 (1H, dd, J=9.6, 15.2 Hz), 5.68-5.78 (1H, m), 5.87 (1H, d, J=15.2 Hz), 6.13 (1H, d, J=11.2 Hz), 6.53 (1H, dd, J=11.2, 15.2 Hz); ESI-MS m/z 677 (M+H)$^+$.

Example 51

(8E,12E,14E)-3,6,16,21-Tetrahydroxy-6,10,12,16,20-pentamethyl-7-((4-(3-methyl-2-buten-1-yl)piperazin-1-yl)carbonyl)oxy-18,19-epoxytricosa-8,12,14-trien-11-olide (Compound 51)

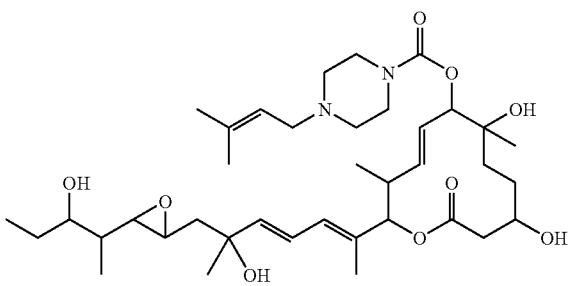

The title compound (a colorless oil) was synthesized by a similar method as described for Example 3.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.2 Hz), 1.21 (3H, s), 1.34 (3H, s), 1.24-1.64 (8H, m), 1.67 (3H, s), 1.75 (3H, s), 1.77 (3H, s), 1.86 (1H, dd, J=5.6, 14.0 Hz), 2.38-2.48 (4H, m), 2.50-2.53 (2H, m), 2.54-2.62 (1H, m), 2.67 (1H, dd, J=2.4, 8.0 Hz), 2.89 (1H, dt, J=2.0, 6.0 Hz), 3.00 (2H, d, J=6.8 Hz), 3.42-3.66 (5H, m), 3.74-3.82 (1H, m), 4.93 (1H, d, J=9.6 Hz), 5.06 (1H, d, J=10.4 Hz), 5.25 (1H, t, J=6.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=10.4 Hz), 6.53 (1H, dd, J=10.8, 15.2 Hz); ESI-MS m/z 691 (M+H)$^+$.

Example 52

(8E,12E,14E)-3,6,16,21-Tetrahydroxy-6,10,12,16,20-pentamethyl-7-((morpholin-4-yl)carbonyl)oxy-18,19-epoxytricosa-8,12,14-trien-11-olide (Compound 52)

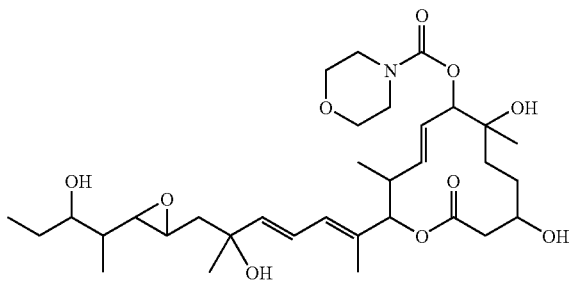

The title compound (a colorless oil) was synthesized by a similar method as described for Example 3.

$^1$H-NMR Spectrum (CD$_3$OD, 400 MHz) δ(ppm): 0.89 (3H, d, J=6.8 Hz), 0.90 (3H, d, J=7.2 Hz), 0.93 (3H, t, J=7.2 Hz), 1.21 (3H, s), 1.34 (3H, s), 1.24-1.70 (8H, m), 1.78 (3H, s), 1.86 (1H, dd, J=5.6, 14.0 Hz), 2.50-2.62 (3H, m), 2.67 (1H, dd, J=2.4, 8.0 Hz), 2.86-2.92 (1H, m), 3.42-3.56 (5H, m), 3.58-3.68 (4H, m), 3.76-3.82 (1H, m), 4.95 (1H, d, J=9.6 Hz), 5.06 (1H, d, J=10.4 Hz), 5.58 (1H, dd, J=10.0, 15.2 Hz), 5.72 (1H, dd, J=9.6, 15.6 Hz), 5.87 (1H, d, J=15.2 Hz), 6.13 (1H, d, J=10.8 Hz), 6.53 (1H, dd, J=10.8, 15.2 Hz); ESI-MS m/z 646 (M+Na)$^+$.

Example 53

(8E,12E,14E)-3,6,16,21-Tetrahydroxy-7-((4-isopropylhomopiperazin-1-yl)carbonyl)oxy-6,10,12,16,20-pentamethyl-18,19-epoxytricosa-8,12,14-trien-11-olide (Compound 53)

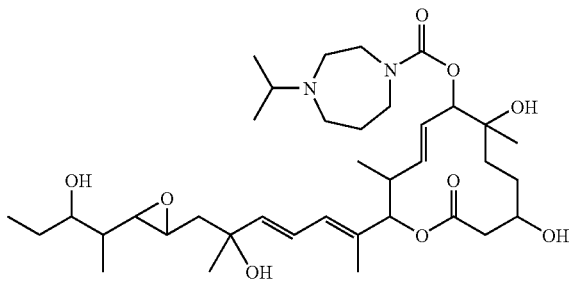

The title compound (a colorless oil) was synthesized by a similar method as described for Example 3.

$^1$H-NMR Spectrum (CD$_3$OD, 40 MHz) δ(ppm): 0.88 (3H, d, J=6.4 Hz), 0.90 (3H, d, J=6.8 Hz), 0.94 (3H, t, J=7.6 Hz), 1.04 (6H, d, J=6.4 Hz), 1.23 (3H, s), 1.23-1.69 (9H, m), 1.34 (3H, s), 1.77 (3H, s), 1.77-1.90 (2H, m), 2.47-2.76 (8H, m), 2.84-2.98 (2H, m), 3.42-3.68 (5H, m), 3.74-3.82 (1H, m), 4.94 (1H, d, J=9.6 Hz), 5.05 (1H, d, J=10.8 Hz), 5.57 (1H, dd, J=9.6, 15.6 Hz), 5.73 (1H, dd, J=9.6, 15.6 Hz), 5.87 (1H, d, J=15.6 Hz), 6.13 (1H, d, J=11.2 Hz), 6.52 (1H, dd, J=11.2, 15.6 Hz); ESI-MS m/z 679 (M+H)$^+$.

Example 54

(8E,12E,14E)-3,6,16,21-Tetrahydroxy-7-((4-isobutylhomopiperazin-1-yl)carbonyl)oxy-6,10,12,16,20-pentamethyl-18,19-epoxytricosa-8,12,14-trien-11-olide (Compound 54)

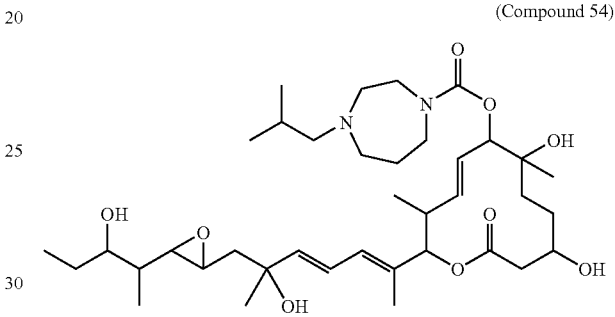

The title compound (a colorless oil) was synthesized by a similar method as described for Example 3.

$^1$H-NMR Spectrum (CD$_3$OD, 400 MHz) δ(ppm): 0.87-0.97 (15H, m), 1.23 (3H, s), 1.23-1.69 (10H, m), 1.34 (3H, s), 1.77 (3H, s), 1.69-1.90 (2H, m), 2.23 (2H, d, J=6.8 Hz), 2.50-2.70 (8H, m), 2.89 (1H, dt, J=2.0, 6.0 Hz), 3.43-3.66 (5H, m), 3.74-3.82 (1H, m), 4.94 (1H, d, J=10.0 Hz), 5.06 (1H, d, J=10.8 Hz), 5.57 (1H, dd, J=9.6, 15.6 Hz), 5.73 (1H, dd, J=9.6, 15.6 Hz), 5.87 (1H, d, J=15.6 Hz), 6.13 (1H, d, J=11.2 Hz), 6.52 (1H, dd, J=11.2, 15.6 Hz); ESI-MS m/z 693 (M+H)$^+$.

Example 55

(8E,12E,14E)-7-((4-(Cyclopentylmethyl)homopiperazin-1-yl)carbonyl)oxy-3,6,16,21-tetrahydroxy-6,10,12,16,20-pentamethyl-18,19-epoxytricosa-8,12,14-trien-11-olide (Compound 55)

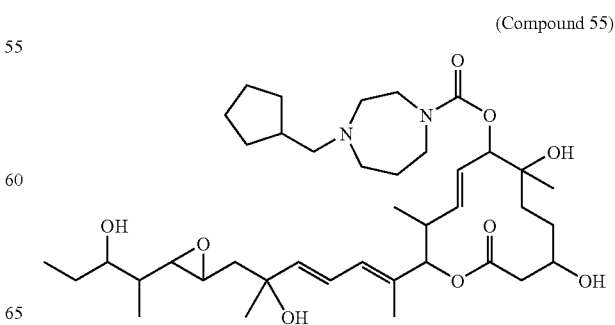

The title compound (a colorless oil) was synthesized by a similar method as described for Example 3.

¹H-NMR Spectrum (CD₃OD, 400 MHz) δ(ppm): 0.89 (3H, d, J=6.4 Hz), 0.90 (3H, d, J=6.8 Hz), 0.94 (3H, t, J=7.2 Hz), 1.15-2.20 (20H, m), 1.23 (3H, s), 1.34 (3H, s), 1.77 (3H, s), 2.42 (2H, d, J=7.2 Hz), 2.46-2.74 (8H, m), 2.86-2.92 (1H, m), 3.40-3.68 (5H, m), 3.75-3.82 (1H, m), 4.94 (1H, d, J=9.6 Hz), 5.07 (1H, d, J=10.8 Hz), 5.57 (1H, dd, J=9.6, 15.2 Hz), 5.73 (1H, dd, J=9.6, 15.6 Hz), 5.87 (1H, d, J=15.6 Hz), 6.13 (1H, d, J=10.8 Hz), 6.52 (1H, dd, J=10.8, 15.6 Hz); ESI-MS m/z 719 (M+H)⁺.

Example 56

(8E,12E,14E)-7-(N-((3S)-1-Ethylpyrrolidin-3-yl)-N-methylcarbamoyloxy)-3,6,16,21-tetrahydroxy-6,10,12,16,20-pentamethyl-18,19-epoxytricosa-8,12,14-trien-11-olide

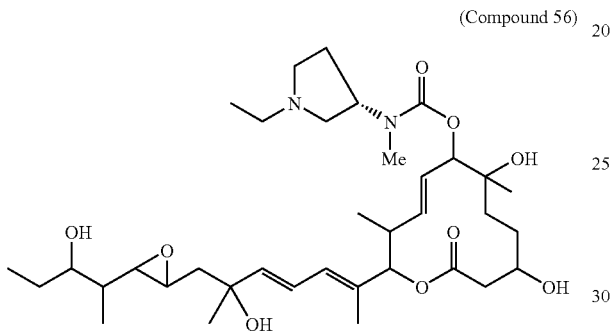

(Compound 56)

The title compound (a colorless oil) was synthesized by a similar method as described for Example 3.

¹H-NMR Spectrum (CD₃OD, 400 MHz) δ(ppm): 0.89 (3H, d, J=6.8 Hz), 0.90 (3H, d, J=6.8 Hz), 0.94 (3H, t, J=7.2 Hz), 1.12 (3H, t, J=7.6 Hz), 1.23 (3H, s), 1.23-1.70 (9H, m), 1.34 (3H, s), 1.77 (3H, s), 1.86 (1H, dd, J=5.2, 14.0 Hz), 2.08-2.22 (1H, m), 2.38-2.90 (11H, m), 2.90 (3H, s), 3.28-3.33 (1H, covered with CD₃OD), 3.49-3.56 (1H, m), 3.75-3.82 (1H, m), 4.87-4.93 (1H, covered with H₂O), 5.06 (1H, d, J=10.4 Hz), 5.58 (1H, dd, J=9.6, 15.2 Hz), 5.71 (1H, dd, J=9.6, 15.6 Hz), 5.87 (1H, d, J=15.6 Hz), 6.13 (1H, d, J=11.2 Hz), 6.52 (1H, dd, J=11.2, 15.6 Hz); ESI-MS m/z 665 (M+H)⁺.

Example 57

(8E,12E,14E)-7-((4-(Cyclobutylmethyl)homopiperazin-1-yl)carbonyl)oxy-3,6,16,21-tetrahydroxy-6,10,12,16,20-pentamethyl-18,19-epoxytricosa-8,12,14-trien-11-olide

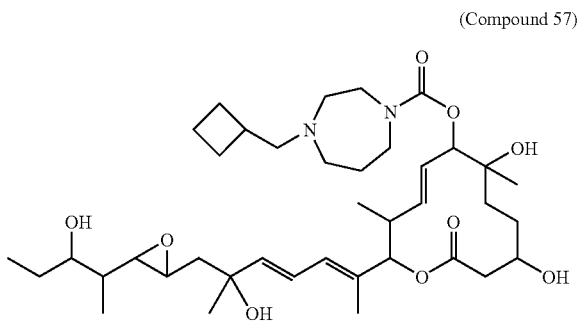

(Compound 57)

The title compound (a colorless oil) was synthesized by a similar method as described for Example 3.

¹H-NMR Spectrum (CD₃OD, 400 MHz) δ(ppm): 0.89 (6H, d, J=6.8 Hz), 0.94 (3H, t, J=7.2 Hz), 1.23 (3H, s), 1.23-1.96 (16H, m), 1.34 (3H, s), 1.77 (3H, s), 2.02-2.12 (2H, m), 2.50-2.64 (8H, m), 2.64-2.70 (2H, m), 2.86-2.92 (1H, m), 3.40-3.68 (5H, m), 3.75-3.82 (1H, m), 4.94 (1H, d, J=9.6 Hz), 5.07 (1H, d, J=10.8 Hz), 5.57 (1H, dd, J=9.6, 15.2 Hz), 5.72 (1H, dd, J=9.6, 15.6 Hz), 5.87 (1H, d, J=15.2 Hz), 6.13 (1H, d, J=10.8 Hz), 6.52 (1H, dd, J=10.8, 15.2 Hz); ESI-MS m/z 705 (M+H)⁺.

Example 58

(8E,12E,14E)-3,6,16,21-Tetrahydroxy-6,10,12,16,20-pentamethyl-7-(((2S)-2-((pyrrolidin-1-yl)methyl)pyrrolidin-1-yl)carbonyl)oxy-18,19-epoxytricosa-8,12,14-trien-11-olide

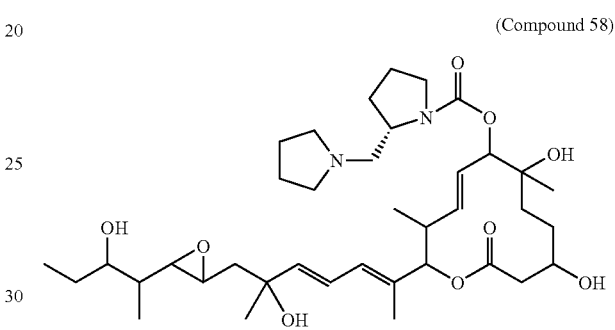

(Compound 58)

The title compound (a colorless oil) was synthesized by a similar method as described for Example 3.

¹H-NMR Spectrum (CD₃OD, 400 MHz) δ(ppm): 0.89 (3H, d, J=6.8 Hz), 0.90 (3H, d, J=7.2 Hz), 0.94 (3H, t, J=7.2 Hz), 1.20-2.03 (17H, m), 1.23 (3H, s), 1.34 (3H, s), 1.77 (3H, s), 2.38-2.70 (10H, m), 2.85-2.92 (1H, m), 3.33-3.44 (1H, m), 3.49-3.56 (1H, m), 3.75-3.82 (1H, m), 3.93-4.08 (2H, m), 4.93 (1H, d, J=9.6 Hz), 5.06 (1H, d, J=10.4 Hz), 5.57 (1H, dd, J=9.6, 15.2 Hz), 5.73 (1H, dd, J=9.6, 15.6 Hz), 5.87 (1H, d, J=15.2 Hz), 6.13 (1H, d, J=10.8 Hz), 6.53 (1H, dd, J=10.8, 15.2 Hz); ESI-MS m/z 691 (M+H)⁺.

Example 59

(8E,12E,14E)-7-(((3S)-3,4-Dimethylpiperazin-1-yl)carbonyl)oxy-3,6,16,21-tetrahydroxy-6,10,12,16,20-pentamethyl-18,19-epoxytricosa-8,12,14-trien-11-olide

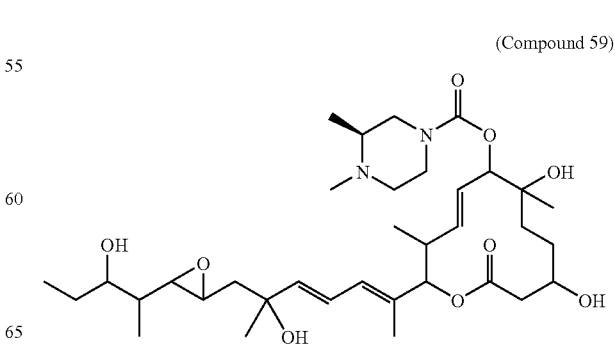

(Compound 59)

The title compound (a colorless oil) was synthesized by a similar method as described for Examples 46 and 47.

$^1$H-NMR Spectrum (CD$_3$OD, 400 MHz) δ(ppm): 0.89 (3H, d, J=6.8 Hz), 0.90 (3H, d, J=7.2 Hz), 0.94 (3H, t, J=7.6 Hz), 1.08 (3H, d, J=6.4 Hz), 1.21 (3H, s), 1.221-1.69 (8H, m), 1.34 (3H, s), 1.77 (3H, s), 1.86 (1H, dd, J=5, 2, 14.0 Hz), 2.02-2.23 (2H, m), 2.30 (3H, s), 2.46-2.84 (6H, m), 2.89 (1H, dt, J=2.0, 5.6 Hz), 2.94-3.12 (1H, m), 3.48-3.55 (1H, m), 3.75-3.82 (1H, m), 3.82-4.20 (2H, m), 4.93 (1H, d, J=9.6 Hz), 5.06 (1H, d, J=10.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, d, J=10.8 Hz), 6.52 (1H, dd, J=10.8, 15.2 Hz); ESI-MS m/z 651 (M+H)$^+$.

Example 60

(8E,12E,14E)-3,6,16,21-Tetrahydroxy-6,10,12,16,20-pentamethyl-7-((4-(prop-2-yn-1-yl)piperazin-1-yl)carbonyl)oxy-18,19-epoxytricosa-8,12,14-trien-11-olide (Compound 60)

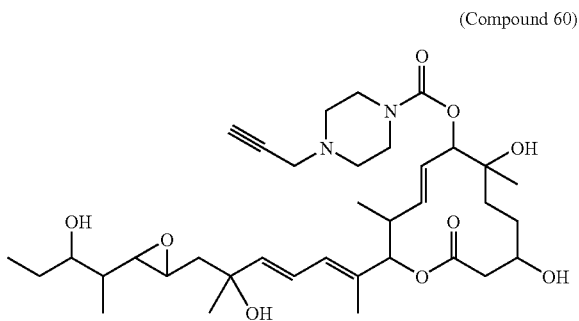

The title compound (a colorless oil) was synthesized by a similar method as described for Examples 46 and 47.

$^1$H-NMR Spectrum (CD$_3$OD, 400 MHz) δ(ppm): 0.89 (3H, d, J=6.8 Hz), 0.90 (3H, d, J=7.2 Hz), 0.94 (3H, t, J=7.6 Hz), 1.22 (3H, s), 1.22-1.69 (8H, m), 1.34 (3H, s), 1.77 (3H, s), 1.86 (1H, dd, J=5, 6, 14.0 Hz), 2.50-2.64 (7H, m), 2.64-2.70 (2H, m), 2.89 (1H, dt, J=2.0, 5.6 Hz), 3.30 (2H, d, J=2.4 Hz), 3.40-3.74 (5H, m), 3.75-3.82 (1H, m), 4.93 (1H, d, J=9.6 Hz), 5.06 (1H, d, J=10.8 Hz), 5.58 (1H, dd, J=9.6, 15.2 Hz), 5.71 (1H, dd, J=9.6, 15.2 Hz), 5.87 (1H, d, J=15.2 Hz), 6.13 (1H, d, J=10.8 Hz), 6.52 (1H, dd, J=11.2, 15.2 Hz); ESI-MS m/z 661 (M+H)$^+$.

Example 61

(8E,12E,14E)-7-((4-(But-2-yn-1-yl)piperazin-1-yl)carbonyl)oxy-3,6,16,21-tetrahydroxy-6,10,12,16,20-pentamethyl-18,19-epoxytricosa-8,12,14-trien-11-olide (Compound 61)

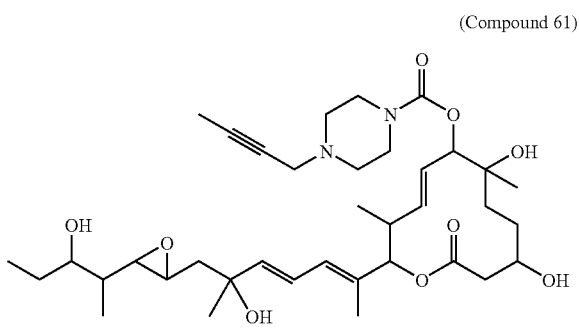

The title compound (a colorless oil) was synthesized by a similar method as described for Examples 46 and 47.

$^1$H-NMR Spectrum (CD$_3$OD, 400 MHz) δ(ppm): 0.89 (3H, d, J=6.8 Hz), 0.90 (3H, d, J=7.2 Hz), 0.94 (3H, t, J=7.6 Hz), 1.22 (3H, s), 1.22-1.69 (8H, m), 1.34 (3H, s), 1.77 (3H, s), 1.80 (3H, t, J=2.4 Hz), 1.86 (1H, dd, J=14.0, 5, 6 Hz), 2.45-2.64 (7H, m), 2.66 (1H, dd, J=2.0, 8.0 Hz), 2.89 (1H, dt, J=2.0, 6.0 Hz), 3.25 (2H, q, J=2.4 Hz) 3.40-3.72 (5H, m), 3.74-3.82 (1H, m), 4.93 (1H, d, J=9.6 Hz), 5.06 (1H, d, J=10.4 Hz), 5.57 (1H, dd, J=10.0, 15.2 Hz), 5.73 (1H, dd, J=10.6, 15.2 Hz), 5.87 (1H, d, J=15.2 Hz), 6.13 (1H, d, J=11.2 Hz), 6.52 (1H, dd, J=11.2, 15.2 Hz); ESI-MS m/z 675 (M+H)$^+$.

Example 62

(8E,12E,14E)-7-((4-Cyclobutylhomopiperazin-1-yl)carbonyl)oxy-3,6,16,21-tetrahydroxy-6,10,12,16,20-pentamethyl-18,19-epoxytricosa-8,12,14-trien-11-olide (Compound 62)

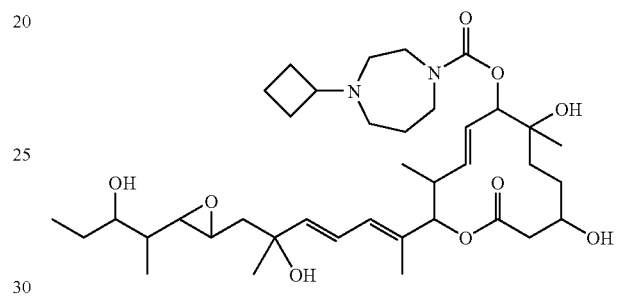

The title compound (a colorless oil) was synthesized by a similar method as described for Example 3.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.2 Hz), 1.23 (3H, s), 1.25-1.29 (1H, m), 1.34 (3H, s), 1.34-1.71 (9H, m), 1.77 (3H, brs), 1.80-1.90 (5H, m), 2.01-2.12 (2H, m), 2.38-2.62 (7H, m), 2.66 (1H, dd, J=2.0, 7.6 Hz), 2.86-2.97 (2H, m), 3.42-3.67 (5H, m), 3.75-3.82 (1H, m), 4.94 (1H, d, J=9.6 Hz), 5.06 (1H, d, J=10.8 Hz), 5.57 (1H, dd, J=9.6, 15.2 Hz), 5.72 (1H, dd, J=10.0, 15.2 Hz), 5.87 (1H, d, J=15.2 Hz), 6.13 (1H, d, J=10.8 Hz), 6.52 (1H, dd, J=10.8, 15.2 Hz); ESI-MS m/z 691 (M+H)$^+$.

Example 63

(8E,12E,14E)-7-((4-Ethylhomopiperazin-1-yl)carbonyl)oxy-3,6,16,21-tetrahydroxy-6,10,12,16,20-pentamethyl-18,19-epoxytricosa-8,12,14-trien-11-olide (Compound 63)

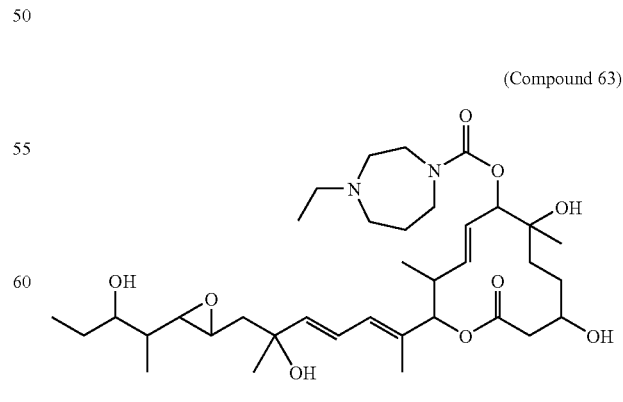

The title compound (a colorless oil) was synthesized by a similar method as described for Example 3.

¹H-NMR Spectrum (CD₃OD, 400 MHz) δ(ppm): 0.89 (3H, d, J=6.8 Hz), 0.90 (3H, d, J=7.2 Hz), 0.94 (3H, t, J=7.2 Hz), 1.09 (3H, t, J=7.2 Hz), 1.23 (3H, s), 1.23-1.30 (1H, m), 1.34 (3H, s), 1.34-1.69 (7H, m), 1.77 (3H, s), 1.83-1.92 (3H, m), 2.47-2.78 (10H, m), 2.89 (1H, dt, J=2.4, 6.4 Hz), 3.44-3.68 (5H, m), 3.75-3.83 (1H, m), 4.94 (1H, d, J=9.6 Hz), 5.06 (1H, d, J=10.8 Hz), 5.58 (1H, dd, J=9.6, 15.2 Hz), 5.73 (1H, dd, J=9.6, 15.2 Hz), 5.87 (1H, d, J=15.2 Hz), 6.13 (1H, d, J=10.8 Hz), 6.52 (1H, dd, J=10.8, 15.2 Hz); ESI-MS m/z 665 (M+H)⁺.

Example 64

(8E,12E,14E)-7-((4-Butylhomopiperazin-1-yl)carbonyl)oxy-3,6,16,21-tetrahydroxy-6,10,12,16,20-pentamethyl-18,19-epoxytricosa-8,12,14-trien-11-olide (Compound 64)

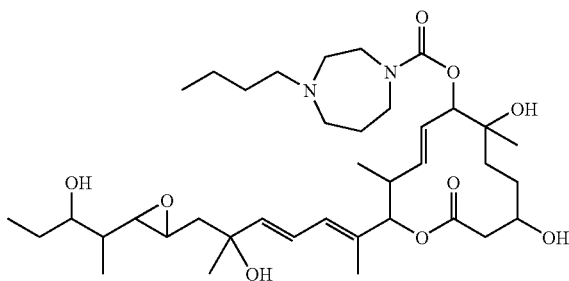

The title compound (a colorless oil) was synthesized by a similar method as described for Example 3.

¹H-NMR Spectrum (CD₃OD, 400 MHz) δ(ppm): 0.89 (3H, d, J=6.4 Hz), 0.90 (3H, d, J=7.2 Hz), 0.94 (3H, t, J=7.6 Hz), 0.95 (3H, t, J=7.2 Hz), 1.23 (3H, s), 1.23-1.30 (1H, m), 1.34 (3H, s), 1.30-1.69 (11H, m), 1.77 (3H, s), 1.86 (1H, dd, J=5.6, 14.0 Hz), 1.90-1.98 (2H, m), 2.47-2.62 (3H, m), 2.62-2.73 (3H, m), 2.78-2.98 (5H, m), 3.44-3.73 (5H, m), 3.76-3.82 (1H, m), 4.95 (1H, d, J=10.4 Hz), 5.06 (1H, d, J=10.4 Hz), 5.58 (1H, dd, J=9.6, 15.2 Hz), 5.73 (1H, dd, J=9.6, 15.2 Hz), 5.87 (1H, d, J=15.2 Hz), 6.13 (1H, d, J=10.8 Hz), 6.52 (1H, dd, J=10.8, 15.2 Hz); ESI-MS m/z 693 (M+H)⁺.

Example 65

(8E,12E,14E)-7-((4-Cyclohexylhomopiperazin-1-yl)carbonyl)oxy-3,6,16,21-tetrahydroxy-6,10,12,16,20-pentamethyl-18,19-epoxytricosa-8,12,14-trien-11-olide (Compound 65)

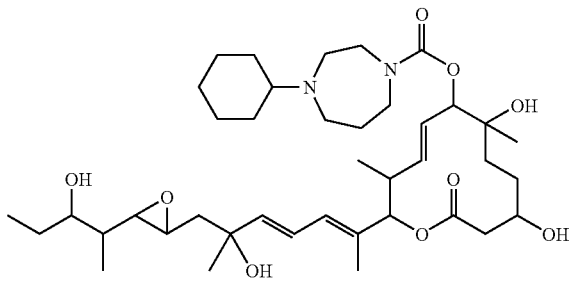

The title compound (a colorless oil) was synthesized by a similar method as described for Example 3.

¹H-NMR Spectrum (CD₃OD, 400 MHz) δ(ppm): 0.89 (3H, d, J=6.8 Hz), 0.90 (3H, d, J=7.2 Hz), 0.94 (3H, t, J=7.6 Hz), 1.06-1.69 (20H, m), 1.74-1.90 (10H, m), 2.44-2.85 (9H, m), 2.89 (1H, dt, J=2.0, 5.6 Hz), 3.40-3.67 (5H, m), 3.74-3.83 (1H, m), 4.94 (1H, d, J=10.0 Hz), 5.06 (1H, d, J=10.8 Hz), 5.57 (1H, dd, J=9.6, 15.2 Hz), 5.72 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 719 (M+H)⁺.

Example 66

(8E,12E,14E)-3,6,16,21-Tetrahydroxy-6,10,12,16,20-pentamethyl-7-((4-(3-methyl-2-buten-1-yl)homopiperazin-1-yl)carbonyl)oxy-18,19-epoxytricosa-8,12,14-trien-11-olide (Compound 66)

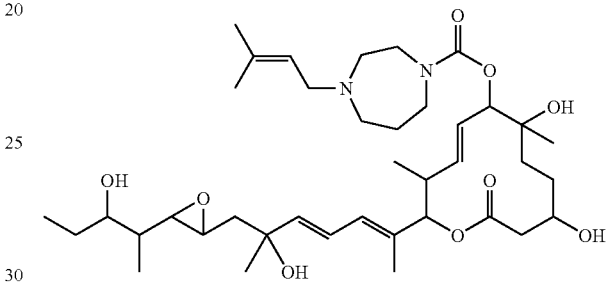

The title compound (a colorless oil) was synthesized by a similar method as described for Example 3.

¹H-NMR Spectrum (CD₃OD, 400 MHz) δ(ppm): 0.89 (3H, d, J=6.4 Hz), 0.90 (3H, d, J=6.8 Hz), 0.94 (3H, t, J=7.2 Hz), 1.16-1.67 (14H, m), 1.67 (3H, s), 1.76 (3H, s), 1.77 (3H, s), 1.82-1.93 (3H, m), 2.44-2.80 (8H, m), 2.89 (1H, dd, J=2.4, 5.6 Hz), 3.17 (2H, d, J=7.2 Hz), 3.43-3.70 (5H, m), 3.72-3.83 (1H, m), 4.95 (1H, d, J=10.0 Hz), 5.06 (1H, d, J=10.4 Hz), 5.20-5.30 (1H, m), 5.57 (1H, dd, J=10.0, 15.2 Hz), 5.72 (1H, dd, J=10.0, 15.2 Hz), 5.87 (1H, d, J=15.2 Hz), 6.13 (1H, d, J=11.2 Hz), 6.53 (1H, dd, J=11.2, 15.2 Hz); ESI-MS m/z 705 (M+H)⁺.

Example 67

(8E,12E,14E)-7-((4-(2-(N,N-Dimethylamino)ethyl)piperazin-1-yl)carbonyl)oxy-3,6,16,21-tetrahydroxy-6,10,12,16,20-pentamethyl-18,19-epoxytricosa-8,12,14-trien-11-olide (Compound 67)

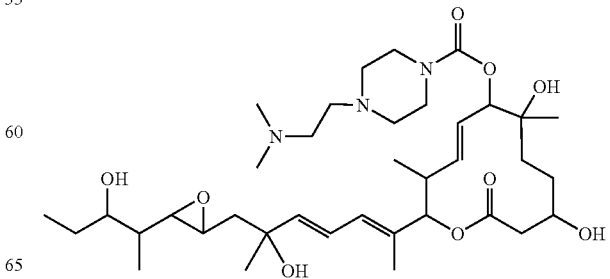

The title compound (a colorless oil) was synthesized by a similar method as described for Example 3.

$^1$H-NMR Spectrum (CD$_3$OD, 400 MHz) δ(ppm): 0.89 (3H, d, J=6.4 Hz), 0.90 (3H, d, J=6.8 Hz), 0.94 (3H, t, J=7.2 Hz), 1.98-1.69 (14H, m), 1.77 (3H, s), 1.86 (1H, dd, J=6.0, 15.2 Hz), 2.33 (6H, s), 2.40-2.62 (11H, m), 2.66 (1H, dd, J=2.4, 8.0 Hz), 2.89 (1H, dt, J=2.4, 6.4 Hz), 3.38-3.70 (5H, m), 3.74-3.82 (1H, m), 4.93 (1H, d, J=10.0 Hz), 5.06 (1H, d, J=10.4 Hz), 5.57 (1H, dd, J=10.0, 15.2 Hz), 5.71 (1H, dd, J=10.0, 15.2 Hz), 5.86 (1H, d, J=15.2 Hz), 6.13 (1H, d, J=10.8 Hz), 6.52 (1H, dd, J=10.8, 15.2 Hz); ESI-MS m/z 694 (M+H)$^+$.

Example 68

(8E,12E,14E)-7-((4-(2-(N,N-Diethylamino)ethyl)piperazin-1-yl)carbonyl)oxy-3,6,16,21-tetrahydroxy-6,10,12,16,20-pentamethyl-18,19-epoxytricosa-8,12,14-trien-11-olide (Compound 68)

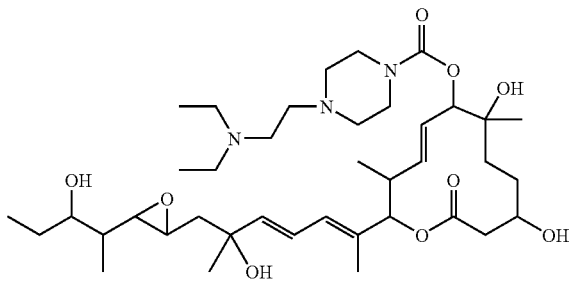

The title compound (a colorless oil) was synthesized by a similar method as described for Example 3.

$^1$H-NMR Spectrum (CD$_3$OD, 400 MHz) δ(ppm): 0.89 (3H, d, J=6.8 Hz), 0.90 (3H, d, J=6.8 Hz), 0.94 (3H, t, J=7.6 Hz), 1.08 (6H, t, J=7.2 Hz), 1.21 (3H, s), 1.22-1.30 (1H, m), 1.34 (3H, s), 1.34-1.68 (7H, m), 1.77 (3H, s), 1.86 (1H, dd, J=5.2, 14.0 Hz), 2.40-2.72 (16H, m), 2.89 (1H, dt, J=2.0, 6.0 Hz), 3.38-3.70 (5H, m), 3.74-3.82 (1H, m), 4.93 (1H, d, J=9.6 Hz), 5.06 (1H, d, J=10.8 Hz), 5.57 (1H, dd, J=9.6, 15.2 Hz), 5.71 (1H, dd, J=9.6, 15.2 Hz), 5.86 (1H, d, J=15.2 Hz), 6.13 (1H, d, J=10.8 Hz), 6.52 (1H, dd, J=10.8, 15.2 Hz); ESI-MS m/z 722 (M+H)$^+$.

Example 69

(8E,12E,14E)-7-((4-(2,2-Dimethylpropyl)homopiperazin-1-yl)carbonyl)oxy-3,6,16,21-tetrahydroxy-6,10,12,16,20-pentamethyl-18,19-epoxytricosa-8,12,14-trien-11-olide

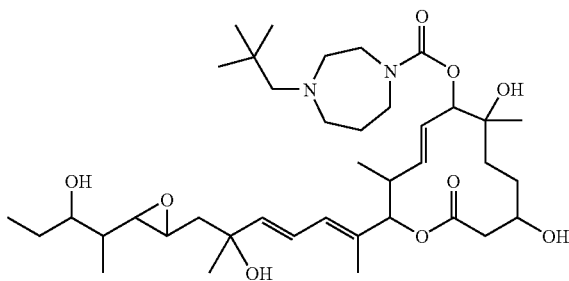

The title compound (a colorless oil) was synthesized by a similar method as described for Example 3.

$^1$H-NMR Spectrum (CD$_3$OD, 400 MHz) δ(ppm): 0.85 (6H, s), 0.86 (3H, s), 0.89 (3H, d, J=6.8 Hz), 0.90 (3H, d, J=6.8 Hz), 0.94 (3H, t, J=7.2 Hz), 1.18-1.68 (14H, m), 1.72-1.82 (5H, m), 1.86 (1H, dd, J=5.6, 14.0 Hz), 2.28 (2H, s), 2.46-2.62 (3H, m), 2.66 (1H, dd, J=2.4, 8.0 Hz), 2.68-2.75 (2H, m), 2.81 (2H, dd, J=5.2, 10.4 Hz), 2.89 (1H, dt, J=2.0, 6.0 Hz), 3.36-3.68 (5H, m), 3.72-3.82 (1H, m), 4.94 (1H, d, J=9.6 Hz), 5.06 (1H, d, J=10.8 Hz), 5.57 (1H, dd, J=9.6, 14.8 Hz), 5.73 (1H, dd, J=9.6, 14.8 Hz), 5.87 (1H, d, J=15.2 Hz), 6.13 (1H, d, J=10.8 Hz), 6.53 (1H, dd, J=10.8, 15.2 Hz); ESI-MS m/z 707 (M+H)$^+$.

Example 70

(8E,12E,14E)-7-((4-Cyclopentylhomopiperazin-1-yl)carbonyl)oxy-3,6,16,21-tetrahydroxy-6,10,12,16,20-pentamethyl-18,19-epoxytricosa-8,12,14-trien-11-olide (Compound 70)

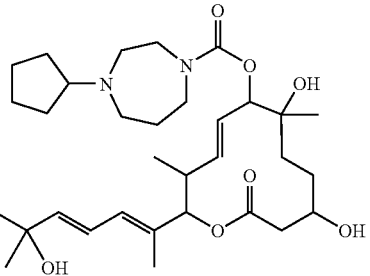

The title compound (a colorless oil) was synthesized by a similar method as described for Example 3.

$^1$H-NMR Spectrum (CD$_3$OD, 400 MHz) δ(ppm): 0.89 (3H, d, J=6.8 Hz), 0.90 (3H, d, J=7.2 Hz), 0.94 (3H, t, J=7.2 Hz), 1.18-1.68 (18H, m), 1.70-1.77 (2H, m), 1.77 (3H, s), 1.86 (1H, dd, J=5.6, 14.0 Hz), 1.88-2.02 (4H, m), 2.46-2.62 (3H, m), 2.66 (1H, dd, J=2.0, 8.0 Hz), 2.82-3.02 (5H, m), 3.08-3.22 (1H, m), 3.42-3.73 (5H, m), 3.73-3.84 (1H, m), 4.95 (1H, d, J=9.6 Hz), 5.06 (1H, d, J=10.4 Hz), 5.58 (1H, dd, J=9.6, 15.2 Hz), 5.73 (1H, dd, J=9.6, 15.2 Hz), 5.87 (1H, d, J=15.2 Hz), 6.13 (1H, d, J=1.2 Hz), 6.53 (1H, dd, J=11.2, 15.2 Hz); ESI-MS m/z 705 (M+H)$^+$.

Example 71

(8E,12E,14E)-7-((4-Cyclopropylpiperazin-1-yl)carbonyl)oxy-3,6,16,21-tetrahydroxy-6,10,12,16,20-pentamethyl-18,19-epoxytricosa-8,12,14-trien-11-olide (Compound 71)

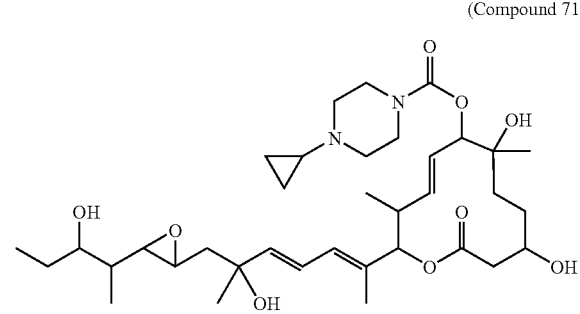

The title compound (a colorless oil) was synthesized by a similar method as described for Example 3.

¹H-NMR Spectrum (CD₃OD, 400 MHz) δ(ppm): 0.34-0.52 (4H, m), 0.89 (3H, d, J=6.8 Hz), 0.90 (3H, d, J=6.8 Hz), 0.94 (3H, t, J=7.6 Hz), 1.13-1.70 (15H, m), 1.77 (3H, s), 1.86 (1H, dd, J=5.2, 14.0 Hz), 2.35-2.72 (8H, m), 2.80-2.92 (1H, m), 3.30-3.68 (5H, m), 3.70-3.82 (1H, m), 4.92 (1H, d, J=10.0 Hz), 5.05 (1H, d, J=10.4 Hz), 5.57 (1H, dd, J=9.6, 15.2 Hz), 5.70 (1H, dd, J=9.6, 15.2 Hz), 5.86 (1H, d, J=15.2 Hz), 6.13 (1H, d, J=1.2 Hz), 6.52 (1H, dd, J=11.2, 15.2 Hz); ESI-MS m/z 663 (M+H)⁺, 685 (M+Na)⁺.

Example 72

(8E,12E,14E)-7-((4-(1,1-Dimethylethyl)piperazin-1-yl)carbonyl)oxy-3,6,16,21-tetrahydroxy-6,10,12,16,20-pentamethyl-18,19-epoxytricosa-8,12,14-trien-11-olide (Compound 72)

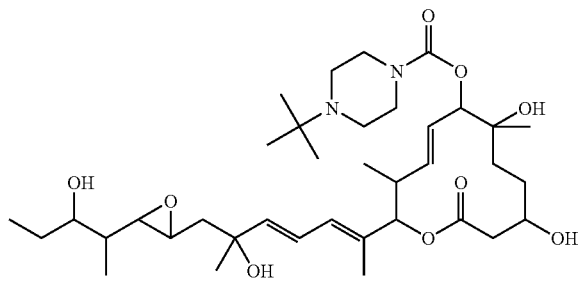

The title compound (a colorless oil) was synthesized by a similar method as described for Example 3.

¹H-NMR Spectrum (CD₃OD, 400 MHz) δ(ppm): 0.89 (3H, d, J=6.8 Hz), 0.90 (3H, d, J=6.8 Hz), 0.94 (3H, t, J=7.2 Hz), 1.10 (9H, s), 1.22 (3H, s), 1.22-1.30 (1H, m), 1.34 (3H, s), 1.35-1.69 (7H, m), 1.77 (3H, s), 1.86 (1H, dd, J=5.2, 14.0 Hz), 2.50-2.64 (7H, m), 2.67 (1H, dd, J=2.4, 8.0 Hz), 2.89 (1H, dt, J=2.0, 6.0 Hz), 3.38-3.68 (5H, m), 3.74-3.82 (1H, m), 4.93 (1H, d, J=10.0 Hz), 5.06 (1H, d, J=10.4 Hz), 5.57 (1H, dd, J=9.6, 15.2 Hz), 5.71 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 679 (M+H)⁺.

Example 73

(8E,12E,14E)-7-((4-Cyclopropylhomopiperazin-1-yl)carbonyl)oxy-3,6,16,21-tetrahydroxy-6,10,12,16,20-pentamethyl-18,19-epoxytricosa-8,12,14-trien-11-olide (Compound 73)

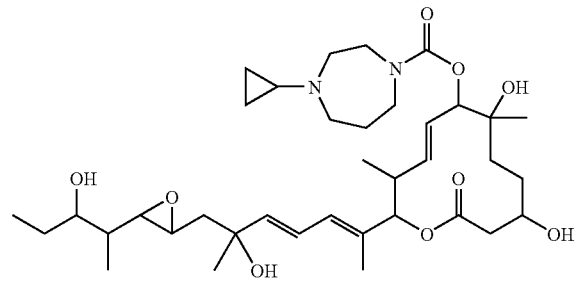

The title compound (a colorless oil) was synthesized by a similar method as described for Example 3.

¹H-NMR Spectrum (CD₃OD, 400 MHz) δ(ppm): 0.32-0.54 (4H, m), 0.89 (3H, d, J=6.8 Hz), 0.90 (3H, d, J=6.8 Hz), 0.94 (3H, t, J=7.2 Hz), 1.14-1.68 (15H, m), 1.69-1.93 (6H, m), 2.42-2.62 (3H, m), 2.66 (1H, dd, J=2.4, 8.0 Hz), 2.70-2.92 (5H, m), 3.38-3.68 (5H, m), 3.68-3.82 (1H, m), 4.94 (1H, d, J=10.4 Hz), 5.06 (1H, d, J=10.4 Hz), 5.57 (1H, dd, J=10.0, 15.2 Hz), 5.72 (1H, dd, J=9.6, 15.2 Hz), 5.87 (1H, d, J=15.2 Hz), 6.13 (1H, d, J=11.2 Hz), 6.52 (1H, dd, J=11.2, 15.2 Hz); ESI-MS m/z 677 (M+H)⁺.

Example 74

(8E,12E,14E)-7-((4-(2,2-Dimethylpropyl)piperazin-1-yl)carbonyl)oxy-3,6,16,21-tetrahydroxy-6,10,12,16,20-pentamethyl-18,19-epoxytricosa-8,12,14-trien-11-olide (Compound 74)

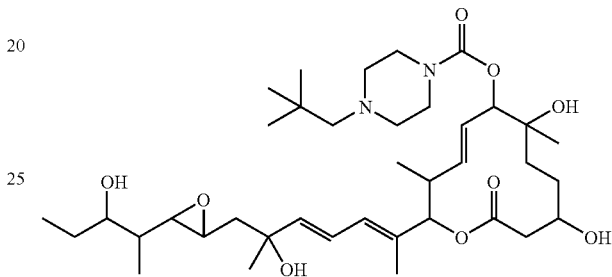

The title compound (a colorless oil) was synthesized by a similar method as described for Example 3.

¹H-NMR Spectrum (CD₃OD, 400 MHz) δ(ppm): 0.87-0.92 (15H, m), 0.94 (3H, t, J=7.6 Hz), 1.20-1.29 (4H, m), 1.31-1.69 (10H, m), 1.77 (3H, d, J=1.2 Hz), 1.86 (1H, dd, J=5.2, 14.0 Hz), 2.09 (2H, s), 2.45-2.64 (7H, m), 2.67 (1H, dd, J=2.4, 8.0 Hz), 2.89 (1H, dt, J=2.4, 6.0 Hz), 3.36-3.67 (5H, m), 3.75-3.83 (1H, m), 4.92 (1H, d, J=9.6 Hz), 5.06 (1H, d, J=10.8 Hz), 5.57 (1H, dd, J=10.0, 15.2 Hz), 5.71 (1H, dd, J=9.6, 15.2 Hz), 5.87 (1H, d, J=15.2 Hz), 6.13 (1H, dd, J=1.6, 10.8 Hz), 6.53 (1H, dd, J=10.8, 15.2 Hz); ESI-MS m/z 693 (M+H)⁺.

Example 75

(8E,12E,14E)-7-(N-(2-(N',N'-Diethylamino)ethyl)-N-methylcarbamoyloxy)-3,6,16,21-tetrahydroxy-6,10,12,16,20-pentamethyl-18,19-epoxytricosa-8,12,14-trien-11-olide (Compound 75)

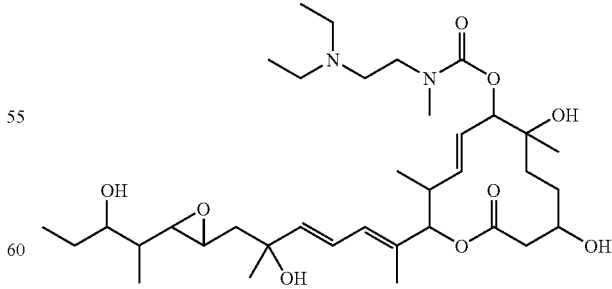

The title compound (a colorless oil) was synthesized by a similar method as described for Example 3.

¹H-NMR Spectrum (CD₃OD, 400 MHz) δ(ppm): 0.88 (3H, d, J=6.6 Hz), 0.89 (3H, d, J=7.0 Hz), 0.93 (3H, t, J=7.3 Hz), 1.06 (6H, brt, J=7.0 Hz), 1.15-1.65 (7H, m), 1.22 (3H, brs), 1.33 (3H, s), 1.65 (1H, dd, J=6.2, 14.3H), 1.77 (3H, s), 1.86 (1H, dd, J=6.2, 14.3 Hz), 2.46-2.65 (5H, m), 2.59 (4H, q, J=7.0 Hz), 2.66 (1H, dd, J=2.2, 8.1 Hz), 2.89 (1H, dt, J=2.2, 6.2 Hz), 2.92 (1.6H, s), 2.99 (1.4H, s), 3.28-3.40 (1H, m), 3.52 (1H, dt, J=4.0, 8.4 Hz), 3.52-3.62 (1H, m), 3.74-3.81 (1H, m), 4.92 (1H, d, J=9.5 Hz), 5.06 (1H, d, J=10.6 Hz), 5.56 (1H, dd, J=9.9, 15.0 Hz), 5.72 (1H, dd, J=9.5, 15.0 Hz), 5.86 (1H, d, J=15.4 Hz), 6.13 (1H, d, J=11.0 Hz), 6.52 (1H, dd, J=11.0, 15.4 Hz); ESI-MS m/z 667 (M+H)⁺.

Example 76

(8E,12E,14E)-3,6,16,21-Tetrahydroxy-6,10,12,16,20-pentamethyl-7-(N-methyl-N-(2-(morpholin-4-yl)ethyl)carbamoyloxy)-18,19-epoxytricosa-8,12,14-trien-11-olide (Compound 76)

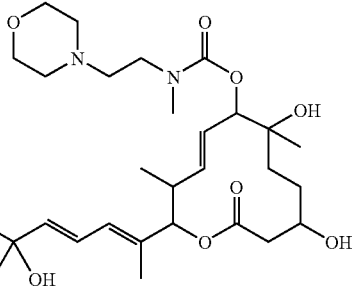

The title compound (a colorless oil) was synthesized by a similar method as described for Example 3.

¹H-NMR Spectrum (CD₃OD, 400 MHz) δ(ppm): 0.888 (3H, d, J=6.6 Hz), 0.894 (3H, d, J=7.0 Hz), 0.93 (3H, t, J=7.3 Hz), 1.19-1.65 (7H, m), 1.22 (3H, s), 1.33 (3H, s), 1.65 (1H, dd, J=6.6, 13.9 Hz), 1.77 (3H, d, J=0.7 Hz), 1.86 (1H, dd, J=6.2, 13.9 Hz), 2.45-2.61 (9H, m), 2.66 (1H, dd, J=2.6, 7.7 Hz), 2.89 (1H, dt, J=2.6, 6.2 Hz), 2.91 (1.6H, s), 2.98 (1.4H, s), 3.30-3.45 (1H, m), 3.52 (1H, dt, J=4.4, 8.1 Hz), 3.60-3.71 (5H, m), 3.74-3.81 (1H, m), 4.92 (1H, d, J=9.9 Hz), 5.06 (1H, d, J=10.6 Hz), 5.51-5.60 (1H, m), 5.67-5.77 (1H, m), 5.86 (1H, d, J=15.0 Hz), 6.13 (1H, d, J=11.0 Hz), 6.52 (1H, dd, J=11.0, 15.0 Hz); ESI-MS m/z 681 (M+H)⁺.

Example 77

(8E,12E,14E)-3,6,16,21-Tetrahydroxy-6,10,12,16,20-pentamethyl-7-(N-methyl-N-(2-(piperidin-1-yl)ethyl)carbamoyloxy)-18,19-epoxytricosa-8,12,14-trien-11-olide (Compound 77)

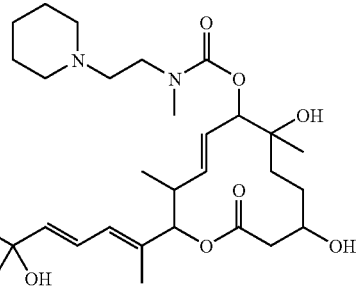

The title compound (a colorless oil) was synthesized by a similar method as described for Example 3.

¹H-NMR Spectrum (CD₃OD, 400 MHz) δ(ppm): 0.88 (3H, d, J=7.0 Hz), 0.89 (3H, d, J=7.0 Hz), 0.93 (3H, t, J=7.3 Hz), 1.19-1.68 (17H, m), 1.33 (3H, s), 1.77 (3H, d, J=0.7 Hz), 1.86 (1H, dd, J=5.5, 13.9 Hz), 2.4-2.62 (9H, m), 2.66 (1H, dd, J=2.6, 7.7 Hz), 2.87-2.92 (1H, m), 2.90 (1.6H, s), 2.98 (1.4H, s), 3.36-3.45 (1H, m), 3.52 (1H, dt, J=4.4, 8.4 Hz), 3.55-3.62 (1H, m), 3.74-3.81 (1H, m), 4.86-4.93 (1H, m), 5.05 (1H, d, J=10.6 Hz), 5.56 (1H, dd, J=9.9, 15.0 Hz), 5.71 (1H, dd, J=10.6, 15.0 Hz), 5.86 (1H, d, J=15.4 Hz), 6.13 (1H, d, J=11.0 Hz), 6.52 (1H, dd, J=11.0, 15.4 Hz); ESI-MS m/z 679 (M+H)⁺.

Example 78

(8E,12E,14E)-7-(N-Ethyl-N-(2-(morpholin-4-yl)ethyl)carbamoyloxy)-3,6,16,21-tetrahydroxy-6,10,12,16,20-pentamethyl-18,19-epoxytricosa-8,12,14-trien-11-olide (Compound 78)

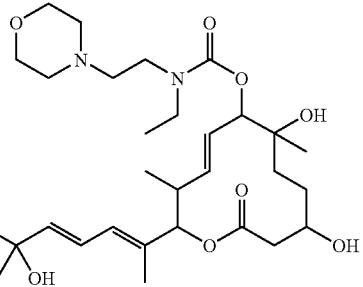

The title compound (a colorless oil) was synthesized by a similar method as described for Example 3.

¹H-NMR Spectrum (CD₃OD, 400 MHz) δ(ppm): 0.886 (3H, d, J=6.6 Hz), 0.893 (3H, d, J=7.0 Hz), 0.93 (3H, t, J=7.3 Hz), 1.08-1.17 (3H, m), 1.18-1.65 (7H, m), 1.22 (3H, s), 1.33 (3H, s), 1.65 (1H, dd, J=5.5, 13.9 Hz), 1.77 (3H, d, J=10.1 Hz), 1.86 (1H, dd, J=5.5, 13.9 Hz), 2.44-2.62 (9H, m), 2.66 (1H, dd, J=2.2, 8.1 Hz), 2.89 (1H, dt, J=2.2, 5.5 Hz), 3.30-3.54 (3H, m), 3.52 (1H, dt, J=4.4, 8.4 Hz), 3.54-3.71 (5H, m), 3.73-3.81 (1H, m), 4.92 (1H, brd, J=9.5 Hz), 5.06 (1H, d, J=10.6 Hz), 5.57 (1H, dd, J=9.9, 15.0 Hz), 5.67-5.78 (1H, m), 5.86 (1H, d, J=15.0 Hz), 6.13 (1H, d, J=11.0 Hz), 6.52 (1H, dd, J=11.0, 15.0 Hz); ESI-MS m/z 695 (M+H)⁺.

Example 79

(8E,12E,14E)-3,6,16,21-Tetrahydroxy-6,10,12,16,20-pentamethyl-7-(N-methyl-N-(2-(pyrrolidin-1-yl)ethyl)carbamoyloxy)-18,19-epoxytricosa-8,12,14-trien-11-olide (Compound 79)

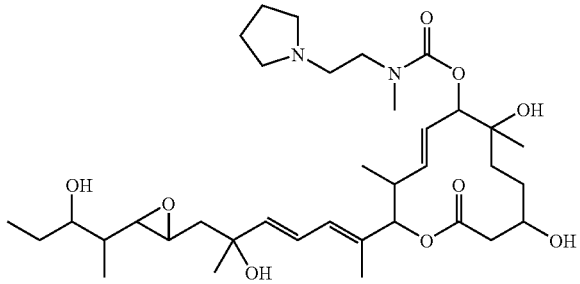

The title compound (a colorless oil) was synthesized by a similar method as described for Example 3.

¹H-NMR Spectrum (CD₃OD, 400 MHz) δ(ppm): 0.88 (3H, d, J=6.6 Hz), 0.89 (3H, d, J=7.0 Hz), 0.93 (3H, t, J=7.3 Hz), 1.19-1.65 (10H, m), 1.33 (3H, s), 1.65 (1H, dd, J=5.5, 14.3 Hz), 1.74-1.85 (4H, m), 1.77 (3H, s), 1.86 (1H, dd, J=5.5, 14.3 Hz), 2.49-2.68 (10H, m), 2.86-2.92 (1H, m), 2.91 (1.6H, s), 2.99 (1.4H, s), 3.39-3.60 (2H, m), 3.52 (1H, dt, J=4.4, 8.4 Hz), 3.73-3.81 (1H, m), 4.91 (1H, d, J=9.5 Hz), 5.05 (1H, d, J=10.6 Hz), 5.56 (1H, dd, J=9.9, 15.4 Hz), 5.72 (1H, dd, J=9.5, 15.4 Hz), 5.86 (1H, d, J=15.4 Hz), 6.13 (1H, d, J=11.0 Hz), 6.52 (1H, dd, J=11.0, 15.4 Hz); ESI-MS m/z 665 (M+H)⁺.

Example 80

(8E,12E,14E)-7-(N-(3-(N',N'-Diethylamino)propyl)-N-methylcarbamoyloxy)-3,6,16,21-tetrahydroxy-6,10,12,16,20-pentamethyl-18,19-epoxytricosa-8,12,14-trien-11-olide (Compound 80)

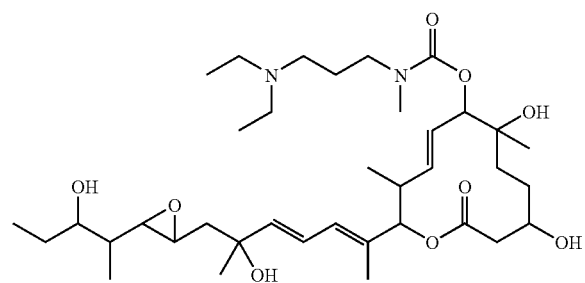

The title compound (a colorless oil) was synthesized by a similar method as described for Example 3.

¹H-NMR Spectrum (CD₃OD, 400 MHz) δ(ppm): 0.88 (3H, d, J=6.6 Hz), 0.89 (3H, d, J=7.0 Hz), 0.93 (3H, t, J=7.3 Hz), 1.05 (6H, t, J=7.3 Hz), 1.21-1.81 (10H, m), 1.21 (3H, s), 1.33 (3H, s), 1.77 (3H, s), 1.86 (1H, dd, J=5.5, 13.6 Hz), 2.46-2.62 (5H, m), 2.58 (4H, q, J=7.3 Hz), 2.66 (1H, dd, J=2.2, 8.1 Hz), 2.87-2.95 (1H, m), 2.89 (1.6H, s), 2.97 (1.4H, s), 3.20-3.32 (1H, m), 3.50-3.59 (1H, m), 3.52 (1H, dt, J=4.4, 8.4 Hz), 3.74-3.82 (1H, m), 4.93 (1H, d, J=9.9 Hz), 5.06 (1H, d, J=10.6 Hz), 5.56 (1H, dd, J=9.9, 15.0 Hz), 5.73 (1H, dd, J=9.9, 15.0 Hz), 5.86 (1H, d, J=15.4 Hz), 6.13 (1H, d, J=11.0 Hz), 6.52 (1H, dd, J=11.0, 15.4 Hz); ESI-MS m/z 681 (M+H)⁺.

Example 81

(8E,12E,14E)-3,6,16,21-Tetrahydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide (Compound 81)

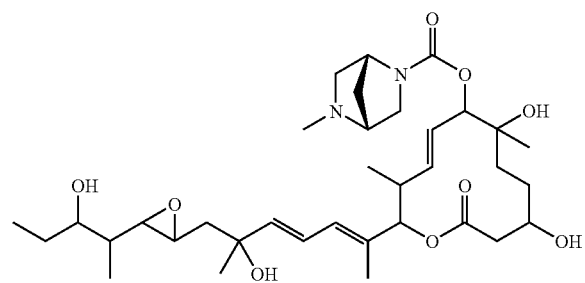

The title compound (a colorless oil) was synthesized by a similar method as described for Example 3.

¹H-NMR Spectrum (CD₃OD, 400 MHz) δ(ppm): 0.88 (3H, d, J=6.6 Hz), 0.89 (3H, d, J=7.0 Hz), 0.93 (3H, t, J=7.3 Hz), 1.19-1.70 (7H, m), 1.20 (1.2H, s), 1.22 (1.8H, s), 1.33 (3H, s), 1.65 (1H, dd, J=6.2, 14.3 Hz), 1.72-1.77 (1H, m), 1.77 (3H, d, J=0.7 Hz), 1.86 (1H, dd, J=6.2, 14.3 Hz), 1.86-1.92 (1H, m), 2.38 (1.2H, s), 2.40 (1.8H, s), 2.50-2.62 (3H, m), 2.63-2.70 (2H, m), 2.74-2.83 (1H, m), 2.89 (1H, dt, J=2.2, 6.2 Hz), 3.21 (0.6H, dd, J=1.8, 10.6 Hz), 3.36 (0.4H, dd, J=1.8, 10.6 Hz), 3.47-3.59 (3H, m), 3.75-3.82 (1H, m), 4.32 (0.4H, s), 4.55 (0.6H, s), 4.91 (1H, d, J=9.9 Hz), 5.06 (1H, d, J=10.6 Hz), 5.68-5.77 (1H, m), 5.51-5.61 (1H, m), 5.86 (1H, d, J=15.0 Hz), 6.13 (1H, d, J=11.0 Hz), 6.52 (1H, dd, J=11.0, 15.0 Hz); ESI-MS m/z 649 (M+H)⁺.

Example 82

(8E,12E,14E)-7-(((1S,4S)-5-Ethyl-2,5-diazabicyclo[2.2.1]heptan-2-yl)carbonyl)oxy-3,6,16,21-tetrahydroxy-6,10,12,16,20-pentamethyl-18,19-epoxytricosa-8,12,14-trien-11-olide (Compound 82)

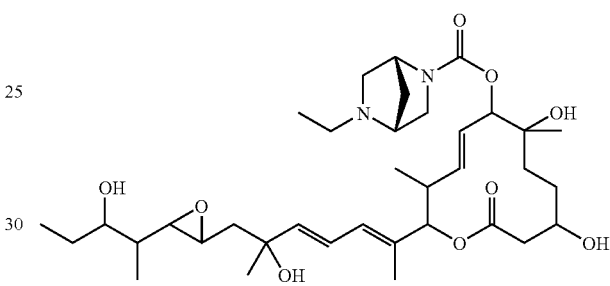

The title compound (a colorless oil) was synthesized by a similar method as described for Examples 46 and 47.

¹H-NMR Spectrum (CD₃OD, 400 MHz) δ(ppm): 0.93 (3H, d, J=6.8 Hz), 0.94 (3H, d, J=6.8 Hz), 0.98 (3H, t, J=7.2 Hz), 110-1.18 (3H, m), 1.22-1.74 (14H, m), 1.80 (1H, brs), 1.82 (3H, s) 1.87-1.95 (2H, m), 2.51-2.77 (7H, m), 2.87-2.97 (2H, m), 3.23-3.29 (0.5H, m), 3.37-3.43 (0.5H, m), 3.51-3.63 (2H, m), 3.63-3.69 (1H, m), 3.79-3.87 (1H, m), 4.37 (0.5H, brs), 4.60 (0.5H, brs), 4.96 (1H, d, J=9.6 Hz), 5.11 (1H, d, J=10.4 Hz), 5.57-5.67 (1H, m), 5.72-5.67 (1H, m), 5.91 (1H, d, J=15.2 Hz), 6.18 (1H, d, J=11.2 Hz), 6.57 (1H, dd, J=11.2, 15.2 Hz); ESI-MS m/z 663 (M+H)+.

Example 83

(8E,12E,14E)-7-((4-Cyclooctylpiperazin-1-yl)carbonyl)oxy-3,6,16,21-tetrahydroxy-6,10,12,16,20-pentamethyl-18,19-epoxytricosa-8,12,14-trien-11-olide (Compound 83)

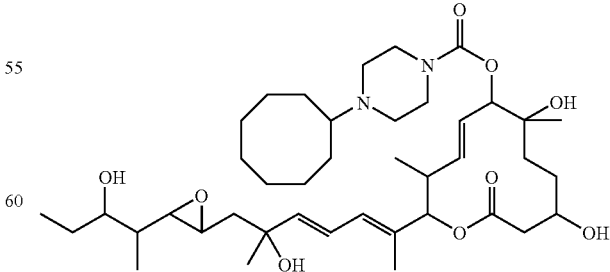

The title compound (a colorless oil) was synthesized by a similar method as described for Examples 46 and 47.

¹H-NMR Spectrum (CD₃OD, 400 MHz) δ(ppm): 0.94 (3H, d, J=6.8 Hz), 0.94 (3H, d, J=6.8 Hz), 0.98 (3H, t, J=7.2

Hz), 1.25 (3H, s), 1.25-1.87 (28H, m), 1.91 (1H, dd, J=5.6, 14.4 Hz), 2.50-2.76 (9H, m), 2.93 (1H, dt, J=2.0, 6.0 Hz), 3.42-3.74 (5H, m), 3.78-3.88 (1H, m), 4.97 (1H, d, J=9.6 Hz), 5.11 (1H, d, J=10.4 Hz), 5.61 (1H, dd, J=9.6, 15.2 Hz), 5.76 (1H, dd, J=9.6, 15.2 Hz), 5.91 (1H, d, J=15.2 Hz), 6.18 (1H, d, J=11.2 Hz), 6.57 (1H, dd, J=11.2, 15.2 Hz); ESI-MS m/z 733 (M+H)$^+$.

Example 84

(8E,12E,14E)-7-((4-(Ethoxycarbonylmethyl)piperazin-1-yl)carbonyl)oxy-3,6,16,21-tetrahydroxy-6,10,12,16,20-pentamethyl-18,19-epoxytricosa-8,12,14-trien-11-olide (Compound 84)

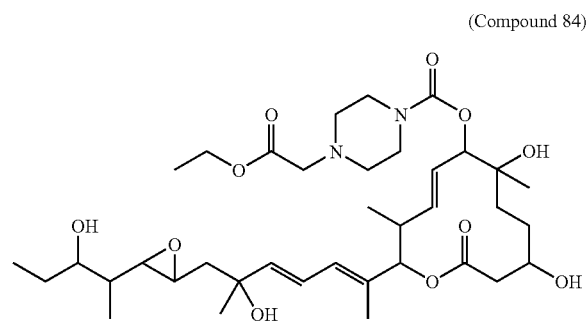

The title compound (a colorless oil) was synthesized by a similar method as described for Examples 46 and 47.

$^1$H-NMR Spectrum (CD$_3$OD, 400 MHz) δ(ppm): 0.89 (3H, d, J=6.4 Hz), 0.90 (3H, d, J=6.8 Hz), 0.94 (3H, t, J=7.2 Hz), 1.20-1.42 (3H, m), 1.21 (3H, s), 1.26 (3H, t, J=7.2 Hz), 1.34 (3H, s), 1.44-1.54 (2H, m), 1.56-1.64 (2H, m), 1.65 (1H, dd, J=6.5, 14.4 Hz), 1.78 (3H, s), 1.86 (1H, dd, J=5.0, 14.4 Hz), 2.50-2.62 (7H, m), 2.67 (1H, dd, J=2.4, 8.0 Hz), 2.87-2.91 (1H, m), 3.26 (2H, s), 3.40-3.70 (4H, m), 3.50-3.55 (1H, m), 3.75-3.81 (1H, m), 4.17 (2H, q, J=7.2 Hz), 4.93 (1H, d, J=10.0 Hz), 5.06 (1H, d, J=10.4 Hz), 5.57 (1H, dd, J=10.0, 15.2 Hz), 5.71 (1H, dd, J=9.8, 15.2 Hz) 5.87 (1H, d, J=15.6 Hz), 6.13 (1H, d, J=10.0 Hz), 6.53 (1H, dd, J=10.8, 15.2 Hz); ESI-MS m/z 731 (M+Na)$^+$.

Example 85

(8E,12E,14E)-3,16,21-Trihydroxy-6-methoxy-6,10,12,16,20-pentamethyl-7-((4-methylpiperazin-1-yl)carbonyl)oxy-18,19-epoxytricosa-8,12,14-trien-11-olide (Compound 85)

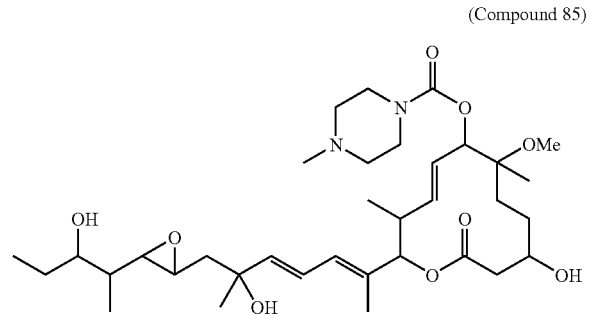

First Step (8E,12E,14E)-7-Acetoxy-6-methoxy-6,10,12,16,20-pentamethyl-3,16,21-tris(triethylsiloxy)-18,19-epoxytricosa-8,12,14-trien-11-olide (Compound 85-1)

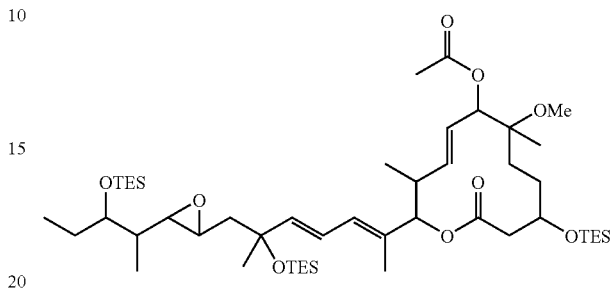

To a solution of Compound 46-1 (8E,12E,14E)-7-acetoxy-6-hydroxy-6,10,12,16,20-pentamethyl-3,16,21-tris(triethylsiloxy)-18,19-epoxytricosa-8,12,14-trien-11-olide (171 mg, 0.19 mmol) obtained in the first step of Example 46 in toluene (6 mL) were added methyl trifluoromethanesulfonate (188 mg, 1.14 mmol) and 1,8-bis(N,N-dimethylamino)naphthalene (368 mg, 1.71 mmol) at room temperature, and the reaction mixture was stirred at 65° C. for 14 hours. Further, methyl trifluoromethanesulfonate (304 mg, 1.9 mmol) and 1,8-bis(N,N-dimethylamino)naphthalene (400 mg, 1.9 mmol) were added to this mixture at room temperature, and the reaction mixture was stirred at 65° C. for 6 hours. The reaction mixture was diluted with diethyl ether and was filtrated through a glass filter. The filtrate was mixed with 28% aqueous ammonia (1 mL), and the reaction mixture was stirred at room temperature for one hour and sequentially washed with brine, a 0.1M aqueous solution of citric acid, a saturated aqueous solution of sodium bicarbonate and brine. The organic layer was dried over anhydrous magnesium sulfate, filtrated and concentrated. The resulting residue was purified by silica gel column chromatography (Kanto silica gel 60N, 40-100 μm; ethyl acetate:hexane=10:90) to give the title compound (141 mg, 84%) as a colorless oil.

ESI-MS m/z 932 (M+Na)$^+$.

Second Step (8E,12E,14E)-7-Hydroxy-6-methoxy-6,10,12,16,20-pentamethyl-3,16,21-tris(triethylsiloxy)-18,19-epoxytricosa-8,12,14-trien-11-olide (Compound 85-2)

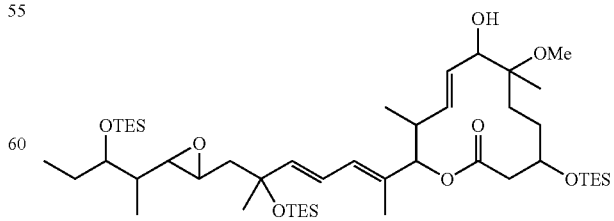

To a solution of Compound 85-1 (8E,12E,14E)-7-acetoxy-6-methoxy-6,10,12,16,20-pentamethyl-3,16,21-tris(triethylsiloxy)-18,19-epoxytricosa-8,12,14-trien-11-olide (158 mg, 0.17 mmol) obtained in the first step in methanol (5 mL) was added potassium carbonate (120 mg, 0.87 mmol) at room temperature, then the reaction mixture was stirred at the same temperature for three hours. The reaction mixture was diluted with ethyl acetate and washed with brine. The organic layer was dried over anhydrous magnesium sulfate and concentrated. The crude product was purified by silica gel column chromatography (Kanto silica gel 60N, 40-100 μm; ethyl acetate:hexane=10:90) to give the title compound (91 mg, 61%) as a colorless oil.

ESI-MS m/z 890 (M+Na)$^+$.

Third Step (8E,12E,14E)-6-Methoxy-6,10,12,16,20-pentamethyl-7-(4-nitrophenoxy)carboxy-3,16,21-tris(triethylsiloxy)-18,19-epoxytricosa-8,12,14-trien-11-olide (Compound 85-3)

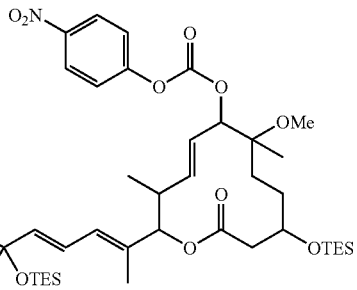

To a solution of Compound 85-2 (8E,12E,14E)-7-hydroxy-6-methoxy-6,10,12,16,20-pentamethyl-3,16,21-tris(triethylsiloxy)-18,19-epoxytricosa-8,12,14-trien-11-olide (91 mg, 0.11 mmol) obtained in the second step in dichloromethane (4 mL) were added triethylamine (64 mg, 0.52 mmol), N,N-dimethylaminopyridine (64 mg, 0.52 mmol) and 4-nitrophenyl chloroformate (63 mg, 0.31 mmol) at room temperature, and the reaction mixture was stirred at the same temperature for 2.5 hours. The reaction mixture was diluted with ethyl acetate and washed with a saturated aqueous solution of sodium bicarbonate and brine. The organic layer was dried over anhydrous magnesium sulfate and concentrated. The resulting residue was purified by silica gel column chromatography (Kanto silica gel 60N, 40-100 μm; ethyl acetate:hexane=10:90) to give the title compound (97 mg, 89%) as a colorless oil.

ESI-MS m/z 1055 (M+Na)$^+$.

Fourth Step (8E,12E,14E)-6-Methoxy-6,10,12,16,20-pentamethyl-7-((4-methylpiperazin-11-yl)carbonyl)oxy-3,16,21-tris(triethylsiloxy)-18,19-epoxytricosa-8,12,14-trien-11-olide (Compound 85-4)

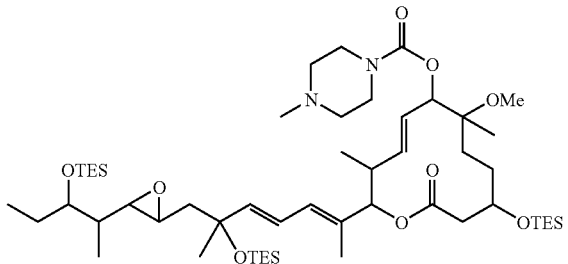

To a solution of Compound 85-3 (8E,12E,14E)-6-methoxy-6,10,12,16,20-pentamethyl-7-(4-nitrophenoxy)carboxy-3,16,21-tris(triethylsiloxy)-18,19-epoxytricosa-8,12,14-trien-11-olide (30 mg, 29 μmol) obtained in the third step in tetrahydrofuran (2 mL) were added triethylamine (11 mg, 0.12 mmol) and 1-methylpiperazine (5.8 mg, 58 μmol) at room temperature, and the reaction mixture was stirred at the same temperature for one hour. The reaction mixture was diluted with ethyl acetate and washed with a saturated aqueous solution of sodium bicarbonate and brine. The organic layer was dried over anhydrous magnesium sulfate, filtrated and concentrated. The resulting residue was purified by silica gel column chromatography (Kanto silica gel 60N, 40-100 μm; methanol:dichloromethane=3:97) to give the title compound (26 mg, 89%) as a colorless oil.

ESI-MS m/z 994 (M+H)$^+$.

Fifth Step (8E,12E,14E)-3,16,21-Trihydroxy-6-methoxy-6,10,12,16,20-pentamethyl-7-((4-methylpiperazin-1-yl)carbonyl)oxy-18,19-epoxytricosa-8,12,14-trien-11-olide (Compound 85)

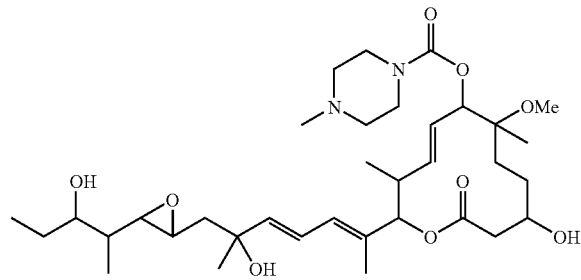

To a solution of Compound 85-4 (8E,12E,14E)-6-methoxy-6,10,12,16,20-pentamethyl-7-((4-methylpiperazin-1-yl)carbonyl)oxy-3,16,21-tris(triethylsiloxy)-18,19-epoxytricosa-8,12,14-trien-11-olide (25 mg, 25 μmol) obtained in the fourth step in tetrahydrofuran (3 mL) was added tetrabutylammonium fluoride (83 μl, 1.0 M tetrahydrofuran solution) at room temperature, then the reaction mixture was stirred at the same temperature for 1.5 hours. The reaction mixture was diluted with ethyl acetate and washed with a saturated aqueous solution of sodium bicarbonate and brine. The organic layer was dried over anhydrous magnesium sulfate, filtrated and concentrated. The resulting residue was purified by thin layer chromatography (Fuji Silysia, NH Silica gel Plate; methanol:dichloromethane=5:95) to give the title compound (11 mg, 67%) as a colorless oil.

$^1$H-NMR Spectrum (CD$_3$OD, 400 MHz) δ(ppm): 0.88 (3H, d, J=6.4 Hz), 0.90 (3H, d, J=6.8 Hz), 0.94 (3H, t, J=7.2 Hz), 1.21 (3H, s), 1.34 (3H, s), 1.22-1.69 (8H, m), 1.78 (3H, s), 1.86 (1H, dd, J=5.6, 14.0 Hz), 2.29 (3H, s), 2.36-2.44 (4H, m), 2.45-2.60 (3H, m), 2.67 (1H, dd, J=2.4, 8.0 Hz), 2.86-2.92 (1H, m), 3.34 (3H, s), 3.44-3.58 (5H, m), 3.78-3.86 (1H, m), 5.01 (1H, d, J=9.6 Hz), 5.06 (1H, d, J=11.2 Hz), 5.56 (1H, dd, J=9.6, 15.2 Hz), 5.73 (1H, dd, J=10.0, 15.2 Hz), 5.87 (1H, d, J=15.2 Hz), 6.13 (1H, d, J=9.2 Hz), 6.53 (1H, dd, J=11.2, 15.2 Hz); ESI-MS m/z 651 (M+H)$^+$.

Example 86

(8E,12E,14E)-3,16,21-Trihydroxy-6-methoxy-6,10,12,16,20-pentamethyl-7-((piperazin-1-yl)carbonyl)oxy-18,19-epoxytricosa-8,12,14-trien-11-olide

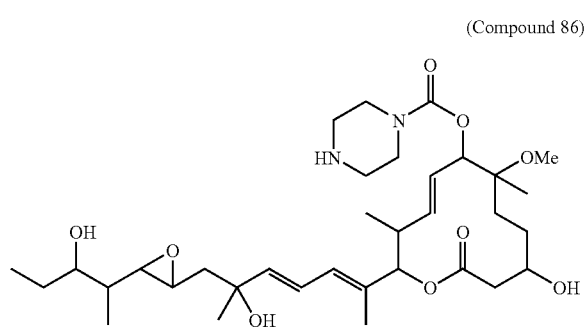
(Compound 86)

The title compound (a colorless oil) was synthesized by a similar method as described for Example 85.

$^1$H-NMR Spectrum (CD$_3$OD, 400 MHz) δ(ppm): 0.88 (3H, d, J=6.4 Hz), 0.90 (3H, d, J=6.8 Hz), 0.94 (3H, t, J=7.6 Hz), 1.22 (3H, s), 1.22-1.82 (8H, m), 1.34 (3H, s), 1.77 (3H, s), 1.86 (1H, dd, J=6.0, 14.0 Hz), 2.44-2.62 (3H, m), 2.66 (1H, dd, J=2.0, 8.0 Hz), 2.70-2.82 (4H, m), 2.89 (1H, dt, J=2.4, 5.6 Hz) 3.25-3.36 (3H, covered with CD$_3$OD), 3.38-3.55 (5H, m), 3.78-3.86 (1H, m), 5.02 (1H, d, J=9.6 Hz), 5.06 (1H, d, J=10.8 Hz), 5.57 (1H, dd, J=9.6, 15.6 Hz), 5.73 (1H, dd, J=9.6, 15.6 Hz), 5.86 (1H, d, J=15.6 Hz), 6.13 (1H, d, J=11.2 Hz), 6.52 (1H, dd, J=11.2, 15.6 Hz); ESI-MS m/z 637 (M+H)$^+$.

Example 87

(8E,12E,14E)-7-(N-(2-(N',N'-Diethylamino)ethyl)carbamoyloxy)-3,16,21-trihydroxy-6-methoxy-6,10,12,16,20-pentamethyl-18,19-epoxytricosa-8,12,14-trien-11-olide

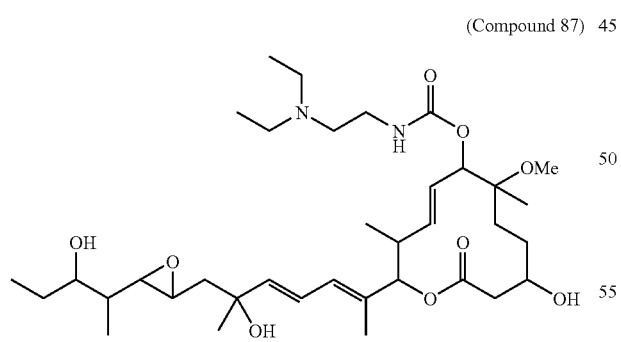
(Compound 87)

The title compound (a colorless oil) was synthesized by a similar method as described for Example 85.

$^1$H-NMR Spectrum (CD$_3$OD, 400 MHz) δ(ppm): 0.88 (3H, d, J=6.0 Hz), 0.90 (3H, d, J=7.2 Hz), 0.94 (3H, t, J=7.6 Hz), 1.06 (6H, t, J=7.2 Hz), 1.22 (3H, s), 1.22-1.70 (8H, m), 1.34 (3H, s), 1.78 (3H, s), 1.86 (1H, dd, J=5.2, 14.0 Hz), 2.44-2.64 (9H, m), 2.66 (1H, dd, J=2.0, 8.0 Hz), 2.89 (1H, dt, J=2.4, 6.0 Hz), 3.21 (2H, t, J=7.2 Hz) 3.25-3.36 (3H, covered with CD$_3$OD), 3.48-3.56 (1H, m), 3.77-3.85 (1H, m), 4.97 (1H, d, J=9.6 Hz), 5.06 (1H, d, J=10.8 Hz), 5.54 (1H, dd, J=10.0, 15.2 Hz), 5.71 (1H, dd, J=9.6, 15.6 Hz), 5.86 (1H, d, J=15.6 Hz), 6.13 (1H, d, J=10.8 Hz), 6.52 (1H, dd, J=11.2, 15.6 Hz); ESI-MS m/z 667 (M+H)$^+$.

Example 88

(8E,12E,14E)-3,16,21-Trihydroxy-6-methoxy-6,10,12,16,20-pentamethyl-7-(N-methyl-N-(1-methylpiperidin-4-yl)carbamoyloxy)-18,19-epoxytricosa-8,12,14-trien-1-olide

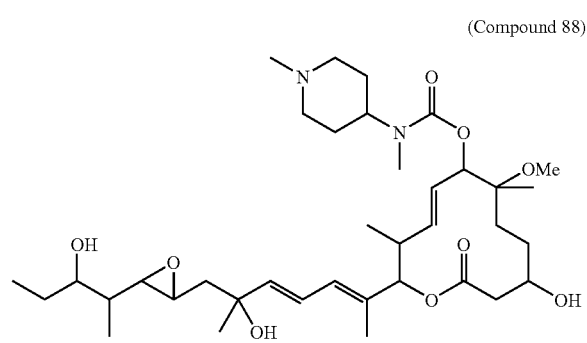
(Compound 88)

The title compound (a colorless oil) was synthesized by a similar method as described for Example 85.

$^1$H-NMR Spectrum (CD$_3$OD, 400 MHz) δ(ppm): 0.88 (3H, d, J=6.4 Hz), 0.90 (3H, d, J=7.2 Hz), 0.94 (3H, t, J=7.2 Hz), 1.17-1.69 (16H, m), 1.72-1.90 (6H, m), 2.10-2.26 (2H, m), 2.33 (3H, s), 2.44-2.62 (3H, m), 2.66 (1H, dd, J=2.4, 8.0 Hz), 2.82 (3H, s), 2.89 (1H, dt, J=2.4, 6.0 Hz), 2.95-3.03 (2H, m), 3.35 (3H, s), 3.52 (1H, dt, J=4.4, 8.0 Hz), 3.78-3.85 (1H, m), 3.92-4.04 (1H, m), 5.03 (1H, d, J=10.0 Hz), 5.06 (1H, d, J=10.4 Hz), 5.56 (1H, dd, J=10.0, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 679 (M+H)$^+$.

Example 89

(8E,12E,14E)-7-((4-(N,N-Dimethylamino)piperidin-1-yl)carbonyl)oxy-3,16,21-trihydroxy-6-methoxy-6,10,12,16,20-pentamethyl-18,19-epoxytricosa-8,12,14-trien-11-olide

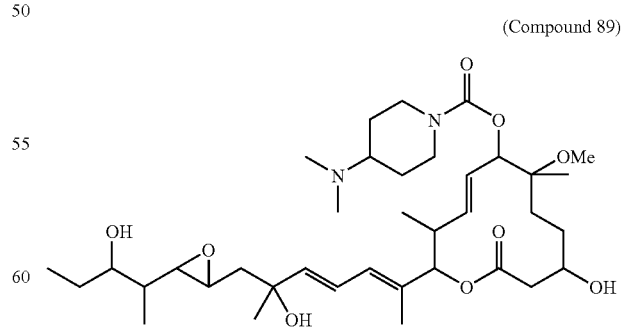
(Compound 89)

The title compound (a colorless oil) was synthesized by a similar method as described for Example 85.

$^1$H-NMR Spectrum (CD$_3$OD, 400 MHz) δ(ppm): 0.88 (3H, d, J=6.0 Hz), 0.89 (3H, d, J=7.2 Hz), 0.94 (3H, t, J=7.6

Hz), 1.17-1.68 (16H, m), 1.78 (3H, s), 1.81-1.94 (3H, m), 2.29 (6H, s), 2.34-2.63 (4H, m), 2.67 (1H, dd, J=2.4, 8.0 Hz), 2.73-2.89 (2H, m), 2.89 (1H, dt, J=2.4, 6.0 Hz), 3.33 (3H, s), 3.52 (1H, dt, J=4.4, 7.6 Hz), 3.78-3.85 (1H, m), 4.10-4.30 (2H, m), 5.01 (1H, d, J=9.2 Hz), 5.06 (1H, d, J=10.8 Hz), 5.56 (1H, dd, J=10.0, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/Z 679 (M+H)$^+$.

Example 90

(8E,12E,14E)-3,16,21-Trihydroxy-6-methoxy-6,10,12,16,20-pentamethyl-7-((4-propylhomopiperazin-1-yl)carbonyl)oxy-18,19-epoxytricosa-8,12,14-trien-11-olide

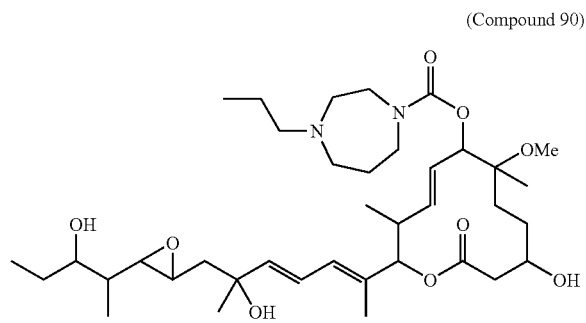

(Compound 90)

The title compound (a colorless oil) was synthesized by a similar method as described for Example 85.

$^1$H-NMR Spectrum (CD$_3$OD, 400 MHz) δ(ppm): 0.84-0.92 (9H, m), 0.94 (3H, t, J=7.2 Hz), 1.24 (3H, s), 1.34 (3H, s), 1.22-1.69 (10H, m), 1.78 (3H, d, J=0.8 Hz), 1.82-1.90 (3H, m), 2.40-2.72 (10H, m), 2.89 (1H, dt, J=2.0, 6.0 Hz), 3.24-3.36 (3H, covered with CD$_3$OD), 3.44-3.60 (5H, m), 3.78-3.86 (1H, m), 5.03 (1H, d, J=9.6 Hz), 5.07 (1H, d, J=10.8 Hz), 5.56 (1H, dd, J=9.6, 15.2 Hz), 5.74 (1H, dd, J=9.6, 15.2 Hz), 5.87 (1H, d, J=15.6 Hz), 6.13 (1H, d, J=10.8 Hz), 6.53 (1H, dd, J=10.8, 15.6 Hz); ESI-MS m/z 693 (M+H)$^+$.

Example 91

(8E,12E,14E)-7-((4-Butylhomopiperazin-1-yl)carbonyl)oxy-3,16,21-trihydroxy-6-methoxy-6,10,12,16,20-pentamethyl-18,19-epoxytricosa-8,12,14-trien-11-olide

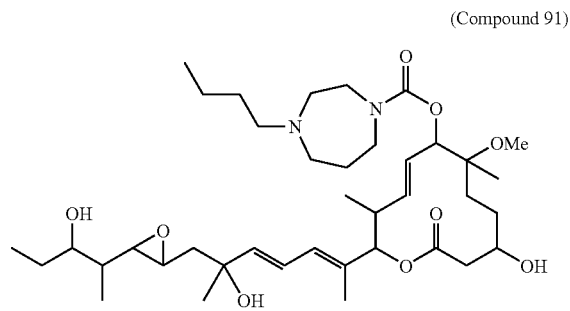

(Compound 91)

The title compound (a colorless oil) was synthesized by a similar method as described for Example 85.

$^1$H-NMR Spectrum (CD$_3$OD, 400 MHz) δ(ppm): 0.86-0.98 (12H, m), 1.23 (3H, brs), 1.34 (3H, s), 1.22-1.70 (12H, m), 1.78 (3H, d, J=0.8 Hz), 1.82-1.89 (3H, m), 2.44-2.74 (10H, m), 2.89 (1H, dt, J=2.0, 6.0 Hz), 3.30 (3H, s), 3.42-3.58 (5H, m), 3.79-3.85 (1H, m), 5.03 (1H, d, J=9.2 Hz), 5.07 (1H, d, J=10.4 Hz), 5.56 (1H, dd, J=10.0, 15.2 Hz), 5.74 (1H, dd, J=9.6, 15.2 Hz), 5.87 (1H, d, J=15.2 Hz), 6.13 (1H, d, J=11.2 Hz), 6.53 (1H, dd, J=11.2, 15.2 Hz); ESI-MS m/z 707 (M+H)$^+$.

Example 92

(8E,12E,14E)-7-((4-Cyclopropylhomopiperazin-1-yl)carbonyl)oxy-3,16,21-trihydroxy-6-methoxy-6,10,12,16,20-pentamethyl-18,19-epoxytricosa-8,12,14-trien-11-olide

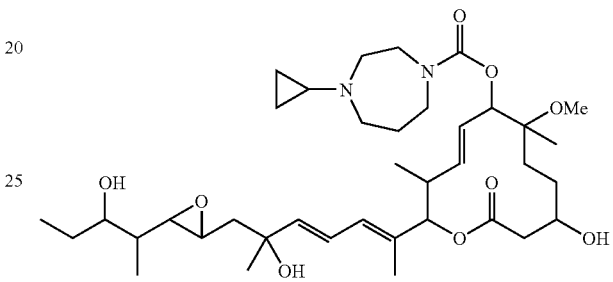

(Compound 92)

The title compound (a colorless oil) was synthesized by a similar method as described for Example 85.

$^1$H-NMR Spectrum (CD$_3$OD, 400 MHz) δ(ppm): 0.38-0.42 (2H, m), 0.47-0.52 (2H, m), 0.88 (3H, d, J=6.4 Hz), 0.90 (3H, d, J=7.2 Hz), 0.94 (3H, t, J=7.2 Hz), 1.23 (3H, s), 1.34 (3H, s), 1.22-1.68 (9H, m), 1.78 (3H, d, J=0.8 Hz), 1.80-1.92 (3H, m), 2.44-2.60 (3H, m), 2.66 (1H, dd, J=2.0, 7.6 Hz), 2.74-2.87 (4H, m), 2.89 (1H, dt, J=1.6, 5.6 Hz), 3.33 (3H, s), 3.44-3.60 (5H, m), 3.78-3.86 (1H, m), 5.03 (1H, d, J=9.6 Hz), 5.06 (1H, d, J=10.4 Hz), 5.56 (1H, dd, J=10.0, 15.6 Hz), 5.74 (1H, dd, J=10.0, 15.2 Hz), 5.87 (1H, d, J=15.2 Hz), 6.13 (1H, d, J=11.2 Hz), 6.53 (1H, dd, J=11.2, 15.2 Hz); ESI-MS m/z 691 (M+H)$^+$.

Example 93

(8E,12E,14E)-7-((4-Cyclobutylhomopiperazin-1-yl)carbonyl)oxy-3,16,21-trihydroxy-6-methoxy-6,10,12,16,20-pentamethyl-18,19-epoxytricosa-8,12,14-trien-11-olide

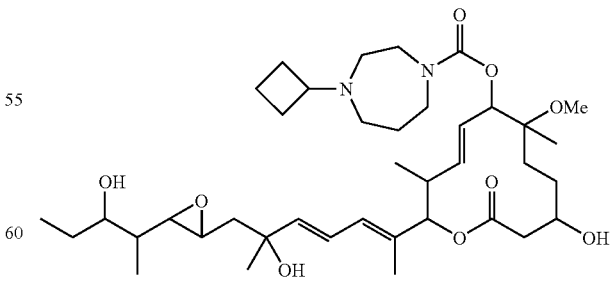

(Compound 93)

The title compound (a colorless oil) was synthesized by a similar method as described for Example 85.

$^1$H-NMR Spectrum (CD$_3$OD, 400 MHz) δ(ppm): 0.88 (3H, d, J=6.8 Hz), 0.90 (3H, d, J=6.8 Hz), 0.94 (3H, t, J=7.6 Hz), 1.23 (3H, s), 1.34 (3H, s), 1.22-1.72 (10H, m), 1.78 (3H, s), 1.80-1.90 (5H, m), 2.02-2.10 (2H, m), 2.41-2.60 (7H, m), 2.67 (1H, dd, J=2.4, 8.0 Hz), 2.86-2.94 (2H, m), 3.24-3.36 (3H, covered with CD₃OD), 3.44-3.60 (5H, m), 3.78-3.86 (1H, m), 5.03 (1H, dd, J=2.0, 9.6 Hz), 5.07 (1H, d, J=10.8 Hz), 5.56 (1H, dd, J=10.0, 15.2 Hz), 5.74 (1H, dd, J=9.6, 15.6 Hz), 5.87 (1H, d, J=15.2 Hz), 6.14 (1H, d, J=10.8 Hz), 6.53 (1H, dd, J=10.8, 15.2 Hz); ESI-MS m/z 705 (M+H)⁺.

Example 94

(8E,12E,14E)-7-((4-Cyclopentylhomopiperazin-1-yl)carbonyl)oxy-3,16,21-trihydroxy-6-methoxy-6,10,12,16,20-pentamethyl-18,19-epoxytricosa-8,12,14-trien-11-olide (Compound 94)

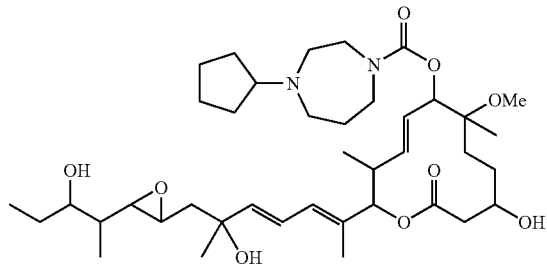

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=7.2 Hz), 0.94 (3H, t, J=7.6 Hz), 1.23 (3H, s), 1.34 (3H, s), 1.36-1.72 (16H, m), 1.78 (3H, d, J=0.8 Hz), 1.82-1.90 (3H, m), 2.44-2.60 (3H, m), 2.64-2.70 (3H, m), 2.73-2.82 (2H, m), 2.84-2.94 (2H, m), 3.24-3.36 (3H, covered with CD₃OD), 3.44-3.60 (5H, m), 3.78-3.86 (1H, m), 5.04 (1H, d, J=11.6 Hz), 5.07 (1H, d, J=10.8 Hz), 5.56 (1H, dd, J=9.6, 15.6 Hz), 5.74 (1H, dd, J=10.0, 15.2 Hz), 5.87 (1H, d, J=15.2 Hz), 6.13 (1H, d, J=11.2 Hz), 6.53 (1H, dd, J=11.2, 15.2 Hz); ESI-MS m/z 719 (M+H)⁺.

Example 95

(8E,12E,14E)-7-((4-Cyclohexylhomopiperazin-1-yl)carbonyl)oxy-3,16,21-trihydroxy-6-methoxy-6,10,12,16,20-pentamethyl-18,19-epoxytricosa-8,12,14-trien-11-olide (Compound 95)

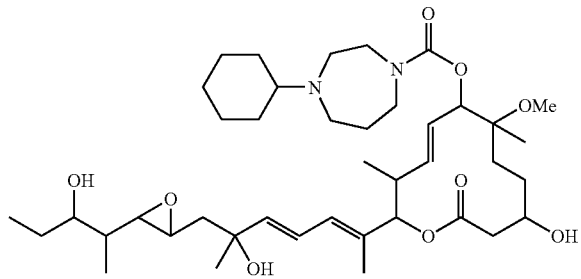

The title compound (a colorless oil) was synthesized by a similar method as described for Example 85.

¹H-NMR Spectrum (CD₃OD, 400 MHz) δ(ppm): 0.88 (3H, d, J=6.0 Hz), 0.90 (3H, d, J=6.8 Hz), 0.94 (3H, t, J=7.2 Hz), 1.23 (3H, s), 1.34 (3H, s), 1.12-1.68 (18H, m), 1.78 (3H, d, J=0.8 Hz), 1.75-1.89 (3H, m), 2.42-2.60 (4H, m), 2.64-2.72 (3H, m), 2.75-2.82 (2H, m), 2.89 (1H, dt, J=1.2, 5.2 Hz), 3.26-3.36 (3H, covered with CD₃OD), 3.42-3.56 (5H, m), 3.78-3.86 (1H, m), 5.03 (1H, dd, J=3.2, 9.6 Hz), 5.07 (1H, d, J=10.8 Hz), 5.56 (1H, dd, J=10.0, 15.2 Hz), 5.74 (1H, dd, J=10.0, 14.8 Hz), 5.87 (1H, d, J=15.2 Hz), 6.13 (1H, d, J=10.8 Hz), 6.53 (1H, dd, J=11.2, 15.2 Hz); ESI-MS m/z 733 (M+H)⁺.

Example 96

(8E,12E,14E)-3,16,21-Trihydroxy-7-((4-isopropylhomopiperazin-1-yl)carbonyl)oxy-6-methoxy-6,10,12,16,20-pentamethyl-18,19-epoxytricosa-8,12,14-trien-11-olide (Compound 96)

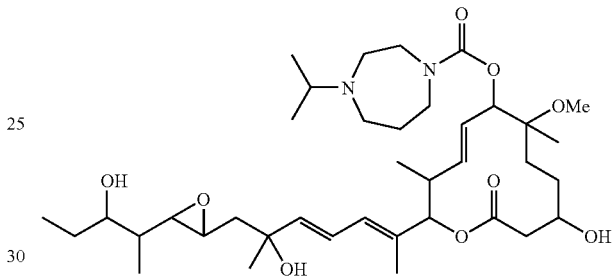

The title compound (a colorless oil) was synthesized by a similar method as described for Example 85.

¹H-NMR Spectrum (CD₃OD, 400 MHz) δ(ppm): 0.88 (3H, d, J=6.0 Hz), 0.90 (3H, d, J=7.2 Hz), 0.94 (3H, t, J=7.6 Hz), 1.03 (6H, d, J=6.4 Hz), 1.24 (3H, s), 1.34 (3H, s), 1.22-1.69 (8H, m), 1.78 (3H, s), 1.76-1.90 (3H, m), 2.44-2.74 (8H, m), 2.86-2.94 (2H, m), 3.33 (3H, s), 3.44-3.60 (5H, m), 3.79-3.86 (1H, m), 5.03 (1H, dd, J=4.4, 9.6 Hz), 5.07 (1H, d, J=10.8 Hz), 5.56 (1H, dd, J=10.8, 16.0 Hz), 5.74 (1H, dd, J=9.6, 15.6 Hz), 5.87 (1H, d, J=15.2 Hz), 6.13 (1H, d, J=11.6 Hz), 6.53 (1H, dd, J=10.8, 15.2 Hz); ESI-MS m/z 693 (M+H)⁺.

Example 97

(8E,12E,14E)-3,16,21-Trihydroxy-7-((4-isobutylhomopiperazin-1-yl)carbonyl)oxy-6-methoxy-6,10,12,16,20-pentamethyl-18,19-epoxytricosa-8,12,14-trien-11-olide (Compound 97)

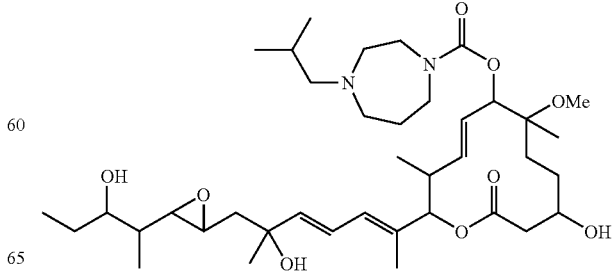

The title compound (a colorless oil) was synthesized by a similar method as described for Example 85.

$^1$H-NMR Spectrum (CD$_3$OD, 400 MHz) δ(ppm): 0.84-0.95 (15H, m), 1.26 (3H, s), 1.34 (3H, s), 1.22-1.76 (9H, m), 1.78 (3H, s), 1.78-1.90 (3H, m), 2.23 (2H, d, J=6.8 Hz), 2.44-2.72 (8H, m), 2.89 (1H, dt, J=2.0, 5.2 Hz), 3.24-3.38 (3H, covered with CD$_3$OD), 3.42-3.58 (5H, m), 3.78-3.86 (1H, m), 5.03 (1H, d, J=9.6 Hz), 5.07 (1H, d, J=10.4 Hz), 5.56 (1H, dd, J=9.6, 15.2 Hz), 5.74 (1H, dd, J=9.2, 14.8 Hz), 5.87 (1H, d, J=15.2 Hz), 6.13 (1H, d, J=10.8 Hz), 6.53 (1H, dd, J=10.8, 15.2 Hz); ESI-MS m/z 707 (M+H)$^+$.

Example 98

(8E,12E,14E)-3,16,21-Trihydroxy-6-methoxy-6,10,12,16,20-pentamethyl-7-((4-(morpholin-4-yl)piperidin-1-yl)carbonyl)oxy-18,19-epoxytricosa-8,12,14-trien-11-olide (Compound 98)

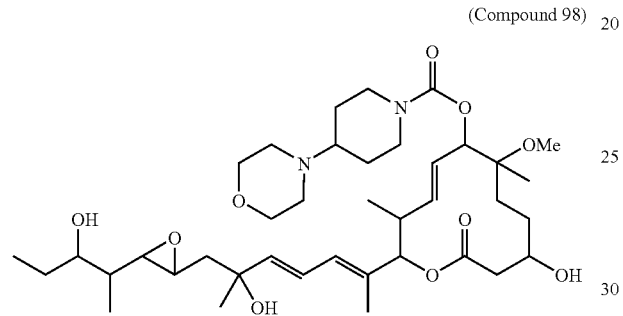

The title compound (a colorless oil) was synthesized by a similar method as described for Example 85.

$^1$H-NMR Spectrum (CD$_3$OD, 400 MHz) δ(ppm): 0.88 (3H, d, J=5.2 Hz), 0.90 (3H, d, J=7.2 Hz), 0.94 (3H, t, J=7.6 Hz), 1.21 (3H, s), 1.34 (3H, s), 1.24-1.68 (10H, m), 1.78 (3H, d, J=1.2 Hz), 1.82-1.96 (3H, m), 2.32-2.43 (1H, m), 2.44-2.62 (7H, m), 2.67 (1H, dd, J=2.4, 8.0 Hz), 2.74-2.92 (3H, m), 3.32 (3H, s), 3.52 (1H, dt, J=3.6, 8.0 Hz), 3.64-3.74 (4H, m), 3.78-3.86 (1H, m), 4.08-4.28 (2H, m), 5.01 (1H, d, J=9.6 Hz), 5.06 (1H, d, J=10.8 Hz), 5.54 (1H, dd, J=9.6, 15.2 Hz), 5.73 (1H, dd, J=9.6, 15.2 Hz), 5.87 (1H, d, J=15.2 Hz), 6.13 (1H, d, J=11.2 Hz), 6.53 (1H, dd, J=10.8, 15.2 Hz); ESI-MS m/z 721 (M+H)$^+$.

Example 99

(8E,12E,14E)-3,16,21-Trihydroxy-6-methoxy-6,10,12,16,20-pentamethyl-7-((4-(pyrrolidin-1-yl)piperidin-1-yl)carbonyl)oxy-18,19-epoxytricosa-8,12,14-trien-11-olide (Compound 99)

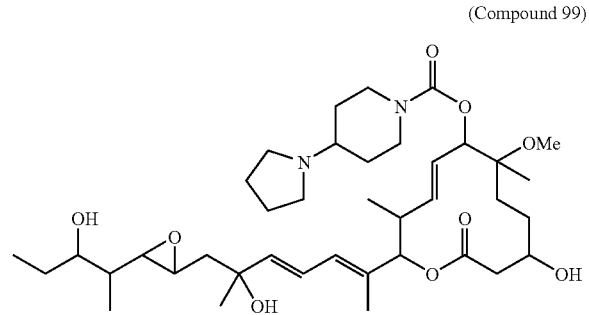

The title compound (a colorless oil) was synthesized by a similar method as described for Example 85.

$^1$H-NMR Spectrum (CD$_3$OD, 400 MHz) δ(ppm): 0.88 (3H, d, J=5.6 Hz), 0.90 (3H, d, J=6.8 Hz), 0.94 (3H, t, J=7.6 Hz), 1.22 (3H, s), 1.34 (3H, s), 1.23-1.70 (10H, m), 1.78 (3H, s), 1.79-1.90 (5H, m), 1.92-2.00 (2H, m), 2.20-2.30 (1H, m), 2.44-2.68 (8H, m), 2.76-2.92 (3H, m), 3.24-3.36 (3H, covered with CD$_3$OD), 3.52 (1H, dt, J=4.8, 8.0 Hz), 3.77-3.86 (1H, m), 4.04-4.24 (2H, m), 5.01 (1H, d, J=10.0 Hz), 5.06 (1H, d, J=10.4 Hz), 5.56 (1H, dd, J=9.6, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 705 (M+H)$^+$.

Example 100

(8E,12E,14E)-3,16,21-Trihydroxy-7-((4-(4-hydroxypiperidin-1-yl)piperidin-1-yl)carbonyl)oxy-6-methoxy-6,10,12,16,20-pentamethyl-18,19-epoxytricosa-8,12,14-trien-11-olide (Compound 100)

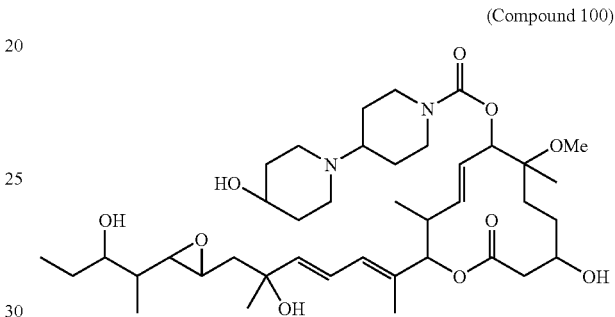

The title compound (a colorless oil) was synthesized by a similar method as described for Example 85.

$^1$H-NMR Spectrum (CD$_3$OD, 400 MHz) δ(ppm): 0.88 (3H, d, J=6.0 Hz), 0.90 (3H, d, J=7.2 Hz), 0.94 (3H, t, J=7.6 Hz), 1.21 (3H, s), 1.34 (3H, s), 1.22-1.69 (12H, m), 1.78 (3H, s), 1.82-1.93 (5H, m), 2.28-2.38 (2H, m), 2.43-2.58 (4H, m), 2.67 (1H, dd, J=2.0, 7.6 Hz), 2.72-2.83 (5H, m), 3.24-3.39 (3H, covered with CD$_3$OD), 3.52 (1H, dt, J=4.8, 8.0 Hz), 3.56-3.64 (1H, m), 3.78-3.86 (1H, m), 4.10-4.30 (2H, m), 5.00 (1H, d, J=9.6 Hz), 5.06 (1H, d, J=10.8 Hz), 5.55 (1H, dd, J=10.4, 15.2 Hz), 5.73 (1H, dd, J=10.0, 15.6 Hz), 5.87 (1H, d, J=15.2 Hz), 6.13 (1H, d, J=10.8 Hz), 6.53 (1H, dd, J=10.8, 15.2 Hz); ESI-MS m/z 735 (M+H)$^+$.

Example 101

(8E,12E,14E)-7-(N-(3-(N',N'-Dimethylamino)propyl)-N-methylcarbamoyloxy)-3,16,21-trihydroxy-6-methoxy-6,10,12,16,20-pentamethyl-18,19-epoxytricosa-8,12,14-trien-11-olide (Compound 101)

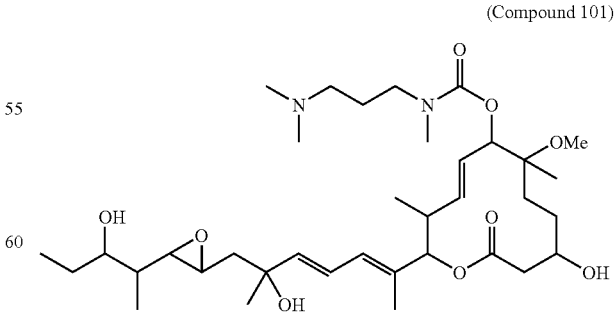

The title compound (a colorless oil) was synthesized by a similar method as described for Example 85.

$^1$H-NMR Spectrum (CD$_3$OD, 400 MHz) δ(ppm): 0.88 (3H, d, J=6.0 Hz), 0.90 (3H, d, J=7.2 Hz), 0.94 (3H, t, J=7.6

Hz), 1.22 (3H, s), 1.34 (3H, s), 1.20-1.78 (10H, m), 1.78 (3H, s), 1.86 (1H, dd, J=6.3, 14.5 Hz), 2.24 (6H, s), 2.31 (2H, t, J=8.8 Hz), 2.44-2.60 (3H, m), 2.66 (1H, dd, J=2.4, 8.0 Hz), 2.85-2.96 (4H, m), 3.22-3.38 (5H, covered with CD₃OD), 3.52 (1H, dd, J=3.6, 8.0 Hz), 3.78-3.85 (1H, m), 5.01 (1H, d, J=10.0 Hz), 5.06 (1H, d, J=10.4 Hz), 5.55 (1H, dd, J=9.6, 15.2 Hz), 5.74 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 667 (M+H)⁺.

Example 102

(8E,12E,14E)-3,16,21-Trihydroxy-6-methoxy-6,10,12,16,20-pentamethyl-7-(N-methyl-N-(2-(morpholin-4-yl)ethyl)carbamoyloxy)-18,19-epoxytricosa-8,12,14-trien-11-olide (Compound 102)

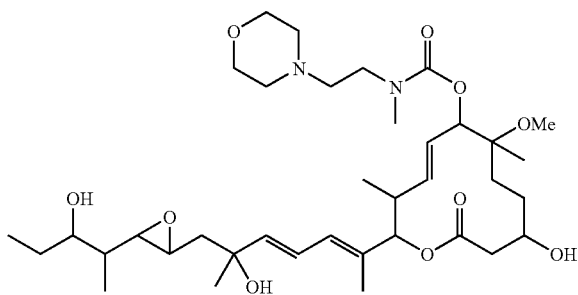

The title compound (a colorless oil) was synthesized by a similar method as described for Example 85.

¹H-NMR Spectrum (CD₃OD, 400 MHz) δ(ppm): 0.89 (3H, d, J=6.8 Hz), 0.90 (3H, d, J=6.8 Hz), 0.94 (3H, t, J=7.2 Hz), 1.22 (3H, s), 1.34 (3H, s), 1.23-1.69 (8H, m), 1.78 (3H, s), 1.86 (1H, dd, J=4.6, 12.7 Hz), 2.44-2.56 (9H, m), 2.66 (1H, dd, J=2.4, 7.6 Hz), 2.86-2.96 (4H, m), 3.22-3.38 (2H, covered with CD₃OD), 3.34 (3H, s), 3.52 (1H, dt, J=4.0, 8.0 Hz), 3.62-3.72 (4H, m), 3.78-3.84 (1H, m), 5.01 (1H, d, J=10.0 Hz), 5.06 (1H, d, J=10.8 Hz), 5.55 (1H, dd, J=10.0, 15.2 Hz), 5.68-5.79 (1H, m), 5.87 (1H, d, J=15.2 Hz), 6.13 (1H, d, J=10.4 Hz), 6.53 (1H, dd, J=10.8, 15.2 Hz); ESI-MS m/z 695 (M+H)⁺.

Example 103

(8E,12E,14E)-3,16,21-Trihydroxy-6-methoxy-6,10,12,16,20-pentamethyl-7-(N-methyl-N-(2-(pyrrolidin-1-yl)ethyl)carbamoyloxy)-18,19-epoxytricosa-8,12,14-trien-11-olide (Compound 103)

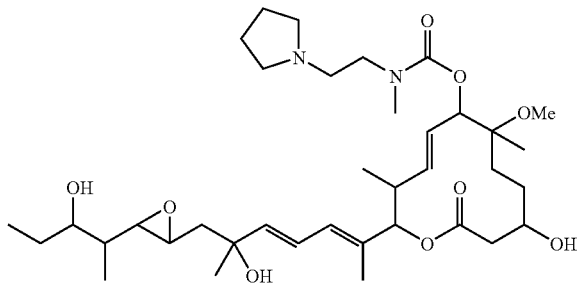

The title compound (a colorless oil) was synthesized by a similar method as described for Example 85.

¹H-NMR Spectrum (CD₃OD, 40 MHz) δ(ppm): 0.88 (3H, d, J=6.8 Hz), 0.90 (3H, d, J=7.2 Hz), 0.94 (3H, t, J=7.6 Hz), 1.22 (3H, s), 1.34 (3H, s), 1.23-1.68 (8H, m), 1.78 (3H, d, J=0.8 Hz), 1.78-1.83 (4H, m), 1.86 (1H, dd, J=5.4, 13.1 Hz), 2.44-2.68 (10H, m), 2.86-2.97 (4H, m), 3.34 (3H, s), 3.40-3.48 (2H, m), 3.52 (1H, dt, J=4.0, 7.6 Hz), 3.78-3.86 (1H, m), 5.00 (1H, d, J=9.6 Hz), 5.06 (1H, d, J=10.4 Hz), 5.55 (1H, dd, J=10.0, 14.8 Hz), 5.74 (1H, dd, J=9.6, 14.8 Hz), 5.87 (1H, d, J=15.2 Hz), 6.13 (1H, d, J=10.8 Hz), 6.53 (1H, dd, J=11.2, 15.2 Hz); ESI-MS m/z 679 (M+H)⁺.

Example 104

(8E,12E,14E)-7-(N-(3-(N',N'-Eiethylamino)propyl)-N-methylcarbamoyloxy)-3,16,21-trihydroxy-6-methoxy-6,10,12,16,20-pentamethyl-18,19-epoxytricosa-8,12,14-trien-11-olide (Compound 104)

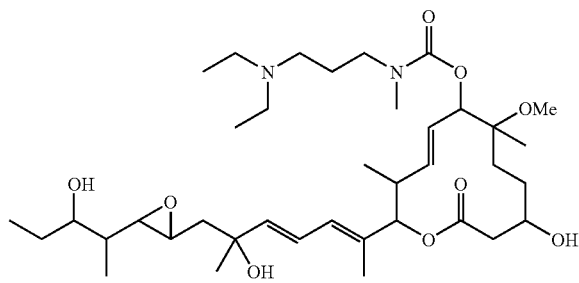

The title compound (a colorless oil) was synthesized by a similar method as described for Example 85.

¹H-NMR Spectrum (CD₃OD, 400 MHz) δ(ppm): 0.88 (3H, d, J=6.4 Hz), 0.90 (3H, d, J=7.2 Hz), 0.94 (3H, t, J=7.6 Hz), 1.05 (6H, t, J=7.2 Hz), 1.22 (3H, s), 1.34 (3H, s), 1.20-1.82 (10H, m), 1.78 (3H, s), 1.86 (1H, dd, J=5.6, 14.4 Hz), 2.42-2.60 (9H, m), 2.66 (1H, dd, J=2.4, 8.0 Hz), 2.84-2.96 (4H, m), 3.22-3.40 (5H, covered with CD₃OD), 3.52 (1H, dt, J=3.6, 8.0 Hz), 3.78-3.86 (1H, m), 5.01 (1H, d, J=9.6 Hz), 5.06 (1H, d, J=10.4 Hz), 5.55 (1H, dd, J=10.0, 15.6 Hz), 5.74 (1H, dd, J=9.6, 15.6 Hz), 5.87 (1H, d, J=15.2 Hz), 6.13 (1H, d, J=10.0 Hz), 6.53 (1H, dd, J=11.2, 15.2 Hz); ESI-MS m/z 695 (M+H)⁺.

Example 105

(8E,12E,14E)-3,16,21-Trihydroxy-6-methoxy-6,10,12,16,20-pentamethyl-7-((4-methylhomopiperazin-1-yl)carbonyl)oxy-18,19-epoxytricosa-8,12,14-trien-11-olide (Compound 105)

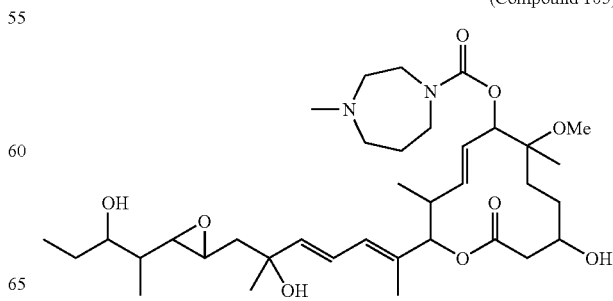

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.19-1.29 (4H, m), 1.34 (3H, s), 1.38-1.69 (7H, m), 1.78 (3H, d, J=0.8 Hz), 1.83-1.93 (3H, m), 2.35 (3H, s), 2.45-2.65 (7H, m), 2.67 (1H, dd, J=2.4, 8.0 Hz), 2.89 (1H, dt, J=2.4, 6.0 Hz), 3.32 (1.5H, s), 3.33 (1.5H, s), 3.46-3.62 (5H, m), 3.79-3.86 (1H, m), 5.01-5.06 (1H, m), 5.07 (1H, d, J=10.4 Hz), 5.56 (1H, dd, J=9.6, 15.2 Hz), 5.74 (1H, dd, J=9.6, 15.2 Hz), 5.87 (1H, d, J=15.2 Hz), 6.13 (1H, dd, J=1.2, 11.2 Hz), 6.53 (1H, dd, J=10.8, 15.2 Hz); ESI-MS m/z 665 (M+H)⁺.

Example 106

(8E,12E,14E)-7-((4-Ethylpiperazin-1-yl)carbonyl)oxy-3,16,21-trihydroxy-6-methoxy-6,10,12,16,20-pentamethyl-18,19-epoxytricosa-8,12,14-trien-11-olide (Compound 106)

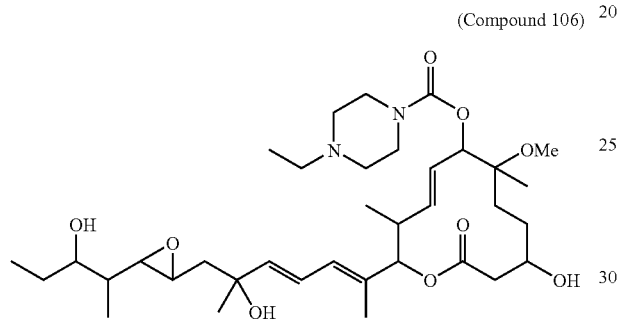

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.11 (3H, t, J=7.6 Hz), 1.20-1.29 (4H, m), 1.34 (3H, s), 1.37-1.69 (7H, m), 1.78 (3H, d, J=0.8 Hz), 1.86 (1H, dd, J=5.2, 14.0 Hz), 2.41-2.63 (9H, m), 2.67 (1H, dd, J=2.4, 8.0 Hz), 2.89 (1H, dt, J=2.4, 6.0 Hz), 3.32 (3H, s), 3.43-3.59 (5H, m), 3.79-3.86 (1H, m), 5.01 (1H, d, J=9.6 Hz), 5.06 (1H, d, J=10.8 Hz), 5.56 (1H, dd, J=9.6, 15.2 Hz), 5.73 (1H, dd, J=9.6, 15.2 Hz), 5.87 (1H, d, J=15.2 Hz), 6.13 (1H, dd, J=1.2, 10.8 Hz), 6.53 (1H, dd, J=10.8, 15.2 Hz); ESI-MS m/z 665 (M+H)⁺.

Example 107

(8E,12E,14E)-7-((4-Ethylhomopiperazin-1-yl)carbonyl)oxy-3,16,21-trihydroxy-6-methoxy-6,10,12,16,20-pentamethyl-18,19-epoxytricosa-8,12,14-trien-11-olide (Compound 107)

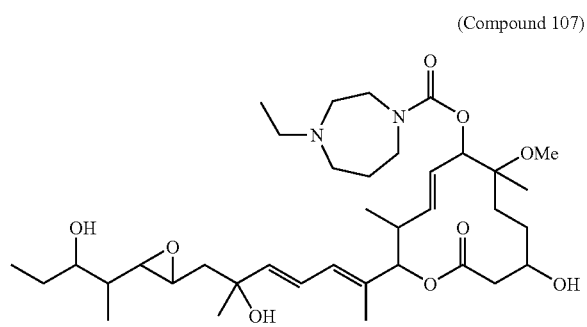

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.08 (3H, t, J=7.2 Hz), 1.19-1.29 (4H, m), 1.34 (3H, s), 1.38-1.70 (7H, m), 1.78 (3H, d, J=0.8 Hz), 1.82-1.90 (3H, m), 2.45-2.73 (10H, m), 2.89 (1H, dt, J=2.4, 6.0 Hz), 3.33 (1.5H, s), 3.33 (1.5Hs), 3.46-3.62 (5H, m), 3.79-3.85 (1H, m), 5.00-5.06 (1H, m), 5.07 (1H, d, J=10.8 Hz), 5.56 (1H, dd, J=10.0, 15.2 Hz), 5.74 (1H, dd, J=10.0, 15.2 Hz), 5.87 (1H, d, J=15.2 Hz), 6.13 (1H, d, J=10.8 Hz), 6.53 (1H, dd, J=11.2, 15.2 Hz); ESI-MS m/z 679 (M+H)⁺.

Example 108

(8E,12E,14E)-7-(N-(2-(N',N'-Dimethylamino)ethyl)-N-methylcarbamoyloxy)-3,16,21-trihydroxy-6-methoxy-6,10,12,16,20-pentamethyl-18,19-epoxytricosa-8,12,14-trien-11-olide (Compound 108)

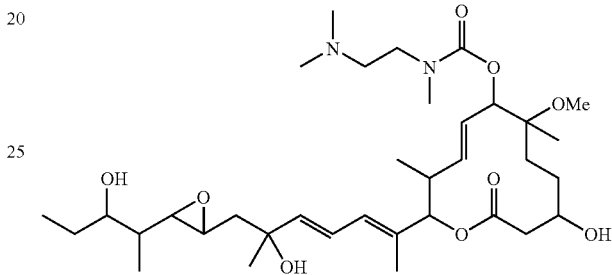

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.19-1.29 (4H, m), 1.34 (3H, s), 1.38-1.70 (7H, m), 1.78 (3H, d, J=0.8 Hz), 1.86 (1H, dd, J=5.2, 14.0 Hz), 2.27 (6H, s), 2.45-2.63 (5H, m), 2.67 (1H, dd, J=2.4, 8.0 Hz), 2.87-2.97 (4H, m), 3.30-3.36 (3H, m), 3.37-3.46 (2H, m), 3.52 (1H, td, J=4.4, 8.0 Hz), 3.78-3.85 (1H, m), 5.00 (1H, d, J=9.6 Hz), 5.06 (1H, d, J=10.4 Hz), 5.55 (1H, dd, J=9.6, 15.2 Hz), 5.69-5.79 (1H, m), 5.87 (1H, d, J=15.2 Hz), 6.13 (1H, d, J=10.8 Hz), 6.53 (1H, dd, J=10.8, 15.2 Hz); ESI-MS m/z 653 (M+H)⁺.

Example 109

(8E,12E,14E)-3,16,21-Trihydroxy-6-methoxy-6,10,12,16,20-pentamethyl-7-((4-(piperidin-1-yl)piperidin-1-yl)carbonyl)oxy-18,19-epoxytricosa-8,12,14-trien-11-olide (Compound 109)

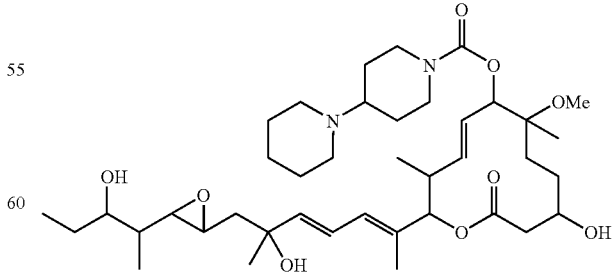

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6

Hz), 1.19-1.29 (4H, m), 1.31-1.69 (18H, m), 1.78 (3H, s), 1.83-1.93 (3H, m), 2.41-2.61 (8H, m), 2.67 (1H, dd, J=2.4, 8.0 Hz), 2.70-2.88 (2H, m), 2.89 (1H, dt, J=2.0, 6.0 Hz), 3.33 (3H, s), 3.52 (1H, td, J=4.4, 8.0 Hz), 3.78-3.85 (1H, m), 4.11-4.29 (2H, m), 5.00 (1H, d, J=9.6 Hz), 5.06 (1H, d, J=10.4 Hz), 5.56 (1H, dd, J=9.6, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 719 (M+H)$^+$.

Example 110

(8E,12E,14E)-3,16,21-Trihydroxy-7-(4-(isopropylpiperazin-1-yl)carbonyl)oxy-6-methoxy-6,10,12,16,20-pentamethyl-18,19-epoxytricosa-8,12,14-trien-11-olide (Compound 110)

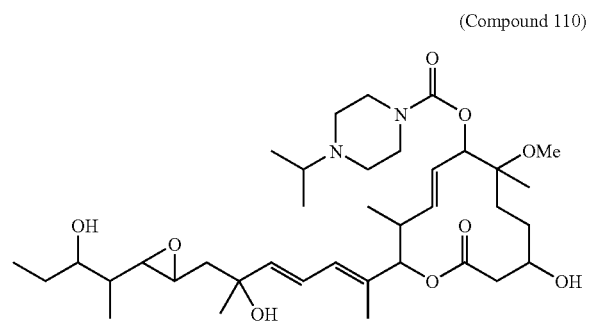

The title compound (a colorless oil) was synthesized by a similar method as described for Example 85.

$^1$H-NMR Spectrum (CD$_3$OD, 400 MHz) δ(ppm): 0.88 (3H, d, J=6.8 Hz), 0.90 (3H, d, J=6.8 Hz), 0.94 (3H, t, J=7.6 Hz), 1.07 (6H, d, J=6.8 Hz), 1.20-1.29 (4H, m), 1.32-1.76 (10H, m), 1.78 (3H, d, J=0.8 Hz), 1.86 (1H, dd, J=5.6, 14.0 Hz), 2.45-2.63 (7H, m), 2.64-2.75 (2H, m), 2.89 (1H, dt, J=2.4, 6.0 Hz), 3.32 (3H, s), 3.42-3.59 (5H, m), 3.78-3.86 (1H, m), 5.01 (1H, d, J=9.6 Hz), 5.06 (1H, d, J=10.4 Hz), 5.56 (1H, dd, J=9.6, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 679 (M+H)$^+$.

Example 111

(8E,12E,14E)-3,16,21-Trihydroxy-6-methoxy-6,10,12,16,20-pentamethyl-7-((4-propylpiperazin-1-yl)carbonyl)oxy-18,19-epoxytricosa-8,12,14-trien-11-olide (Compound 111)

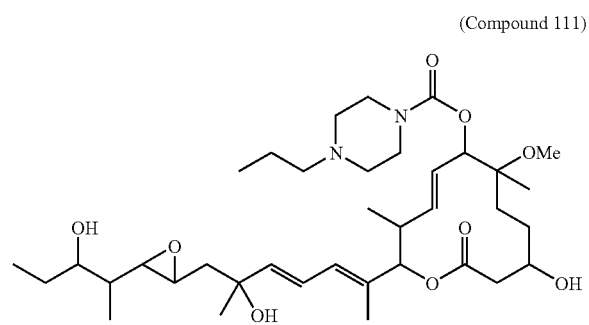

The title compound (a colorless oil) was synthesized by a similar method as described for Example 85.

$^1$H-NMR Spectrum (CD$_3$OD, 400 MHz) δ(ppm): 0.89 (3H, d, J=6.8 Hz), 0.90 (3H, d, J=7.2 Hz), 0.93 (3H, t, J=7.2 Hz), 0.94 (3H, t, J=7.2 Hz), 1.20-1.30 (4H, m), 1.34 (3H, s), 1.39-1.69 (9H, m), 1.78 (3H, d, J=1.2 Hz), 1.87 (1H, dd, J=5.2, 14.0 Hz), 2.31-2.37 (2H, m), 2.40-2.63 (7H, m), 2.67 (1H, dd, J=2.4, 8.0 Hz), 2.90 (1H, dt, J=2.0, 6.0 Hz), 3.32 (3H, s), 3.42-3.60 (5H, m), 3.79-3.86 (1H, m), 5.02 (1H, d, J=9.6 Hz), 5.07 (1H, d, J=10.4 Hz), 5.57 (1H, dd, J=10.0, 15.2 Hz), 5.74 (1H, dd, J=9.6, 15.2 Hz), 5.87 (1H, d, J=15.2 Hz), 6.14 (1H, d, J=11.2 Hz), 6.53 (1H, dd, J=11.2, 15.2 Hz); ESI-MS m/z 679 (M+H)$^+$.

Example 112

(8E,12E,14E)-7-((4-Butylpiperazin-1-yl)carbonyl)oxy-3,16,21-trihydroxy-6-methoxy-6,10,12,16,20-pentamethyl-18,19-epoxytricosa-8,12,14-trien-11-olide (Compound 112)

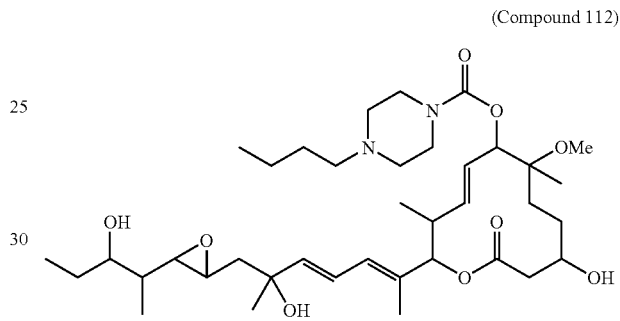

The title compound (a colorless oil) was synthesized by a similar method as described for Example 85.

$^1$H-NMR Spectrum (CD$_3$OD, 400 MHz) δ(ppm): 0.88 (3H, d, J=6.8 Hz), 0.90 (3H, d, J=6.8 Hz), 0.94 (3H, t, J=7.2 Hz), 0.94 (3H, t, J=7.2 Hz), 1.19-1.29 (4H, m), 1.29-1.69 (14H, m), 1.78 (3H, d, J=0.8 Hz), 1.86 (1H, dd, J=5.2, 14.0 Hz), 2.34-2.39 (2H, m), 2.40-2.63 (7H, m), 2.67 (1H, dd, J=2.4, 8.0 Hz), 2.89 (1H, dt, J=2.0, 6.0 Hz), 3.32 (3H, s), 3.41-3.60 (5H, m), 3.79-3.85 (1H, m), 5.01 (1H, d, J=10.0 Hz), 5.06 (1H, d, J=10.8 Hz), 5.56 (1H, dd, J=10.0, 15.2 Hz), 5.73 (1H, dd, J=9.6, 15.2 Hz), 5.87 (1H, d, J=15.2 Hz), 6.13 (1H, d, J=11.2 Hz), 6.53 (1H, dd, J=10.8, 15.2 Hz); ESI-MS m/z 693 (M+H)$^+$.

Example 113

(8E,12E,14E)-3,16,21-Trihydroxy-7-((4-isobutylpiperazin-1-yl)carbonyl)oxy-6-methoxy-6,10,12,16,20-pentamethyl-18,19-epoxytricosa-8,12,14-trien-11-olide (Compound 113)

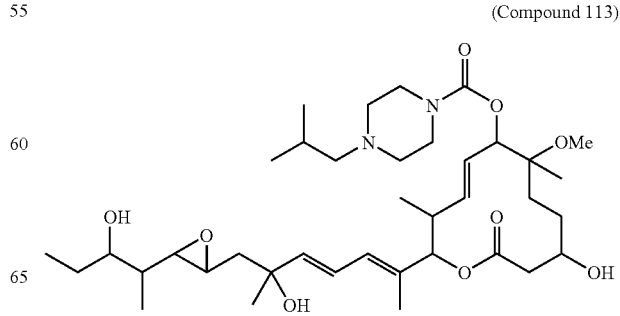

The title compound (a colorless oil) was synthesized by a similar method as described for Example 85.

¹H-NMR Spectrum (CD₃OD, 400 MHz) δ(ppm): 0.89 (3H, d, J=6.8 Hz), 0.90 (3H, d, J=6.8 Hz), 0.91 (6H, d, J=6.4 Hz), 0.94 (3H, t, J=7.6 Hz), 1.19-1.29 (4H, m), 1.34 (3H, s), 1.39-1.69 (7H, m), 1.76-1.90 (5H, m), 2.11 (2H, d, J=7.2 Hz), 2.33-2.41 (4H, m), 2.45-2.63 (3H, m), 2.67 (1H, dd, J=2.4, 8.0 Hz), 2.89 (1H, dt, J=2.4, 6.0 Hz), 3.32 (3H, s), 3.40-3.58 (5H, m), 3.79-3.86 (1H, m), 5.01 (1H, d, J=9.6 Hz), 5.06 (1H, d, J=10.8 Hz), 5.56 (1H, dd, J=10.0, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 693 (M+H)⁺.

Example 114

(8E,12E,14E)-3,16,21-Trihydroxy-6-methoxy-7-((4-(2-methoxyethyl)piperazin-1-yl)carbonyl)oxy-6,10,12,16,20-pentamethyl-18,19-epoxytricosa-8,12,14-trien-11-olide (Compound 114)

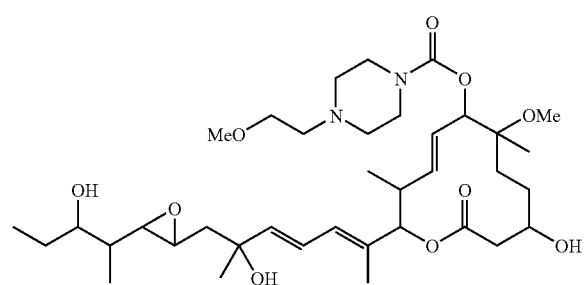

The title compound (a colorless oil) was synthesized by a similar method as described for Example 85.

¹H-NMR Spectrum (CD₃OD, 400 MHz) δ(ppm): 0.89 (3H, d, J=6.8 Hz), 0.90 (3H, d, J=6.8 Hz), 0.94 (3H, t, J=7.6 Hz), 1.19-1.29 (4H, m), 1.34 (3H, s), 1.38-1.69 (7H, m), 1.78 (3H, d, J=0.8 Hz), 1.86 (1H, dd, J=5.6, 14.0 Hz), 2.44-2.63 (9H, m), 2.67 (1H, dd, J=2.4, 8.0 Hz), 2.89 (1H, dt, J=2.0, 6.0 Hz), 3.32 (3H, s), 3.33 (3H, s), 3.41-3.59 (7H, m), 3.78-3.85 (1H, m), 5.01 (1H, d, J=9.6 Hz), 5.06 (1H, d, J=10.8 Hz), 5.56 (1H, dd, J=10.0, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 695 (M+H)⁺.

Example 115

(8E,12E,14E)-3,16,21-Trihydroxy-6-methoxy-6,10,12,16,20-pentamethyl-7-((4-(tetrahydropyran-4-yl)piperazin-1-yl)carbonyl)oxy-18,19-epoxytricosa-8,12,14-trien-11-olide (Compound 115)

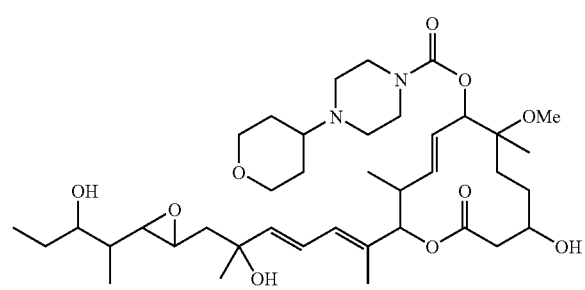

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.19-1.29 (4H, m), 1.34 (3H, s), 1.38-1.69 (9H, m), 1.77-1.85 (5H, m), 1.86 (1H, dd, J=5.2, 14.0 Hz), 2.43-2.63 (8H, m), 2.67 (1H, dd, J=2.4, 8.0 Hz), 2.89 (1H, dt, J=2.4, 6.0 Hz), 3.32 (3H, s), 3.35-3.43 (2H, m), 3.43-3.59 (5H, m), 3.78-3.85 (1H, m), 3.98 (2H, dd, J=4.4, 11.2 Hz), 5.01 (1H, d, J=10.0 Hz), 5.06 (1H, d, J=10.4 Hz), 5.56 (1H, dd, J=10.0, 15.2 Hz), 5.73 (1H, dd, J=9.6, 15.2 Hz), 5.87 (1H, d, J=15.2 Hz), 6.13 (1H, dd, J=1.2, 11.2 Hz), 6.53 (1H, dd, J=10.8, 15.2 Hz); ESI-MS m/z 721 (M+H)⁺.

Example 116

(8E,12E,14E)-7-((4-Cyclopropylpiperazin-1-yl)carbonyl)oxy-3,16,21-trihydroxy-6-methoxy-6,10,12,16,20-pentamethyl-18,19-epoxytricosa-8,12,14-trien-11-olide (Compound 116)

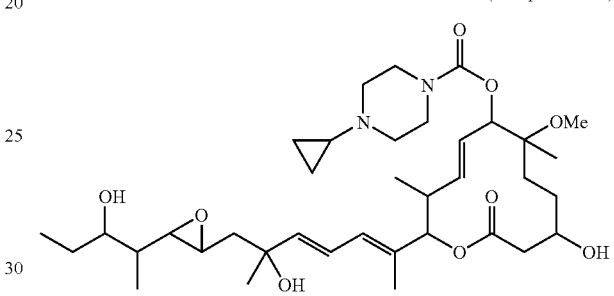

The title compound (a colorless oil) was synthesized by a similar method as described for Example 85.

¹H-NMR Spectrum (CD₃OD, 400 MHz) δ(ppm): 0.40-0.46 (2H, m), 0.46-0.53 (2H, m), 0.89 (3H, d, J=6.4 Hz), 0.90 (3H, d, J=6.8 Hz), 0.94 (3H, t, J=7.6 Hz), 1.19-1.29 (4H, m), 1.34 (3H, s), 1.38-1.70 (8H, m), 1.78 (3H, d, J=0.8 Hz), 1.86 (1H, dd, J=5.2, 14.0 Hz), 2.45-2.63 (7H, m), 2.67 (1H, dd, J=2.4, 8.0 Hz), 2.89 (1H, dt, J=2.4, 6.0 Hz), 3.32 (3H, s), 3.37-3.56 (5H, m), 3.78-3.85 (1H, m), 5.01 (1H, d, J=9.6 Hz), 5.06 (1H, d, J=10.8 Hz), 5.56 (1H, dd, J=9.6, 15.2 Hz), 5.73 (1H, dd, J=10.0, 15.2 Hz), 5.87 (1H, d, J=15.2 Hz), 6.13 (1H, dd, J=1.2, 10.8 Hz), 6.53 (1H, dd, J=10.8, 15.2 Hz); ESI-MS m/z 677 (M+H)⁺.

Example 117

(8E,12E,14E)-7-((4-Cyclobutylpiperazin-1-yl)carbonyl)oxy-3,16,21-trihydroxy-6-methoxy-6,10,12,16,20-pentamethyl-18,19-epoxytricosa-8,12,14-trien-11-olide (Compound 117)

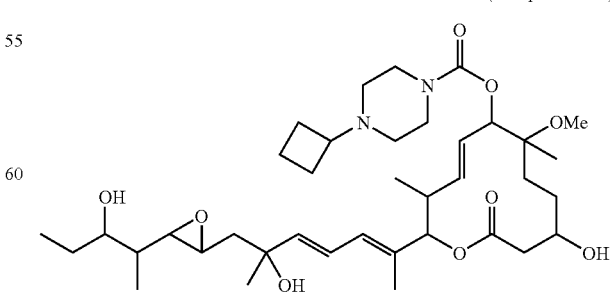

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.19-1.29 (4H, m), 1.34 (3H, s), 1.39-1.78 (9H, m), 1.78 (3H, d, J=0.8 Hz), 1.83-1.95 (3H, m), 2.02-2.10 (2H, m), 2.31 (4H, t, J=4.8 Hz), 2.45-2.63 (3H, m), 2.67 (1H, dd, J=2.4, 8.0 Hz), 2.72-2.81 (1H, m), 2.89 (1H, dt, J=2.0, 6.0 Hz), 3.31 (3H, s), 3.40-3.58 (5H, m), 3.78-3.85 (1H, m), 5.01 (1H, d, J=9.6 Hz), 5.06 (1H, d, J=10.8 Hz), 5.56 (1H, dd, J=10.0, 15.2 Hz), 5.73 (1H, dd, J=9.6, 15.2 Hz), 5.87 (1H, d, J=15.2 Hz), 6.13 (1H, d, J=11.2 Hz), 6.53 (1H, dd, J=10.8, 15.2 Hz); ESI-MS m/z 691 (M+H)⁺.

Example 118

(8E,12E,14E)-7-((4-Cyclopentylpiperazin-1-yl)carbonyl)oxy-3,16,21-trihydroxy-6-methoxy-6,10,12,16,20-pentamethyl-18,19-epoxytricosa-8,12,14-trien-11-olide (Compound 118)

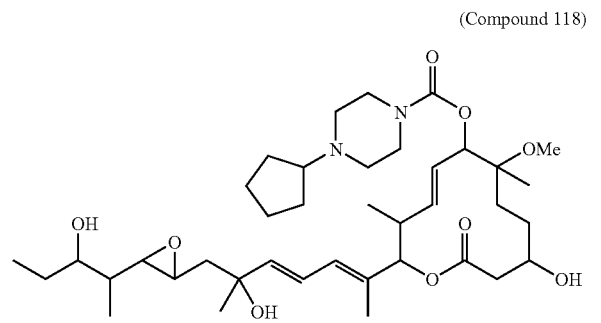

The title compound (a colorless oil) was synthesized by a similar method as described for Example 85.

¹H-NMR Spectrum (CD₃OD, 400 MHz) δ(ppm): 0.89 (3H, d, J=6.8 Hz), 0.90 (3H, d, J=6.8 Hz), 0.94 (3H, t, J=7.2 Hz), 1.19-1.29 (4H, m), 1.34 (3H, s), 1.36-1.77 (13H, m), 1.78 (3H, d, J=0.8 Hz), 1.86 (1H, dd, J=5.2, 14.0 Hz), 1.86-1.95 (2H, m), 2.44-2.63 (8H, m), 2.67 (1H, dd, J=2.4, 8.0 Hz), 2.89 (1H, dt, J=2.0, 6.0 Hz), 3.32 (3H, s), 3.42-3.59 (5H, m), 3.78-3.85 (1H, m), 5.01 (1H, d, J=10.0 Hz), 5.06 (1H, d, J=10.4 Hz), 5.56 (1H, dd, J=9.6, 15.2 Hz), 5.73 (1H, dd, J=9.6, 15.2 Hz), 5.87 (1H, d, J=15.2 Hz), 6.13 (1H, dd, J=1.2, 10.8 Hz), 6.53 (1H, dd, J=11.2, 15.2 Hz); ESI-MS m/z 705 (M+H)⁺.

Example 119

(8E,12E,14E)-7-((4-Cyclohexylpiperazin-1-yl)carbonyl)oxy-3,16,21-trihydroxy-6-methoxy-6,10,12,16,20-pentamethyl-18,19-epoxytricosa-8,12,14-trien-11-olide (Compound 119)

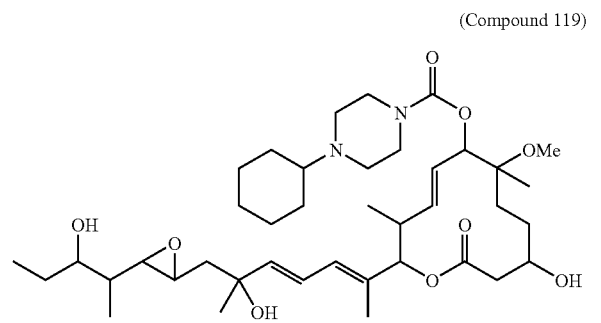

The title compound (a colorless oil) was synthesized by a similar method as described for Example 85.

¹H-NMR Spectrum (CD₃OD, 400 MHz) δ(ppm): 0.89 (3H, d, J=6.8 Hz), 0.90 (3H, d, J=6.8 Hz), 0.94 (3H, t, J=7.6 Hz), 1.09-1.33 (10H, m), 1.34 (3H, s), 1.39-1.69 (7H, m), 1.78 (3H, d, J=0.8 Hz) 1.78-1.93 (5H, m), 2.27-2.35 (1H, m), 2.45-2.65 (7H, m), 2.67 (1H, dd, J=2.4, 8.0 Hz), 2.89 (1H, dt, J=2.4, 6.0 Hz), 3.32 (3H, s), 3.39-3.58 (5H, m), 3.79-3.86 (1H, m), 5.01 (1H, d, J=9.6 Hz), 5.07 (1H, d, J=10.8 Hz), 5.57 (1H, dd, J=10.0, 15.2 Hz), 5.74 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 719 (M+H)⁺.

Example 120

(8E,12E,14E)-7-((4-Cycloheptylpiperazin-1-yl)carbonyl)oxy-3,16,21-trihydroxy-6-methoxy-6,10,12,16,20-pentamethyl-18,19-epoxytricosa-8,12,14-trien-11-olide (Compound 120)

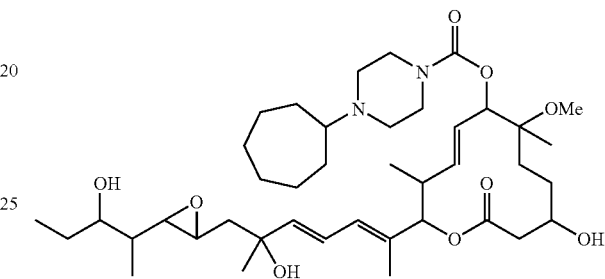

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.19-1.30 (4H, m), 1.34 (3H, s), 1.38-1.75 (17H, m), 1.78 (3H, d, J=0.8 Hz), 1.79-1.86 (2H, m), 1.86 (1H, dd, J=5.2, 14.0 Hz), 2.45-2.64 (8H, m), 2.67 (1H, dd, J=2.4, 8.0 Hz), 2.89 (1H, dt, J=2.4, 6.0 Hz), 3.32 (3H, s), 3.39-3.57 (5H, m), 3.78-3.85 (1H, m), 5.01 (1H, d, J=9.6 Hz), 5.06 (1H, d, J=10.8 Hz), 5.56 (1H, dd, J=9.6, 15.2 Hz), 5.73 (1H, dd, J=9.6, 15.2 Hz), 5.87 (1H, d, J=15.2 Hz), 6.13 (1H, d, J=10.8 Hz), 6.53 (1H, dd, J=10.8, 15.2 Hz); ESI-MS m/z 733 (M+H)⁺.

Example 121

(8E,12E,14E)-3,16,21-Trihydroxy-6-methoxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide (Compound 121)

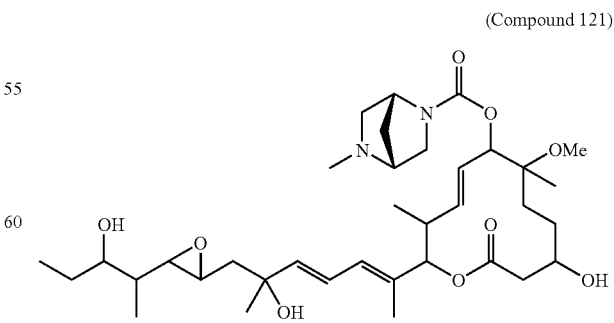

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.20-1.29 (4H, m), 1.34 (3H, s), 1.40-1.69 (7H, m), 1.74-1.82 (4H, m), 1.83-1.93 (2H, m), 2.38 (1.2H, s), 2.41 (1.8H, s), 2.44-2.63 (3H, m), 2.65-2.71 (2H, m), 2.75-2.85 (1H, m), 2.89 (1H, dt, J=2.0, 6.0 Hz), 3.20-3.30 (1H, m), 3.33 (1.8H, s), 3.34 (1.2H, s), 3.46-3.59 (3H, m), 3.79-3.85 (1H, m), 4.32 (0.4H, s), 4.42 (0.6H, s), 4.98-5.04 (1H, m), 5.06 (1H, d, J=10.4 Hz), 5.56 (1H, dd, J=9.6, 15.2 Hz), 5.74 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 663 (M+H)⁺.

Example 122

(8E,12E,14E)-7-(((1S,4S)-5-Ethyl-2,5-diazabicyclo[2.2.1]heptan-2-yl)carbonyl)oxy-3,16,21-trihydroxy-6-methoxy-6,10,12,16,20-pentamethyl-18,19-epoxytricosa-8,12,14-trien-11-olide (Compound 122)

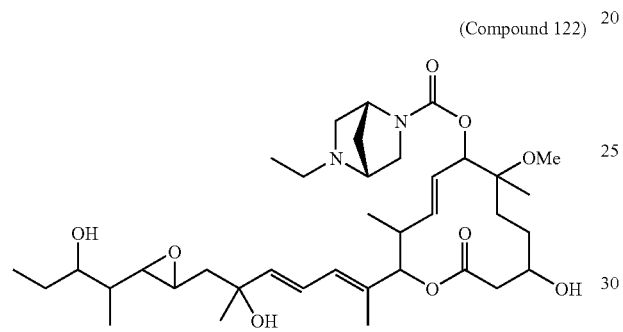

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=6.8 Hz), 0.94 (3H, t, J=7.6 Hz), 1.05-1.13 (3H, m), 1.20-1.30 (4H, m), 1.34 (3H, s), 1.38-1.69 (7H, m), 1.78 (3H, d, J=0.8 Hz), 1.83-1.91 (2H, m), 2.45-2.72 (8H, m), 2.82-2.93 (2H, m), 3.20-3.31 (1H, m), 3.33 (1.5H, s), 3.34 (1.5H, s), 3.50-3.64 (3H, m), 3.79-3.85 (1H, m), 4.32 (0.5H, s), 4.42 (0.5H, s), 4.98-5.04 (1H, m), 5.06 (1H, d, J=10.8 Hz), 5.56 (1H, dd, J=10.0, 15.2 Hz), 5.74 (1H, dd, J=10.0, 15.2 Hz), 5.87 (1H, d, J=15.2 Hz), 6.13 (1H, dd, J=1.2, 10.8 Hz), 6.53 (1H, dd, J=10.8, 15.2 Hz); ESI-MS m/z 677 (M+H)⁺.

Example 123

(8E,12E,14E)-3,16,21-Trihydroxy-7-(((1S,4S)-5-isopropyl-2,5-diazabicyclo[2.2.1]heptan-2-yl)carbonyl)oxy-6-methoxy-6,10,12,16,20-pentamethyl-18,19-epoxytricosa-8,12,14-trien-11-olide (Compound 123)

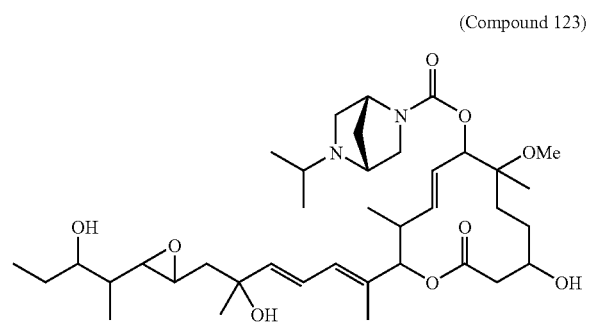

The title compound (a colorless oil) was synthesized by a similar method as described for Example 85.

¹H-NMR Spectrum (CD₃OD, 400 MHz) δ(ppm): 0.88 (3H, d, J=6.4 Hz), 0.90 (3H, d, J=6.8 Hz), 0.94 (3H, t, J=7.6 Hz), 1.05-1.11 (6H, m), 1.19-1.30 (4H, m), 1.34 (3H, s), 1.37-1.69 (7H, m), 1.73-1.90 (5H, m), 2.45-2.65 (6H, m), 2.67 (1H, dd, J=2.4, 8.0), 2.89 (1H, dt, J=2.0, 6.0 Hz), 3.01-3.20 (1H, m), 3.18-3.29 (1H, m), 3.32-3.35 (3H, m), 3.52 (1H, td, J=4.4, 8.4 Hz), 3.54-3.65 (1H, m), 3.76-3.86 (2H, m), 4.30 (0.5H, s), 4.40 (0.5H, s), 4.98-5.09 (2H, m), 5.57 (1H, dd, J=9.6, 15.2 Hz), 5.70-5.79 (1H, m), 5.87 (1H, d, J=15.2 Hz), 6.13 (1H, d, J=10.8 Hz), 6.53 (1H, dd, J=10.8, 15.2 Hz); ESI-MS m/z 691 (M+H)⁺.

Example 124

(8E,12E,14E)-7-((4-(2-(N,N-Dimethylamino)ethyl)piperazin-1-yl)carbonyl)oxy-3,16,21-trihydroxy-6-methoxy-6,10,12,16,20-pentamethyl-18,19-epoxytricosa-8,12,14-trien-11-olide (Compound 124)

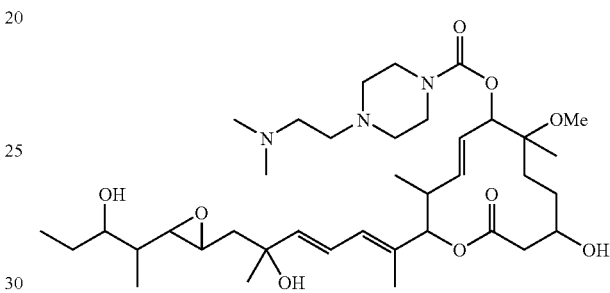

The title compound (a colorless oil) was synthesized by a similar method as described for Example 85.

¹H-NMR Spectrum (CD₃OD, 400 MHz) δ(ppm): 0.88 (3H, d, J=6.8 Hz), 0.90 (3H, d, J=7.2 Hz), 0.94 (3H, t, J=7.6 Hz), 1.19-1.30 (4H, m), 1.34 (3H, s), 1.37-1.69 (7H, m), 1.78 (3H, d, J=0.8 Hz), 1.86 (1H, dd, J=5.2, 14.0 Hz), 2.27 (6H, s), 2.43-2.48 (4H, m), 2.48-2.62 (7H, m), 2.67 (1H, dd, J=2.4, 8.0 Hz), 2.89 (1H, dt, J=2.0, 6.0 Hz), 3.32 (3H, s), 3.41-3.59 (5H, m), 3.78-3.85 (1H, m), 5.01 (1H, d, J=9.6 Hz), 5.06 (1H, d, J=10.8 Hz), 5.56 (1H, dd, J=10.0, 15.2 Hz), 5.73 (1H, dd, J=10.0, 15.2 Hz), 5.87 (1H, d, J=15.2 Hz), 6.13 (1H, d, J=10.8 Hz), 6.53 (1H, dd, J=10.8, 15.2 Hz); ESI-MS m/z 708 (M+H)⁺.

Example 125

(8E,12E,14E)-3,16,21-Trihydroxy-6-methoxy-6,10,12,16,20-pentamethyl-7-((4-(1-methylpiperidin-4-yl)piperazin-1-yl)carbonyl)oxy-18,19-epoxytricosa-8,12,14-trien-11-olide (Compound 125)

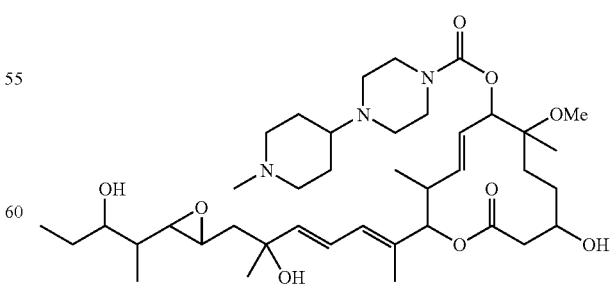

The title compound (a colorless oil) was synthesized by a similar method as described for Example 85.

¹H-NMR Spectrum (CD₃OD, 40 MHz) δ(ppm): 0.88 (3H, d, J=6.8 Hz), 0.90 (3H, d, J=7.2 Hz), 0.94 (3H, t, J=7.6 Hz), 1.19-1.30 (4H, m), 1.34 (3H, s), 1.39-1.69 (9H, m), 1.78 (3H, d, J=1.2 Hz), 1.83-1.90 (3H, m), 1.98-2.07 (2H, m), 2.24-2.33 (1H, m), 2.25 (3H, s), 2.45-2.62 (7H, m), 2.67 (1H, dd, J=2.4, 8.0 Hz), 2.87-2.96 (3H, m), 3.32 (3H, s), 3.41-3.58 (5H, m), 3.79-3.86 (1H, m), 5.01 (1H, d, J=9.6 Hz), 5.06 (1H, d, J=10.8 Hz), 5.56 (1H, dd, J=10.0, 15.2 Hz), 5.73 (1H, dd, J=10.0, 15.2 Hz), 5.87 (1H, d, J=15.2 Hz), 6.13 (1H, dd, J=1.2, 10.8 Hz), 6.53 (1H, dd, J=10.8, 15.2 Hz); ESI-MS m/z 734 (M+H)$^+$.

Example 126

(8E,12E,14E)-3,16,21-Trihydroxy-6-methoxy-6,10,12,16,20-pentamethyl-7-((4-(pyridin-4-yl)piperazin-1-yl)carbonyl)oxy-18,19-epoxytricosa-8,12,14-trien-11-olide (Compound 126)

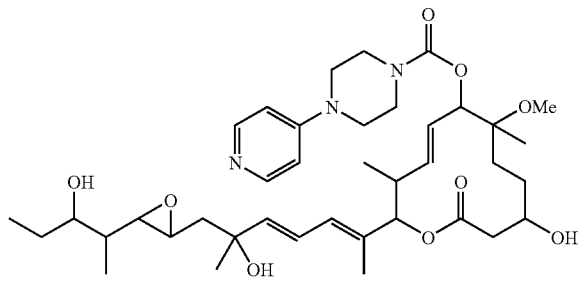

The title compound (a colorless oil) was synthesized by a similar method as described for Example 85.

$^1$H-NMR Spectrum (CD$_3$OD, 400 MHz) δ(ppm): 0.88 (3H, d, J=6.8 Hz), 0.90 (3H, d, J=6.8 Hz), 0.94 (3H, t, J=7.6 Hz), 1.19-1.29 (4H, m), 1.34 (3H, s), 1.38-1.69 (7H, m), 1.78 (3H, d, J=1.2 Hz), 1.86 (1H, dd, J=5.2, 14.0 Hz), 2.45-2.63 (3H, m), 2.66 (1H, dd, J=2.4, 8.0 Hz), 2.89 (1H, dt, J=2.0, 6.0 Hz), 3.34 (3H, s), 3.40-3.47 (4H, m), 3.52 (1H, td, J=4.4, 8.4 Hz), 3.56-3.72 (4H, m), 3.80-3.87 (1H, m), 5.05 (1H, d, J=9.2 Hz), 5.07 (1H, d, J=10.4 Hz), 5.58 (1H, dd, J=10.0, 15.2 Hz), 5.76 (1H, dd, J=10.0, 15.2 Hz), 5.87 (1H, d, J=15.2 Hz), 6.13 (1H, dd, J=1.2, 11.2 Hz), 6.53 (1H, dd, J=11.2, 15.2 Hz), 6.86 (2H, d, J=6.4 Hz), 8.02-8.04 (2H, m); ESI-MS m/z 714 (M+H)$^+$.

Example 127

(8E,12E,14E)-6-Ethoxy-3,16,21-trihydroxy-6,10,12,16,20-pentamethyl-7-((4-methylpiperazin-1-yl)carbonyl)oxy-18,19-epoxytricosa-8,12,14-trien-11-olide (Compound 127)

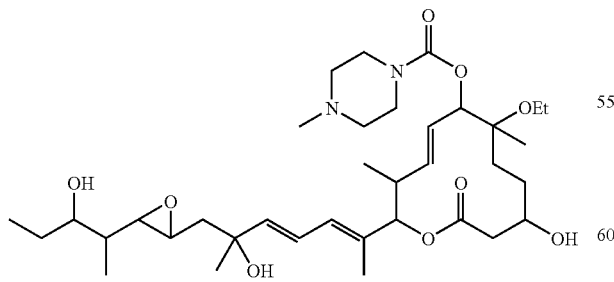

The title compound (a colorless oil) was synthesized by a similar method as described for Example 85 except for using ethyl trifluoromethanesulfonate in the first step.

$^1$H-NMR Spectrum (CD$_3$OD, 400 MHz) δ(ppm): 0.88 (3H, d, J=6.8 Hz), 0.90 (3H, d, J=6.8 Hz), 0.94 (3H, t, J=7.6 Hz), 1.16 (3H, t, J=7.2 Hz), 1.22 (3H, s), 1.22-1.60 (7H, m), 1.34 (3H, s), 1.65 (1H, dd, J=6.4, 14.0 Hz), 1.78 (3H, s), 1.86 (1H, dd, J=5.6, 13.6 Hz), 2.30 (3H, s), 2.36-2.43 (4H, m), 2.43-2.69 (4H, m), 2.89 (1H, dt, J=2.4, 5.6 Hz), 3.43-3.61 (7H, m), 3.77-3.84 (1H, m), 4.98 (1H, d, J=9.6 Hz), 5.06 (1H, d, J=10.8 Hz), 5.55 (1H, dd, J=10.0, 15.2 Hz), 5.76 (1H, dd, J=9.6, 15.2 Hz), 5.86 (1H, d, J=15.2 Hz), 6.13 (1H, d, J=11.2 Hz), 6.52 (1H, dd, J=11.2, 15.2 Hz); ESI-MS m/z 665 (M+H)$^+$.

Example 128

(8E,12E,14E)-6-Ethoxy-3,16,21-trihydroxy-6,10,12,16,20-pentamethyl-7-((4-(piperidin-1-yl)piperidin-1-yl)carbonyl)oxy-18,19-epoxytricosa-8,12,14-trien-11-olide (Compound 128)

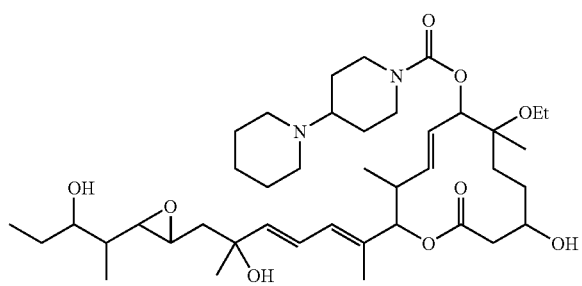

The title compound (a colorless oil) was synthesized by a similar method as described for Example 127.

$^1$H-NMR Spectrum (CD$_3$OD, 400 MHz) δ(ppm): 0.88 (3H, d, J=6.0 Hz), 0.90 (3H, d, J=6.8 Hz), 0.94 (3H, t, J=7.6 Hz), 1.17 (3H, t, J=6.8 Hz), 1.22 (3H, s), 1.22-1.69 (16H, m), 1.34 (3H, s), 1.78 (3H, s), 1.83-1.93 (3H, m), 2.42-2.63 (8H, m), 2.67 (1H, dd, J=2.4, 7.6 Hz), 2.70-2.92 (3H, m), 3.49-3.62 (3H, m), 3.77-3.84 (1H, m), 4.13-4.27 (2H, m), 4.98 (1H, d, J=9.6 Hz), 5.06 (1H, d, J=10.4 Hz), 5.54 (1H, dd, J=10.0, 15.2 Hz), 5.76 (1H, dd, J=9.6, 15.6 Hz), 5.86 (1H, d, J=15.2 Hz), 6.13 (1H, d, J=10.0 Hz), 6.52 (1H, dd, J=11.2, 15.2 Hz); ESI-MS m/z 733 (M+H)$^+$.

Example 129

(8E,12E,14E)-7-Acetoxy-6,16-dihydroxy-6,10,12,16,20-pentamethyl-3,21-bis(triethylsiloxy)-18,19-epoxytricosa-8,12,14-trien-11-olide (Compound 129)

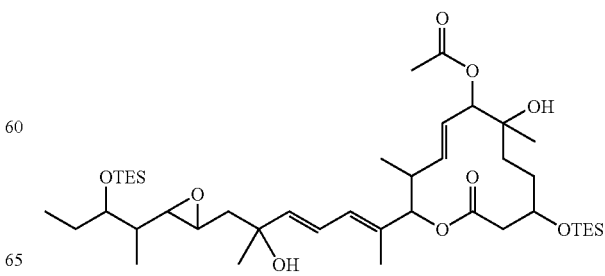

A solution of (8E,12E,14E)-7-acetoxy-3,6,16,21-tetrahydroxy-6,10,12,16,20-pentamethyl-18,19-epoxytricosa-8,12,14-trien-11-olide (221 mg, 0.4 mmol), N,N-dimethylaminopyridine (25 mg, 0.2 mmol) and triethylamine (613 mg, 6 mmol) in dichloromethane (7 mL) was cooled to 5° C., a solution of chlorotriethylsilane (609 mg, 4 mmol) in dichloromethane (3 mL) was added dropwise thereto, and the reaction mixture was stirred at room temperature for one hour. The reaction mixture was diluted with ethyl acetate, washed with water and a saturated aqueous solution of sodium bicarbonate, dried over anhydrous magnesium sulfate and evaporated. The resulting residue was purified by silica gel column chromatography (Kanto silica gel 60N, 40 to 50 μm; ethyl acetate-hexane, 1:9 to 1:4 to 1:3) to give the title compound (320 mg, quantitative) as a colorless oil.

ESI-MS m/z 803 (M+Na)$^+$.

Example 130

(8E,12E,14E)-3,6,16-Trihydroxy-7-((4-isopropylpiperazin-1-yl)carbonyl)oxy-21-methoxy-6,10,12,16,20-pentamethyl-18,19-epoxytricosa-8,12,14-trien-11-olide (Compound 130)

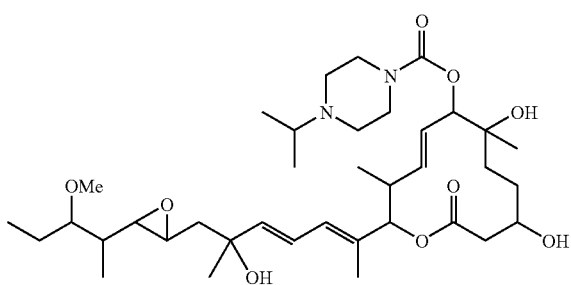

First Step (8E,12E,14E)-7-Acetoxy-6,16-bis(1-ethoxyethoxy)-6,10,12,16,20-pentamethyl-3,21-bis(triethylsiloxy)-18,19-epoxytricosa-8,12,14-trien-11-olide (Compound 130-1)

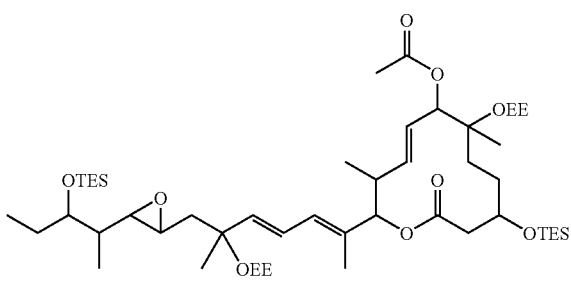

To a solution of Compound 129 (8E,12E,14E)-7-acetoxy-6,16-dihydroxy-6,10,12,16,20-pentamethyl-3,21-bis(triethylsiloxy)-18,19-epoxytricosa-8,12,14-trien-11-olide (320 mg, 0.41 mmol) obtained in Example 129 and ethylvinyl ether (589 mg, 8 mmol) in dichloromethane (6 mL) was added a solution of pyridinium p-toluenesulfonate (5 mg, 20 μmol) in dichloromethane (1 mL) at room temperature, and the reaction mixture was stirred at the same temperature overnight. The reaction mixture was diluted with ethyl acetate, washed with water and a saturated aqueous solution of sodium bicarbonate, dried over anhydrous magnesium sulfate and evaporated. The resulting residue was purified by silica gel column chromatography (Kanto silica gel 60N, 40 to 50 μm; ethyl acetate-hexane, 1:9 to 1:7) to give the title compound (252 mg, 67%) as a colorless oil.

ESI-MS m/z 947 (M+Na)$^+$.

Second Step (8E,12E,14E)-7-Acetoxy-6,16-bis(1-ethoxyethoxy)-3,21-dihydroxy-6,10,12,16,20-pentamethyl-18,19-epoxytricosa-8,12,14-trien-11-olide (Compound 130-2)

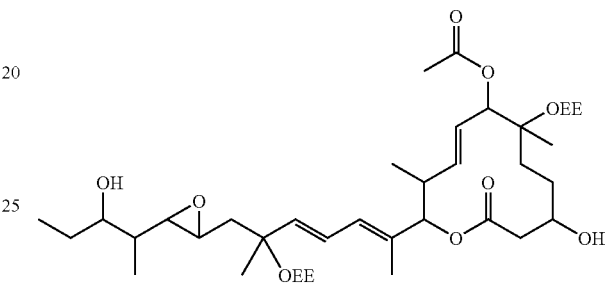

A solution of Compound 130-1 (8E,12E,14E)-7-acetoxy-6,16-bis(1-ethoxyethoxy)-6,10,12,16,20-pentamethyl-3,21-bis(triethylsiloxy)-18,19-epoxytricosa-8,12,14-trien-11-olide (107 mg, 0.1156 mmol) obtained in the first step in tetrahydrofuran (6 mL) was cooled to 5° C., tetrabutylammonium fluoride (1.0 M tetrahydrofuran solution, 0.25 mL, 0.25 mmol) was added dropwise thereto, and the reaction mixture was stirred at room temperature for 1.5 hours. The reaction mixture was diluted with ethyl acetate and then washed with water and a saturated aqueous solution of sodium bicarbonate, dried over anhydrous magnesium sulfate and evaporated. The resulting residue was purified by silica gel column chromatography (Kanto silica gel 60N, 40 to 50 μm; ethyl acetate-hexane, 1:1 to 2:1) to give the title compound (81 mg, 100%) as a colorless oil.

ESI-MS m/z 719 (M+Na)$^+$.

Third Step (8E,12E,14E)-7-Acetoxy-3-diethylisopropylsiloxy-6,16-bis(1-ethoxyethoxy)-21-hydroxy-6,10,12,16,20-pentamethyl-18,19-epoxytricosa-8,12,14-trien-11-olide (Compound 130-3)

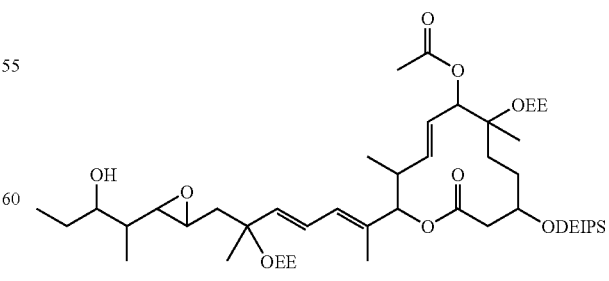

A solution of Compound 130-2 (8E,12E,14E)-7-acetoxy-6,16-bis(1-ethoxyethoxy)-3,21-dihydroxy-6,10,12,16,20-pentamethyl-18,19-epoxytricosa-8,12,14-trien-11-olide (33.2 mg, 47.6 μmol) obtained in the second step, N,N-dimethylaminopyridine (3 mg, 23.8 μmol) and triethylamine (49 mg, 0.476 mmol) in dichloromethane (1 mL) was cooled to −20° C., diethylisopropylsilyl chloride (10.3 mg, 59.5 μmol) was added dropwise thereto, and the reaction mixture was stirred at −20° C. to 5° C. for 1.2 hours. Next, diethylisopropylsilyl chloride (31 mg, 179 μmol) was added dropwise to the reaction mixture at the same temperature, followed by stirring for 4.5 hours. Further, diethylisopropylsilyl chloride (41.2 mg, 238 μmol) was added dropwise to the reaction mixture at the same temperature, followed by stirring for 1.3 hours, and then stirring at room temperature for one hour. The reaction mixture was diluted with ethyl acetate, washed with water and a saturated aqueous solution of sodium bicarbonate, dried over anhydrous magnesium sulfate and evaporated. The resulting residue was purified by thin layer chromatography (Merck Art 1.05628; ethyl acetate-hexane, 1:2) to give the title compound (19.1 mg, 49%) as a colorless oil.

ESI-MS m/z 847 (M+Na)$^+$.

Fourth Step (8E,12E,14E)-7-Acetoxy-3-diethylisopropylsiloxy-6,16-bis(1-ethoxyethoxy)-21-methoxy-6,10,12,16,20-pentamethyl-18,19-epoxytricosa-8,12,14-trien-11-olide

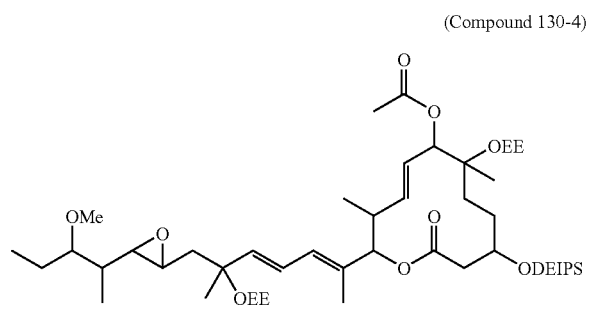

(Compound 130-4)

A solution of Compound 130-3 (8E,12E,14E)-7-acetoxy-3-diethylisopropylsiloxy-6,16-bis(1-ethoxyethoxy)-21-hydroxy-6,10,12,16,20-pentamethyl-18,19-epoxytricosa-8,12,14-trien-11-olide (33.2 mg, 40 μmol) obtained in the third step and 1,8-bis(N,N-dimethylamino)naphthalene (51.4 mg, 0.24 mmol) in toluene (0.7 mL) was cooled to 5° C., and methyl trifluoromethanesulfonate (20 mg, 0.12 mmol) was added dropwise to the reaction mixture, followed by addition of 0.5 mL of toluene. The reaction mixture was stirred at 50° C. for 12.5 hours. The reaction mixture was cooled to room temperature, diluted with toluene, and 0.06 N aqueous ammonia (5 mL) was added at 5° C., followed by stirring at room temperature for about 20 minutes. Ethyl acetate, water and a saturated aqueous solution of ammonium chloride were added thereto, the mixture was stirred for a while, and the organic layer was separated. The organic layer was washed with a 0.05 M aqueous solution of citric acid and an aqueous solution of sodium bicarbonate successively, dried over anhydrous magnesium sulfate and evaporated. The resulting residue was purified by silica gel column chromatography (Kanto silica gel 60N, 40 to 50 μm; ethyl acetate-hexane, 1:9 to 1:7 to 1:4 to 1:3) to give the title compound (15.8 mg, 47%) as a colorless oil.

ESI-MS m/z 861 (M+Na)$^+$.

<Fifth Step>

(8E,12E,14E)-3-Diethylisopropylsiloxy-6,16-bis(1-ethoxyethoxy)-7-hydroxy-21-methoxy-6,10,12,16,20-pentamethyl-18,19-epoxytricosa-8,12,14-trien-11-olide

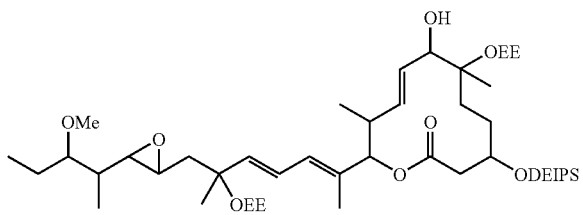

(Compound 130-5)

To Compound 130-4 (8E,12E,14E)-7-acetoxy-3-diethylisopropylsiloxy-6,16-bis(1-ethoxyethoxy)-21-methoxy-6,10,12,16,20-pentamethyl-18,19-epoxytricosa-8,12,14-trien-11-olide (21.5 mg, 25.6 μmol) obtained in the fourth step was added a 0.2M solution of guanidine/guanidine nitrate (methanol-dichloromethane, 9:1) (0.26 mL, 52 μmol), followed by stirring at room temperature for 12.5 hours. The reaction mixture was diluted with ethyl acetate, washed with water and a saturated aqueous solution of ammonium chloride, dried over anhydrous magnesium sulfate and evaporated. The resulting residue was purified by silica gel column chromatography (Kanto silica gel 60N, 40 to 50 μm; ethyl acetate-hexane, 1:7 to 1:5 to 1:4) to give the title compound (19.3 mg, 95%) as a colorless oil.

ESI-MS m/z 819 (M+Na)$^+$.

Sixth Step (8E,12E,14E)-3-Diethylisopropylsiloxy-6,16-bis(1-ethoxyethoxy)-21-methoxy-6,10,12,16,20-pentamethyl-7-(4-nitrophenoxy)carboxy-18,19-epoxytricosa-8,12,14-trien-11-olide

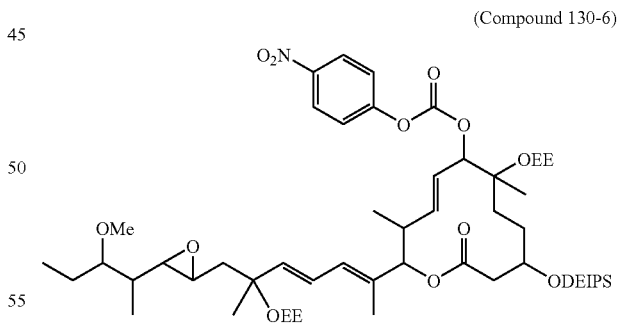

(Compound 130-6)

A solution of Compound 130-5 (8E,12E,14E)-3-diethylisopropylsiloxy-6,16-bis(1-ethoxyethoxy)-7-hydroxy-21-methoxy-6,10,12,16,20-pentamethyl-18,19-epoxytricosa-8,12,14-trien-11-olide (19.3 mg, 24.2 μmol) obtained in the fifth step, N,N-dimethylaminopyridine (3 mg, 24.2 μmol) and triethylamine (25 mg, 0.242 mmol) in dichloromethane (1.2 mL) was cooled to 5° C., a solution of 4-nitrophenyl chloroformate (25 mg, 121 μmol) in dichloromethane (0.3 mL) was added dropwise thereto, followed by stirring at room temperature for three hours. The reaction mixture was diluted with ethyl acetate and then washed with an aqueous solution of sodium bicarbonate. Further the organic layer was sequentially washed with an aqueous solution of ammonium chloride, an aqueous solution of sodium bicarbonate and water in this order. The organic layer was dried over anhydrous magnesium sulfate and evaporated to give a residue of the title compound (40.7 mg) as a pale yellow solid.

This solid was subjected to the subsequent reaction without purification.

Seventh Step (8E,12E,14E)-3-Diethylisopropylsiloxy-6,16-bis(1-ethoxyethoxy)-7-((4-isopropylpiperazin-1-yl)carbonyl)oxy-21-methoxy-6,10,12,16,20-pentamethyl-18,19-epoxytricosa-8,12,14-trien-11-olide (Compound 130-7)

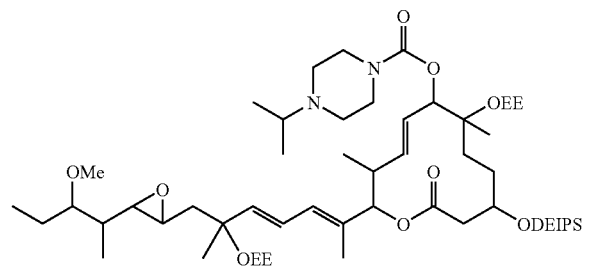

A solution of the crude product of Compound 130-6 (8E,12E,14E)-3-diethylisopropylsiloxy-6,16-bis(1-ethoxyethoxy)-21-methoxy-7-(4-nitrophenoxy)carboxy-6,10,12,16,20-pentamethyl-18,19-epoxytricosa-8,12,14-trien-11-olide (20.4 mg, 12.1 µmol) obtained in the sixth step in tetrahydrofuran (0.9 mL) was cooled to 5° C., and a solution of 1-isopropylpiperazine (2.4 mg, 18.2 µmol) in tetrahydrofuran (0.1 mL) and triethylamine (3.7 mg, 36.3 µmol) were added dropwise thereto, followed by stirring at room temperature for 6.5 hours. The reaction mixture was diluted with ethyl acetate, washed with water and a saturated aqueous solution of sodium bicarbonate, dried over anhydrous magnesium sulfate and evaporated. The resulting residue was purified by thin layer chromatography (Fuji Silysia NH Silica gel plate; ethyl acetate-hexane, 1:3) to give the title compound (10.0 mg, 87%, two steps) as a colorless oil.

ESI-MS m/z 951 (M+H)$^+$.

Eighth Step (8E,12E,14E)-6,16-Bis(1-ethoxyethoxy)-3-hydroxy-7-((4-isopropylpiperazin-1-yl)carbonyl)oxy-21-methoxy-6,10,12,16,20-pentamethyl-18,19-epoxytricosa-8,12,14-trien-11-olide (Compound 130-8)

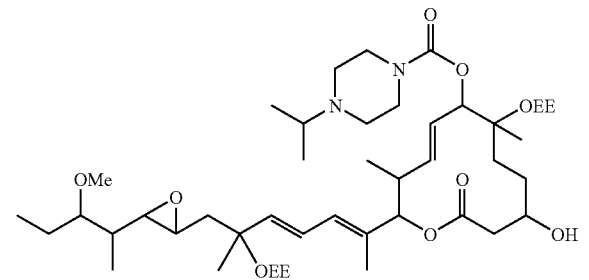

A solution of Compound 130-7 (8E,12E,14E)-3-diethylisopropylsiloxy-6,16-bis(1-ethoxyethoxy)-7-((4-isopropylpiperazin-1-yl)carbonyl)oxy-21-methoxy-6,10,12,16,20-pentamethyl-18,19-epoxytricosa-8,12,14-trien-11-olide (10 mg, 10.5 µmol) obtained in the seventh step in tetrahydrofuran (1.0 mL) was cooled to 5° C., and tetrabutylammonium fluoride (1.0 M tetrahydrofuran solution, 11.6 µl, 11.6 µmol) was added dropwise thereto, followed by stirring at room temperature for 1.5 hours. The reaction mixture was diluted with ethyl acetate, washed with water and a saturated aqueous solution of sodium bicarbonate, dried over anhydrous magnesium sulfate and evaporated. The resulting residue was purified by thin layer chromatography (Merck Art 1.05628; methanol-dichloromethane, 1:29) to give the title compound (7.4 mg, 86%) as a colorless oil.

ESI-MS m/z 823 (M+H)$^+$.

Ninth Step (8E,12E,14E)-3,6,16-Trihydroxy-7-((4-isopropylpiperazin-1-yl)carbonyl)oxy-21-methoxy-6,10,12,16,20-pentamethyl-18,19-epoxytricosa-8,12,14-trien-11-olide (Compound 130)

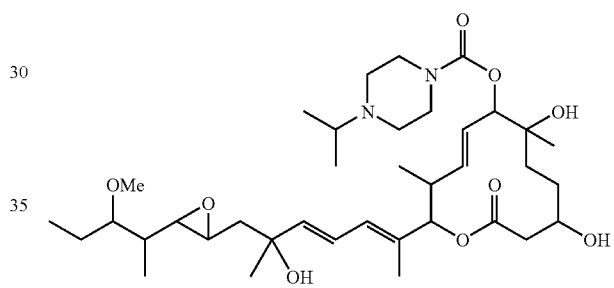

To a solution of Compound 130-8 (8E,12E,14E)-6,16-bis(1-ethoxyethoxy)-3-hydroxy-7-((4-isopropylpiperazin-1-yl)carbonyl)oxy-21-methoxy-6,10,12,16,20-pentamethyl-18,19-epoxytricosa-8,12,14-trien-11-olide (7.4 mg, 9 µmol) obtained in the eighth step in a mixture of tetrahydrofuran:2-methyl-2-propanol=1:1 (0.7 mL) was added pyridinium p-toluenesulfonate (6.8 mg, 27 µmol), followed by stirring at room temperature for 24 hours. The reaction mixture was diluted with ethyl acetate, washed with water and a saturated aqueous solution of sodium bicarbonate, dried over anhydrous magnesium sulfate and evaporated. The resulting residue was purified by thin layer chromatography (Fuji Silysia NH Silica gel plate; methanol-dichloromethane, 1:39) to give the title compound (4.2 mg, 69%) as a colorless oil.

$^1$H-NMR Spectrum (CD$_3$OD, 400 MHz) δ(ppm): 0.88 (3H, d, J=7.2 Hz), 0.88 (3H, t, J=7.6 Hz), 0.89 (3H, d, J=6.8 Hz), 1.07 (6H, d, J=6.4 Hz), 1.21 (3H, s), 1.28-1.70 (11H, m), 1.77 (3H, d, J=1.2 Hz), 1.85 (1H, dd, J=5.2, 14.0 Hz), 2.47-2.62 (7H, m), 2.64 (1H, dd, J=2.4, 8.0 Hz), 2.67-2.74 (1H, m), 2.88 (1H, dt, J=2.4, 6.0 Hz), 3.14-3.19 (1H, m), 3.38 (3H, s), 3.42-3.70 (4H, m), 3.75-3.82 (1H, m), 4.93 (1H, d, J=10.0 Hz), 5.06 (1H, d, J=10.8 Hz), 5.57 (1H, dd, J=10.0, 15.2 Hz), 5.72 (1H, dd, J=9.6, 15.2 Hz), 5.87 (1H, d, J=15.2 Hz), 6.13 (1H, d, J=10.8 Hz), 6.53 (1H, dd, J=11.2, 15.2 Hz); ESI-MS m/z 679 (M+H)$^+$.

Example 131

(8E,12E,14E)-3,6,16-Trihydroxy-21-methoxy-6,10,12,16,20-pentamethyl-7-((4-methylpiperazin-1-yl)carbonyl)oxy-18,19-epoxytricosa-8,12,14-trien-11-olide (Compound 131)

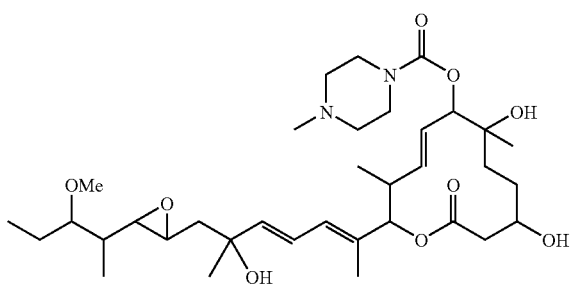

The title compound (a colorless oil) was synthesized by a similar method as described for Example 130.

$^1$H-NMR Spectrum (CD$_3$OD, 400 MHz) δ(ppm): 0.88 (3H, d, J=7.2 Hz), 0.88 (3H, t, J=7.6 Hz), 0.89 (3H, d, J=6.8 Hz), 1.21 (3H, s), 1.29-1.70 (11H, m), 1.77 (3H, d, J=1.2 Hz), 1.85 (1H, dd, J=5.2, 14.0 Hz), 2.30 (3H, s), 2.35-2.63 (7H, m), 2.64 (1H, dd, J=2.4, 8.0 Hz), 2.88 (1H, dt, J=2.4, 6.0 Hz), 3.14-3.20 (1H, m), 3.38 (3H, s), 3.39-3.71 (4H, m), 3.75-3.82 (1H, m), 4.93 (1H, d, J=10.0 Hz), 5.06 (1H, d, J=10.8 Hz), 5.57 (1H, dd, J=9.6, 15.2 Hz), 5.72 (1H, dd, J=9.6, 15.2 Hz), 5.87 (1H, d, J=15.2 Hz), 6.13 (1H, dd, J=1.2, 10.8 Hz), 6.53 (1H, dd, J=10.8, 15.2 Hz); ESI-MS m/z 651 (M+H)$^+$.

Example 132

(8E,12E,14E)-3,6,16-Trihydroxy-21-methoxy-6,10,12,16,20-pentamethyl-7-((4-methylhomopiperazin-1-yl)carbonyl)oxy-18,19-epoxytricosa-8,12,14-trien-11-olide (Compound 132)

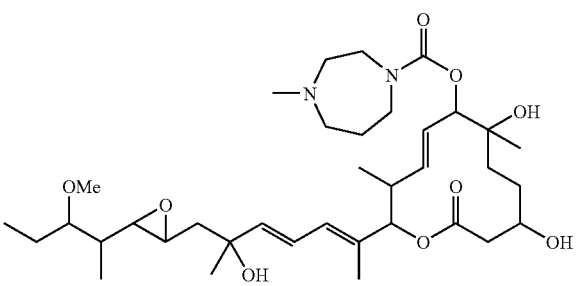

The title compound (a colorless oil) was synthesized by a similar method as described for Example 130.

$^1$H-NMR Spectrum (CD$_3$OD, 400 MHz) δ(ppm): 0.88 (3H, d, J=7.2 Hz), 0.88 (3H, t, J=7.6 Hz), 0.89 (3H, d, J=6.8 Hz), 1.22 (1.2H, s), 1.23 (1.8H, s), 1.28-1.71 (11H, m), 1.77 (3H, d, J=0.8 Hz), 1.81-1.93 (3H, m), 2.34 (1.2H, s), 2.35 (1.8H, s), 2.50-2.67 (8H, m), 2.88 (1H, dt, J=2.0, 6.0 Hz), 3.14-3.20 (1H, m), 3.38 (3H, s), 3.47-3.56 (2H, m), 3.58-3.67 (2H, m), 3.75-3.82 (1H, m), 4.95 (1H, d, J=10.0 Hz), 5.07 (1H, d, J=10.8 Hz), 5.57 (1H, dd, J=9.6, 15.2 Hz), 5.73 (1H, dd, J=9.6, 15.2 Hz), 5.87 (1H, d, J=15.2 Hz), 6.13 (1H, d, J=11.2 Hz), 6.53 (1H, dd, J=10.8, 15.2 Hz); ESI-MS m/z 665 (M+H)$^+$.

Example 133

(8E,12E,14E)-7-((4-Ethylhomopiperazin-1-yl)carbonyl)oxy-3,6,16-trihydroxy-21-methoxy-6,10,12,16,20-pentamethyl-18,19-epoxytricosa-8,12,14-trien-11-olide (Compound 133)

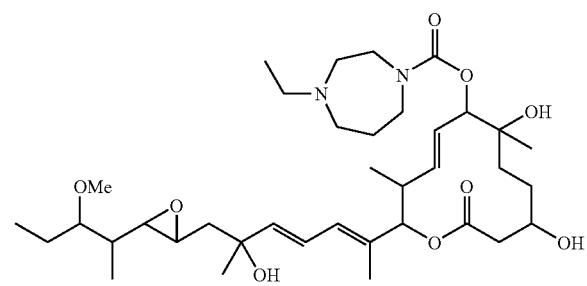

The title compound (a colorless oil) was synthesized by a similar method as described for Example 130.

$^1$H-NMR Spectrum (CD$_3$OD, 400 MHz) δ(ppm): 0.88 (3H, d, J=7.2 Hz), 0.88 (3H, t, J=7.6 Hz), 0.89 (3H, d, J=6.8 Hz), 1.08 (1.5H, t, J=7.2 Hz), 1.09 (1.5H, t, J=7.2 Hz), 1.22 (1.5H, s), 1.23 (1.5H, s), 1.28-1.70 (11H, m), 1.77 (3H, d, J=1.2 Hz), 1.82-1.91 (3H, m), 2.47-2.76 (10H, m), 2.88 (1H, dt, J=2.4, 6.0 Hz), 3.14-3.19 (1H, m), 3.38 (3H, s), 3.45-3.67 (4H, m), 3.75-3.82 (1H, m), 4.95 (1H, d, J=9.6 Hz), 5.07 (1H, d, J=10.8 Hz), 5.57 (1H, dd, J=9.6, 15.2 Hz), 5.73 (1H, dd, J=9.6, 15.2 Hz), 5.87 (1H, d, J=15.2 Hz), 6.13 (1H, d, J=11.2 Hz), 6.53 (1H, dd, J=10.8, 15.2 Hz); ESI-MS m/z 679 (M+H)$^+$.

Example 134

(8E,12E,14E)-7-Acetoxy-3,16,21-trihydroxy-6,10,12,16,20-pentamethyl-6-((4-methylpiperazin-1-yl)carbonyl)oxy-18,19-epoxytricosa-8,12,14-trien-11-olide (Compound 134)

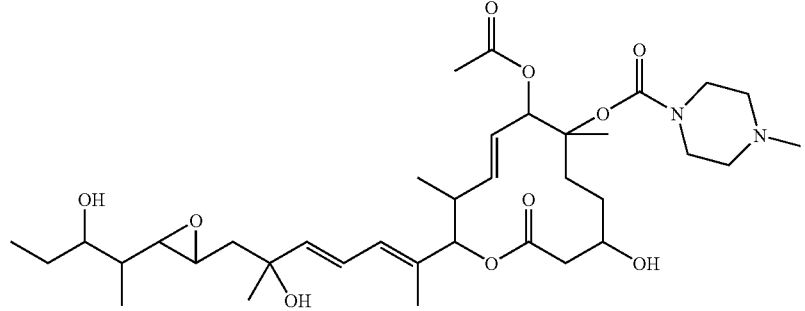

First Step (8E,12E,14E)-7-Acetoxy-6,10,12,16,20-pentamethyl-6-(4-nitrophenoxy)carboxy-3,16,21-tris(triethylsiloxy)-18,19-epoxytricosa-8,12,14-trien-11-olide (Compound 134-1)

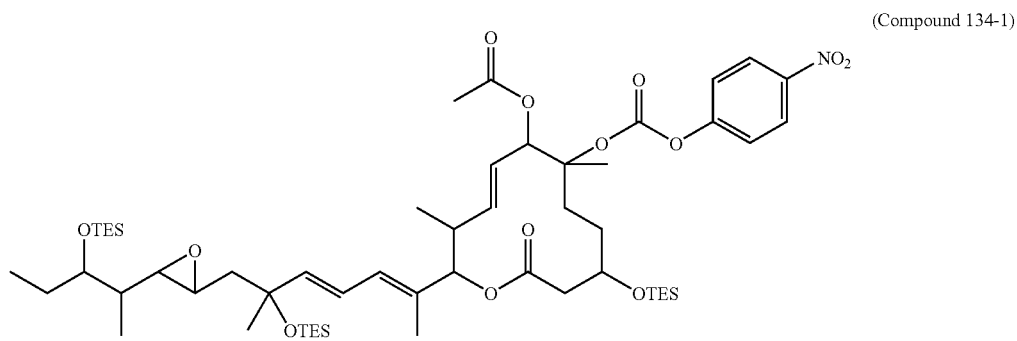

To a solution of Compound 46-1 (8E,12E,14E)-7-acetoxy-6-hydroxy-6,10,12,16,20-pentamethyl-3,16,21-tris(triethylsiloxy)-18,19-epoxytricosa-8,12,14-trien-11-olide (44 mg, 49 μmol) obtained in the first step of Example 46 in dichloromethane (2.0 mL) were added triethylamine (30 mg, 0.29 mmol), N,N-dimethylaminopyridine (90 mg, 0.73 mmol) and 4-nitrophenyl chloroformate (90 mg, 0.44 mmol) under ice-cooling, and the reaction mixture was stirred at room temperature under nitrogen atmosphere for three days. The reaction mixture was diluted with ethyl acetate and washed with a saturated aqueous solution of sodium bicarbonate and brine. The organic layer was dried over anhydrous magnesium sulfate, filtrated and evaporated. The resulting residue was purified by silica gel column chromatography (Kanto silica gel 60N, 40 to 100 μm; ethyl acetate:hexane=10:90) to give the title compound (19 mg, 36%) as a colorless oil.

ESI-MS m/z 1082 (M+Na)$^+$.

Second Step (8E,12E,14E)-7-Acetoxy-6,10,12,16,20-pentamethyl-6-((4-methylpiperazin-1-yl)carbonyl)oxy-3,16,21-tris(triethylsiloxy)-18,19-epoxytricosa-8,12,14-trien-11-olide (Compound 134-2)

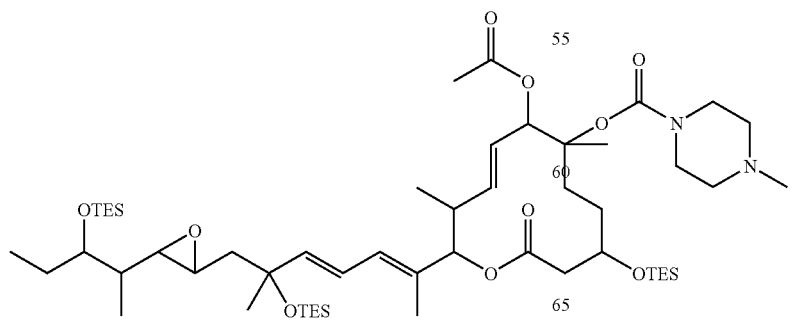

To a solution of Compound 134-1 (8E,12E,14E)-7-acetoxy-6,10,12,16,20-pentamethyl-6-(4-nitrophenyl)carboxy-3,16,21-tris(triethylsiloxy)-18,19-epoxytricosa-8,12,14-trien-11-olide (9 mg, 8.5 μmol) obtained in the first step in tetrahydrofuran (1 mL) were added triethylamine (8 mg, 85 μmol) and 1-methylpiperazine (1.7 mg, 17 μmol) at room temperature, followed by stirring at the same temperature under nitrogen atmosphere for 4 hours. The reaction mixture was diluted with ethyl acetate and then washed with brine. The organic layer was dried over anhydrous sodium sulfate, filtrated and evaporated. The resulting residue was purified by silica gel column chromatography (Kanto silica gel 60N, 40 to 100 μm; ethyl acetate:hexane=50:50) to give the title compound (8.6 mg, 100%) as a colorless oil.

ESI-MS m/z 1021 (M+H)$^+$.

Third Step (8E,12E,14E)-7-Acetoxy-3,16,21-trihydroxy-6,10,12,16,20-pentamethyl-6-((4-methylpiperazin-1-yl)carbonyl)oxy-18,19-epoxytricosa-8,12,14-trien-11-olide anhydrous sodium sulfate, filtrated and evaporated. The resulting residue was purified by silica gel column chromatography (Kanto silica gel 60N, 40 to 100 μm; methanol:dichloromethane=5:95) to give the title compound (4.4 mg, 77%) as a colorless oil.

$^1$H-NMR Spectrum (CD$_3$OD, 400 MHz) δ(ppm): 0.89 (6H, d, J=6.8 Hz), 0.94 (3H, t, J=7.2 Hz), 1.20-1.28 (1H, m), 1.34 (3H, s), 1.38-1.70 (10H, m), 1.78 (3H, s), 1.86 (1H, dd, J=5.2, 14.0 Hz), 2.04 (3H, s), 2.31 (3H, s), 2.38-2.48 (4H, m), 2.48-2.52 (2H, m), 2.56-2.65 (1H, m), 2.66 (1H, dd, J=2.0, 7.6 Hz), 2.89 (1H, dt, J=2.0, 6.4 Hz), 3.42-3.62 (5H, m), 3.76-3.84 (1H, m), 5.01 (1H, d, J=9.6 Hz), 5.06 (1H, d, J=10.8

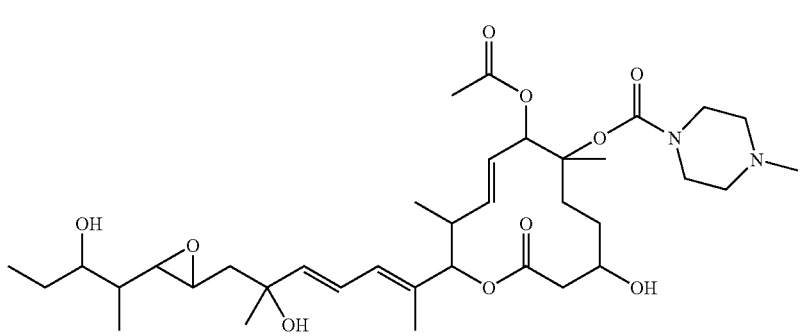

(Compound 134)

To a solution of Compound 134-2 (8E,12E,14E)-7-acetoxy-6,10,12,16,20-pentamethyl-6-((4-methylpiperazin-1-yl)carbonyl)oxy-3,16,21-tris(triethylsiloxy)-18,19-epoxytricosa-8,12,14-trien-11-olide (9 mg, 8.5 μmol) obtained in the second step in tetrahydrofuran (1 mL) was added tetrabutylammonium fluoride (1.0 M tetrahydrofuran solution, 48 μL, 48 μmol) at room temperature, and the reaction mixture was stirred at the same temperature under nitrogen atmosphere for 5 hours. The reaction mixture was diluted with ethyl acetate and washed with brine. The organic layer was dried over Hz), 5.63 (1H, dd, J=9.6, 15.2 Hz), 5.75 (1H, dd, J=9.2, 15.2 Hz), 5.87 (1H, d, J=15.2 Hz), 6.14 (1H, d, J=10.8 Hz), 6.52 (1H, dd, J=10.8, 15.2 Hz); ESI-MS m/z 679 (M+H)$^+$.

Example 135

(8E,12E,14E)-7-Acetoxy-6-((4-cycloheptylpiperazin-1-yl)carbonyl)oxy-3,16,21-trihydroxy-6,10,12,16,20-pentamethyl-18,19-epoxytricosa-8,12,14-trien-11-olide

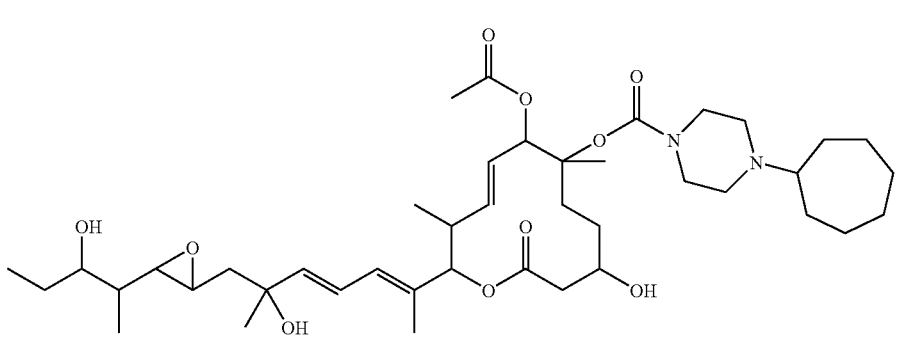

(Compound 135)

The title compound (a colorless oil) was synthesized by a similar method as described for Example 134.

¹H-NMR Spectrum (CD₃OD, 40 MHz) δ(ppm): 0.89 (3H, d, J=6.8 Hz), 0.90 (3H, d, J=6.8 Hz), 0.94 (3H, t, J=7.2 Hz), 1.22-1.32 (1H, m), 1.34 (3H, m), 1.40-1.78 (20H, m), 1.79 (3H, s), 1.82-1.93 (3H, m), 2.05 (3H, s), 2.39-2.47 (1H, m), 2.50 (2H, d, J=3.6 Hz), 2.54-2.66 (6H, m), 2.89 (1H, dt, J=2.0, 6.4 Hz), 3.37-3.64 (5H, m), 3.76-3.83 (1H, m), 5.07 (1H, d, J=10.8 Hz), 5.15 (1H, d, J=9.2 Hz), 5.63 (1H, dd, J=9.2, 15.2 Hz), 5.71 (1H, dd, J=9.2, 15.2 Hz), 5.87 (1H, d, J=15.2 Hz), 6.14 (1H, d, J=10.8 Hz), 6.53 (1H, dd, J=10.8, 15.2 Hz); ESI-MS m/z 761 (M+H)⁺.

Example 136

(8E,12E,14E)-7-Acetoxy-6-((4-ethylhomopiperazin-1-yl)carbonyl)oxy-3,16,21-trihydroxy-6,10,12,16,20-pentamethyl-18,19-epoxytricosa-8,12,14-trien-11-olide (Compound 136)

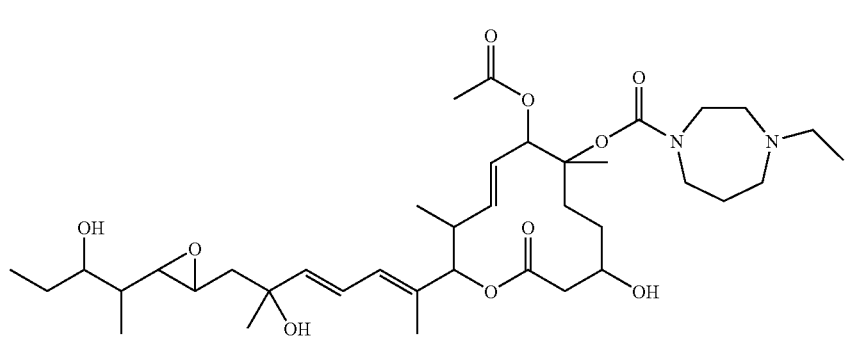

The title compound (a colorless oil) was synthesized by a similar method as described for Example 134.

¹H-NMR Spectrum (CD₃OD, 400 MHz) δ(ppm): 0.89 (6H, d, J=7.2 Hz), 0.94 (3H, t, J=7.2 Hz), 1.08 (3H, t, J=7.2 Hz), 1.20-1.28 (1H, m), 1.34 (3H, s), 1.38-1.70 (10H, m), 1.78 (3H, s), 1.83-1.91 (3H, m), 2.03 (3H, s), 2.33-2.42 (1H, m), 2.50 (2H, d, J=3.9 Hz), 2.58-2.80 (7H, m), 2.89 (1H, dt, J=2.4, 6.4 Hz), 3.45-3.65 (5H, m), 3.75-3.84 (1H, m), 5.02 (1H, d, J=9.6 Hz), 5.07 (1H, d, J=10.4 Hz), 5.63 (1H, dd, J=9.6, 15.2 Hz), 5.76 (1H, dd, J=9.6, 15.6 Hz), 5.87 (1H, d, J=15.6 Hz), 6.14 (1H, d, J=11.2 Hz), 6.53 (1H, dd, J=11.2, 15.6 Hz); ESI-MS m/z 707 (M+H)⁺.

Example 137

(8E,12E,14E)-3,6,16,21-Tetrahydroxy-7-(N-isopropylthiocarbamoyloxy)-6,10,12,16,20-pentamethyl-18,19-epoxytricosa-8,12,14-trien-11-olide (Compound 137)

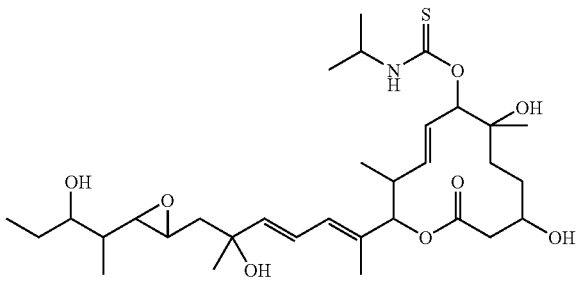

First Step (8E,12E,14E)-3,6,16,21-Tetrakis(1-ethoxyethoxy)-7-(N-isopropylthiocarbamoyloxy)-6,10,12,16,20-pentamethyl-18,19-epoxytricosa-8,12,14-trien-11-olide (Compound 137-1)

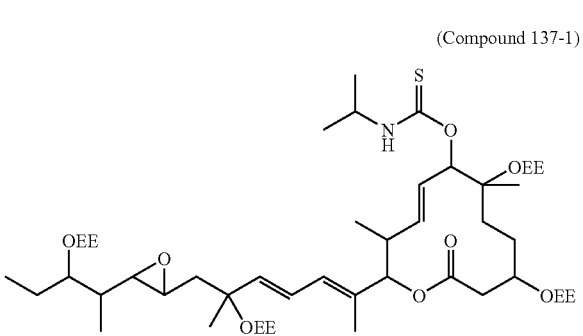

To a suspension of sodium hydride (60% oil dispersion, 2 mg, 0.052 mmol) in tetrahydrofuran (0.5 mL) was added dropwise a solution of (8E,12E,14E)-3,6,16,21-tetra(1-ethoxyethoxy)-7-hydroxy-6,10,12,16,20-pentamethyl-18,19-epoxytricosa-8,12,14-trien-11-olide (19 mg, 0.019 mmol) obtained in Example 3-(2) in tetrahydrofuran (0.5 mL) under ice-cooling and stirring, and the reaction mixture was stirred at room temperature for 10 minutes. Then, isopropyl isothiocyanate (6.6 mg, 0.066 mmol) was added dropwise thereto, and the reaction mixture was stirred at room temperature for three hours. Water was added to the reaction mixture under ice-cooling to terminate the reaction, followed by diluting with ethyl acetate and washing with brine. The organic layer was dried over anhydrous sodium sulfate and evaporated. The resulting residue was purified by silica gel column chromatography (Kanto silica gel 60N, 40 to 100 μm; ethyl acetate: hexane=25:75) to give the title compound (10 mg, 60%) as a colorless oil.

ESI-MS m/z 922 (M+Na)$^+$.

Second Step (8E,12E,14E)-3,6,16,21-Tetrahydroxy-7-(N-isopropylthiocarbamoyloxy)-6,10,12,16,20-pentamethyl-18,19-epoxytricosa-8,12,14-trien-11-olide (Compound 137)

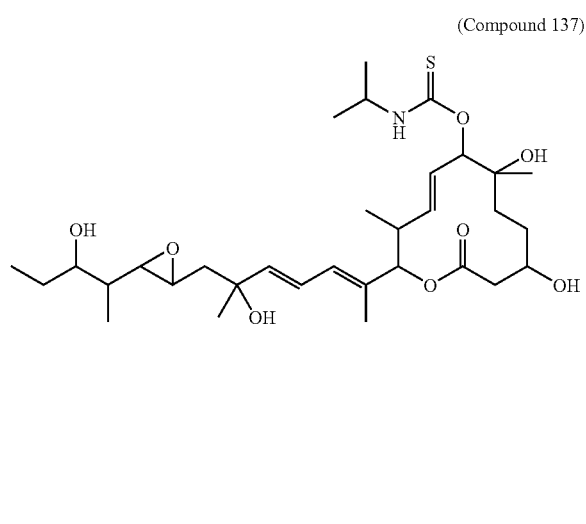

The title compound (a colorless oil) was obtained by a similar method as described for Example 3-5.

$^1$H-NMR Spectrum (CD$_3$ OD, 400 MHz) δ(ppm): 0.89 (3H, d, J=6.4 Hz), 0.90 (3H, d, J=6.8 Hz), 0.94 (3H, t, J=7.2 Hz), 1.14-1.69 (20H, m), 1.77 (3H, s), 1.86 (1H, dd, J=5.2, 14.0 Hz), 2.48-2.60 (3H, m), 2.66 (1H, dd, J=2.0, 8.0 Hz), 2.89 (1H, dt, J=2.0, 6.0 Hz), 3.49-4.08 (1H, m), 3.73-3.83 (1H, m), 4.23-4.34 (1H, m) 4.95 (1H, d, J=9.6 Hz), 5.07 (1H, d, J=10.4 Hz), 5.60-5.92 (3H, m), 6.13 (1H, d, J=10.8 Hz), 6.52 (1H, dd, J=10.8, 15.2 Hz); ESI-MS m/z 634 (M+Na)$^+$.

Example 138

(8E,12E,14E)-7-(N-Butylthiocarbamoyloxy)-3,6,16,21-tetrahydroxy-6,10,12,16,20-pentamethyl-18,19-epoxytricosa-8,12,14-trien-11-olide (Compound 138)

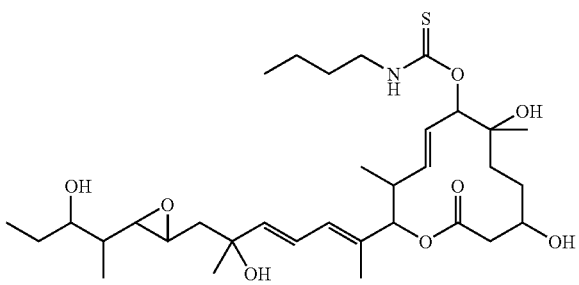

The title compound (a colorless oil) was obtained by a similar method as described for Example 137.

$^1$H-NMR Spectrum (CD$_3$OD, 400 MHz) δ(ppm): 0.88 (3H, d, J=6.4 Hz), 0.90 (3H, d, J=7.2 Hz), 0.937 (3H, t, J=7.2 Hz), 0.942 (3H, t, J=7.2 Hz), 1.19 (3H, s), 1.19-1.69 (15H, m), 1.77 (3H, s), 1.86 (1H, dd, J=5.6, 14.0 Hz), 2.49-2.62 (3H, m), 2.66 (1H, dd, J=2.0, 8.0 Hz), 2.89 (1H, dt, J=2.0, 6.0 Hz), 3.42-3.57 (3H, m), 3.73-3.83 (1H, m), 4.95 (1H, d, J=9.6 Hz), 5.07 (1H, d, J=10.4 Hz), 5.62-5.92 (3H, m), 6.14 (1H, d, J=10.8 Hz), 6.52 (1H, dd, J=10.8, 15.2 Hz); ESI-MS m/z 648 (M+Na)$^+$.

Example 139

(8E,12E,14E)-7-(N-(3-(N',N'-Diethylamino)propyl)thiocarbamoyloxy)-3,6,16,21-tetrahydroxy-6,10,12,16,20-pentamethyl-18,19-epoxytricosa-8,12,14-trien-11-olide (Compound 139)

The title compound (a colorless oil) was obtained by a similar method as described for Example 137.

$^1$H-NMR Spectrum (CD$_3$OD, 400 MHz) δ(ppm): 0.88 (3H, d, J=6.4 Hz), 0.90 (3H, d, J=7.2 Hz), 0.94 (3H, t, J=7.2 Hz), 1.14 (6H, t, J=6.8 Hz), 1.19 (3H, s), 1.21-1.69 (13H, m), 1.77 (3H, s), 1.86 (1H, dd, J=5.2, 14.0 Hz), 2.48-2.61 (3H, m), 2.66 (1H, dd, J=2.4, 8.0 Hz), 3.70-3.86 (6H, m), 2.89 (1H, dt, J=2.4, 5.6 Hz), 3.44-3.58 (3H, m), 3.75-3.83 (1H, m), 4.96 (1H, d, J=8.4 Hz), 5.07 (1H, d, J=10.4 Hz), 5.64-5.92 (3H, m), 6.14 (1H, d, J=10.8 Hz), 6.52 (1H, dd, J=10.8, 15.2 Hz); ESI-MS m/z 683 (M+H)$^+$.

Example 140

(8E,12E,14E)-7-Benzoyloxy-3,6,16,21-tetrahydroxy-6,10,12,16,20-pentamethyl-18,19-epoxytricosa-8,12,14-trien-11-olide

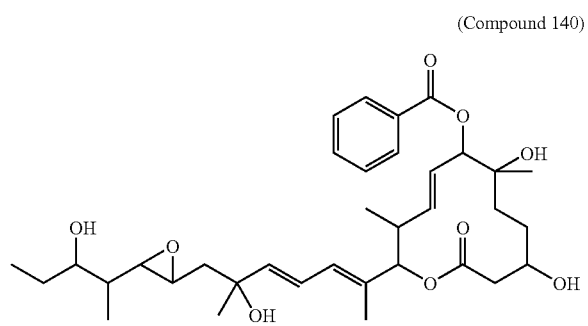
(Compound 140)

First Step (8E,12E,14E)-7-Benzoyloxy-3,6,16,21-tetrakis(1-ethoxyethoxy)-6,10,12,16,20-pentamethyl-18,19-epoxytricosa-8,12,14-trien-11-olide

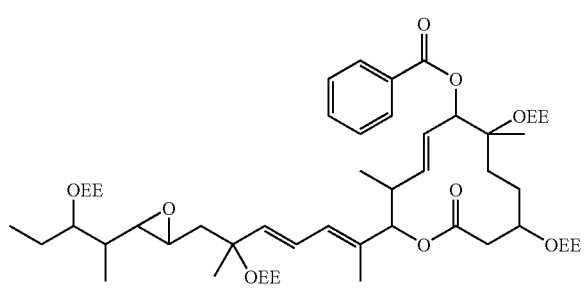
(Compound 140-1)

To a solution of (8E,12E,14E)-3,6,16,21-tetrakis(1-ethoxyethoxy)-7-hydroxy-6,10,12,16,20-pentamethyl-18,19-epoxytricosa-8,12,14-trien-11-olide (10 mg, 12.5 µmol) obtained in Example 3-2 in pyridine (0.5 mL) were added N,N-dimethylaminopyridine (8 mg, 62.5 µmol) and benzyl chloride (17.6 mg, 125 µmol) at room temperature, and the reaction mixture was stirred at the same temperature under nitrogen atmosphere for 12 hours. The reaction mixture was diluted with ethyl acetate and washed with a saturated aqueous solution of ammonium chloride and brine. The organic layer was dried over anhydrous magnesium sulfate and evaporated. The resulting residue was purified by silica gel column chromatography (Kanto silica gel 60N, 40 to 100 µm; ethyl acetate:hexane=25:75) to give the title compound (6 mg, 55%) as a colorless oil.

ESI-MS m/z 925 (M+Na)$^+$.

Second Step (8E,12E,14E)-7-Benzoyloxy-3,6,16,21-tetrahydroxy-6,10,12,16,20-pentamethyl-18,19-epoxytricosa-8,12,14-trien-11-olide

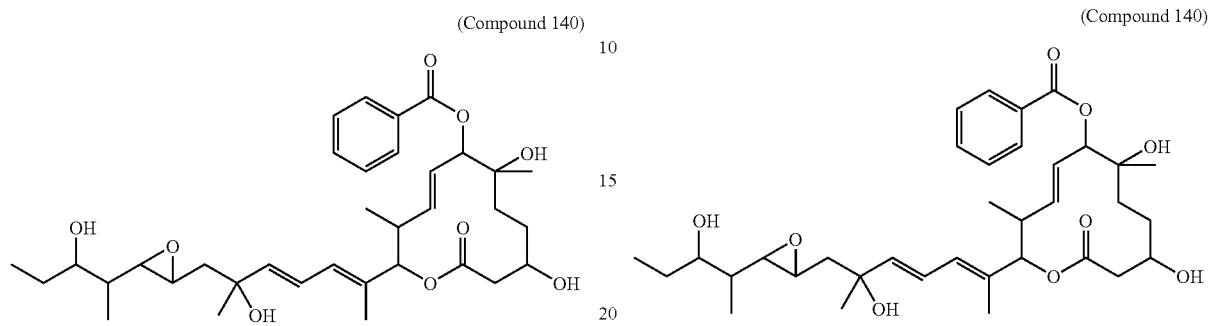
(Compound 140)

The title compound (a colorless oil) was obtained by a similar method as described for Example 3-5.

$^1$H-NMR Spectrum (CD$_3$OD, 400 MHz) δ(ppm): 0.88 (3H, d, J=6.8 Hz), 0.89 (3H, d, J=7.2 Hz), 0.93 (3H, t, J=7.2 Hz), 1.20-1.76 (14H, m), 1.78 (3H, s), 1.86 (1H, dd, J=5.6, 14.0 Hz), 2.53-2.64 (3H, m), 2.66 (1H, dd, J=2.4, 8.0 Hz), 2.89 (1H, dt, J=2.4, 5.6 Hz), 3.52 (1H, dt, J=4.8, 8.0 Hz), 3.78-3.85 (1H, m), 5.09 (1H, d, J=10.8 Hz), 5.29 (1H, d, J=9.6 Hz), 5.69 (1H, dd, J=9.6, 15.2 Hz), 5.83 (1H, dd, J=9.6, 15.2 Hz), 5.87 (1H, d, J=15.2 Hz), 6.14 (1H, d, J=10.4 Hz), 6.53 (1H, dd, J=10.8, 15.2 Hz), 7.47 (2H, dd, J=7.6, 7.6 Hz), 7.60 (1H, dd, J=7.6, 7.6 Hz), 8.12 (2H, d, J=7.6 Hz); ESI-MS m/z 637 (M+Na)$^+$.

Example 141

(8E,12E,14E)-3,6,16,21-Tetrahydroxy-6,10,12,16,20-pentamethyl-7-propanoyloxy-18,19-epoxytricosa-8,12,14-trien-11-olide

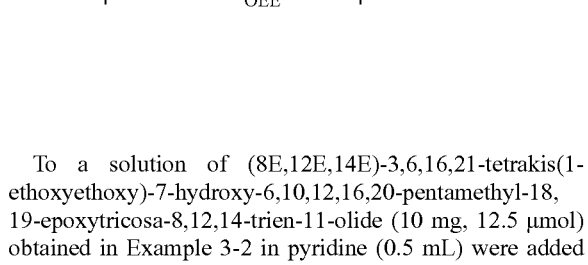
(Compound 141)

The title compound (a colorless oil) was obtained by a similar method as described for Example 140.

$^1$H-NMR Spectrum (CD$_3$OD, 400 MHz) δ(ppm): 0.88 (3H, d, J=6.8 Hz), 0.89 (3H, d, J=7.2 Hz), 0.94 (3H, t, J=7.2 Hz), 1.18 (3H, t, J=8.0 Hz), 1.18 (3H, s), 1.22-1.68 (11H, m), 1.77 (3H, s), 1.86 (1H, dd, J=5.2, 14.0 Hz), 2.28-2.45 (2H, m), 2.50-2.61 (3H, m), 2.66 (1H, dd, J=2.4, 8.0 Hz), 2.89 (1H, dt, J=2.0, 6.0 Hz), 3.52 (1H, dt, J=4.8, 8.0 Hz), 3.75-3.82 (1H, m), 4.95 (1H, d, J=9.6 Hz), 5.05 (1H, d, J=9.6 Hz), 5.57 (1H, dd, J=10.0, 15.2 Hz), 5.70 (1H, dd, J=9.6, 15.2 Hz), 5.87 (1H, d, J=15.2 Hz), 6.13 (1H, d, J=10.8 Hz), 6.52 (1H, dd, J=10.8, 15.2 Hz); ESI-MS m/z 589 (M+Na)$^+$.

Example 142

(8E,12E,14E)-3,6,16,21-Tetrahydroxy-6,10,12,16,20-pentamethyl-7-(3-phenylpropanoyl)oxy-18,19-epoxytricosa-8,12,14-trien-11-olide (Compound 142)

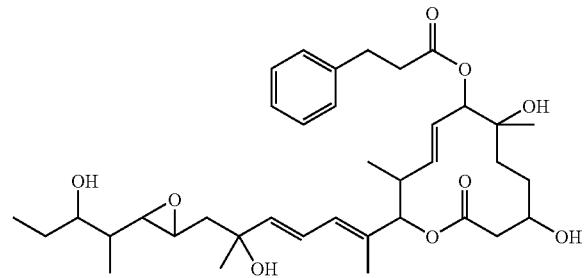

The title compound (a colorless oil) was obtained by a similar method as described for Example 140.

$^1$H-NMR Spectrum (CD$_3$OD, 400 MHz) δ(ppm): 0.86 (3H, d, J=6.8 Hz), 0.90 (3H, d, J=6.8 Hz), 0.94 (3H, t, J=7.2 Hz), 1.09 (3H, s), 1.20-1.69 (11H, m), 1.77 (3H, s), 1.86 (1H, dd, J=5.2, 14.0 Hz), 2.46-2.59 (3H, m), 2.62-2.70 (3H, m), 2.85-2.96 (3H, m), 3.48-3.56 (1H, m), 3.72-3.80 (1H, m), 5.03 (1H, d, J=9.2 Hz), 5.05 (1H, d, J=10.8 Hz), 5.54 (1H, dd, J=9.6, 15.2 Hz), 5.66 (1H, dd, J=9.2, 15.2 Hz), 5.87 (1H, d, J=14.8 Hz), 6.13 (1H, d, J=10.8 Hz), 6.53 (1H, dd, J=10.8, 14.8 Hz), 7.12-7.28 (5H, m); ESI-MS m/z 665 (M+Na)$^+$.

Example 143

(8E,12E,14E)-7-(Hexanoyl)oxy-3,6,16,21-tetrahydroxy-6,10,12,16,20-pentamethyl-18,19-epoxytricosa-8,12,14-trien-11-olide (Compound 143)

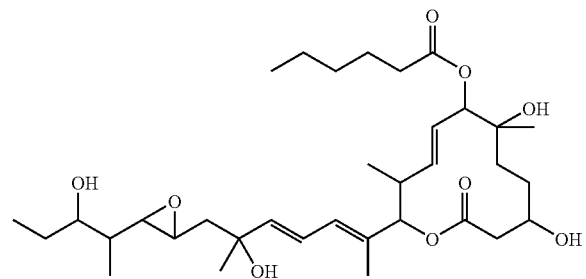

The title compound (a colorless oil) was obtained by a similar method as described for Example 140.

$^1$H-NMR Spectrum (CD$_3$OD, 400 MHz) δ(ppm): 0.76-0.83 (9H, m), 0.98 (3H, t, J=7.2 Hz), 1.23 (3H, s), 1.24-1.74 (17H, m), 1.82 (3H, brs), 1.91 (1H, dd, J=5.6, 14.4 Hz), 2.32-2.44 (2H, m), 2.52-2.69 (3H, m), 2.71 (1H, dd, J=2.4, 8.0 Hz), 2.94 (1H, dt, J=2.4, 6.0 Hz), 3.53-3.60 (1H, m), 3.78-3.86 (1H, m), 5.10 (1H, d, J=9.6 Hz), 5.11 (1H, d, J=9.6 Hz), 5.61 (1H, dd, J=9.6, 15.2 Hz), 5.74 (1H, dd, J=9.6, 15.2 Hz), 5.91 (1H, d, J=15.2 Hz), 6.18 (1H, d, J=11.2 Hz), 6.57 (1H, dd, J=11.2, 15.2 Hz); ESI-MS m/z 631 (M+Na)$^+$.

Example 144

(8E,12E,14E)-7,21-Diacetoxy-3,6,16-trihydroxy-6,10,12,16,20-pentamethyl-18,19-epoxytricosa-8,12,14-trien-11-olide (Compound 144-1) and (8E,12E,14E)-3,7,21-triacetoxy-6,16-dihydroxy-6,10,12,16,20-pentamethyl-18,19-epoxytricosa-8,12,14-trien-11-olide (Compound 144-2)

Compound 144-1

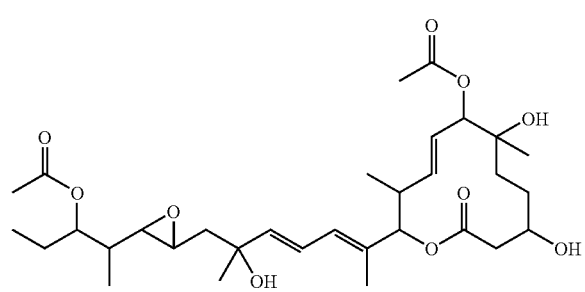

Compound 144-2

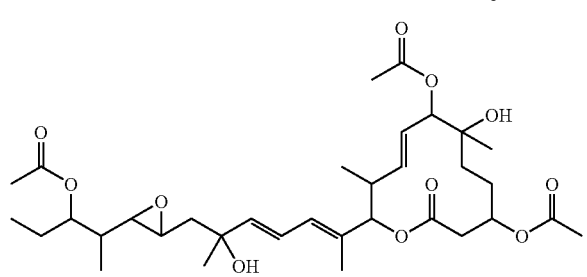

A solution of (8E,12E,14E)-7-acetoxy-3,6,16,21-tetrahydroxy-6,10,12,16,20-pentamethyl-18,19-epoxytricosa-8,12,14-trien-11-olide (276 mg, 0.5 mmol), N,N-dimethylaminopyridine (31 mg, 0.25 mmol) and triethylamine (256 mg, 2.5 mmol) in dichloromethane (15 mL) was cooled to −20° C., a solution of acetic anhydride (53 mg, 0.5 mmol) in dichloromethane (2 mL) was added dropwise thereto over 30 minutes, and the reaction mixture was stirred at the same temperature for 30 minutes. A solution of acetic anhydride (10.5 mg, 0.1 mmol) in dichloromethane (1 mL) was added dropwise to the reaction mixture over 30 minutes, followed by stirring at the same temperature for 2.5 hours. Further, a solution of acetic anhydride (10.5 mg, 0.1 mmol) in dichloromethane (1 mL) was added dropwise to the reaction mixture over 5 minutes, followed by stirring at the same temperature for 30 minutes. Furthermore, a solution of acetic anhydride (21 mg, 0.2 mmol) in dichloromethane (1 mL) was added dropwise to the reaction mixture over 5 minutes, followed by stirring at the same temperature for 30 minutes. The reaction mixture was diluted with ethyl acetate, washed with water and a saturated aqueous solution of sodium bicarbonate, dried over anhydrous magnesium sulfate and evaporated. The resulting residue was purified by silica gel column chromatography (Kanto silica gel 60N, 40 to 50 µm; ethyl acetate-hexane, 2:1 to 3:1 to 4:1 to 9:1) to give the residue of Compound 144-1 as a colorless oil, and Compound 144-2 (67.7 mg, 21%) as colorless crystals. The residue of Compound 144-1 was then purified by thin layer chromatography (Merck Art 1.13792; ethyl acetate-hexane, 8:1 to 9:1) to give Compound 144-1 (214.3 mg, 72%) as a colorless oil.

Compound 144-1

$^1$H-NMR Spectrum (CD$_3$OD, 400 MHz) δ(ppm): 0.87 (3H, t, J=7.6 Hz), 0.88 (3H, d, J=7.2 Hz), 0.92 (3H, d, J=6.8 Hz), 1.18 (3H, s), 1.31-1.68 (11H, m), 1.77 (3H, d, J=0.8 Hz), 1.82 (1H, dd, J=5.2, 14.0 Hz), 2.05 (3H, s), 2.06 (3H, s), 2.46-2.63 (4H, m), 2.88 (1H, dt, J=2.0, 6.0 Hz), 3.75-3.81 (1H, m), 4.84-4.92 (1H, covered with H$_2$O), 5.04 (1H, d, J=9.6 Hz), 5.05 (1H, d, J=10.8 Hz), 5.56 (1H, dd, J=9.6, 15.2 Hz), 5.70 (1H, dd, J=9.6, 15.2 Hz), 5.86 (1H, d, J=15.2 Hz), 6.13 (1H, d, J=11.2 Hz), 6.52 (1H, dd, J=10.8, 15.2 Hz); ESI-MS m/z 617 (M+Na)$^+$.

Compound 144-2

$^1$H-NMR Spectrum (CD$_3$OD, 400 MHz) δ(ppm): 0.87 (3H, t, J=7.6 Hz), 0.89 (3H, d, J=6.8 Hz), 0.91 (3H, d, J=6.8 Hz), 1.18 (3H, s), 1.33 (3H, s), 1.34-1.73 (8H, m), 1.77 (3H, d, J=0.8 Hz), 1.83 (1H, dd, J=5.6, 14.0 Hz), 2.04 (3H, s), 2.05 (3H, s), 2.06 (3H, s), 2.53-2.68 (4H, m), 2.88 (1H, dt, J=2.0, 6.0 Hz), 4.78-4.96 (2H, covered with H$_2$O), 4.99 (1H, d, J=10.4 Hz), 5.02 (1H, d, J=9.6 Hz), 5.57 (1H, dd, J=9.6, 15.2 Hz), 5.72 (1H, dd, J=9.6, 15.2 Hz), 5.86 (1H, d, J=15.2 Hz), 6.14 (1H, dd, J=1.2, 10.8 Hz), 6.52 (1H, dd, J=11.2, 15.2 Hz); ESI-MS m/z 659 (M+Na)$^+$.

Example 145

(8E,12E,14E)-21-Acetoxy-3,6,16-trihydroxy-7-((4-isopropylpiperazin-1-yl)carbonyl)oxy-6,10,12,16,20-pentamethyl-18,19-epoxytricosa-8,12,14-trien-11-olide (Compound 145-1) and (8E,12E,14E)-3,21-diacetoxy-6,16-dihydroxy-7-((4-isopropylpiperazin-1-yl)carbonyl)oxy-6,10,12,16,20-pentamethyl-18,19-epoxytricosa-8,12,14-trien-11-olide (Compound 145-2)

Compound 145-1

$^1$H-NMR Spectrum (CD$_3$OD, 400 MHz) δ(ppm): 0.91 (3H, t, J=7.2 Hz), 0.93 (3H, d, J=6.8 Hz), 0.96 (3H, d, J=7.2 Hz), 1.12 (6H, d, J=6.4 Hz), 1.26 (3H, s), 1.30-1.56 (6H, m), 1.58-1.76 (5H, m), 1.82 (3H, s), 1.87 (1H, dd, J=5.6, 14.0 Hz), 2.10 (3H, s), 2.48-2.70 (8H, m), 2.70-2.82 (1H, m) 2.93 (1H, dt, J=2.0, 5.6 Hz), 3.44-3.76 (4H, m), 3.78-3.88 (1H, m), 4.86-4.98 (1H, covered with H$_2$O), 4.97 (1H, d, J=9.6 Hz), 5.10 (1H, d, J=10.8 Hz), 5.62 (1H, dd, J=10.0, 15.2 Hz), 5.76 (1H, dd, J=9.6, 15.2 Hz), 5.90 (1H, d, J=15.2 Hz), 6.18 (1H, d, J=10.8 Hz), 6.57 (1H, dd, J=10.8, 15.2 Hz); ESI-MS m/z 707 (M+H)$^+$.

Compound 145-2

$^1$H-NMR Spectrum (CD$_3$OD, 400 MHz) δ(ppm): 0.91 (3H, t, J=7.6 Hz), 0.93 (3H, d, J=6.8 Hz), 0.96 (3H, d, J=7.2 Hz), 1.12 (6H, d, J=6.4 Hz), 1.25 (3H, s), 1.30-1.92 (15H, m), 2.088 (3H, s), 2.094 (3H, s), 2.50-2.80 (9H, m), 2.93 (1H, dt, J=2.0, 6.0 Hz), 3.40-3.76 (4H, m), 4.80-4.96 (2H, covered with H$_2$O), 4.96 (1H, d, J=9.6 Hz), 5.04 (1H, d, J=10.8 Hz), 5.63 (1H, dd, J=10.0, 15.2 Hz), 5.78 (1H, dd, J=9.6, 15.2 Hz), 5.91 (1H, d, J=15.2 Hz), 6.18 (1H, d, J=10.8 Hz), 6.56 (1H, dd, J=10.8, 15.2 Hz); ESI-MS m/z 749 M$^+$.

Example 146

(8E,12E,14E)-6,16-Dihydroxy-7-((4-isopropylpiperazin-1-yl)carbonyl)oxy-6,10,12,16,20-pentamethyl-3,21-dioxo-18,19-epoxytricosa-8,12,14-trien-11-olide (Compound 146-1) and (8E,12E,14E)-3,6,16-trihydroxy-7-((4-isopropylpiperazin-1-yl)carbonyl)oxy-6,10,12,16,20-pentamethyl-21-oxo-18,19-epoxytricosa-8,12,14-trien-11-olide (Compound 146-2)

(Compound 145-1)

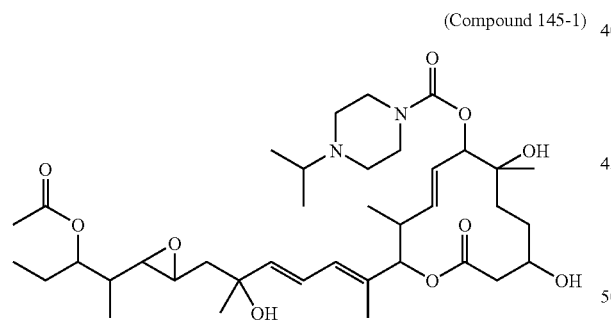

Compound 145-2

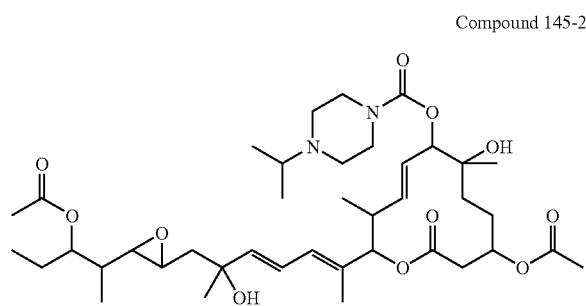

The title compounds (each a colorless oil) were synthesized by a similar method as described for Example 144 except for using Compound 44 obtained in Example 44.

Compound 146-1

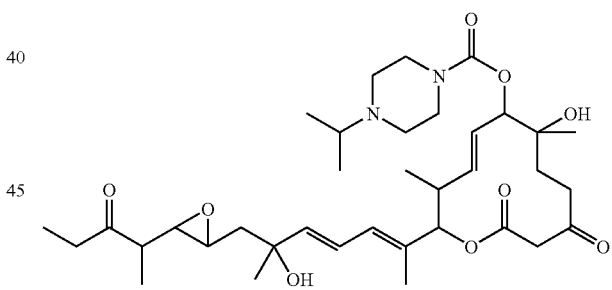

Compound 146-2

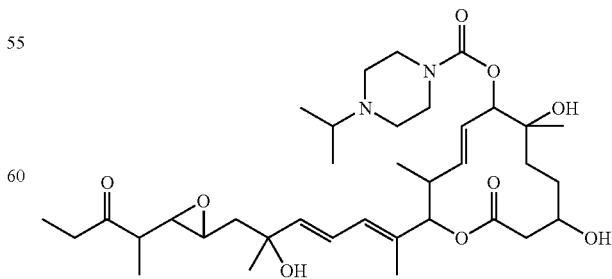

To a solution of Compound 44 (20 mg, 30 μmol) obtained in Example 44 in dichloromethane (2.0 mL) was added Dess- Martin reagent (43 mg, 0.101 mmol) under ice-cooling and stirring, and the reaction mixture was stirred at room temperature under nitrogen atmosphere for six hours. The reaction mixture was diluted with ethyl acetate and then washed with a saturated aqueous solution of sodium bicarbonate and brine. The organic layer was dried over anhydrous sodium sulfate and evaporated. The resulting residue was purified by silica gel column chromatography (Kanto silica gel 60N, 40 to 100 μm; dichloromethane:methanol=95:5 to 90:10) to give the title compounds, Compound 146-1 (9.6 mg, 48%) and Compound 146-2 (8.9 mg, 45%), each as a colorless oil.

Compound 146-1

$^1$H-NMR Spectrum (CD$_3$OD, 400 MHz) δ(ppm): 0.91 (3H, d, J=6.8 Hz), 1.00 (3H, t, J=7.2 Hz), 1.07 (3H, d, J=7.2 Hz), 1.10 (6H, d, J=6.4 Hz), 1.30 (3H, s), 1.33 (3H, s), 1.63 (1H, dd, J=6.8, 14.4 Hz), 1.74-1.80 (1H, m), 1.80 (3H, s), 1.89 (1H, dd, J=5.6, 14.4 Hz), 2.00-2.08 (1H, m), 2.37 (1H, m), 2.46 (2H, d, J=12.4 Hz), 2.52-2.70 (7H, m), 2.72-2.84 (3H, m), 2.92 (1H, dt, J=2.0, 6.4 Hz), 3.31-3.33 (1H, m), 3.42-3.64 (4H, m), 4.94 (1H, d, J=8.0 Hz), 4.96 (1H, d, J=10.8 Hz), 5.23 (1H, dd, J=8.8, 15.6 Hz), 5.50 (1H, dd, J=8.4, 15.6 Hz), 5.86 (1H, d, J=15.2 Hz), 6.10 (1H, d, J=10.8 Hz), 6.54 (1H, dd, J=10.8, 15.2 Hz); ESI-MS M/Z 661 (M+H)$^+$, 683 (M+Na)$^+$.

Compound 146-2

$^1$H-NMR Spectrum (CD$_3$OD, 400 MHz) δ(ppm): 0.88 (3H, d, J=6.8 Hz), 1.00 (3H, t, J=7.2 Hz), 1.07 (3H, d, J=6.8 Hz), 1.10 (6H, d, J=7.2 Hz), 1.21 (3H, s), 1.38-1.42 (5H, m), 1.54-1.68 (3H, m) 1.77 (3H, s), 1.89 (1H, dd, J=4.8, 14.0 Hz), 2.28-2.36 (1H, m), 2.50-2.64 (8H, m), 2.75 (1H, dd, J=2.0, 8.4 Hz), 2.76-2.84 (1H, m), 2.91 (1H, dt, J=2.4, 7.6 Hz), 3.31-3.33 (1H, m), 3.42-3.64 (4H, m), 3.75-3.82 (1H, m), 4.93 (1H, d, J=9.6 Hz), 5.06 (1H, d, J=10.4 Hz), 5.57 (1H, dd, J=10.0, 15.2 Hz), 5.72 (1H, dd, J=10.0, 15.2 Hz), 5.86 (1H, d, J=15.2 Hz), 6.14 (1H, d, J=10.8 Hz), 6.53 (1H, dd, J=10.8, 15.2 Hz); ESI-MS m/z 663 (M+H)$^+$, 685 (M+Na)$^+$.

Example 147

(8E,12E,14E)-7-Acetoxy-6-ethoxy-3,16,21-trihydroxy-6,10,12,16,20-pentamethyl-18,19-epoxytricosa-8,12,14-trien-11-olide (Compound 147)

The title compound (a colorless oil) was synthesized by a similar method as described for Example 43 except for using ethyl trifluoromethanesulfonate.

$^1$H-NMR Spectrum (CD$_3$OD, 400 MHz) δ(ppm): 0.87 (3H, d, J=6.4 Hz), 0.90 (3H, d, J=6.8 Hz), 0.94 (3H, t, J=7.6 Hz), 1.17 (3H, t, J=7.2 Hz), 1.20 (3H, s), 1.22-1.60 (7H, m), 1.34 (3H, s), 1.65 (1H, dd, J=6.4, 14.0 Hz), 1.78 (3H, s), 1.86 (1H, dd, J=5.2, 14.0 Hz), 2.04 (3H, s), 2.44-2.68 (4H, m), 2.89 (1H, dt, J=2.4, 5.2 Hz), 3.49-3.66 (3H, m), 3.77-3.84 (1H, m), 5.06 (1H, d, J=10.4 Hz), 5.10(H, d, J=9.6 Hz), 5.55 (1H, dd, J=9.6, 15.6 Hz), 5.75 (1H, dd, J=10.0, 15.6 Hz), 5.86 (1H, d, J=15.2 Hz), 6.13 (1H, d, J=11.2 Hz), 6.52 (1H, dd, J=11.2, 15.6 Hz); ESI-MS m/z 603 (M+Na)$^+$.

Formulation Example

Formulation Examples of the compounds of the present invention will be illustrated below, but the formulation of the compounds of the present invention is not limited to these Formulation Examples.

Formulation Example 1

Compound of Example 44 45 (part)

Heavy magnesium oxide 15

Lactose 75 were mixed homogeneously and formulated into a powdered medicine in the form of a powder or fine granules having a size of 350 μm or less. The powdered medicine was charged into capsules to give capsule form.

Formulation Example 2

Compound of Example 75 45 (part)

Starch 15

Lactose 16

Crystalline cellulose 21

Poly(vinyl alcohol) 3

Distilled water 30 were mixed homogeneously, pulverized, granulated, dried and then sieved to give granules having a size of 1410 to 177 μm.

Formulation Example 3

Granules were produced by a similar method as described for Formulation Example 2, 4 parts of calcium stearate was added to 96 parts of the granules, compressed and molded to give tablets having a diameter of 10 mm.

Formulation Example 4

To 90 parts of granules obtained by the method of Formulation Example 2 were added 10 parts of crystalline cellulose and 3 parts of calcium stearate, compressed and molded to give tables having a diameter of 8 mm. Then, a mixed suspension of syrup, gelatin and precipitated calcium carbonate was added thereto to give sugar-coated tablets.

Formulation Example 5

Compound of Example 45 0.6 (part)

Nonionic surfactant 2.4

Isotonic sodium chloride solution 97

Referential Examples

Referential Example 1

1-(Cyclopropylmethyl)piperazine

The compound was synthesized by the following three steps.

Referential Example 1-1

Benzyl 4-(cyclopropylcarbonyl)piperazin-1-carboxylate

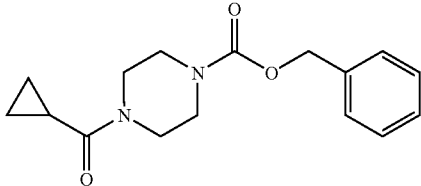

In 35 mL of N,N-dimethylformamide were dissolved benzyl 1-piperazinecarboxylate (5.00 g, 22.7 mmol) and cyclopropanecarboxylic acid (2.54 g, 29.5 mmol), and 1-ethyl-3-(3-(N,N-dimethylamino)propyl)-carbodiimide hydrochloride (6.53 g, 34.1 mmol), 1-hydroxybenzotriazole (4.52 g, 29.5 mmol) and triethylamine (3.60 g, 35.9 mmol) were added thereto at room temperature, followed by stirring at the same temperature for three hours. The reaction mixture was mixed with water, and extracted twice with ethyl acetate. The organic layer was sequentially washed with water twice, with a saturated aqueous solution of sodium bicarbonate once and with brine once, and then dried over anhydrous sodium sulfate. The organic layer was passed through a silica gel column (Fuji Silysia, NH Silica gel) and evaporated to give the title compound (6.10 g, 93.1%) as a white amorphous.

$^1$H-NMR Spectrum (CDCl$_3$, 400 MHz) δ(ppm): 0.75-0.83 (2H, m), 0.95-1.03 (2H, m), 1.65-1.75 (1H, m), 3.40-3.80 (8H, m), 5.16 (2H, s), 7.30-7.40 (5H, m).

Referential Example 1-2

1-(Cyclopropylcarbonyl)piperazine

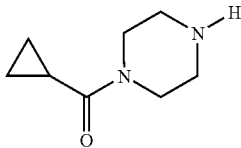

In 100 mL of ethanol was dissolved benzyl 4-(cyclopropylcarbonyl)piperazine-1-carboxylate (3.00 g, 10.4 mmol), and 1.5 g of 10% palladium-carbon was added thereto, followed by stirring at room temperature under hydrogen atmosphere overnight. The palladium-carbon was removed by filtration, and the filtrate was evaporated to give the title compound (1.50 g, 97.3%) as a colorless oil.

$^1$H-NMR Spectrum (CDCl$_3$, 400 MHz) δ(ppm): 0.73-0.80 (2H, m), 0.96-1.03 (2H, m), 1.67-1.77 (1H, m), 2.82-2.97 (4H, m), 3.60-3.71 (4H, m).

Referential Example 1-3

1-(Cyclopropylmethyl)piperazine

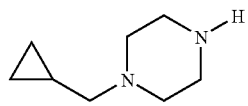

Lithium aluminium hydride (770 mg, 20.3 mmol) was suspended in tetrahydrofuran (150 mL), 1-(cyclopropylcarbonyl)piperazine (1.56 g, 10.1 mmol) was gradually added thereto, and the reaction mixture was heated under reflux for 30 minutes. The reaction mixture was cooled to room temperature, and 0.8 mL of water, 0.8 mL of a 15% aqueous solution of sodium hydroxide and 2.3 mL of water were sequentially gradually added thereto. The precipitated insoluble matter was removed by filtration through Celite, and the filtrate was evaporated to give the title compound (1.40 g) as a colorless oil. The product was used for the synthesis of (8E,12E,14E)-7-((4-cyclopropylmethylpiperazin-1-yl)carbonyl)oxy-3,6,16,21-tetrahydroxy-6,10,12,16,20-pentamethyl-18,19-epoxytricosa-8,12,14-trien-11-olide (the compound of Example 27) without further purification.

$^1$H-NMR Spectrum (CDCl$_3$, 400 MHz) δ(ppm): 0.09-0.15 (2H, m), 0.48-0.56 (2H, m), 0.82-0.93 (1H, m), 2.25 (2H, d, J=7.2 Hz) 2.48-2.65 (4H, m), 2.90-2.99 (4H, m).

Referential Example 2

1-Isobutylpiperazine

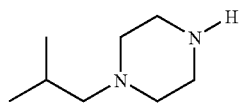

Benzyl 1-piperazinecarboxylate (1.1 g, 5.00 mmol) and isobutylaldehyde (0.91 mL, 10.0 mmol) were dissolved in 30 mL of tetrahydrofuran, and acetic acid (0.57 mL, 10.0 mmol) and sodium triacetoxyborohydride (2.11 g, 10.0 mmol) were added thereto, and the reaction mixture was stirred at room temperature for two hours. The reaction mixture was mixed with a 1N aqueous solution of sodium hydroxide, extracted with ethyl acetate twice, and the combined organic layers were washed with brine once. The mixture was dried over anhydrous sodium sulfate and evaporated. The resulting residue was purified by silica gel column chromatography (Fuji Silysia, NH Silica gel; ethyl acetate:hexane=50:50) to give benzyl 4-isobutylpiperazin-1-carboxylate (1.05 g) as a colorless oil.

The resulting benzyl 4-isobutylpiperazin-1-carboxylate (1.05 g) was dissolved in 35 mL of ethanol, 10% palladium-carbon (750 mg) was added thereto, and the reaction mixture was stirred at room temperature under hydrogen atmosphere (1 atm) for 12 hours. The palladium-carbon was removed by filtration, and the filtrate was evaporated to give the title compound (610 mg) as a colorless oil.

¹H-NMR Spectrum (CDCl₃, 400 MHz) δ(ppm): 0.90 (6H, d, J=6.8 Hz), 1.71-1.86 (1H, m), 2.07 (2H, d, J=7.6 Hz), 2.33-2.43 (4H, m), 2.86-2.93 (4H, m).

Referential Example 3

1-(Tetrahydropyran-4-yl)piperazine

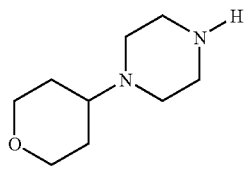

The title compound was synthesized by a similar method as described for the compound of Referential Example 2 (1-isobutylpiperazine).

¹H-NMR Spectrum (CDCl₃, 400 MHz) δ(ppm): 1.50-1.64 (2H, m), 1.72-1.80 (2H, m), 2.36-2.46 (1H, m), 2.54-2.64 (4H, m), 2.91-2.97 (4H, m), 3.37 (2H, dt, J=2.0, 11, 6 Hz), 4.03 (2H, dd, J=4.4, 11.6 Hz).

Referential Example 4

1-(Cyclopropylmethyl)homopiperazine

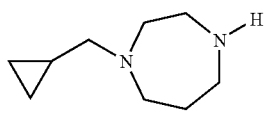

Benzyl 1-homopiperazinecarboxylate (1.95 g, 8.32 mmol) and cyclopropanecarboxyaldehyde (700 mg, 10.0 mmol) were dissolved in 40 mL of tetrahydrofuran. Acetic acid (600 mg, 10.0 mmol) and sodium triacetoxyborohydride (2.11 g, 10.0 mmol) were added thereto, and the reaction mixture was stirred at room temperature for two hours. The reaction mixture was mixed with 1 N aqueous solution of sodium hydroxide, extracted with ethyl acetate twice, and the combined organic layers were washed with brine once. The mixture was dried over anhydrous sodium sulfate and evaporated. The resulting residue was purified by silica gel column chromatography (Fuji Silysia, NH Silica gel; ethyl acetate:hexane=50:50) to give benzyl 4-(cyclopropylmethyl)homopiperazin-1-carboxylate (2.5 g) as a colorless oil.

The resulting benzyl 4-(cyclopropylmethyl)homopiperazin-1-carboxylate (2.5 g) was dissolved in 50 mL of ethanol, 10% palladium-carbon (500 mg) was added, and the reaction mixture was stirred at room temperature under hydrogen atmosphere (1 atm) for 12 hours. The palladium-carbon was removed by filtration, and the filtrate was evaporated to give the title compound (1.4 g) as a colorless oil.

¹H-NMR Spectrum (CDCl₃, 400 MHz) δ(ppm): 0.08-0.15 (2H, m), 0.47-0.56 (2H, m), 0.82-0.95 (1H, m), 1.80-1.89 (2H, m), 2.44 (2H, d, J=6.4 Hz) 2.75-2.85 (4H, m), 2.94-3.03 (4H, m).

Referential Example 5

1-(2,2,2-Trifluoroethyl)piperazine

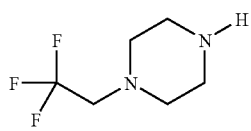

Benzyl 1-piperazinecarboxylate (2.0 g, 9.08 mmol), 2,2,2-trifluoroethyl trifluoromethanesulfonate (2.5 g, 10.8 mmol) and triethylamine (1.9 mL, 13.8 mmol) were dissolved in 50 mL of tetrahydrofuran, and the reaction mixture was stirred at 60° C. for two hours. After cooling to room temperature, the reaction mixture was mixed with a saturated aqueous solution of sodium bicarbonate and extracted with ethyl acetate twice. The combined organic layers were sequentially washed with water and brine in this order. The mixture was dried over anhydrous sodium sulfate and evaporated. The resulting residue was purified by silica gel column chromatography (Fuji Silysia, NH Silica gel; ethyl acetate:hexane=50:50) to give 4-(2,2,2-trifluoroethyl)piperazin-1-carboxylic acid benzyl ester (3.1 g) as a colorless oil.

Resulting benzyl 4-(2,2,2-trifluoroethyl)piperazin-1-carboxylate (3.1 g) was dissolved in 50 mL of ethanol, and 10% palladium-carbon (900 mg) was added, followed by stirring at room temperature under hydrogen atmosphere (1 atm) overnight. The palladium-carbon was removed by filtration, and the filtrate was evaporated to give the title compound (1.4 g) as a colorless oil.

¹H-NMR Spectrum (CDCl₃, 400 MHz) δ(ppm): 2.64-2.77 (4H, m), 2.90-3.01 (6H, m).

Referential Example 6

One loopful of the slant culture [0.5% of soluble starch, 0.5% of glucose, 0.1% of fish meat extract (manufactured by Wako Pure Chemical Industries, Ltd.), 0.1% of yeast extract (manufactured by Oriental Yeast Co., Ltd.), 0.2% of NZ-case (manufactured by Humko Sheffield Chemical Co.), 0.2% of sodium chloride, 0.1% of calcium carbonate, and 1.6% of agar (manufactured by Wako Pure Chemical Industries, Ltd.)] of *Streptomyces* sp. AB-1704 strain (FERM P-18999) isolated from the soil was inoculated into a 65 mL test tube containing 7 mL of a seed medium [2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate], and it was cultured at 28° C. for three days in a shaking incubator to give a seed culture.

Further, 0.5 mL of the seed culture was inoculated into a 65 mL test tube containing 7 mL of a production medium [2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate], and it was cultured at 28° C. for three days in a shaking incubator.

Next, a 25 mg/mL solution of the substrate 11107B substance (the compound of Example A4 of WO 02/060890) in ethanol was prepared, and 0.2 mL of the solution was added to the culture. After addition, it was shaken at 28° C. for 48 hours to carry out conversion reaction.

After the reaction, the reaction mixture was analyzed by HPLC under the following analytic HPLC condition (a) to verify that 11107D substance was formed in the reaction mixture.

Analytic HPLC Condition (a)

Column: CAPCELL PAK C18 SG120 φ4.6 mm×250 mm (manufactured by SHISEIDO Co.)
Temperature: 40° C.
Flow rate: 1 mL/min.
Detection: 240 nm
Eluent:acetonitrile/0.15% potassium dihydrogenphosphate (pH 3.5) (3:7 to 5:5, v/v, 0 to 18 minutes, linear gradient), acetonitrile/0.15% potassium dihydrogenphosphate (pH 3.5) (5:5 to 85:15, v/v, 18 to 22 minutes, linear gradient)
Retention time: 11107D substance 9.9 min., 11107B substance 19.4 min.

Referential Example 7

One loopful of the slant culture (yeast-malt agar medium) of A-1545 strain (FERM P-18944) isolated from the soil was inoculated into a 250 mL Erlenmeyer flask containing 20 mL of a seed medium [2.4% of soluble starch, 0.1% of glucose, 0.5% of soybean meal (ESUSAN-MEAT manufactured by Ajinomoto Co., Ltd.), 0.3% of beef extract (manufactured by Difco), 0.5% of yeast extract (manufactured by Difco), 0.5% of triptone-peptone (manufactured by Difco), and 0.4% of calcium carbonate], and it was cultured at 28° C. for three days in a shaking incubator to give a seed culture.

Further, 0.6 mL of the seed culture was inoculated into a 500 mL Erlenmeyer flask containing 60 mL of a production medium [2% of soluble starch, 2% of glucose, 2% of soybean meal (ESUSAN-MEAT manufactured by Ajinomoto Co., Ltd.), 0.5% of yeast extract (manufactured by Oriental Yeast Co., Ltd.), 0.25% of sodium chloride, 0.32% of calcium carbonate, 0.0005% of copper sulfate, 0.0005% of manganese chloride, 0.0005% of zinc sulfate, pH 7.4 before sterilization], and it was cultured at 28° C. for four days in a shaking incubator. Each 2 mL of the resulting culture was dispensed into 15 mL test tubes. Next, a 20 mg/mL solution of the substrate 11107B substance in dimethyl sulfoxide was prepared, and 0.05 mL of the solution was added. After the addition, it was shaken at 28° C. for 23 hours to carry out conversion. After the reaction, the reaction mixture was analyzed by HPLC under the following analytic HPLC condition (b) to verify that the 11107D substance was formed in the reaction mixture.

Analytic HPLC Condition (b)

Column: CAPCELL PAK C18 SG120 φ 4.6 mm×250 mm (manufactured by SHISEIDO Co.)
Temperature: 40° C.
Flow rate: 1 mL/min.
Detection: 240 nm
Eluent: acetonitrile/water (50:50, v/v) isocratic
Retention time: 11107B substance 7.2 min., 11107D substance 3.6 min.

Referential Example 8

One loopful of the slant culture [0.5% of soluble starch, 0.5% of glucose, 0.1% of fish meat extract (manufactured by Wako Pure Chemical Industries, Ltd.), 0.1% of yeast extract (manufactured by Oriental Yeast Co., Ltd.), 0.2% of NZ-case (manufactured by Humko Sheffield Chemical Co.), 0.2% of sodium chloride, 0.1% of calcium carbonate, and 1.6% of agar (manufactured by Wako Pure Chemical Industries, Ltd.)] of *Streptomyces* sp. AB-1704 strain (FERM P-18999) isolated from the soil was inoculated into a 500-mL Erlenmeyer flask containing 100 mL of a seed medium [2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate], and it was cultured at 28° C. for three days in a shaking incubator to give a seed culture. Further, each 2 mL of the seed culture was inoculated into 500 mL Erlenmeyer flasks (150 flasks) each containing 100 mL of a production medium [2.0% of soluble starch, 1.0% of glucose, 0.5% of polypeptone (manufactured by Nihon Pharmaceutical Co., Ltd.), 0.5% of yeast extract (manufactured by Oriental Yeast Co., Ltd.), and 0.1% of calcium carbonate], and it was cultured at 28° C. for two days in a shaking incubator.

A 20 mg/mL solution of the substrate 11107B substance in ethanol was prepared, and each 0.44 mL of the solution was added to the culture (100 mL/500 mL Erlenmeyer flask, 150 flasks). After the addition, it was shaken at 28° C. for 9 hours to carry out conversion. After the completion of reaction, the cultures were collected and separated into the culture supernatant and the mycelium cake by centrifugation at 2700 rpm for 10 minutes. The mycelium cake was extracted with 5 L of methanol and filtrated to give the methanol extract. This methanol extract was evaporated to remove methanol, combined with the culture supernatant and extracted with 10 L of ethyl acetate. The resulting ethyl acetate solution was evaporated to give 2090 mg of a crude active fraction. The crude active fraction was dissolved in 4 mL of a mixture of tetrahydrofuran-methanol (1:1, v/v) and 6 mL of a 50% aqueous solution of acetonitrile, subjected to ODS column chromatography (manufactured by YMC Co., ODS-AM 120-S50 φ3.6 cm×43 cm) and eluted with a 40% aqueous solution of acetonitrile. An eluted fraction from 336 mL to 408 mL was concentrated to dryness under reduced pressure to give 560 mg of a residue. Further, the residue was dissolved in 10 mL of a 50% aqueous solution of methanol, subjected to ODS column chromatography (manufactured by YMC Co., ODS-AM 120-S50 φ3.6 cm×40 cm) and eluted with a 50% aqueous solution of methanol. An eluted fraction from 1344 mL to 1824 mL was concentrated to dryness under reduced pressure to give 252 mg of 11107D substance.

Referential Example 9

One loopful of the slant culture (yeast-malt agar medium) of A-1544 strain (FERM P-18943) was inoculated into a 250 mL Erlenmeyer flask containing 25 mL of a seed medium [2% of soluble starch, 2% of glucose, 2% of soybean meal (ESUSAN-MEAT manufactured by Ajinomoto Co., Ltd.), 0.5% of yeast extract (manufactured by Difco), 0.25% of sodium chloride, and 0.32% of calcium carbonate, pH 7.4 before sterilization], and it was cultured at 28° C. for two days in a shaking incubator to give a seed culture. Each 0.75 mL of the culture was dispensed into 2 mL serum tubes (manufactured by Sumitomo Bakelite Co., Ltd.), and an equal amount of a 40% aqueous solution of glycerol was added. After stirring, it was frozen at −70° C. to give a frozen seed culture. The frozen seed culture was melted, 0.25 mL thereof was inoculated into a 250 mL Erlenmeyer flask containing 25 mL of a seed medium [2% of soluble starch, 2% of glucose, 2% of soybean meal (ESUSAN-MEAT manufactured by Ajinomoto Co., Ltd.), 0.5% of yeast extract (manufactured by Oriental Yeast Co., Ltd.), 0.25% of sodium chloride, and 0.32% of calcium carbonate, pH 7.4 before sterilization], and it was cultured at 28° C. for two days in a shaking incubator to give a seed culture. Further, the seed culture (0.5 mL) was inoculated into a 500 mL Erlenmeyer flask containing 100 mL of production medium [2% of soluble starch, 2% of glucose, 2% of soybean meal (ESUSAN-MEAT manufactured by Ajinomoto Co., Ltd.), 0.5% of yeast extract (manufactured by Oriental Yeast Co., Ltd.), 0.25% of sodium chloride, and 0.32% of calcium carbonate, pH 7.4 before sterilization], and it was cultured at 28° C. for three days in a shaking incubator.

Each of the resulting cultures (100 mL/500 mL Erlenmeyer flask, 10 flasks) was subjected to centrifugation at 3000 rpm for 10 minutes to collect cells, and the cells were suspended into 100 mL of a 50 mM phosphate buffer solution (pH 6.0). Next, a 100 mg/mL solution of the substrate 11107B substance in dimethyl sulfoxide was prepared, and each 0.5 mL of the solution was added. After the addition, it was shaken at 28° C. for 24 hours to carry out conversion. After the completion of the reaction, the reaction mixtures were collected and separated into the supernatant and mycelium cake by centrifugation at 5000 rpm for 20 minutes. The supernatant was extracted with 1 L of ethyl acetate. The mycelium cake was extracted with 500 mL of methanol and then filtrated to give a methanol extract. The methanol extract was evaporated to remove methanol and extracted with 1 L of ethyl acetate. Each of the ethyl acetate layers was washed with water, dried over anhydrous sodium sulfate, and the combined layers were evaporated to give 937 mg of a crude active fraction. The crude active fraction was subjected to silica gel column chromatography (Kiesel gel 60, 50 g) and eluted with 1200 mL of a mixture of ethyl acetate and n-hexane (90:10; v/v) to give 234 mg of an active fraction. The resulting active fraction was subjected to preparative high performance liquid chromatography (HPLC) under the following preparative HPLC condition (C), and the resulting eluate was analyzed by HPLC under the following analytic HPLC condition (c). The solvent was removed from the fraction containing the 11107D substance thus obtained, to give 80 mg of the 11107D substance.

Preparative HPLC Condition (C)
  Column: CAPCELL PAK C18 UG120 φ 30×250 mm (manufactured by SHISEIDO Co.)
  Flow rate: 20 mL/min.
  Detection: 240 nm
  Eluent: acetonitrile/water (30:70, v/v) isocratic Analytic HPLC Condition (c)
  Column: CAPCELL PAK C18 SG120 φ4.6 mm×250 mm (manufactured by SHISEIDO Co.)
  Temperature: 40° C.
  Flow rate: 1 mL/min.
  Detection: 240 nm
  Eluent: acetonitrile/water (35:65, v/v) isocratic
  Retention time: 11107D substance 7.8 min.

Referential Example 10

Each of cultures of A-1545 strain (FERM P-18944) (100 mL/500 mL Erlenmeyer flask, 10 flasks) obtained by a similar method as described for Referential Example 9 was subjected to centrifugation at 3000 rpm for 10 minutes to collect cells, and the cells were suspended into 100 mL of a 50 mM phosphate buffer solution (pH 6.0). Next, a 100 mg/mL solution of the substrate 11107B in dimethyl sulfoxide was prepared, and each 1 mL of the solution was added. After the addition, it was shaken at 28° C. for 24 hours to carry out conversion. After the completion of the reaction, the reaction mixtures were collected and separated into the supernatant and mycelium cake by centrifugation at 5000 rpm for 20 minutes. The supernatant was extracted with 1 L of ethyl acetate. The mycelium cake was extracted with 500 mL of acetone, and then filtrated to give an acetone extract. The acetone extract was evaporated to remove acetone, and extracted with 1 L of ethyl acetate. Each of the ethyl acetate layers was washed with water, dried and dehydrated over anhydrous sodium sulfate, and the combined layers were evaporated to give 945 mg of a crude active fraction. The crude active fraction was subjected to silica gel column chromatography (Kiesel gel 60, 50 g), eluted with 100 mL of a mixture of ethyl acetate and n-hexane (50:50; v/v), 200 mL of a mixture of ethyl acetate and n-hexane (75:25; v/v), and 600 mL of a mixture of ethyl acetate and n-hexane (90:10; v/v), to give 463 mg of an active fraction. The obtained active fraction was subjected to preparative high performance liquid chromatography (HPLC) under the preparative HPLC condition (C) described in Example 4, the resulting eluate was analyzed by HPLC under the analytic HPLC condition described in Example 4. The solvent was removed from the fraction containing 11107D substance thus obtained, to give 304 mg of 11107D substance.

The invention claimed is:
1. A compound represented by the formula (I):

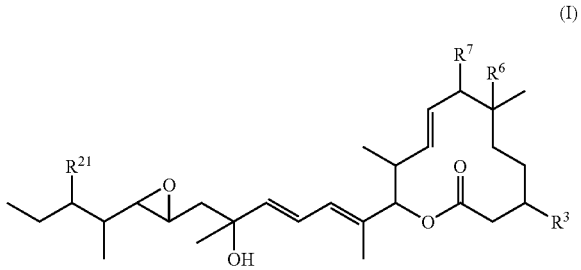

(in the formula, $R^3$, $R^6$, $R^7$ and $R^{21}$ are the same as or different from one another and each represents
  1) a hydroxyl group or an oxo group formed together with the carbon atom to which each of $R^3$, $R^6$, $R^7$ and $R^{21}$ is bound, provided that $R^6$ is limited to hydroxyl group,
  2) an optionally substituted $C_{1-22}$ alkoxy group,
  3) an optionally substituted unsaturated $C_{2-22}$ alkoxy group,
  4) an optionally substituted $C_{7-22}$ aralkyloxy group,
  5) an optionally substituted 5 to 14-membered heteroaralkyloxy group,
  6) RCO—O— (wherein R represents
    a) a hydrogen atom,
    b) an optionally substituted $C_{1-22}$ alkyl group,
    c) an optionally substituted unsaturated $C_{2-22}$ alkyl group,
    d) an optionally substituted $C_{6-14}$ aryl group,
    e) an optionally substituted 5 to 14-membered heteroaryl group,
    f) an optionally substituted $C_{7-22}$ aralkyl group,
    g) an optionally substituted 5 to 14-membered heteroaralkyl group,
    h) an optionally substituted $C_{1-22}$ alkoxy group,
    i) an optionally substituted unsaturated $C_{2-22}$ alkoxy group,
    j) an optionally substituted $C_{6-14}$ aryloxy group or
    k) an optionally substituted 5 to 14-membered heteroaryloxy group), 7) $R^{S1}R^{S2}R^{S3}SiO—$ (wherein $R^{S1}$, $R^{S2}$ and $R^{S3}$ are the same as or different from one another and each represents
   a) a $C_{1-6}$ alkyl group or
   b) a $C_{6-14}$ aryl group),
8) a halogen atom,
9) $R^{N1}R^{N2}N—R^M—$ (wherein $R^M$ represents
   a) a single bond,
   b) —CO—O—,
   c) —S$_2$—O—,
   d) —CS—O— or
   e) —CO—NR$^{N3}$— (wherein $R^{N3}$ represents a hydrogen atom or an optionally substituted $C_{1-6}$ alkyl group), provided that each of the leftmost bond in b) to e) is bound to the nitrogen atom; and
   $R^{N1}$ and $R^{N2}$ are the same as or different from each other and each represents
   a) a hydrogen atom,
   b) an optionally substituted $C_{1-22}$ alkyl group,
   c) an optionally substituted unsaturated $C_{2-22}$ alkyl group,
   d) an optionally substituted aliphatic $C_{2-22}$ acyl group,
   e) an optionally substituted aromatic $C_{7-15}$ acyl group,
   f) an optionally substituted $C_{6-14}$ aryl group,
   g) an optionally substituted 5 to 14-membered heteroaryl group,
   h) an optionally substituted $C_{7-22}$ aralkyl group,
   i) an optionally substituted $C_{1-22}$ alkylsulfonyl group,
   j) an optionally substituted $C_{6-14}$ arylsulfonyl group,
   k) an optionally substituted 3 to 14-membered non-aromatic heterocyclic group formed by $R^{N1}$ and $R^{N2}$ together with the nitrogen atom to which $R^{N1}$ and $R^{N2}$ are bound, and the non-aromatic heterocyclic group may have substituents,
   l) an optionally substituted 5 to 14-membered heteroaralkyl group,
   m) an optionally substituted $C_{3-14}$ cycloalkyl group or
   n) an optionally substituted 3 to 14-membered non-aromatic heterocyclic group),
10) $R^{N4}SO_2—O—$ (wherein $R^{N4}$ represents
    a) an optionally substituted $C_{1-22}$ alkyl group,
    b) an optionally substituted $C_{6-14}$ aryl group,
    c) an optionally substituted $C_{1-22}$ alkoxy group,
    d) an optionally substituted unsaturated $C_{2-22}$ alkoxy group,
    e) an optionally substituted $C_{6-14}$ aryloxy group,
    f) an optionally substituted 5 to 14-membered heteroaryloxy group,
    g) an optionally substituted $C_{7-22}$ aralkyloxy group or
    h) an optionally substituted 5 to 14-membered heteroaralkyloxy group),
11) $(R^{N5}O)_2PO—O—$ (wherein $R^{N5}$ represents
    a) an optionally substituted $C_{1-22}$ alkyl group,
    b) an optionally substituted unsaturated $C_{2-22}$ alkyl group,
    c) an optionally substituted $C_{6-14}$ aryl group,
    d) an optionally substituted 5 to 14-membered heteroaryl group,
    e) an optionally substituted $C_{7-22}$ aralkyl group or
    f) an optionally substituted 5 to 14-membered heteroaralkyl group),
12) $(R^{N1}R^{N2}N)_2PO—O—$ (wherein $R^{N1}$ and $R^{N2}$ have the same meanings as defined above) or
13) $(R^{N1}R^{N2}N)(R^{N5}O)PO—O—$ (wherein $R^{N1}$, $R^{N2}$ and R have the same meanings as defined above), provided that a compound in which $R^3$, $R^6$, $R^7$ and $R^{21}$ are all hydroxyl groups, and a compound in which $R^3$, $R^6$ and $R^{21}$ are all hydroxyl groups and $R^7$ is an acetoxy group and a compound in which $R^3$ and $R^6$ are hydroxyl groups, $R^7$ is an acetoxy group and $R^{21}$ is an oxo group formed together with the carbon atom to which $R^{21}$ is bound are excluded), or a pharmacologically acceptable salt thereof.

2. The compound according to claim 1 represented by the formula (I-a):

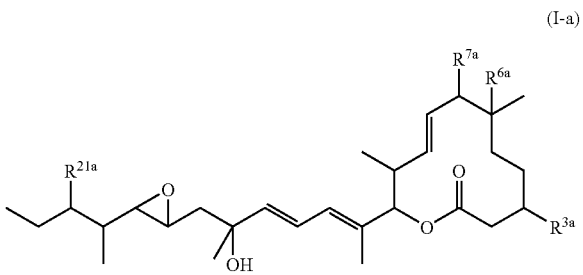

(I-a)

(in the formula, $R^{3a}$, $R^{6a}$, $R^{7a}$ and $R^{21a}$ are the same as or different from one another and each represents
   1) a hydroxyl group or an oxo group formed together with the carbon atom to which each of $R^{3a}$, $R^{6a}$, $R^{7a}$ and $R^{21a}$ is bound, provided that $R^{6a}$ is limited to a hydroxyl group,
   2) an optionally substituted $C_{1-22}$ alkoxy group,
   3) $R^aCO—O—$ (wherein $R^a$ represents
      a) a hydrogen atom,
      b) an optionally substituted $C_{1-22}$ alkyl group,
      c) an optionally substituted unsaturated $C_{2-22}$ alkyl group,
      d) an optionally substituted $C_{6-14}$ aryl group,
      e) an optionally substituted 5 to 14-membered heteroaryl group,
      f) an optionally substituted $C_{7-22}$ aralkyl group,
      g) an optionally substituted 5 to 14-membered heteroaralkyl group,
      h) an optionally substituted $C_{1-22}$ alkoxy group,
      i) an optionally substituted unsaturated $C_{2-22}$ n alkoxy group,
      j) an optionally substituted $C_{6-14}$ aryloxy group or
      k) an optionally substituted 5 to 14-membered heteroaryloxy group),
   4) $R^{aS1}R^{aS2}R^{aS3}SiO—$ (wherein $R^{aS1}$, $R^{aS2}$ and $R^{aS3}$ are the same as or different from one another and each represents
      a) a $C_{1-6}$ alkyl group or
      b) a $C_{6-14}$ aryl group),
   5) a halogen atom or
   6) $R^{aN1}R^{aN2}N—R^{aM}—$ (wherein $R^{aM}$ represents
      a) a single bond,
      b) —CO—O—,
      c) —SO$_2$—O—,
      d) —CS—O— or
      e) —CO—NR$^{aN3}$— (wherein $R^{aN3}$ represents a hydrogen atom or an optionally substituted $C_{1-6}$ alkyl group, provided that each of the leftmost bond in b) to e) is bound to the nitrogen atom); and
   $R^{aN1}$ and $R^{aN2}$ are the same as or different from each other and each represents
      a) a hydrogen atom,
      b) an optionally substituted $C_{1-22}$ alkyl group,
      c) an optionally substituted unsaturated $C_{2-22}$ alkyl group, d) an optionally substituted aliphatic $C_{2-22}$ acyl group,
e) an optionally substituted aromatic $C_{7-15}$ acyl group,
f) an optionally substituted $C_{6-14}$ aryl group,
g) an optionally substituted 5 to 14-membered heteroaryl group,
h) an optionally substituted $C_{7-22}$ aralkyl group,
i) an optionally substituted $C_{1-22}$ alkylsulfonyl group,
j) an optionally substituted $C_{6-14}$ arylsulfonyl group,
k) an optionally substituted 3 to 14-membered non-aromatic heterocyclic group formed by $R^{aN1}$ and $R^{aN2}$ together with the nitrogen atom to which $R^{aN1}$ and $R^{aN2}$ are bound, and the non-aromatic heterocyclic group may have substituents,
l) an optionally substituted 5 to 14-membered heteroaralkyl group,
m) an optionally substituted $C_{3-14}$ cycloalkyl group or
n) an optionally substituted 3 to 14-membered non-aromatic heterocyclic group)), or a pharmacologically acceptable salt thereof.

3. The compound according to claim 1 represented by the formula (I-b):

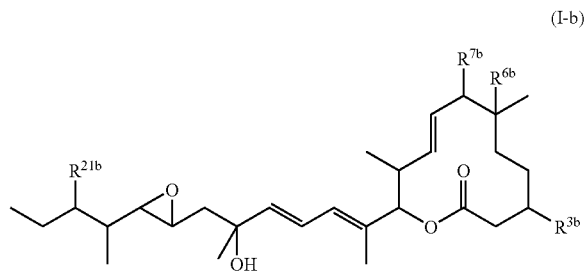

(I-b)

(in the formula, $R^{3b}$, $R^{6b}$, $R^{7b}$ and $R^{21b}$ are the same as or different from one another and each represents
1) a hydroxyl group or an oxo group formed together with the carbon atom to which each of $R^{3b}$, $R^{6b}$, $R^{7b}$ and $R^{21b}$ is bound, provided that $R^{6b}$ is limited to a hydroxyl group,
2) an optionally substituted $C_{1-22}$ alkoxy group,
3) $R^bCO$—O— (wherein $R^b$ represents
   a) a hydrogen atom,
   b) an optionally substituted $C_{1-22}$ alkyl group,
   c) an optionally substituted unsaturated $C_{2-22}$ alkyl group,
   d) an optionally substituted $C_{6-14}$ aryl group,
   e) an optionally substituted 5 to 14-membered heteroaryl group,
   f) an optionally substituted $C_{7-22}$ aralkyl group,
   g) an optionally substituted 5 to 14-membered heteroaralkyl group,
   h) an optionally substituted $C_{1-22}$ alkoxy group,
   i) an optionally substituted unsaturated $C_{2-22}$ alkoxy group,
   j) an optionally substituted $C_{6-14}$ aryloxy group or
   k) an optionally substituted 5 to 14-membered heteroaryloxy group),
4) $R^{bS1}R^{bS2}R^{bS3}SiO$— (wherein $R^{bS1}$, $R^{bS2}$ and $R^{bS3}$ are the same as or different from one another and each represents
   a) a $C_{1-6}$ alkyl group or
   b) a $C_{6-14}$ aryl group) or 5) $R^{bN1}R^{bN2}N$—$R^{bM}$— (wherein $R^{bM}$ represents
   a) —CO—O— or
   b) —CS—O—, provided that each of the leftmost bond in a) and b) is bound to the nitrogen atom; and
$R^{bN1}$ and $R^{bN2}$ are the same as or different from each other and each represents
   a) a hydrogen atom,
   b) an optionally substituted $C_{1-22}$ alkyl group,
   c) an optionally substituted unsaturated $C_{2-22}$ alkyl group,
   d) an optionally substituted aliphatic $C_{2-22}$ acyl group,
   e) an optionally substituted aromatic $C_{7-15}$ acyl group,
   f) an optionally substituted $C_{6-14}$ aryl group,
   g) an optionally substituted 5 to 14-membered heteroaryl group,
   h) an optionally substituted $C_{7-22}$ aralkyl group,
   i) an optionally substituted $C_{1-22}$ alkylsulfonyl group,
   j) an optionally substituted $C_{6-14}$ arylsulfonyl group,
   k) an optionally substituted 3 to 14-membered non-aromatic heterocyclic group formed by $R^{bN1}$ and $R^{bN2}$ together with the nitrogen atom to which $R^{bN1}$ and $R^{bN2}$ are bound, and the non-aromatic heterocyclic group may have substituents,
   l) an optionally substituted 5 to 14-membered heteroaralkyl group,
   m) an optionally substituted $C_{3-14}$ cycloalkyl group or
   n) an optionally substituted 3 to 14-membered non-aromatic heterocyclic group)), or a pharmacologically acceptable salt thereof.

4. The compound according to claim 1 represented by the formula (I-c):

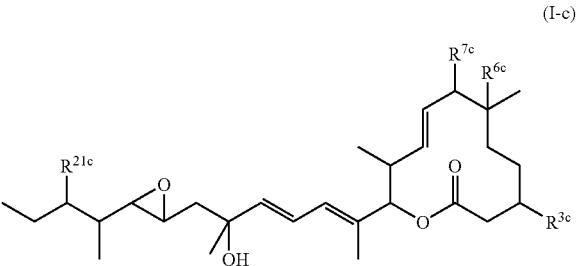

(I-c)

(in the formula, $R^{3c}$, $R^{6c}$, $R^{7c}$ and $R^{21c}$ are the same as or different from one another and each represents
1) a hydroxyl group or an oxo group formed together with the carbon atom to which each of $R^{3c}$, $R^{6c}$, $R^{7c}$ and $R^{21c}$ is bound, provided tat $R^{6c}$ is limited to a hydroxyl group,
2) an optionally substituted $C_{1-22}$ alkoxy group,
3) $R^cCO$—O— (wherein $R^c$ represents
   a) an optionally substituted $C_{1-22}$ alkyl group,
   b) an optionally substituted $C_{6-14}$ aryl group,
   c) an optionally substituted $C_{7-22}$ aralkyl group or
   d) an optionally substituted $C_{6-14}$ aryloxy group),
4) $R^{cS1}R^{cS2}R^{cS3}SiO$— (wherein $R^{cS1}$, $R^{cS2}$ and $R^{cS3}$ are the same as or different from one another and each represents
   a) a $C_{1-6}$ alkyl group or
   b) a $C_{6-14}$ aryl group) or
5) $R^{cN1}R^{cN2}N$—$R^{cM}$— (wherein $R^{cM}$ represents
   a) —CO—O— or
   b) —CS—O—, provided that each of the leftmost bond in a) and b) is bound to the nitrogen atom; and
$R^{cN1}$ and $R^{cN2}$ are the same as or different from each other and each represents a) a hydrogen atom,
b) an optionally substituted $C_{1-22}$ alkyl group,
c) an optionally substituted 3 to 14-membered non-aromatic heterocyclic group formed by $R^{cN1}$ and $R^{cN2}$ together with the nitrogen atom to which $R^{cN1}$ and $R^{cN2}$ are bound, and the non-aromatic heterocyclic group may have substituents,
d) an optionally substituted 5 to 14-membered heteroaralkyl group,
e) an optionally substituted $C_{3-14}$ cycloalkyl group or
f) an optionally substituted 3 to 14-membered non-aromatic heterocyclic group)), or a pharmacologically acceptable salt thereof.

5. The compound according to claim 1 represented by the formula (I-d):

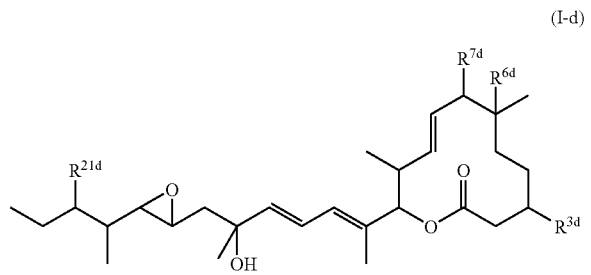

(I-d)

(in the formula, $R^{3d}$ represents
1) a hydroxyl group or an oxo group formed together with the carbon atom to which $R^{3d}$ is bound,
2) an optionally substituted $C_{1-22}$ alkoxy group,
3) an optionally substituted unsaturated $C_{2-22}$ alkoxy group,
4) an optionally substituted $C_{7-22}$ aralkyloxy group,
5) $R^d$CO—O— (wherein $R^d$ represents
    a) a hydrogen atom,
    b) an optionally substituted $C_{1-22}$ alkyl group,
    c) an optionally substituted unsaturated $C_{2-22}$ alkyl group,
    d) an optionally substituted $C_{6-14}$ aryl group,
    e) an optionally substituted 5 to 14-membered heteroaryl group,
    f) an optionally substituted $C_{7-22}$ aralkyl group,
    g) an optionally substituted 5 to 14-membered heteroaralkyl group,
    h) an optionally substituted $C_{1-22}$ alkoxy group,
    i) an optionally substituted unsaturated $C_{2-22}$ alkoxy group,
    j) an optionally substituted $C_{6-14}$ aryloxy group or
    k) an optionally substituted 5 to 14-membered heteroaryloxy group) or
6) $R^{dN1}R^{dN2}$N—CO—O— (wherein $R^{dN1}$ and $R^{dN2}$ are the same as or different from each other and each represents
    a) a hydrogen atom,
    b) an optionally substituted $C_{1-22}$ alkyl group,
    c) an optionally substituted unsaturated $C_{2-22}$ alkyl group,
    d) an optionally substituted $C_{6-14}$ aryl group,
    e) an optionally substituted 5 to 14-membered heteroaryl group,
    f) an optionally substituted $C_{7-22}$ aralkyl group,
    g) an optionally substituted 5 to 14-membered heteroaralkyl group,
    h) an optionally substituted $C_{3-14}$ cycloalkyl group,
    i) an optionally substituted 3 to 14-membered non-aromatic heterocyclic group or
    j) an optionally substituted 3 to 14-membered non-aromatic heterocyclic group formed by $R^{dN1}$ and $R^{dN2}$ together with the nitrogen atom to which $R^{dN1}$ and $R^{dN2}$ are bound, and the non-aromatic heterocyclic group may have substituents); and $R^{6d}$, $R^{7d}$ and $R^{21d}$ are the same as or different from one another and each represents
1) a hydroxyl group or an oxo group formed together with the carbon atom to which each of $R^{6d}$, $R^{7d}$ and $R^{21d}$ is bound, provided that $R^{6d}$ is limited to a hydroxyl group,
2) an optionally substituted $C_{1-22}$ alkoxy group,
3) an optionally substituted unsaturated $C_{2-22}$ alkoxy group,
4) an optionally substituted $C_{7-22}$ aralkyloxy group,
5) $R^d$CO—O— (wherein $R^d$ has the same meaning as defined above),
6) $R^{dN1}R^{dN2}$N—CO—O— (wherein $R^{dN1}$ and $R^{dN2}$ have the same meanings as defined above),
7) $R^{dN1}R^{dn2}$N—SO$_2$—O— (wherein $R^{dn1}$ and $R^{dN2}$ have the same meanings as defined above),
8) $R^{dN1}R^{dN2}$N—CS—O— (wherein $R^{dN1}$ and $R^{dN2}$ have the same meanings as defined above),
9) $R^{dN3}$SO$_2$—O— (wherein $R^{dN3}$ represents
    a) an optionally substituted $C_{1-22}$ alkyl group,
    b) an optionally substituted $C_{1-22}$ alkoxy group,
    c) an optionally substituted unsaturated $C_{2-22}$ alkoxy group,
    d) an optionally substituted $C_{6-14}$ aryl group,
    e) an optionally substituted $C_{6-14}$ aryloxy group,
    f) an optionally substituted 5 to 14-membered heteroaryloxy group,
    g) an optionally substituted $C_{7-22}$ aralkyloxy group or
    h) an optionally substituted 5 to 14-membered heteroaralkyloxy group),
10) $(R^{dN5}O)_2$PO— (wherein $R^{dN5}$ represents
    a) an optionally substituted $C_{1-22}$ alkyl group,
    b) an optionally substituted unsaturated $C_{2-22}$ alkyl group,
    c) an optionally substituted $C_{6-14}$ aryl group,
    d) an optionally substituted 5 to 14-membered heteroaryl group,
    e) an optionally substituted $C_{7-22}$ aralkyl group or
    f) an optionally substituted 5 to 14-membered heteroaralkyl group),
11) $(R^{dN1}R^{dN2}N)_2$PO— (wherein $R^{dN1}$ and $R^{dN2}$ have the same meanings as defined above) or
12) $(R^{dN1}R^{dN2}N)(R^{dN5}O)$PO— (wherein $R^{dN1}$, $R^{dN2}$ and $R^{dN5}$ have the same meanings as defined above), provided that a compound in which $R^{3d}$, $R^{6d}$, $R^{7d}$ and $R^{21d}$ are all hydroxyl groups, and a compound in which $R^{3d}$, $R^{6d}$ and $R^{21d}$ are hydroxyl groups and $R^{7d}$ is an acetoxy group are excluded), or a pharmacologically acceptable salt thereof.

6. The compound according to claim 1, wherein $R^6$ and/or $R^7$ represents $R^{N1}R^{N2}$N—$R^M$— (wherein $R^M$ represents
a) —CO—O— or
b) —CS—O—; and
$R^{N1}$ and $R^{N2}$ have the same meanings as defined above, provided that each of the leftmost bond in a) and b) is bound to the nitrogen atom), or a pharmacologically acceptable salt thereof.

7. The compound according to claim 1, or a pharmacologically acceptable salt thereof, wherein $R^{21}$ is an oxo group formed together with the carbon atom to which $R^{21}$ is bound.

8. The compound according to claim 5 represented by the formula (I-e):

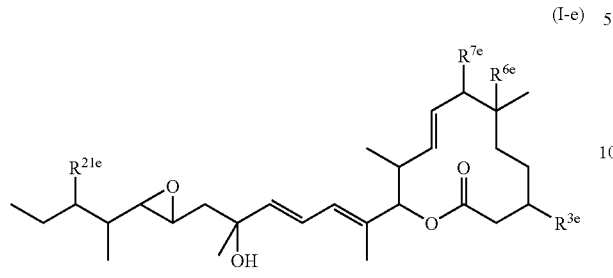

(in the formula, $R^{3e}$ and $R^{21e}$ are the same as or different from each other and each represents
1) a hydroxyl group or an oxo group formed together with the carbon atom to which each of $R^{3e}$ and $R^{21e}$ is bound,
2) an optionally substituted $C_{1-6}$ alkoxy group,
3) an optionally substituted unsaturated $C_{2-10}$ alkoxy group,
4) an optionally substituted $C_{7-10}$ aralkyloxy group,
5) an optionally substituted aliphatic $C_{2-6}$ acyloxy group or
6) $R^{eN1}R^{eN2}N$—CO—O— (wherein $R^{eN1}$ and $R^{eN2}$ are the same as or different from each other and each represents
A) a hydrogen atom or
B) an optionally substituted $C_{1-6}$ alkyl group); and
$R^{6e}$ and $R^{7e}$ are the same as or different from each other and each represents
1) a hydroxyl group or an oxo group formed together with the carbon atom to which each of $R^{6e}$ and $R^{7e}$ is bound, provided that $R^{6e}$ is limited to a hydroxyl group,
2) an optionally substituted $C_{1-6}$ alkoxy group,
3) an optionally substituted unsaturated $C_{2-10}$ alkoxy group,
4) an optionally substituted $C_{7-10}$ aralkyloxy group,
5) an optionally substituted aliphatic $C_{2-6}$ acyloxy group or
6) $R^eC(=Y^e)$—O— (wherein $Y^e$ represents an oxygen atom or a sulfur atom; and $R^e$ represents
a) a hydrogen atom,
b) an optionally substituted $C_{1-6}$ alkyl group,
c) an optionally substituted $C_{7-10}$ aralkyl group,
d) an optionally substituted 5 to 14-membered heteroaralkyl group,
e) the formula (III):

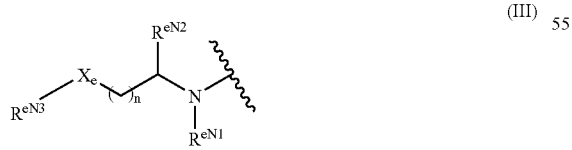

(in the formula,
A) n represents an integer of 0 to 4;
$X_e$ represents
i) —CHR$^{eN4}$—,
ii) —NR$^{eN5}$—,
iii) —O—,
iv) —S—,
v) —SO— or
vi) —SO$_2$—;
$R^{eN1}$ represents
i) a hydrogen atom or
ii) a $C_{1-6}$ alkyl group;
$R^{eN2}$ represents
i) a hydrogen atom or
ii) a $C_{1-6}$ alkyl group;
$R^{eN3}$ and $R^{eN4}$ are the same as or different from each other and each represents
i) a hydrogen atom,
ii) an optionally substituted $C_{1-6}$ alkyl group,
iii) an optionally substituted unsaturated $C_{2-10}$ alkyl group,
iv) an optionally substituted $C_{6-14}$ aryl group,
v) an optionally substituted 5 to 14-membered heteroaryl group,
vi) an optionally substituted $C_{7-10}$ aralkyl group,
vii) an optionally substituted $C_{3-8}$ cycloalkyl group,
viii) an optionally substituted $C_{4-9}$ cycloalkyl alkyl group,
ix) an optionally substituted 5 to 14-membered heteroaralkyl group,
x) an optionally substituted 5 to 14-membered non-aromatic heterocyclic group,
xi) —NR$^{eN6}$R$^{eN7}$ (wherein R$^{eN6}$ and R$^{eN7}$ are the same as or different from each other and each represents a hydrogen atom or an optionally substituted $C_{1-6}$ alkyl group) or
xii) an optionally substituted 5 to 14-membered non-aromatic heterocyclic group formed by R$^{eN3}$ and R$^{eN4}$ together with the carbon atom to which R$^{eN3}$ and R$^{eN4}$ are bound, and the non-aromatic heterocyclic group may have substituents; and
R$^{eN5}$ represents
3) a hydrogen atom,
ii) an optionally substituted $C_{1-6}$ alkyl group,
iii) an optionally substituted unsaturated $C_{2-10}$ alkyl group,
iv) an optionally substituted $C_{6-14}$ aryl group,
v) an optionally substituted 5 to 14-membered heteroaryl group,
vi) an optionally substituted $C_{7-10}$ aralkyl group,
vii) an optionally substituted $C_{3-8}$ cycloalkyl group,
viii) an optionally substituted $C_{4-9}$ cycloalkyl alkyl group,
ix) an optionally substituted 5 to 14-membered heteroaralkyl group,
x) an optionally substituted 5 to 14-membered non-aromatic heterocyclic group or
xi) an optionally substituted 5 to 14-membered non-aromatic heterocyclic group formed by R$^{eN3}$ and R$^{eN5}$ together with the nitrogen atom to which R$^{eN}$3 and R$^{eN5}$ are bound, and the non-aromatic heterocyclic group may have substituents,
B) $X_e$, n, R$^{eN3}$, R$^{eN4}$ and R$^{eN5}$ each represents the group as defined above; and R$^{eN1}$ R$^{eN2}$ together form an optionally substituted 5 to 14-membered non-aromatic heterocyclic group,
C) $X_e$, n, R$^{eN2}$, R$^{eN4}$ and R$^{eNn5}$ each represents the group as defined above; and R$^{eN1}$ and R$^{eN3}$ together form an optionally substituted 5 to 14-membered non-aromatic heterocyclic group or
D) $X_e$, n, R$^{eN1}$, R$^{eN4}$ and R$^{eN5}$ each represents the group as defined above; and R$^{eN2}$ and R$^{eN3}$ together form an optionally substituted 5 to 14-membered non-aromatic heterocyclic group) or f) the formula (IV):

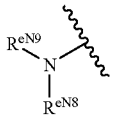

(IV)

(in the formula, $R^{eN8}$ and $R^{eN9}$ are the same as or different from each other and each represents
i) a hydrogen atom,
ii) an optionally substituted $C_{1-6}$ alkyl group,
iii) an optionally substituted $C_{6-14}$ aryl group,
iv) an optionally substituted 5 to 14-membered heteroaryl group,
v) an optionally substituted $C_{7-10}$ aralkyl group or
vi) an optionally substituted 5 to 14-membered heteroaralkyl group))), or a pharmacologically acceptable salt thereof.

9. The compound according to claim 5, wherein $R^{6d}$ and/or $R^{7d}$ represents $R^{d1}C(=Y^{d1})$—O— (wherein $Y^{d1}$ represents an oxygen atom or a sulfur atom; and $R^{d1}$ represents
1) a hydrogen atom,
2) an optionally substituted $C_{1-6}$ alkyl group,
3) an optionally substituted $C_{7-10}$ aralkyl group or
4) an optionally substituted 5 to 14-membered heteroaralkyl group), or a pharmacologically acceptable salt thereof.

10. The compound according to claim 5, wherein $R^{6d}$ and/or $R^{7d}$ represents $R^{d2}C(=Y^{d2})$—O— (wherein $Y^{d2}$ represents an oxygen atom or sulfur atom; and $R^{d2}$ represents the formula (III'):

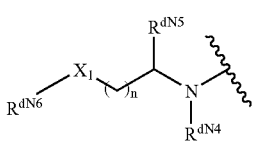

(III')

(in the formula, n represents an integer of 0 to 4; $X_1$ represents
1) —$CHR^{dN7}$—,
2) —$NR^{dN8}$—,
3) —O—,
4) —S—,
5) —SO— or
6) —$SO_2$—;
$R^{dN4}$ and $R^{dN5}$ are the same as or different from each other and each represents
1) a hydrogen atom or
2) a $C_{1-6}$ alkyl group;
$R^{dN6}$ and $R^{dN7}$ are the same as or different from each other and each represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group,
10) an optionally substituted 5 to 14-membered non-aromatic heterocyclic group,
11) —$NR^{dN9}R^{dN10}$ (wherein $R^{dN9}$ and $R^{dN10}$ are the same as or different from each other and each represents a hydrogen atom or an optionally substituted $C_{1-6}$ alkyl group) or
12) an optionally substituted 5 to 14-membered non-aromatic heterocyclic group formed together by $R^{dN6}$ and $R^{dN7}$, and the non-aromatic heterocyclic group may have substituents; and
$R^{dN8}$ represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group,
10) an optionally substituted 5 to 14-membered non-aromatic heterocyclic group,
11) an optionally substituted 5 to 14-membered non-aromatic heterocyclic group formed by $R^{dN4}$, $R^{dN5}$ or $R^{dN6}$ together with the nitrogen atom to which each of $R^{dN4}$, $R^{dN5}$ and $R^{dN6}$ is bound, and the non-aromatic heterocyclic group may have substituents or
12) an optionally substituted 5 to 14-membered non-aromatic heterocyclic group formed by two substituents selected from the group consisting of $R^{dN4}$, $R^{dN5}$ and $R^{dN6}$ together with the nitrogen atom to which it is bound, and the non-aromatic heterocyclic group may have substituents)), or a pharmacologically acceptable salt thereof.

11. The compound according to claim 10 or a pharmacologically acceptable salt thereof, wherein $X_1$ represents —$NR^{dN8}$— (wherein $NR^{dN8}$ has the same meanings as defined above).

12. The compound according to claim 5 represented by the formula (I-f):

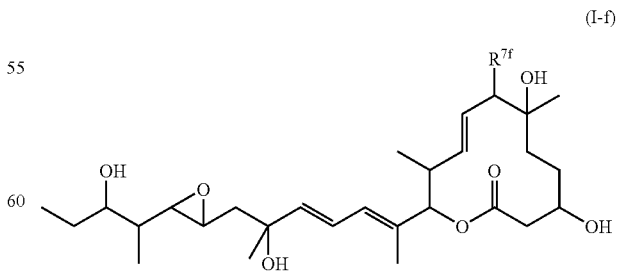

(I-f)

(in the formula, $R^{7f}$ represents $R^{f}C(=Y^{f})$—O— (wherein $Y^{f}$ represents an oxygen atom or a sulfur atom; and $R^{f}$ represents the formula (V):

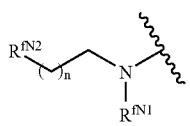

(V)

(wherein n represents an integer of 0 to 4;
$R^{fN1}$ represents
1) a hydrogen atom,
2) a methyl group or
3) an ethyl group; and
$R^{fN2}$ represents
1) a hydrogen atom,
2) a methylamino group,
3) a dimethylamino group,
4) an ethylamino group,
5) a diethylamino group,
6) an ethylmethylamino group,
7) a pyridinyl group,
8) a pyrrolidin-1-yl group,
9) a piperidin-1-yl group,
10) a morpholin-4-yl group or
11) a 4-methylpiperazin-1-yl group))), or a pharmacologically acceptable salt thereof.

13. The compound according to claim 5, wherein $R^{6d}$ and/or $R^{7d}$ represents $R^{d3}CO\text{—}O\text{—}$ (wherein $R^{d3}$ represents the formula (VI):

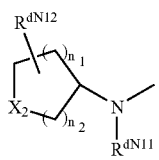

(VI)

(wherein $n_1$ and $n_2$ are the same as or different from each other and each represents an integer of 0 to 4;
$X_2$ represents
1) —$CHR^{dN13}$—,
2) —$NR^{dN14}$—,
3) —O—,
4) —S—,
5) —SO— or
6) —$SO_2$—;
$R^{dN11}$ represents
1) a hydrogen atom or
2) an optionally substituted $C_{1-6}$ alkyl group;
$R^{dN12}$ represents
1) a hydrogen atom,
2) an optionally substituted $C_{1-6}$ alkyl group,
3) an optionally substituted $C_{61-4}$ aryl group or
4) an optionally substituted $C_{7-10}$ aralkyl group;
$R^{dN13}$ represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group,
10) —$NR^{dN15}R^{dN16}$ (wherein $R^{dN15}$ and $R^{dN16}$ are the same as or different from each other and each represents a hydrogen atom or an optionally substituted $C_{1-6}$ alkyl group) or
11) an optionally substituted 5 to 14-membered non-aromatic heterocyclic group; and
$R^{dN14}$ represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group or
10) an optionally substituted 5 to 14-membered non-aromatic heterocyclic group)), or a pharmacologically acceptable salt thereof.

14. The compound according to claim 5 represented by the formula (I-g):

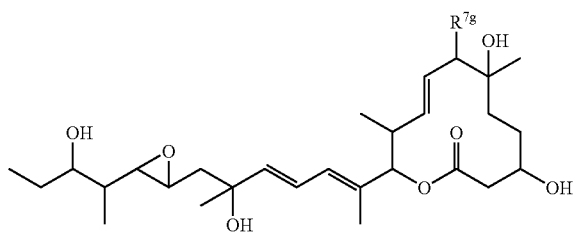

(I-g)

(in the formula, $R^{7g}$ represents $R^gCO\text{—}O\text{—}$ (wherein $R^g$ represents the formula (VII):

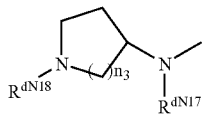

(VII)

(wherein $n_3$ represents 1 or 2;
$R^{dN17}$ represents
1) a hydrogen atom,
2) a methyl group or
3) an ethyl group; and
$R^{dN18}$ represents
1) a hydrogen atom,
2) a methyl group or
3) an ethyl group))), or a pharmacologically acceptable salt thereof.

15. The compound according to claim 5, wherein $R^{6d}$ and/or $R^{7d}$ represents $R^{d4}CO\text{—}O\text{—}$ (wherein $R^{d4}$ represents the formula (VIII):

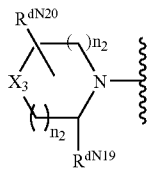

(VIII)

(wherein $n_1$ and $n_2$ are the same as or different from each other and each represents an integer of 0 to 4;
$X_3$ represents
1) —$CHR^{dN21}$—,
2) —$NR^{dN22}$—,
3) —O—,
4) —S—,
5) —SO— or
6) —$SO_2$—;
$R^{dN19}$ represents
1) a hydrogen atom or
2) a $C_{1-6}$ alkyl group;
$R^{dN20}$ represents
1) a hydrogen atom,
2) an optionally substituted $C_{1-6}$ alkyl group,
3) an optionally substituted $C_{6-14}$ aryl group or
4) an optionally substituted $C_{7-10}$ aralkyl group;
$R^{dn21}$ represents
1) a hydrogen atom,
2) an optionally substituted $C_{1-6}$ alkyl group,
3) an optionally substituted unsaturated $C_{2-10}$ alkyl group,
4) an optionally substituted $C_{1-6}$ alkoxy group,
5) an optionally substituted $C_{6-14}$ aryl group,
6) an optionally substituted 5 to 14-membered heteroaryl group,
7) an optionally substituted $C_{7-10}$ aralkyl group,
8) an optionally substituted $C_{3-8}$ cycloalkyl group,
9) an optionally substituted $C_{4-9}$ cycloalkyl alkyl group,
10) an optionally substituted 5 to 14-membered heteroaralkyl group,
11) —$NR^{dN23}R^{dN24}$ (wherein $R^{dN23}$ and $R^{dN24}$ are the same as or different from each other and each represents a hydrogen atom or an optionally substituted $C_{1-6}$ alkyl group) or
12) an optionally substituted 5 to 14-membered non-aromatic heterocyclic group; and
$R^{dN22}$ represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-8}$ cycloalkyl group,
8) an optionally substituted $C_{4-9}$ cycloalkyl alkyl group,
9) an optionally substituted 5 to 14-membered heteroaralkyl group or
10) an optionally substituted 5 to 14-membered non-aromatic heterocyclic group)), or a pharmacologically acceptable salt thereof.

16. The compound according to claim 5 represented by the formula (I-h):

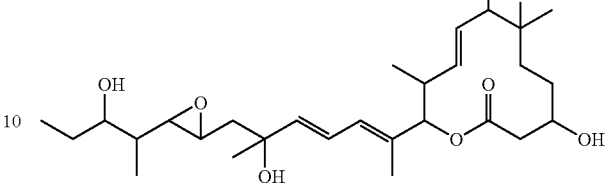

(I-h)

(in the formula, $R^{7h}$ represents $R^hCO$—O— (wherein $R^h$ represents the formula (IX):

(IX)

(wherein $n_4$ represents an integer of 1 to 3; and
$R^{dN25}$ represents
1) an amino group,
2) a methylamino group,
3) a dimethylamino group,
4) a pyrrolidin-1-yl group,
5) a piperidin-1-yl group or
6) a morpholin-4-yl group))), or a pharmacologically acceptable salt thereof.

17. The compound according to claim 5 represented by the formula (I-i):

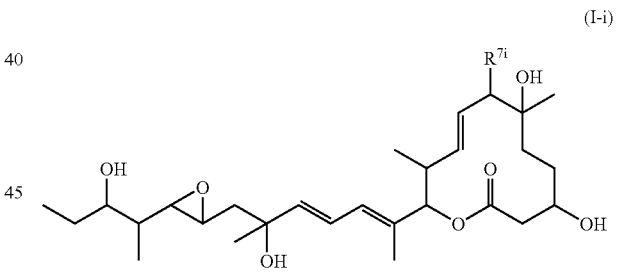

(I-i)

(in the formula, $R^{7i}$ represents $R^iCO$—O— (wherein $R^i$ represents the formula (X):

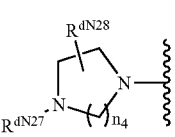

(X)

(wherein $n_4$ represents an integer of 1 to 3;
$R^{dN26}$ represents
1) a hydrogen atom,
2) an optionally substituted $C_{1-6}$ alkyl group,
3) an optionally substituted $C_{6-14}$ aryl group or
4) an optionally substituted $C_{7-10}$ aralkyl group; and $R^{dN27}$ represents
1) a hydrogen atom,
2) an optionally substituted $C_{1-6}$ alkyl group,
3) an optionally substituted $C_{3-8}$ cycloalkyl group,
4) an optionally substituted 3 to 8-membered non-aromatic heterocyclic group,
5) an optionally substituted $C_{6-14}$ aryl group,
6) an optionally substituted 5 to 14-membered heteroaryl group,
7) an optionally substituted $C_{7-10}$ aralkyl group,
8) an optionally substituted 5 to 14-membered heteroaralkyl group or
9) an optionally substituted $C_{4-9}$ cycloalkyl alkyl group))), or a pharmacologically acceptable salt thereof.

18. The compound according to claim 5 represented by the formula (I-j):

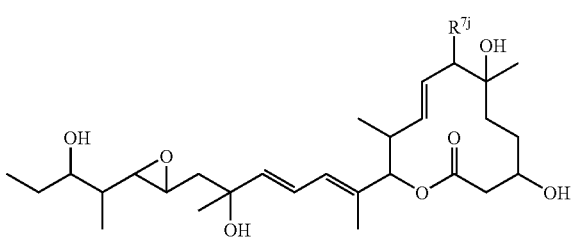

(I-j)

(in the formula, $R^{7j}$ represents $R^jCO$—O— (wherein $R^j$ represents the formula (XI):

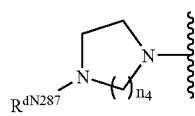

(XI)

(wherein $n_4$ represents an integer of 1 to 3; and $R^{dN28}$ represents
1) a hydrogen atom,
2) an optionally substituted $C_{1-6}$ alkyl group,
3) a $C_{3-8}$ cycloalkyl group,
4) a $C_{4-9}$ cycloalkyl alkyl group,
5) a $C_{7-10}$ aralkyl group,
6) a pyridinyl group or
7) a tetrahydropyranyl group))), or a pharmacologically acceptable salt thereof.

19. The compound according to claim 5 represented by the formula (I-k):

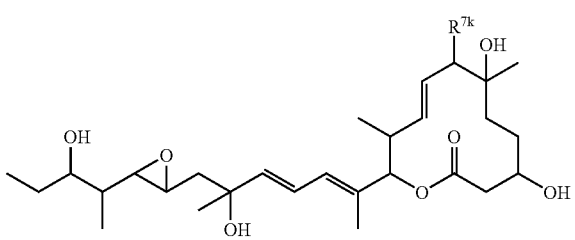

(I-k)

(in the formula, $R^{7k}$ represents $R^kCO$—O— (wherein $R^k$ represents the formula (XII):

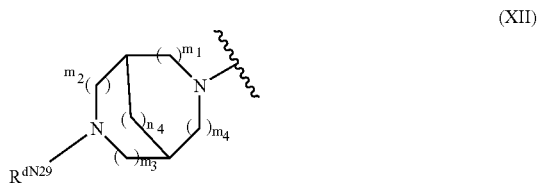

(XII)

(wherein $m_1$, $m_2$, $m_3$ and $m_4$ are the same as or different from one another and each represents 0 or 1;
$n_4$ represents an integer of 1 to 3; and
$R^{dN29}$ represents
1) a hydrogen atom,
2) an optionally substituted $C_{1-6}$ alkyl group,
3) an optionally substituted unsaturated $C_{2-10}$ alkyl group,
4) an optionally substituted $C_{6-14}$ aryl group,
5) an optionally substituted 5 to 14-membered heteroaryl group,
6) an optionally substituted $C_{7-10}$ aralkyl group,
7) an optionally substituted $C_{3-5}$ cycloalkyl group,
8) an optionally substituted $C_{4-9}$ cycloalkyl alkyl group,
9) an optionally substituted 5 to 14-membered heteroaralkyl group or
10) an optionally substituted 5 to 14-membered non-aromatic heterocyclic group))), or a pharmacologically acceptable salt thereof.

20. The compound according to claim 5 represented by the formula (I-m):

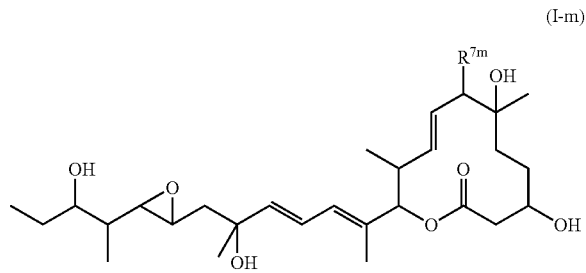

(I-m)

(in the formula, $R^{7m}$ represents $R^mCO$—O— (wherein $R^m$ represents the formula (XIII):

(XIII)

(wherein $m_5$ represents an integer of 1 to 3; and $n_5$ represents 2 or 3))), or a pharmacologically acceptable salt thereof.

21. The compound according to claim 5 represented by the formula (I-n):

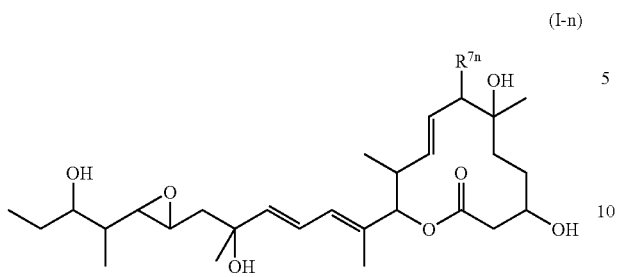

(I-n)

(in the formula, $R^{7n}$ represents R"CO—O— (wherein R" is a group represented by the formula (XIV):

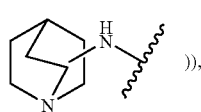

(XIV)

or a pharmacologically acceptable salt thereof.

22. The compound according to claim 1, which is selected from:

(8E,12E,14E)-7-(N-(2-(N',N'-Dimethylamino)ethyl)-N-methylcarbamoyloxy)-3,6,16,21-tetrahydroxy-6,10,12,16,20-pentamethyl-18,19-epoxytricosa-8,12,14-trien-11-olide; (8E,12E,14E)-3,6,16,21-Tetrahydroxy-6,10,12,16,20-pentamethyl-7-((4-methylhomopiperazin-1-yl)carbonyl)oxy-18,19-epoxytricosa-8,12,14-trien-11-olide; (8E,12E,14E)-3,6,16,21-Tetrahydroxy-6,10,12,16,20-pentamethyl-7-((4-methylpiperazin-1-yl)carbonyl)oxy-18,19-epoxytricosa-8,12,14-trien-11-olide; (8E,12E,14E)-7-((4-Butylpiperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-7-((4-Ethylpiperazin-1-yl)carbonyl)oxy-3,6,16,21-tetrahydroxy-6,10,12,16,20-pentamethyl-18,19-epoxytricosa-8,12,14-trien-11-olide; (8E,12E,1 4E)-3,6,16,21-Tetrahydroxy-6,10,12,16,20-pentamethyl-7-((4-propylpiperazin-1-yl)carbonyl)oxy-18,19-epoxytricosa-8,12,14-trien-11-olide; (8E,12E,14E)-7-((4-Cyclohexylpiperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-7-((4-(Cyclopropylmethyl)piperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-3,6,16,21-Tetrahydroxy-6,10,12,16,20-pentamethyl-7-((4-propylhomopiperazin-1-yl)carbonyl)oxy-18,19-epoxytricosa-8,12,14-trien-11-olide; (8E,12E,14E)-7-((4-(Cyclopropylmethyl)homopiperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-7-((4-Cyclopentylpiperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-3,6,16,21-Tetrahydroxy-7-((4-isopropylpiperazin-1-yl)carbonyl)oxy-6,10,12,16,20-pentamethyl-18,19-epoxytricosa-8,12,14-trien-11-olide; (8E,12E,14E)-7-((4-Cycloheptylpiperazin-1-yl)carbonyl)oxy-3,6,16,21-tetrahydroxy-6,10,12,16,20-pentamethyl-8,19-epoxytricosa-8,12,14-trien-11-olide; (8E,12E,14E)-7-(N-(2-(N',N'-Diethylamino)ethyl)-N-methylcarbamoyloxy)-3,6,16,21-tetrahydroxy-6,10,12,16,20-pentamethyl-18,19-epoxytricosa-8,12,14-trien-11-olide; (8E,12E,14E)-3,6,16,21-Tetrahydroxy-7-((4-isobutylhomopiperazin-1-yl)carbonyl)oxy-6,10,12,16,20-pentamethyl-18,19-epoxytricosa-8,12,14-trien-11-olide; (8E,12E,14E)-7-((4-Ethylhomopiperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-7-((4-Butylhomopiperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-3,16,21 -Trihydroxy-6-methoxy-6,10,12,16,20-pentamethyl-7-((4-methylpiperazin-1-yl)carbonyl)oxy-18,19-epoxytricosa-8,12,14-trien-11-olide; (8E,12E,14E)-3,16,21-Trihydroxy-6-methoxy-6,10,12,16,20-pentamethyl-7-((4-(piperidin-1-yl)piperidin-1-yl)carbonyl)oxy-18,19-epoxytricosa-8,12,14-trien-11-olide; (8E,12E,14E)-7-((4-(2,2-Dimethylpropyl)homopiperazin-1-yl)carbonyl)oxy-3,6,16,21-tetrahydroxy-6,10,12,16,20-pentamethyl-18,19-epoxytricosa-8,12,14-trien-11-olide; and (8E,12E,14E)-3,6,16-Trihydroxy-21-methoxy-6,10,12,16,20-pentamethyl-7-((4-methylpiperazin-1-yl)carbonyl)oxy-18,19-epoxytricosa-8,12,14-trien-11-olide.

23. The compound according to claim 1, which is selected from:

(8E,12E,14E)-3,6,16,21-tetrahydroxy-6,10,12,16,20-pentamethyl-7-((4-methylhomopiperazin-1-yl)carbonyl)oxy-18,19-epoxytricosa-8,12,14-trien-11-olide; (8E,12E,14E)-3,6,16,21-tetrahydroxy-6,10,12,16,20-pentamethyl-7-((4-methylpiperazin-1-yl)carbonyl)oxy-18,19-epoxytricosa-8,12,14-trien-11-olide; (8E,12E,14E)-7-((4-cyclohexylpiperazin-1-yl)carbonyl)oxy-3,6,16,21-tetrahydroxy-6,10,12,16,20-pentamethyl-18,19-epoxytricosa-8,12,14-trien-11-olide; (8E,12E,14E)-3,6,16,21-tetrahydroxy-7-((4-isopropylpiperazin-1-yl)carbonyl)oxy-6,10,12,16,20-pentamethyl-18,19-epoxytricosa-8,12,14-trien-11-olide; (8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide; and (8E,12E,14E)-7-(N-(2-(N',N'-Diethylamino)ethyl)-N-methylcarbamoyloxy)-3,6,16,21-tetrahydroxy-6,10,12,16,20-pentamethyl-18,19-epoxytricosa-8,12,14-trien-11-olide.

24. A pharmaceutical composition comprising the compound according to claim 1, or a pharmacologically acceptable salt thereof as an active ingredient.

25. A method for treating a disease against which suppression of VEGF production is efficacious, which comprises administering a pharmacologically effective dose of the compound according to claim 1 to a patient in need thereof, wherein said disease is a cancer, angioma, metastasis, solid cancer, lung cancer, brain tumor, breast cancer, prostate cancer, ovarian cancer, colon cancer, melanoma, or leukemia.

26. A method or treating a disease against which an angiogenesis inhibition is efficacious, which comprises administering a pharmacologically effective dose of the compound according to claim 1 to a patient in need thereof, wherein said disease is a cancer, angioma, metastasis, solid cancer, lung cancer, brain tumor, breast cancer, prostate cancer, ovarian cancer, colon cancer, melanoma, or leukemia.

* * * * *

UNITED STATES PATENT AND TRADEMARK OFFICE
CERTIFICATE OF CORRECTION

PATENT NO. : 7,550,503 B2
APPLICATION NO. : 11/473201
DATED : June 23, 2009
INVENTOR(S) : Yoshihiko Kotake et al.

It is certified that error appears in the above-identified patent and that said Letters Patent is hereby corrected as shown below:

On the title page, please correct the Assignee information as follows:

Item (73) Assignees: Eisai R & D management Co., Ltd., Tokyo (JP); "Merican Corporation" should read --Mercian Corporation--

Please correct the claims as follows:

In Column 181, line 10:
"c) —S$_2$—O—," should read --c) —SO$_2$—O—,--

In Column 181, line 64:
"13) (R$^{N1}$R$^{N2}$N)(R$^{N5}$O)PO—O— (wherein R$^{N1}$, R$^{N2}$ and R" should read --13) (R$^{N1}$R$^{N2}$N)(R$^{N5}$O)PO—O— (wherein R$^{N1}$, R$^{N2}$ and R$^{N5}$--

In Column 182, line 42:
"C$_{2-22}$ n alkoxy" should read --C$_{2-22}$ alkoxy--

In Column 184, line 50 claim 4:
"tat" should read --that--

Signed and Sealed this

Fifteenth Day of June, 2010

David J. Kappos
*Director of the United States Patent and Trademark Office*

In Column 186, line 21 claim 5:

"$R^{dn2}$" should read --$R^{dN2}$--

"$R^{dn1}$" should read --$R^{dN1}$--

In Column 188, line 37 claim 8:

"3)" should read --i)--

In Column 188, line 54 claim 8:

"$R^{eN}3$" should read --$R^{eN3}$--

In Column 188, line 58 claim 8:

"$R^{eN1}\ R^{eN2}$" should read --$R^{eN1}$ and $R^{eN2}$--

In Column 188, line 61 claim 8:

"$R^{eNn5}$" should read --$R^{eN5}$--

In Column 191, line 55 claim 13:

"$C_{61-4}$" should read --$C_{6-14}$--

In Column 195, line 35 claim 18:

in the formula (XI), "$R^{dN287}$" should read --$R^{dN28}$--

In Column 196, line 29 claim 19:

"$C_{3-5}$ cycloalkyl" should read --$C_{3-8}$ cycloalkyl--

UNITED STATES PATENT AND TRADEMARK OFFICE
CERTIFICATE OF CORRECTION

PATENT NO.       : 7,550,503 B2
APPLICATION NO.  : 11/473201
DATED            : June 23, 2009
INVENTOR(S)      : Yoshihiko Kotake et al.

It is certified that error appears in the above-identified patent and that said Letters Patent is hereby corrected as shown below:

On the Title Page, please insert the following:

Item -- (30)   Foreign Application Priority Data

| May 29, 2002  | [JP] | Japan........... 2002-155853 |
| July 31, 2002 | [JP] | Japan........... 2002-223355 |
| March 10, 2003| [JP] | Japan........... 2003-63176 -- |

On the Title Page, please amend the Related U.S. Application Data as follows:

Item -- (63)   Related U.S. Application Data

Continuation of application No. 10/515,647, filed on July 20, 2005, now abandoned, which is the national stage application of PCT/JP03/06779, filed on May 29, 2003.

Column 197, lines 64-66, "(8E,12E,14E)-7-((4-Cycloheptylpiperazin-1-yl)carbonyl)oxy-3,6,16,21-tetrahydroxy-6,10,12,16,20-pentamethyl-8,19-epoxytricosa-8,12,14-trien-11-olide," should read --(8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide;--.

Column 198, line 58, claim 26, "method or treating" should read --method for treating--.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,550,503 B2 |
| APPLICATION NO. | : 11/473201 |
| DATED | : June 23, 2009 |
| INVENTOR(S) | : Yoshihiko Kotake et al. |

It is certified that error appears in the above-identified patent and that said Letters Patent is hereby corrected as shown below:

On the Title Page, please insert the following:

Item --(30)    Foreign Application Priority Data

| | | |
|---|---|---|
| May 29, 2002 | [JP] | Japan............ 2002-155853 |
| July 31, 2002 | [JP] | Japan............ 2002-223355 |
| March 10, 2003 | [JP] | Japan............ 2003-63176-- |

On the Title Page, please amend the Related U.S. Application Data as follows:

Item (63)    Related U.S. Application Data

Continuation of application No. 10/515,647, filed on July 20, 2005, now abandoned, which is the national stage application of PCT/JP03/06779, filed on May 29, 2003.

Column 197, lines 64-66, "(8E,12E,14E)-7-((4-Cycloheptylpiperazin-1-yl)carbonyl)oxy-3,6,16,21-tetrahydroxy-6,10,12,16,20-pentamethyl-8,19-epoxytricosa-8,12,14-trien-11-olide;" should read --(8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide;--.

Column 198, line 58 claim 26, "method or treating" should read --method for treating--.

Signed and Sealed this

Ninth Day of November, 2010

David J. Kappos
*Director of the United States Patent and Trademark Office*